United States Patent
Shelton, IV et al.

(10) Patent No.: US 11,109,866 B2
(45) Date of Patent: Sep. 7, 2021

(54) METHOD FOR CIRCULAR STAPLER CONTROL ALGORITHM ADJUSTMENT BASED ON SITUATIONAL AWARENESS

(71) Applicant: Ethicon LLC, Guaynabo, PR (US)

(72) Inventors: Frederick E. Shelton, IV, Hillsboro, OH (US); Gregory J. Bakos, Mason, OH (US); Jason L. Harris, Lebanon, OH (US); Chester O. Baxter, III, Loveland, OH (US)

(73) Assignee: Cilag GmbH International, Zug (CH)

( * ) Notice: Subject to any disclaimer, the term of this patent is extended or adjusted under 35 U.S.C. 154(b) by 114 days.

(21) Appl. No.: 16/209,491

(22) Filed: Dec. 4, 2018

(65) Prior Publication Data

US 2019/0200998 A1 Jul. 4, 2019

Related U.S. Application Data

(60) Provisional application No. 62/773,742, filed on Nov. 30, 2018, provisional application No. 62/773,778, (Continued)

(51) Int. Cl.
*A61B 17/115* (2006.01)
*A61B 17/32* (2006.01)
(Continued)

(52) U.S. Cl.
CPC ...... *A61B 17/1155* (2013.01); *A61B 1/00009* (2013.01); *A61B 1/00045* (2013.01);
(Continued)

(58) Field of Classification Search
CPC .......... A61M 2230/005; A61M 1/0025; A61B 17/0682; A61B 17/07207; A61B 17/1155;
(Continued)

(56) References Cited

U.S. PATENT DOCUMENTS 3,082,426 A 3/1963 Miles
3,503,396 A 3/1970 Pierie et al.
(Continued)

FOREIGN PATENT DOCUMENTS

AU 2015201140 A1 3/2015
CA 2795323 A1 5/2014
(Continued)

OTHER PUBLICATIONS

US 10,504,709 B2, 12/2019, Karancsi et al. (withdrawn)
(Continued)

*Primary Examiner* — Andrew M Tecco
*Assistant Examiner* — Nicholas E Igbokwe

(57) ABSTRACT

A method of adjusting a staple parameter of a surgical stapling instrument is disclosed. The method includes determining, by a control circuit of the surgical stapling instrument, a first stroke length for a first staple driver of the surgical stapling instrument to drive a first row of staples of a circular stapling head assembly of the surgical stapling instrument; detecting, by the control circuit, a malformed staple in the first row of staples; adjusting, by the control circuit, the staple parameter, based on the detection of the malformed staple; and determining, by the control circuit, a second stroke length for a second staple driver of the surgical stapling instrument to drive a second row of staples of the circular stapling head assembly.

19 Claims, 89 Drawing Sheets

Related U.S. Application Data filed on Nov. 30, 2018, provisional application No. 62/773,728, filed on Nov. 30, 2018, provisional application No. 62/773,741, filed on Nov. 30, 2018, provisional application No. 62/750,555, filed on Oct. 25, 2018, provisional application No. 62/750,529, filed on Oct. 25, 2018, provisional application No. 62/750,539, filed on Oct. 25, 2018, provisional application No. 62/729,186, filed on Sep. 10, 2018, provisional application No. 62/729,183, filed on Sep. 10, 2018, provisional application No. 62/729,195, filed on Sep. 10, 2018, provisional application No. 62/729,177, filed on Sep. 10, 2018, provisional application No. 62/729,182, filed on Sep. 10, 2018, provisional application No. 62/729,176, filed on Sep. 10, 2018, provisional application No. 62/729,185, filed on Sep. 10, 2018, provisional application No. 62/729,184, filed on Sep. 10, 2018, provisional application No. 62/729,191, filed on Sep. 10, 2018, provisional application No. 62/721,996, filed on Aug. 23, 2018, provisional application No. 62/721,994, filed on Aug. 23, 2018, provisional application No. 62/721,999, filed on Aug. 23, 2018, provisional application No. 62/721,995, filed on Aug. 23, 2018, provisional application No. 62/721,998, filed on Aug. 23, 2018, provisional application No. 62/692,768, filed on Jun. 30, 2018, provisional application No. 62/692,747, filed on Jun. 30, 2018, provisional application No. 62/692,748, filed on Jun. 30, 2018, provisional application No. 62/691,219, filed on Jun. 28, 2018, provisional application No. 62/691,228, filed on Jun. 28, 2018, provisional application No. 62/691,230, filed on Jun. 28, 2018, provisional application No. 62/691,262, filed on Jun. 28, 2018, provisional application No. 62/691,257, filed on Jun. 28, 2018, provisional application No. 62/691,227, filed on Jun. 28, 2018, provisional application No. 62/691,251, filed on Jun. 28, 2018, provisional application No. 62/665,129, filed on May 1, 2018, provisional application No. 62/665,128, filed on May 1, 2018, provisional application No. 62/665,177, filed on May 1, 2018, provisional application No. 62/665,134, filed on May 1, 2018, provisional application No. 62/665,192, filed on May 1, 2018, provisional application No. 62/665,139, filed on May 1, 2018, provisional application No. 62/659,900, filed on Apr. 19, 2018, provisional application No. 62/650,877, filed on Mar. 30, 2018, provisional application No. 62/650,898, filed on Mar. 30, 2018, provisional application No. 62/650,887, filed on Mar. 30, 2018, provisional application No. 62/650,882, filed on Mar. 30, 2018, provisional application No. 62/649,320, filed on Mar. 28, 2018, provisional application No. 62/649,309, filed on Mar. 28, 2018, provisional application No. 62/649,307, filed on Mar. 28, 2018, provisional application No. 62/649,313, filed on Mar. 28, 2018, provisional application No. 62/649,296, filed on Mar. 28, 2018, provisional application No. 62/649,327, filed on Mar. 28, 2018, provisional application No. 62/649,310, filed on Mar. 28, 2018, provisional application No. 62/649,294, filed on Mar. 28, 2018, provisional application No. 62/649,315, filed on Mar. 28, 2018, provisional application No. 62/649,323, filed on Mar. 28, 2018, provisional application No. 62/649,333, filed on Mar. 28, 2018, provisional application No. 62/649,302, filed on Mar. 28, 2018, provisional application No. 62/649,291, filed on Mar. 28, 2018, provisional application No. 62/649,300, filed on Mar. 28, 2018, provisional application No. 62/611,340, filed on Dec. 28, 2017, provisional application No. 62/611,341, filed on Dec. 28, 2017, provisional application No. 62/611,339, filed on Dec. 28, 2017.

(51) Int. Cl.

| | | |
|---|---|---|
| *A61B 18/14* | (2006.01) | |
| *A61B 34/32* | (2016.01) | |
| *G16H 40/63* | (2018.01) | |
| *A61B 17/072* | (2006.01) | |
| *A61B 90/98* | (2016.01) | |
| *A61M 1/00* | (2006.01) | |
| *A61B 34/20* | (2016.01) | |
| *A61B 34/00* | (2016.01) | |
| *A61B 90/35* | (2016.01) | |
| *A61B 90/00* | (2016.01) | |
| *G16H 40/67* | (2018.01) | |
| *G16H 10/60* | (2018.01) | |
| *G16H 50/20* | (2018.01) | |
| *G16H 70/20* | (2018.01) | |
| *A61B 1/00* | (2006.01) | |
| *A61B 1/05* | (2006.01) | |
| *A61B 1/06* | (2006.01) | |
| *A61B 5/00* | (2006.01) | |
| *A61B 5/026* | (2006.01) | |
| *A61B 6/00* | (2006.01) | |
| *A61B 17/068* | (2006.01) | |
| *A61B 17/11* | (2006.01) | |
| *A61B 17/128* | (2006.01) | |
| *B25J 9/16* | (2006.01) | |
| *B25J 13/00* | (2006.01) | |
| *H01Q 1/22* | (2006.01) | |
| *H04L 29/06* | (2006.01) | |
| *H04L 29/08* | (2006.01) | |
| *H04N 5/272* | (2006.01) | |
| *H04N 7/18* | (2006.01) | |
| *H05K 1/02* | (2006.01) | |
| *H05K 1/18* | (2006.01) | |
| *A61M 16/00* | (2006.01) | |
| *A61B 17/00* | (2006.01) | |
| *A61B 18/12* | (2006.01) | |
| *G16H 20/40* | (2018.01) | |
| *A61B 34/30* | (2016.01) | |
| *A61B 90/30* | (2016.01) | |
| *A61B 18/00* | (2006.01) | |
| *A61M 13/00* | (2006.01) | |
| *G06K 7/10* | (2006.01) | |
| *G06K 19/077* | (2006.01) | |

(52) U.S. Cl.
CPC ............ *A61B 1/051* (2013.01); *A61B 1/0661* (2013.01); *A61B 5/0066* (2013.01); *A61B 5/0075* (2013.01); *A61B 5/0261* (2013.01); *A61B 6/5247* (2013.01); *A61B 17/0682* (2013.01); *A61B 17/072* (2013.01); *A61B 17/07207* (2013.01); *A61B 17/1114* (2013.01); *A61B 17/1285* (2013.01); *A61B 17/320092* (2013.01); *A61B 34/20* (2016.02); *A61B 34/32* (2016.02); *A61B 34/71* (2016.02); *A61B 90/35* (2016.02); *A61B 90/361* (2016.02); *A61B 90/98* (2016.02); *A61M 1/0025* (2014.02); *A61M 1/0056* (2013.01); *B25J 9/1697* (2013.01); *B25J 13/006* (2013.01); *G16H*

10/60 (2018.01); *G16H 40/63* (2018.01); *G16H 40/67* (2018.01); *G16H 50/20* (2018.01); *G16H 70/20* (2018.01); *H01Q 1/22* (2013.01); *H04L 63/1416* (2013.01); *H04L 67/10* (2013.01); *H04N 5/272* (2013.01); *H04N 7/183* (2013.01); *H05K 1/028* (2013.01); *H05K 1/189* (2013.01); *A61B 18/1206* (2013.01); *A61B 18/1442* (2013.01); *A61B 18/1445* (2013.01); *A61B 34/30* (2016.02); *A61B 2017/0003* (2013.01); *A61B 2017/0011* (2013.01); *A61B 2017/00017* (2013.01); *A61B 2017/00022* (2013.01); *A61B 2017/00026* (2013.01); *A61B 2017/00039* (2013.01); *A61B 2017/00044* (2013.01); *A61B 2017/00057* (2013.01); *A61B 2017/00061* (2013.01); *A61B 2017/00075* (2013.01); *A61B 2017/00084* (2013.01); *A61B 2017/00097* (2013.01); *A61B 2017/00106* (2013.01); *A61B 2017/00115* (2013.01); *A61B 2017/00119* (2013.01); *A61B 2017/00199* (2013.01); *A61B 2017/00203* (2013.01); *A61B 2017/00221* (2013.01); *A61B 2017/00398* (2013.01); *A61B 2017/00402* (2013.01); *A61B 2017/00442* (2013.01); *A61B 2017/00734* (2013.01); *A61B 2017/00809* (2013.01); *A61B 2017/00818* (2013.01); *A61B 2017/07235* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2017/1132* (2013.01); *A61B 2017/32007* (2017.08); *A61B 2017/320074* (2017.08); *A61B 2017/320084* (2013.01); *A61B 2017/320095* (2017.08); *A61B 2017/320097* (2017.08); *A61B 2018/0063* (2013.01); *A61B 2018/00541* (2013.01); *A61B 2018/00589* (2013.01); *A61B 2018/00595* (2013.01); *A61B 2018/00601* (2013.01); *A61B 2018/00607* (2013.01); *A61B 2018/00642* (2013.01); *A61B 2018/00684* (2013.01); *A61B 2018/00791* (2013.01); *A61B 2018/00827* (2013.01); *A61B 2018/00875* (2013.01); *A61B 2018/00892* (2013.01); *A61B 2018/00988* (2013.01); *A61B 2018/00994* (2013.01); *A61B 2034/2055* (2016.02); *A61B 2034/2057* (2016.02); *A61B 2034/301* (2016.02); *A61B 2034/305* (2016.02); *A61B 2090/061* (2016.02); *A61B 2090/064* (2016.02); *A61B 2090/0808* (2016.02); *A61B 2090/309* (2016.02); *A61B 2217/005* (2013.01); *A61B 2217/007* (2013.01); *A61B 2218/002* (2013.01); *A61B 2218/007* (2013.01); *A61B 2218/008* (2013.01); *A61M 1/0066* (2013.01); *A61M 13/003* (2013.01); *A61M 16/00* (2013.01); *A61M 2205/3306* (2013.01); *A61M 2205/3313* (2013.01); *A61M 2205/3327* (2013.01); *A61M 2205/3331* (2013.01); *A61M 2205/3365* (2013.01); *A61M 2205/3368* (2013.01); *A61M 2230/04* (2013.01); *A61M 2230/30* (2013.01); *G05B 2219/40174* (2013.01); *G05B 2219/45119* (2013.01); *G06K 7/10316* (2013.01); *G06K 19/07749* (2013.01); *G16H 20/40* (2018.01); *H04L 67/12* (2013.01)

(58) Field of Classification Search
CPC .......... A61B 2017/00022; A61B 2017/00075; A61B 2017/07235; A61B 2090/064
See application file for complete search history.

(56) References Cited

U.S. PATENT DOCUMENTS

| | | | |
|---|---|---|---|
| 3,584,628 A | 6/1971 | Green | |
| 3,759,017 A | 9/1973 | Young | |
| 4,448,193 A | 5/1984 | Ivanov | |
| 4,523,695 A | 6/1985 | Braun et al. | |
| 4,701,193 A | 10/1987 | Robertson et al. | |
| 4,735,603 A | 4/1988 | Goodson et al. | |
| 4,788,977 A | 12/1988 | Farin et al. | |
| 5,042,460 A | 8/1991 | Sakurai et al. | |
| 5,084,057 A | 1/1992 | Green et al. | |
| 5,100,402 A | 3/1992 | Fan | |
| 5,151,102 A | 9/1992 | Kamiyama et al. | |
| 5,156,315 A | 10/1992 | Green et al. | |
| 5,197,962 A | 3/1993 | Sansom et al. | |
| 5,242,474 A | 9/1993 | Herbst et al. | |
| 5,253,793 A | 10/1993 | Green et al. | |
| RE34,519 E | 1/1994 | Fox et al. | |
| 5,318,516 A | 6/1994 | Cosmescu | |
| 5,322,055 A | 6/1994 | Davison et al. | |
| 5,342,349 A | 8/1994 | Kaufman | |
| 5,383,880 A * | 1/1995 | Hooven | A61B 17/072 227/175.1 |
| 5,396,900 A | 3/1995 | Slater et al. | |
| 5,397,046 A | 3/1995 | Savage et al. | |
| 5,403,312 A | 4/1995 | Yates et al. | |
| 5,403,327 A | 4/1995 | Thornton et al. | |
| 5,413,267 A | 5/1995 | Solyntjes et al. | |
| 5,417,699 A | 5/1995 | Klein et al. | |
| 5,439,468 A | 8/1995 | Schulze et al. | |
| 5,445,304 A | 8/1995 | Plyley et al. | |
| 5,465,895 A | 11/1995 | Knodel et al. | |
| 5,467,911 A | 11/1995 | Tsuruta et al. | |
| 5,474,566 A | 12/1995 | Alesi et al. | |
| 5,496,315 A | 3/1996 | Weaver et al. | |
| 5,503,320 A | 4/1996 | Webster et al. | |
| 5,531,743 A | 7/1996 | Nettekoven et al. | |
| 5,545,148 A | 8/1996 | Wurster | |
| 5,610,379 A | 3/1997 | Muz et al. | |
| 5,613,966 A | 3/1997 | Makower et al. | |
| 5,624,452 A | 4/1997 | Yates | |
| 5,643,291 A | 7/1997 | Pier et al. | |
| 5,654,750 A | 8/1997 | Weil et al. | |
| 5,673,841 A | 10/1997 | Schulze et al. | |
| 5,673,842 A | 10/1997 | Bittner et al. | |
| 5,675,227 A | 10/1997 | Roos et al. | |
| 5,693,052 A | 12/1997 | Weaver | |
| 5,695,502 A | 12/1997 | Pier et al. | |
| 5,697,926 A | 12/1997 | Weaver | |
| 5,706,998 A | 1/1998 | Plyley et al. | |
| 5,725,536 A | 3/1998 | Oberlin et al. | |
| 5,725,542 A | 3/1998 | Yoon | |
| 5,735,848 A | 4/1998 | Yates et al. | |
| 5,746,209 A | 5/1998 | Yost et al. | |
| 5,749,362 A | 5/1998 | Funda et al. | |
| 5,749,893 A | 5/1998 | Vidal et al. | |
| 5,752,644 A | 5/1998 | Bolanos et al. | |
| 5,762,255 A | 6/1998 | Chrisman et al. | |
| 5,766,186 A | 6/1998 | Faraz et al. | |
| 5,769,791 A | 6/1998 | Benaron et al. | |
| 5,797,537 A | 8/1998 | Oberlin et al. | |
| D399,561 S | 10/1998 | Ellingson | |
| 5,817,093 A | 10/1998 | Williamson, IV et al. | |
| 5,820,009 A | 10/1998 | Melling et al. | |
| 5,836,909 A | 11/1998 | Cosmescu | |
| 5,843,080 A | 12/1998 | Fleenor et al. | |
| 5,846,237 A | 12/1998 | Nettekoven | |
| 5,849,022 A | 12/1998 | Sakashita et al. | |
| 5,873,873 A | 2/1999 | Smith et al. | |
| 5,878,938 A | 3/1999 | Bittner et al. | |
| 5,893,849 A | 4/1999 | Weaver | |
| 5,906,625 A | 5/1999 | Bito et al. | |
| 5,942,333 A | 8/1999 | Arnett et al. | |
| 5,947,996 A | 9/1999 | Logeman | |
| 5,968,032 A | 10/1999 | Sleister | |
| 5,980,510 A | 11/1999 | Tsonton et al. | |
| 5,997,528 A | 12/1999 | Bisch et al. | |

(56) References Cited

U.S. PATENT DOCUMENTS

| | | |
|---|---|---|
| 6,010,054 A | 1/2000 | Johnson et al. |
| 6,030,437 A | 2/2000 | Gourrier et al. |
| 6,036,637 A | 3/2000 | Kudo |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,155,473 A | 12/2000 | Tompkins et al. |
| 6,214,000 B1 | 4/2001 | Fleenor et al. |
| 6,273,887 B1 | 8/2001 | Yamauchi et al. |
| 6,301,495 B1 | 10/2001 | Gueziec et al. |
| 6,302,881 B1 | 10/2001 | Farin |
| 6,325,808 B1 | 12/2001 | Bernard et al. |
| 6,325,811 B1 | 12/2001 | Messerly |
| 6,341,164 B1 | 1/2002 | Dilkie et al. |
| 6,391,102 B1 | 5/2002 | Bodden et al. |
| 6,443,973 B1 | 9/2002 | Whitman |
| 6,461,352 B2 | 10/2002 | Morgan et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,585,791 B1 | 7/2003 | Garito et al. |
| 6,618,626 B2 | 9/2003 | West, Jr. et al. |
| 6,648,223 B2 | 11/2003 | Boukhny et al. |
| 6,685,704 B2 | 2/2004 | Greep |
| 6,699,187 B2 | 3/2004 | Webb et al. |
| 6,742,895 B2 | 6/2004 | Robin |
| 6,752,816 B2 | 6/2004 | Culp et al. |
| 6,773,444 B2 | 8/2004 | Messerly |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,852,219 B2 | 2/2005 | Hammond |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,937,892 B2 | 8/2005 | Leyde et al. |
| 6,945,981 B2 | 9/2005 | Donofrio et al. |
| 6,951,559 B1 | 10/2005 | Greep |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,048,775 B2 | 5/2006 | Jornitz et al. |
| 7,053,752 B2 | 5/2006 | Wang et al. |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,118,564 B2 | 10/2006 | Ritchie et al. |
| 7,121,460 B1 | 10/2006 | Parsons et al. |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,208,005 B2 | 4/2007 | Frecker et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,422,139 B2 | 9/2008 | Shelton, IV et al. |
| 7,423,972 B2 | 9/2008 | Shaham et al. |
| 7,457,804 B2 | 11/2008 | Uber, III et al. |
| 7,464,847 B2 | 12/2008 | Viola et al. |
| 7,464,849 B2 | 12/2008 | Shelton, IV et al. |
| 7,515,961 B2 | 4/2009 | Germanson et al. |
| 7,575,144 B2 | 8/2009 | Ortiz et al. |
| 7,621,192 B2 | 11/2009 | Conti et al. |
| 7,621,898 B2 | 11/2009 | Lalomia et al. |
| 7,637,410 B2 | 12/2009 | Marczyk |
| 7,641,092 B2 | 1/2010 | Kruszynski et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,736,357 B2 | 6/2010 | Lee, Jr. et al. |
| 7,742,176 B2 | 6/2010 | Braunecker et al. |
| 7,753,245 B2 | 7/2010 | Boudreaux et al. |
| 7,766,905 B2 | 8/2010 | Paterson et al. |
| 7,770,773 B2 | 8/2010 | Whitman et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,818,041 B2 | 10/2010 | Kim et al. |
| 7,837,079 B2 | 11/2010 | Holsten et al. |
| 7,837,680 B2 | 11/2010 | Isaacson et al. |
| 7,845,537 B2 | 12/2010 | Shelton, IV et al. |
| 7,862,560 B2 | 1/2011 | Marion |
| 7,862,579 B2 | 1/2011 | Ortiz et al. |
| 7,892,337 B2 | 2/2011 | Palmerton et al. |
| 7,913,891 B2 | 3/2011 | Doll et al. |
| 7,918,230 B2 | 4/2011 | Whitman et al. |
| 7,920,706 B2 | 4/2011 | Asokan et al. |
| 7,955,322 B2 | 6/2011 | Devengenzo et al. |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,035,685 B2 | 10/2011 | Jensen |
| 8,038,686 B2 | 10/2011 | Huitema et al. |
| 8,043,560 B2 | 10/2011 | Okumoto et al. |
| 8,054,184 B2 | 11/2011 | Cline et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,075,571 B2 | 12/2011 | Vitali et al. |
| 8,096,459 B2 | 1/2012 | Ortiz et al. |
| 8,120,301 B2 | 2/2012 | Goldberg et al. |
| 8,123,764 B2 | 2/2012 | Meade et al. |
| 8,131,565 B2 | 3/2012 | Dicks et al. |
| 8,147,486 B2 | 4/2012 | Honour et al. |
| 8,157,145 B2 | 4/2012 | Shelton, IV et al. |
| 8,157,150 B2 | 4/2012 | Viola et al. |
| 8,160,098 B1 | 4/2012 | Yan et al. |
| 8,161,977 B2 | 4/2012 | Shelton, IV et al. |
| 8,172,836 B2 | 5/2012 | Ward |
| 8,181,839 B2 | 5/2012 | Beetel |

(56) References Cited

U.S. PATENT DOCUMENTS

| | | |
|---|---|---|
| 8,185,409 B2 | 5/2012 | Putnam et al. |
| 8,206,345 B2 | 6/2012 | Abboud et al. |
| 8,210,411 B2 | 7/2012 | Yates et al. |
| 8,220,688 B2 | 7/2012 | Laurent et al. |
| 8,225,979 B2 | 7/2012 | Farascioni et al. |
| 8,229,549 B2 | 7/2012 | Whitman et al. |
| 8,257,387 B2 | 9/2012 | Cunningham |
| 8,262,560 B2 | 9/2012 | Whitman |
| 8,292,888 B2 | 10/2012 | Whitman |
| 8,308,040 B2 | 11/2012 | Huang et al. |
| 8,321,581 B2 | 11/2012 | Katis et al. |
| 8,328,065 B2 | 12/2012 | Shah |
| 8,335,590 B2 | 12/2012 | Costa et al. |
| 8,346,392 B2 | 1/2013 | Walser et al. |
| 8,364,222 B2 | 1/2013 | Cook et al. |
| 8,365,975 B1 | 2/2013 | Manoux et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,946 B2 | 3/2013 | Whitfield et al. |
| 8,406,859 B2 | 3/2013 | Zuzak et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,476,227 B2 | 7/2013 | Kaplan et al. |
| 8,489,235 B2 | 7/2013 | Moll et al. |
| 8,499,992 B2 | 8/2013 | Whitman et al. |
| 8,503,759 B2 | 8/2013 | Greer et al. |
| 8,505,801 B2 | 8/2013 | Ehrenfels et al. |
| 8,512,365 B2 | 8/2013 | Wiener et al. |
| 8,521,331 B2 | 8/2013 | Itkowitz |
| 8,523,043 B2 | 9/2013 | Ullrich et al. |
| 8,546,996 B2 | 10/2013 | Messerly et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,573,465 B2 | 11/2013 | Shelton, IV |
| 8,591,536 B2 | 11/2013 | Robertson |
| 8,595,607 B2 | 11/2013 | Nekoomaram et al. |
| 8,596,513 B2 | 12/2013 | Olson et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,620,473 B2 | 12/2013 | Diolaiti et al. |
| 8,623,027 B2 | 1/2014 | Price et al. |
| 8,627,483 B2 | 1/2014 | Rachlin et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,632,525 B2 | 1/2014 | Kerr et al. |
| 8,652,086 B2 | 2/2014 | Gerg et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,701,962 B2 | 4/2014 | Kostrzewski |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,794,497 B2 | 8/2014 | Zingman |
| 8,799,008 B2 | 8/2014 | Johnson et al. |
| 8,799,009 B2 | 8/2014 | Mellin et al. |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,840,003 B2 | 9/2014 | Morgan et al. |
| 8,851,354 B2 | 10/2014 | Swensgard et al. |
| 8,852,174 B2 | 10/2014 | Burbank |
| 8,875,973 B2 | 11/2014 | Whitman |
| 8,882,662 B2 | 11/2014 | Charles |
| 8,905,977 B2 | 12/2014 | Shelton et al. |
| 8,912,746 B2 | 12/2014 | Reid et al. |
| 8,914,098 B2 | 12/2014 | Brennan et al. |
| 8,918,207 B2 | 12/2014 | Prisco |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,945,095 B2 | 2/2015 | Blumenkranz et al. |
| 8,945,163 B2 | 2/2015 | Voegele et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,455 B2 | 3/2015 | Zhou |
| 8,968,276 B2 | 3/2015 | Zemlok et al. |
| 8,968,309 B2 | 3/2015 | Roy et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | Dinardo et al. |
| 9,020,240 B2 | 4/2015 | Pettersson et al. |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,358 B2 | 8/2015 | Kerr et al. |
| 9,101,359 B2 | 8/2015 | Smith et al. |

(56) References Cited

U.S. PATENT DOCUMENTS

| | | |
|---|---|---|
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,114,494 B1 | 8/2015 | Mah |
| 9,116,597 B1 | 8/2015 | Gulasky |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,149,322 B2 | 10/2015 | Knowlton |
| 9,161,803 B2 | 10/2015 | Yates et al. |
| 9,168,054 B2 | 10/2015 | Turner et al. |
| 9,179,912 B2 | 11/2015 | Yates et al. |
| 9,183,723 B2 | 11/2015 | Sherman et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,202,078 B2 | 12/2015 | Abuelsaad et al. |
| 9,204,879 B2 | 12/2015 | Shelton, IV |
| 9,204,995 B2 | 12/2015 | Scheller et al. |
| 9,216,062 B2 | 12/2015 | Duque et al. |
| 9,218,053 B2 | 12/2015 | Komuro et al. |
| 9,226,766 B2 | 1/2016 | Aldridge et al. |
| 9,226,767 B2 | 1/2016 | Stulen et al. |
| 9,237,891 B2 | 1/2016 | Shelton, IV |
| 9,241,728 B2 | 1/2016 | Price et al. |
| 9,241,731 B2 | 1/2016 | Boudreaux et al. |
| 9,250,172 B2 | 2/2016 | Harris et al. |
| 9,255,907 B2 | 2/2016 | Heanue et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,280,884 B1 | 3/2016 | Schultz et al. |
| 9,282,974 B2 | 3/2016 | Shelton, IV |
| 9,283,054 B2 | 3/2016 | Morgan et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,307,894 B2 | 4/2016 | von Grunberg et al. |
| 9,307,914 B2 | 4/2016 | Fahey |
| 9,314,246 B2 | 4/2016 | Shelton, IV et al. |
| 9,314,308 B2 | 4/2016 | Parihar et al. |
| 9,326,767 B2 | 5/2016 | Koch et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,345,481 B2 | 5/2016 | Hall et al. |
| 9,345,490 B2 | 5/2016 | Ippisch |
| 9,351,726 B2 | 5/2016 | Leimbach et al. |
| 9,351,727 B2 | 5/2016 | Leimbach et al. |
| 9,358,003 B2 | 6/2016 | Hail et al. |
| 9,358,685 B2 | 6/2016 | Meier et al. |
| 9,360,449 B2 | 6/2016 | Duric |
| 9,364,231 B2 | 6/2016 | Wenchell |
| 9,364,249 B2 | 6/2016 | Kimball et al. |
| 9,364,294 B2 | 6/2016 | Razzaque et al. |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,736 B2 | 9/2016 | Olson |
| 9,450,701 B2 | 9/2016 | Do et al. |
| 9,451,958 B2 | 9/2016 | Shelton, IV et al. |
| 9,463,022 B2 | 10/2016 | Swayze et al. |
| 9,468,438 B2 | 10/2016 | Baber et al. |
| 9,480,492 B2 | 11/2016 | Aranyi et al. |
| 9,485,475 B2 | 11/2016 | Speier et al. |
| 9,492,146 B2 | 11/2016 | Kostrzewski et al. |
| 9,492,237 B2 | 11/2016 | Kang et al. |
| 9,498,215 B2 | 11/2016 | Duque et al. |
| 9,516,239 B2 | 12/2016 | Blanquart et al. |
| 9,519,753 B1 | 12/2016 | Gerdeman et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,572,592 B2 | 2/2017 | Price et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,603,024 B2 | 3/2017 | Wang et al. |
| 9,610,114 B2 | 4/2017 | Baxter, III et al. |
| 9,622,808 B2 | 4/2017 | Beller et al. |
| 9,629,623 B2 | 4/2017 | Lytle, IV et al. |
| 9,629,629 B2 | 4/2017 | Leimbach et al. |
| 9,630,318 B2 | 4/2017 | Ibarz Gabardos et al. |
| 9,636,188 B2 | 5/2017 | Gattani et al. |
| 9,641,596 B2 | 5/2017 | Unagami et al. |
| 9,641,815 B2 | 5/2017 | Richardson et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,706,993 B2 | 7/2017 | Hessler et al. |
| 9,710,644 B2 | 7/2017 | Reybok et al. |
| 9,713,424 B2 | 7/2017 | Spaide |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |

(56) References Cited

U.S. PATENT DOCUMENTS

| | | |
|---|---|---|
| 9,743,947 B2 | 8/2017 | Price et al. |
| 9,750,499 B2 | 9/2017 | Leimbach et al. |
| 9,750,522 B2 | 9/2017 | Scheib et al. |
| 9,750,523 B2 | 9/2017 | Tsubuku |
| 9,753,135 B2 | 9/2017 | Bosch |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,764,164 B2 | 9/2017 | Wiener et al. |
| 9,770,541 B2 | 9/2017 | Carr et al. |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,248 B2 | 11/2017 | Hoffman |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,833,241 B2 | 12/2017 | Huitema et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,470 B2 | 12/2017 | Gilbert et al. |
| 9,839,487 B2 | 12/2017 | Dachs, II |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,867,612 B2 | 1/2018 | Parihar et al. |
| 9,867,651 B2 | 1/2018 | Wham |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,914 B2 | 2/2018 | Martin et al. |
| 9,888,919 B2 | 2/2018 | Leimbach et al. |
| 9,888,921 B2 | 2/2018 | Williams et al. |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,905,000 B2 | 2/2018 | Chou et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,778 B2 | 3/2018 | Walberg et al. |
| 9,918,788 B2 | 3/2018 | Paul et al. |
| 9,922,304 B2 | 3/2018 | Debusk et al. |
| 9,924,941 B2 | 3/2018 | Burbank |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,309 B2 | 4/2018 | Shelton, IV et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,980,778 B2 | 5/2018 | Ohline et al. |
| 9,987,000 B2 | 6/2018 | Shelton, IV et al. |
| 9,993,248 B2 | 6/2018 | Shelton, IV et al. |
| 9,993,258 B2 | 6/2018 | Shelton, IV et al. |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| D826,405 S | 8/2018 | Shelton, IV et al. |
| 10,039,564 B2 | 8/2018 | Hibner et al. |
| 10,039,565 B2 | 8/2018 | Vezzu |
| 10,041,822 B2 | 8/2018 | Zemlok |
| 10,044,791 B2 | 8/2018 | Kamen et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,054,441 B2 | 8/2018 | Schorr et al. |
| 10,076,326 B2 | 9/2018 | Yates et al. |
| 10,080,618 B2 | 9/2018 | Marshall et al. |
| 10,085,748 B2 | 10/2018 | Morgan et al. |
| 10,085,749 B2 | 10/2018 | Cappola et al. |
| 10,098,527 B2 | 10/2018 | Weisenburgh, II et al. |
| 10,098,635 B2 | 10/2018 | Burbank |
| 10,098,705 B2 | 10/2018 | Brisson et al. |
| 10,105,140 B2 | 10/2018 | Malinouskas et al. |
| 10,105,142 B2 | 10/2018 | Baxter, III et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,949 B2 | 11/2018 | Felder et al. |

(56) References Cited

U.S. PATENT DOCUMENTS

| | | |
|---|---|---|
| 10,143,526 B2 | 12/2018 | Walker et al. |
| 10,143,948 B2 | 12/2018 | Bonifas et al. |
| 10,149,680 B2 | 12/2018 | Parihar et al. |
| 10,152,789 B2 | 12/2018 | Carnes et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,169,862 B2 | 1/2019 | Andre et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,194,907 B2 | 2/2019 | Marczyk et al. |
| 10,194,913 B2 | 2/2019 | Nalagatla et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,226,250 B2 | 3/2019 | Beckman et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,251,661 B2 | 4/2019 | Collings et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,035 B2 | 4/2019 | Fehre et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,285,698 B2 | 5/2019 | Cappola et al. |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,771 B2 | 5/2019 | Wood et al. |
| 10,299,792 B2 | 5/2019 | Huitema et al. |
| 10,299,870 B2 | 5/2019 | Connolly et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,335,147 B2 | 7/2019 | Rector et al. |
| 10,335,149 B2 | 7/2019 | Baxter, III et al. |
| 10,335,227 B2 | 7/2019 | Heard |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,190 B2 | 11/2019 | Miller et al. |
| 10,478,544 B2 | 11/2019 | Friederichs et al. |
| 10,485,450 B2 | 11/2019 | Gupta et al. |

(56) References Cited

U.S. PATENT DOCUMENTS

| | | |
|---|---|---|
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,461 B2 | 12/2019 | Gupta et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,548,504 B2 | 2/2020 | Shelton, IV et al. |
| 10,548,612 B2 | 2/2020 | Martinez et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,422 B2 | 2/2020 | Schellin et al. |
| 10,561,471 B2 | 2/2020 | Nichogi |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,582,928 B2 | 3/2020 | Hunter et al. |
| 10,582,931 B2 | 3/2020 | Mujawar |
| 10,586,074 B2 | 3/2020 | Rose et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,595,882 B2 | 3/2020 | Parfett et al. |
| 10,595,887 B2 | 3/2020 | Shelton, IV et al. |
| 10,595,952 B2 | 3/2020 | Forrest et al. |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,484 B2 | 4/2020 | Kilroy et al. |
| 10,624,635 B2 | 4/2020 | Harris et al. |
| 10,624,691 B2 | 4/2020 | Wiener et al. |
| 10,631,423 B2 | 4/2020 | Collins et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,729,458 B2 | 8/2020 | Stoddard et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,651 B2 | 9/2020 | Shelton, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 2002/0049551 A1 | 4/2002 | Friedman et al. |
| 2003/0093503 A1 | 5/2003 | Yamaki et al. |
| 2004/0078236 A1 | 4/2004 | Stoodley et al. |
| 2004/0199180 A1 | 10/2004 | Knodel et al. |
| 2004/0199659 A1 | 10/2004 | Ishikawa et al. |
| 2004/0243148 A1 | 12/2004 | Wasielewski |
| 2004/0243435 A1 | 12/2004 | Williams |
| 2005/0063575 A1 | 3/2005 | Ma et al. |
| 2005/0065438 A1 | 3/2005 | Miller |
| 2005/0131390 A1 | 6/2005 | Heinrich et al. |
| 2005/0149001 A1 | 7/2005 | Uchikubo et al. |
| 2005/0149356 A1 | 7/2005 | Cyr et al. |
| 2005/0222631 A1 | 10/2005 | Dalal et al. |
| 2005/0277913 A1 | 12/2005 | McCary |
| 2006/0020272 A1 | 1/2006 | Gildenberg |
| 2006/0116908 A1 | 6/2006 | Dew et al. |

(56) References Cited

U.S. PATENT DOCUMENTS

| | | |
|---|---|---|
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0027459 A1 | 2/2007 | Horvath et al. |
| 2007/0078678 A1 | 4/2007 | DiSilvestro et al. |
| 2007/0167702 A1 | 7/2007 | Hasser et al. |
| 2007/0168461 A1 | 7/2007 | Moore |
| 2007/0175955 A1 | 8/2007 | Shelton et al. |
| 2007/0225556 A1 | 9/2007 | Ortiz et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0059658 A1 | 3/2008 | Williams |
| 2008/0077158 A1 | 3/2008 | Haider et al. |
| 2008/0083414 A1 | 4/2008 | Messerges |
| 2008/0251569 A1* | 10/2008 | Smith ................ A61B 17/068 227/175.1 |
| 2008/0255413 A1 | 10/2008 | Zemlok et al. |
| 2008/0262654 A1 | 10/2008 | Omori et al. |
| 2008/0281678 A1 | 11/2008 | Keuls et al. |
| 2008/0296346 A1 | 12/2008 | Shelton, IV et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0182577 A1 | 7/2009 | Squilla et al. |
| 2009/0206131 A1 | 8/2009 | Weisenburgh, II et al. |
| 2009/0259149 A1 | 10/2009 | Tahara et al. |
| 2009/0259221 A1 | 10/2009 | Tahara et al. |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0065604 A1 | 3/2010 | Weng |
| 2010/0070417 A1 | 3/2010 | Flynn et al. |
| 2010/0096435 A1* | 4/2010 | Fuchs ................ A61B 17/1114 227/179.1 |
| 2010/0132334 A1 | 6/2010 | Duclos et al. |
| 2010/0191100 A1 | 7/2010 | Anderson et al. |
| 2010/0198248 A1 | 8/2010 | Vakharia |
| 2010/0217991 A1 | 8/2010 | Choi |
| 2010/0235689 A1 | 9/2010 | Tian et al. |
| 2010/0250571 A1 | 9/2010 | Pierce et al. |
| 2010/0292535 A1 | 11/2010 | Paskar |
| 2011/0087238 A1 | 4/2011 | Wang et al. |
| 2011/0105895 A1 | 5/2011 | Kornblau et al. |
| 2011/0118708 A1 | 5/2011 | Burbank et al. |
| 2011/0119075 A1 | 5/2011 | Dhoble |
| 2011/0125149 A1 | 5/2011 | Ei-Galley et al. |
| 2011/0139851 A1 | 6/2011 | McCuen |
| 2011/0237883 A1 | 9/2011 | Chun |
| 2011/0306840 A1 | 12/2011 | Allen et al. |
| 2012/0116381 A1 | 5/2012 | Houser et al. |
| 2012/0130217 A1 | 5/2012 | Kauphusman et al. |
| 2012/0191091 A1 | 7/2012 | Allen |
| 2012/0203785 A1 | 8/2012 | Awada |
| 2012/0211542 A1 | 8/2012 | Racenet |
| 2012/0245958 A1 | 9/2012 | Lawrence et al. |
| 2012/0292367 A1 | 11/2012 | Morgan et al. |
| 2012/0319859 A1 | 12/2012 | Taub et al. |
| 2013/0024213 A1 | 1/2013 | Poon |
| 2013/0046279 A1 | 2/2013 | Niklewski et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0105552 A1 | 5/2013 | Weir et al. |
| 2013/0116218 A1 | 5/2013 | Kaplan et al. |
| 2013/0165776 A1 | 6/2013 | Blomqvist |
| 2013/0178853 A1 | 7/2013 | Hyink et al. |
| 2013/0206813 A1 | 8/2013 | Nalagatla |
| 2013/0214025 A1* | 8/2013 | Zemlok ............ A61B 17/07207 227/175.1 |
| 2013/0253480 A1 | 9/2013 | Kimball et al. |
| 2013/0256373 A1 | 10/2013 | Schmid et al. |
| 2013/0277410 A1 | 10/2013 | Fernandez et al. |
| 2013/0317351 A1 | 11/2013 | Case et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331875 A1 | 12/2013 | Ross et al. |
| 2014/0001234 A1 | 1/2014 | Shelton, IV et al. |
| 2014/0006132 A1 | 1/2014 | Barker |
| 2014/0006943 A1 | 1/2014 | Robbins et al. |
| 2014/0029411 A1 | 1/2014 | Nayak et al. |
| 2014/0035762 A1 | 2/2014 | Shelton, IV et al. |
| 2014/0066700 A1 | 3/2014 | Wilson et al. |
| 2014/0081255 A1 | 3/2014 | Johnson et al. |
| 2014/0081659 A1 | 3/2014 | Nawana et al. |
| 2014/0087999 A1 | 3/2014 | Kaplan et al. |
| 2014/0092089 A1 | 4/2014 | Kasuya et al. |
| 2014/0107471 A1 | 4/2014 | Haider et al. |
| 2014/0107697 A1 | 4/2014 | Patani et al. |
| 2014/0108983 A1 | 4/2014 | William et al. |
| 2014/0187856 A1 | 7/2014 | Holoien et al. |
| 2014/0204190 A1 | 7/2014 | Rosenblatt, III et al. |
| 2014/0246475 A1 | 9/2014 | Hall et al. |
| 2014/0246476 A1* | 9/2014 | Hall ................ A61B 34/30 227/175.1 |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0303660 A1 | 10/2014 | Boyden et al. |
| 2014/0305988 A1* | 10/2014 | Boudreaux .......... A61B 17/068 227/175.3 |
| 2014/0305993 A1* | 10/2014 | Timm ............. A61B 17/00234 227/178.1 |
| 2015/0025549 A1 | 1/2015 | Kilroy et al. |
| 2015/0032150 A1 | 1/2015 | Ishida et al. |
| 2015/0051617 A1 | 2/2015 | Takemura et al. |
| 2015/0053737 A1 | 2/2015 | Leimbach et al. |
| 2015/0066000 A1 | 3/2015 | An et al. |
| 2015/0070187 A1 | 3/2015 | Wiesner et al. |
| 2015/0108198 A1 | 4/2015 | Estrella |
| 2015/0108201 A1* | 4/2015 | Williams ............ A61B 90/98 227/177.1 |
| 2015/0133945 A1 | 5/2015 | Dushyant et al. |
| 2015/0199109 A1 | 7/2015 | Lee |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1* | 10/2015 | Huitema ............ A61B 17/072 227/176.1 |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0332003 A1 | 11/2015 | Stamm et al. |
| 2015/0332196 A1 | 11/2015 | Stiller et al. |
| 2016/0000437 A1 | 1/2016 | Giordano et al. |
| 2016/0015471 A1 | 1/2016 | Piron et al. |
| 2016/0030046 A1* | 2/2016 | Williams ............ A61B 17/072 227/181.1 |
| 2016/0034648 A1 | 2/2016 | Mohlenbrock et al. |
| 2016/0038253 A1 | 2/2016 | Piron et al. |
| 2016/0066913 A1 | 3/2016 | Swayze et al. |
| 2016/0106934 A1 | 4/2016 | Hiraga et al. |
| 2016/0117857 A1 | 4/2016 | State et al. |
| 2016/0192960 A1 | 7/2016 | Bueno et al. |
| 2016/0206202 A1 | 7/2016 | Frangioni |

(56) References Cited

U.S. PATENT DOCUMENTS

| | | |
|---|---|---|
| 2016/0235303 A1 | 8/2016 | Fleming et al. |
| 2016/0249910 A1 | 9/2016 | Shelton, IV et al. |
| 2016/0256184 A1* | 9/2016 | Shelton, IV ......... A61B 17/072 |
| 2016/0270780 A1* | 9/2016 | Hall .................... A61B 34/74 |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310203 A1 | 10/2016 | Gaspredes et al. |
| 2016/0321400 A1 | 11/2016 | Durrant et al. |
| 2016/0323283 A1 | 11/2016 | Kang et al. |
| 2016/0324537 A1 | 11/2016 | Green et al. |
| 2016/0342916 A1 | 11/2016 | Arceneaux et al. |
| 2016/0350490 A1 | 12/2016 | Martinez et al. |
| 2016/0374665 A1 | 12/2016 | DiNardo et al. |
| 2016/0374723 A1 | 12/2016 | Frankhouser et al. |
| 2016/0374762 A1 | 12/2016 | Case et al. |
| 2016/0374775 A1 | 12/2016 | Prpa et al. |
| 2017/0000516 A1 | 1/2017 | Stulen et al. |
| 2017/0000553 A1 | 1/2017 | Wiener et al. |
| 2017/0027603 A1 | 2/2017 | Pandey |
| 2017/0068792 A1 | 3/2017 | Reiner |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0132374 A1 | 5/2017 | Lee et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0151026 A1 | 6/2017 | Panescu et al. |
| 2017/0156076 A1 | 6/2017 | Eom et al. |
| 2017/0164997 A1 | 6/2017 | Johnson et al. |
| 2017/0165012 A1 | 6/2017 | Chaplin et al. |
| 2017/0172565 A1 | 6/2017 | Heneveld |
| 2017/0172614 A1 | 6/2017 | Scheib et al. |
| 2017/0177807 A1 | 6/2017 | Fabian |
| 2017/0181745 A1 | 6/2017 | Penna et al. |
| 2017/0196637 A1 | 7/2017 | Shelton, IV et al. |
| 2017/0202591 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0249432 A1 | 8/2017 | Grantcharov |
| 2017/0252095 A1 | 9/2017 | Johnson |
| 2017/0255751 A1 | 9/2017 | Sanmugalingham |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296177 A1 | 10/2017 | Harris et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304020 A1 | 10/2017 | Ng et al. |
| 2017/0360439 A1 | 12/2017 | Chen et al. |
| 2017/0360499 A1 | 12/2017 | Greep et al. |
| 2017/0367695 A1 | 12/2017 | Shelton, IV et al. |
| 2017/0367697 A1 | 12/2017 | Shelton, IV et al. |
| 2017/0367754 A1 | 12/2017 | Narisawa |
| 2018/0008359 A1 | 1/2018 | Randle |
| 2018/0014848 A1 | 1/2018 | Messerly et al. |
| 2018/0049817 A1 | 2/2018 | Swayze et al. |
| 2018/0049819 A1 | 2/2018 | Harris et al. |
| 2018/0050196 A1 | 2/2018 | Pawsey et al. |
| 2018/0055529 A1 | 3/2018 | Messerly et al. |
| 2018/0065248 A1 | 3/2018 | Barral et al. |
| 2018/0092706 A1 | 4/2018 | Anderson et al. |
| 2018/0098816 A1 | 4/2018 | Govari et al. |
| 2018/0110523 A1 | 4/2018 | Shelton, IV |
| 2018/0116662 A1 | 5/2018 | Shelton, IV et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0161716 A1 | 6/2018 | Li et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168592 A1 | 6/2018 | Overmyer et al. |
| 2018/0168593 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168601 A1 | 6/2018 | Bakos et al. |
| 2018/0168603 A1 | 6/2018 | Morgan et al. |
| 2018/0168605 A1 | 6/2018 | Baber et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168632 A1 | 6/2018 | Harris et al. |
| 2018/0168633 A1 | 6/2018 | Shelton, IV et al. |
| 2018/0168639 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0168715 A1 | 6/2018 | Strobl |
| 2018/0177557 A1 | 6/2018 | Kapadia et al. |
| 2018/0199995 A1 | 7/2018 | Odermatt et al. |
| 2018/0214025 A1 | 8/2018 | Homyk et al. |
| 2018/0221598 A1 | 8/2018 | Silver |
| 2018/0228557 A1 | 8/2018 | Darisse et al. |
| 2018/0242967 A1 | 8/2018 | Meade |
| 2018/0250080 A1 | 9/2018 | Kopp |
| 2018/0250084 A1 | 9/2018 | Kopp et al. |
| 2018/0263710 A1 | 9/2018 | Sakaguchi et al. |
| 2018/0263717 A1 | 9/2018 | Kopp |
| 2018/0271603 A1 | 9/2018 | Nir et al. |
| 2018/0296286 A1 | 10/2018 | Peine et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0317826 A1 | 11/2018 | Muhsin et al. |
| 2018/0317915 A1 | 11/2018 | McDonald, II |
| 2018/0338806 A1 | 11/2018 | Gru Bbs |
| 2018/0358112 A1 | 12/2018 | Sharifi Sedeh et al. |
| 2018/0360449 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360456 A1 | 12/2018 | Shelton, IV et al. |
| 2018/0368930 A1 | 12/2018 | Esterberg et al. |
| 2018/0369511 A1 | 12/2018 | Zergiebel et al. |
| 2019/0000446 A1 | 1/2019 | Shelton, IV et al. |
| 2019/0000448 A1 | 1/2019 | Shelton, IV et al. |
| 2019/0000478 A1 | 1/2019 | Messerly et al. |
| 2019/0000530 A1 | 1/2019 | Yates et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |

(56) References Cited

U.S. PATENT DOCUMENTS

| | | |
|---|---|---|
| 2019/0005641 A1 | 1/2019 | Yamamoto |
| 2019/0006047 A1 | 1/2019 | Gorek et al. |
| 2019/0029712 A1 | 1/2019 | Stoddard et al. |
| 2019/0038364 A1 | 2/2019 | Enoki |
| 2019/0053801 A1 | 2/2019 | Wixey et al. |
| 2019/0053866 A1 | 2/2019 | Seow et al. |
| 2019/0069949 A1 | 3/2019 | Vrba et al. |
| 2019/0069962 A1 | 3/2019 | Tabandeh et al. |
| 2019/0069964 A1 | 3/2019 | Hagn |
| 2019/0070550 A1 | 3/2019 | Lalomia et al. |
| 2019/0070731 A1 | 3/2019 | Bowling et al. |
| 2019/0090969 A1 | 3/2019 | Jarc et al. |
| 2019/0104919 A1 | 4/2019 | Shelton, IV et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125344 A1 | 5/2019 | Dinardo et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125381 A1 | 5/2019 | Scheib et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0162179 A1 | 5/2019 | O'Shea et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201088 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201117 A1 | 7/2019 | Yates et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |

(56) References Cited

U.S. PATENT DOCUMENTS

| | | |
|---|---|---|
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207857 A1 | 7/2019 | Shelton, IV et al. |
| 2019/0207911 A1 | 7/2019 | Wiener et al. |
| 2019/0208641 A1 | 7/2019 | Yates et al. |
| 2019/0254759 A1 | 8/2019 | Azizian |
| 2019/0269476 A1 | 9/2019 | Bowling et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0314015 A1 | 10/2019 | Shelton, IV et al. |
| 2019/0321117 A1 | 10/2019 | Itkowitz et al. |
| 2019/0343594 A1 | 11/2019 | Garcia Kilroy et al. |
| 2019/0374140 A1 | 12/2019 | Tucker et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054327 A1 | 2/2020 | Harris et al. |
| 2020/0054328 A1 | 2/2020 | Harris et al. |
| 2020/0054329 A1 | 2/2020 | Shelton, IV et al. |
| 2020/0054330 A1 | 2/2020 | Harris et al. |
| 2020/0054331 A1 | 2/2020 | Harris et al. |
| 2020/0100830 A1 | 4/2020 | Henderson et al. |
| 2020/0178971 A1 | 6/2020 | Harris et al. |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 2732772 A1 | 5/2014 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| GB | 2509523 A | 7/2014 |
| JP | S5373315 A | 6/1978 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-2007137304 A2 | 11/2007 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014134196 A1 | 9/2014 |
| WO | WO-2015129395 A1 | 9/2015 |
| WO | WO-2016206015 A1 | 12/2016 |
| WO | WO-2017011382 A1 | 1/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018152141 A1 | 8/2018 |

OTHER PUBLICATIONS

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

(56) References Cited

OTHER PUBLICATIONS

Yuyi Mao et al., "A Survey on Mobile Edge Computing: The Communication Perspective," IEEE Communications Surveys & Tutorials, pp. 2322-2358, Jun. 13, 2017.
Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.
Benkmann et al., "Concept of iterative optimization of minimally invasive surgery," 2017 22nd International Conference on Methods and Models in Automation and Robotics (MMAR), IEEE pp. 443-446, Aug. 28, 2017.
Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.
Miksch et al., "Utilizing temporal data abstraction for data validation and therapy planning for artificially ventilated newborn infants," Artificial Intelligence in Medicine, vol. 8, No. 6, pp. 543-576 (1996).
Horn et al., "Effective data validation of high-frequency data: Time-point-time-interval-, and trend-based methods," Computers in Biology and Medic, New York, NY, vol. 27, No. 5, pp. 389-409 (1997).
Stacey et al., "Temporal abstraction in intelligent clinical data analysis: A survey, " Artificial Intelligence in Medicine, vol. 39, No. 1, pp. 1-24 (2006).
Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.
Takahashi et al., "Automatic smoke evacuation in laparoscopic surgery: a simplified method for objective evaluation," Surgical Endoscopy, vol. 27, No. 8, pp. 2980-2987, Feb. 23, 2013.
Zoccali, Bruno, "A Method for Approximating Component Temperatures at Altitude Conditions Based on CFD Analysis at Sea Level Conditions," (white paper), www.tdmginc.com, Dec. 6, 2018 (9 pages).
Slocinski et al., "Distance measure for impedance spectra for quantified evaluations," Lecture Notes on Impedance Spectroscopy, vol. 3, Taylor and Francis Group (Jul. 2012—Book Not Attached.
Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.
Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].
Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.
Phumzile Malindi, "5. QoS in Telemedicine," "Telemedicine," Jun. 20, 2011, IntechOpen, pp. 119-138.
Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode,"Article, Oct. 8, 2010, pp. 1-9, Microwave Journal.
Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.
Hsiao-Wei Tang, "ARCM", Video, Sep. 2012, YouTube, 5 screenshots, Retrieved from. internet: <https://www.youtube.com/watch?v=UldQaxb3fRw&feature=youtu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
Shi et al., An intuitive control console for robotic syrgery system, 2014, IEEE, p. 404-407 (Year: 2014).

(56) References Cited

OTHER PUBLICATIONS

Choi et al., A haptic augmented reality surgeon console for a laparoscopic surgery robot system, 2013, IEEE, p. 355-357 (Year: 2013).

Xie et al., Development of stereo vision and master-slave controller for a compact surgical robot system, 2015, IEEE, p. 403-407 (Year: 2015).

Sun et al., Innovative effector design for simulation training in robotic surgery, 2010, IEEE, p. 1735-1759 (Year: 2010).

* cited by examiner

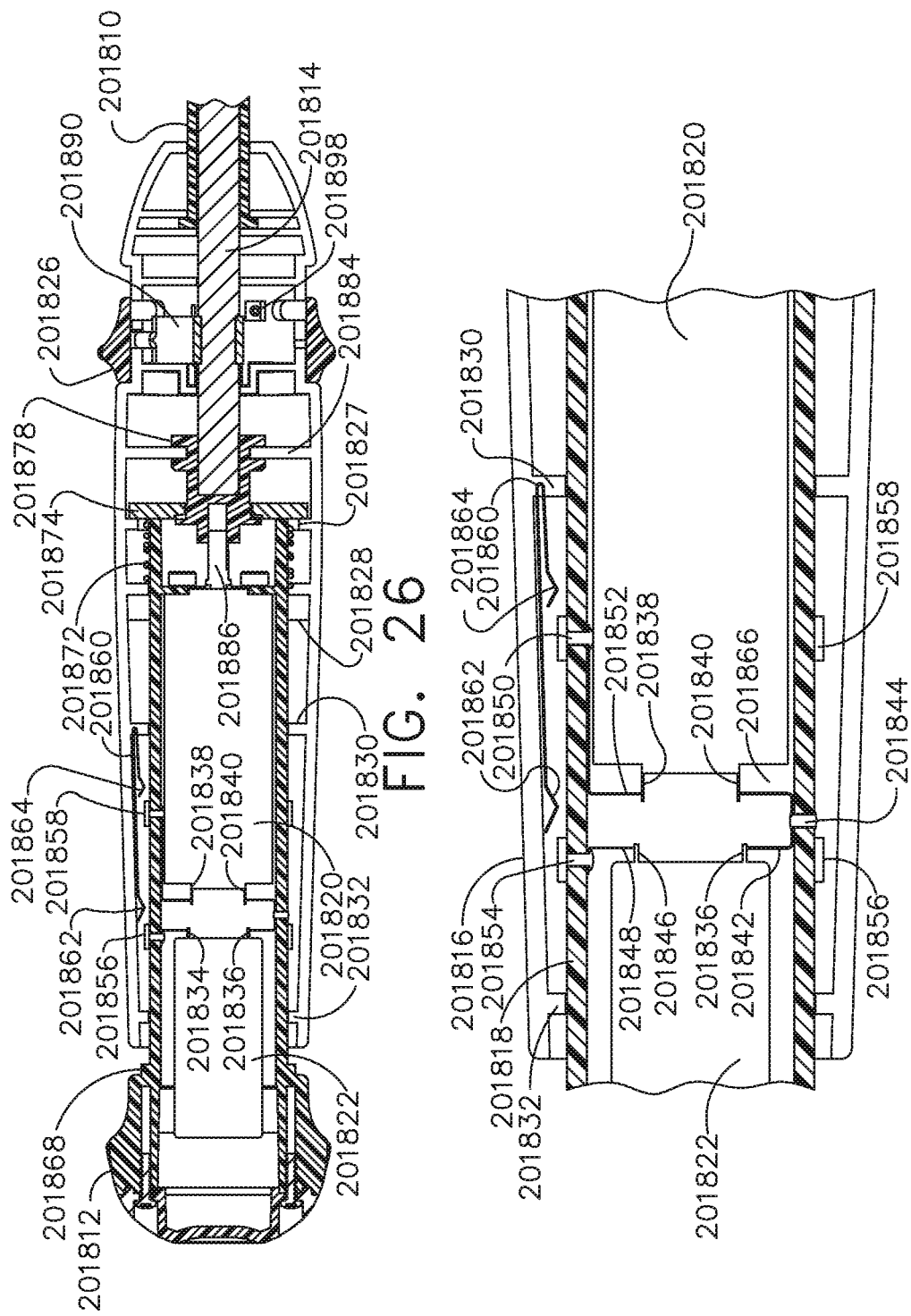

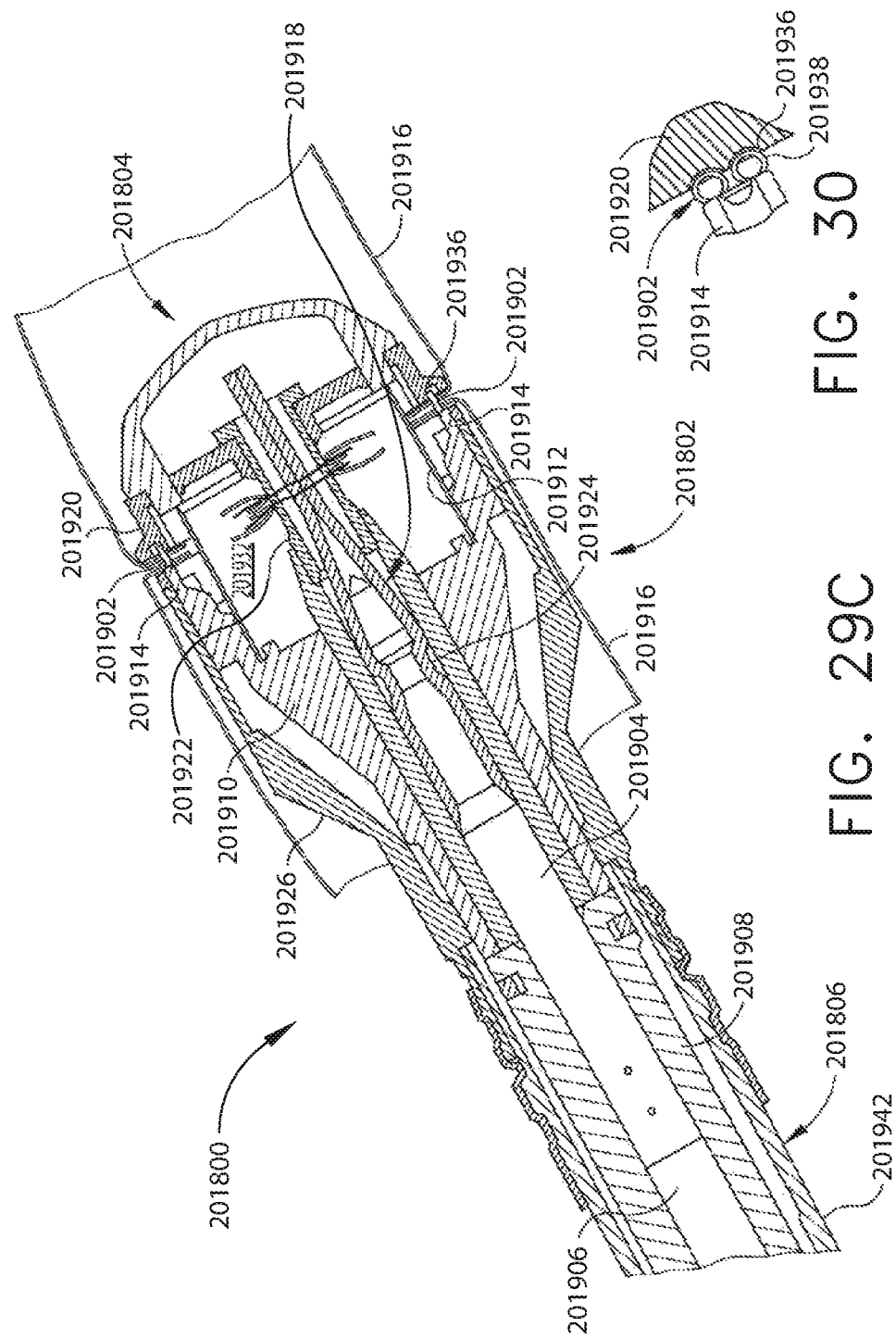

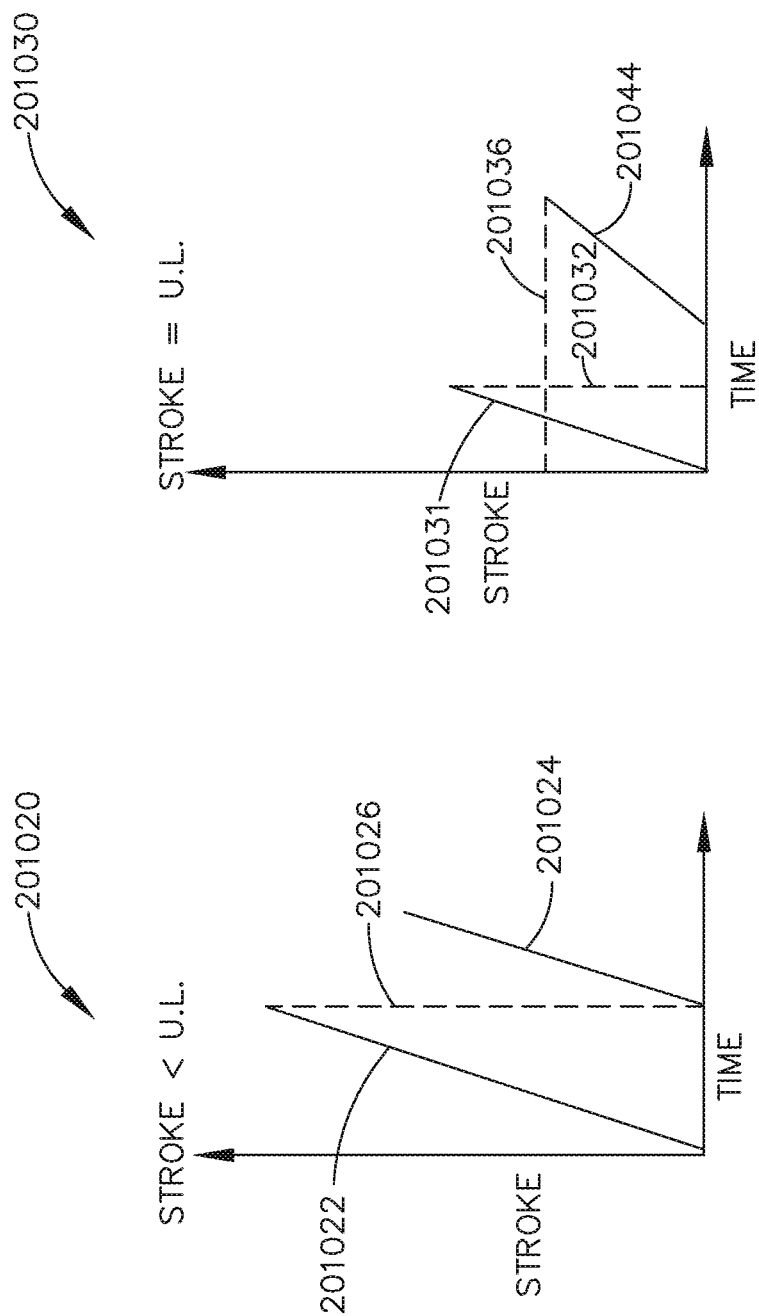

| STROKE | | INNER STAPLE | OUTER STAPLE | ALGORITHM |
|---|---|---|---|---|
| UPPER LIMIT | if | | | NO ADJUSTMENT |
| | if | | | SLOWER RATE OR DELAYED START |
| LOWER LIMIT | if | | | NO ADJUSTMENT |
| | if | | | TALLER |
| MED. LIMIT | if | | | NO ADJUSTMENT |
| | if | | | TALLER |

FIG. 35

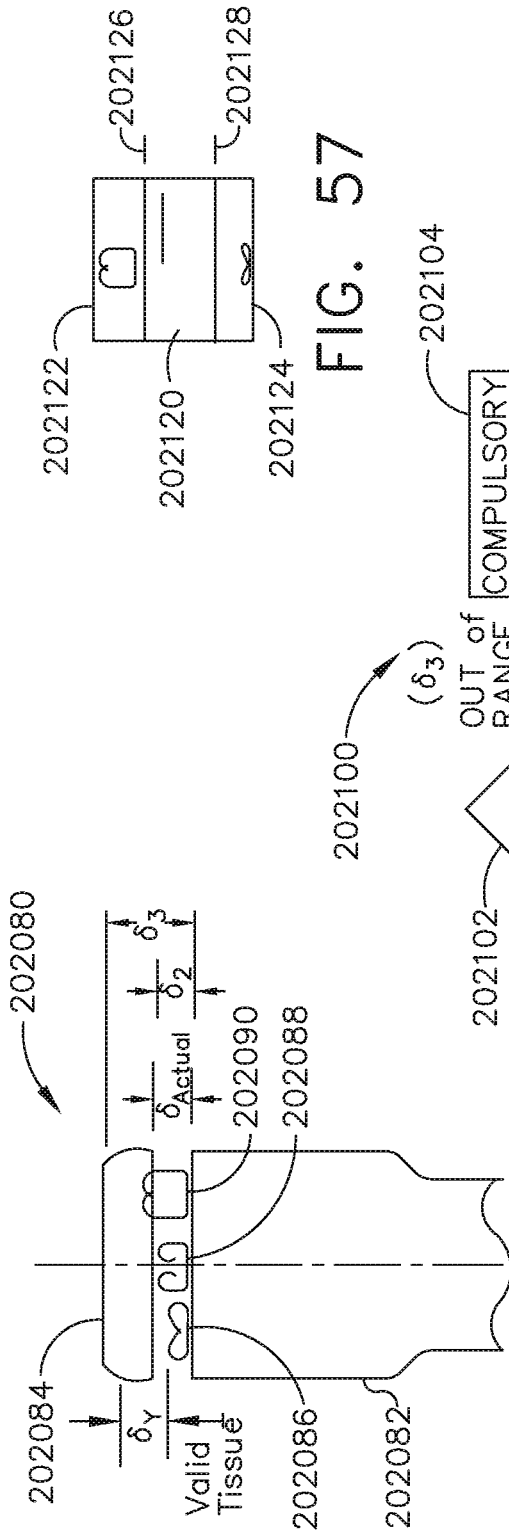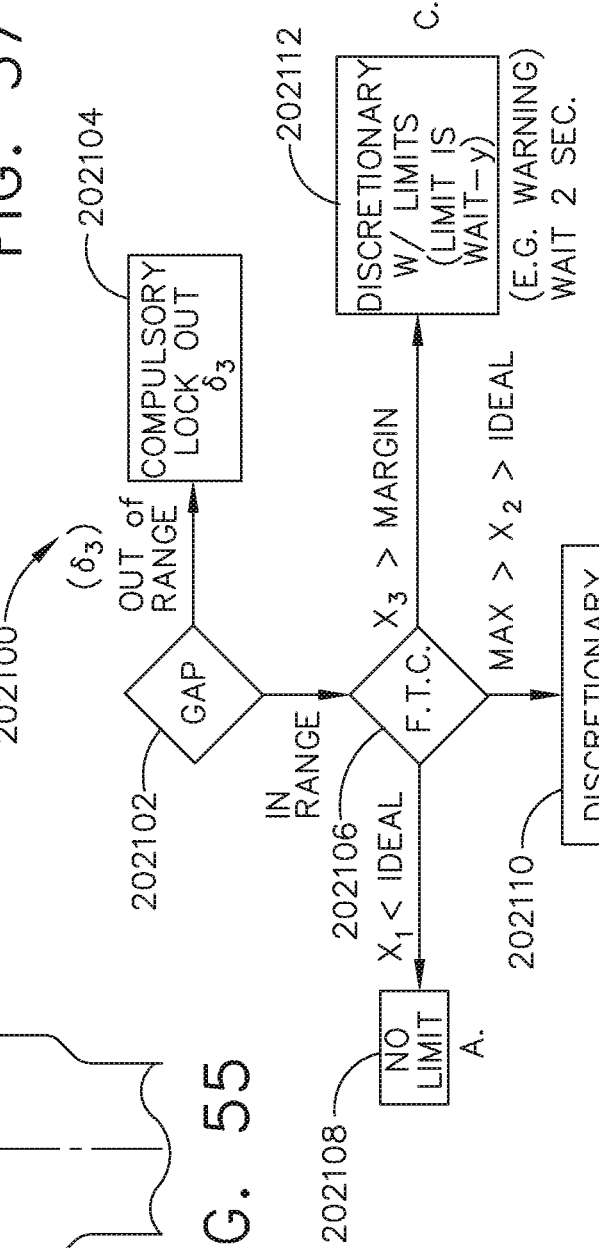
FIG. 55
FIG. 56
FIG. 57

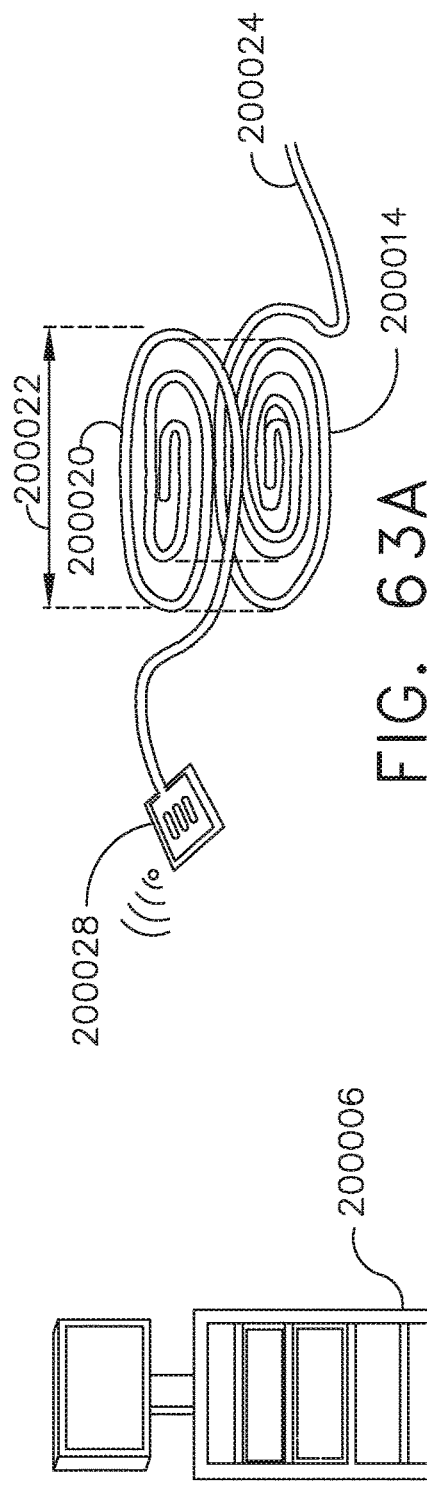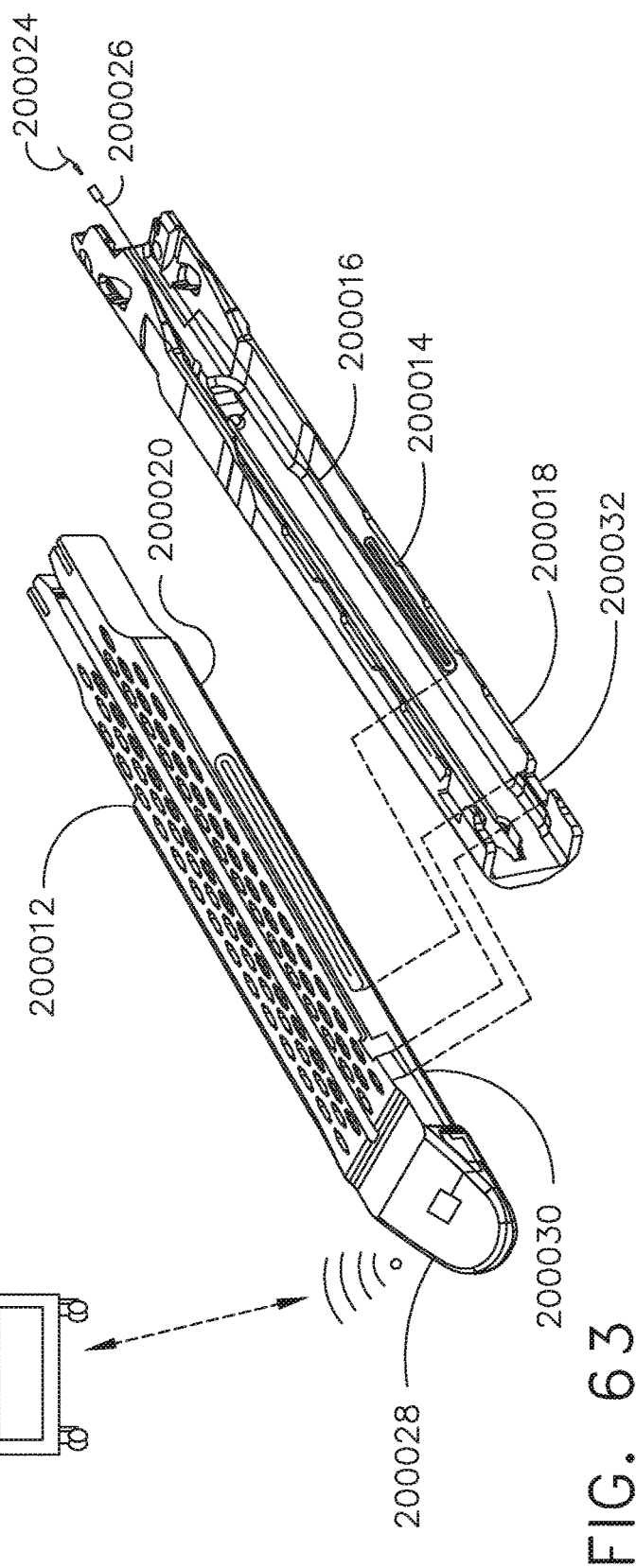

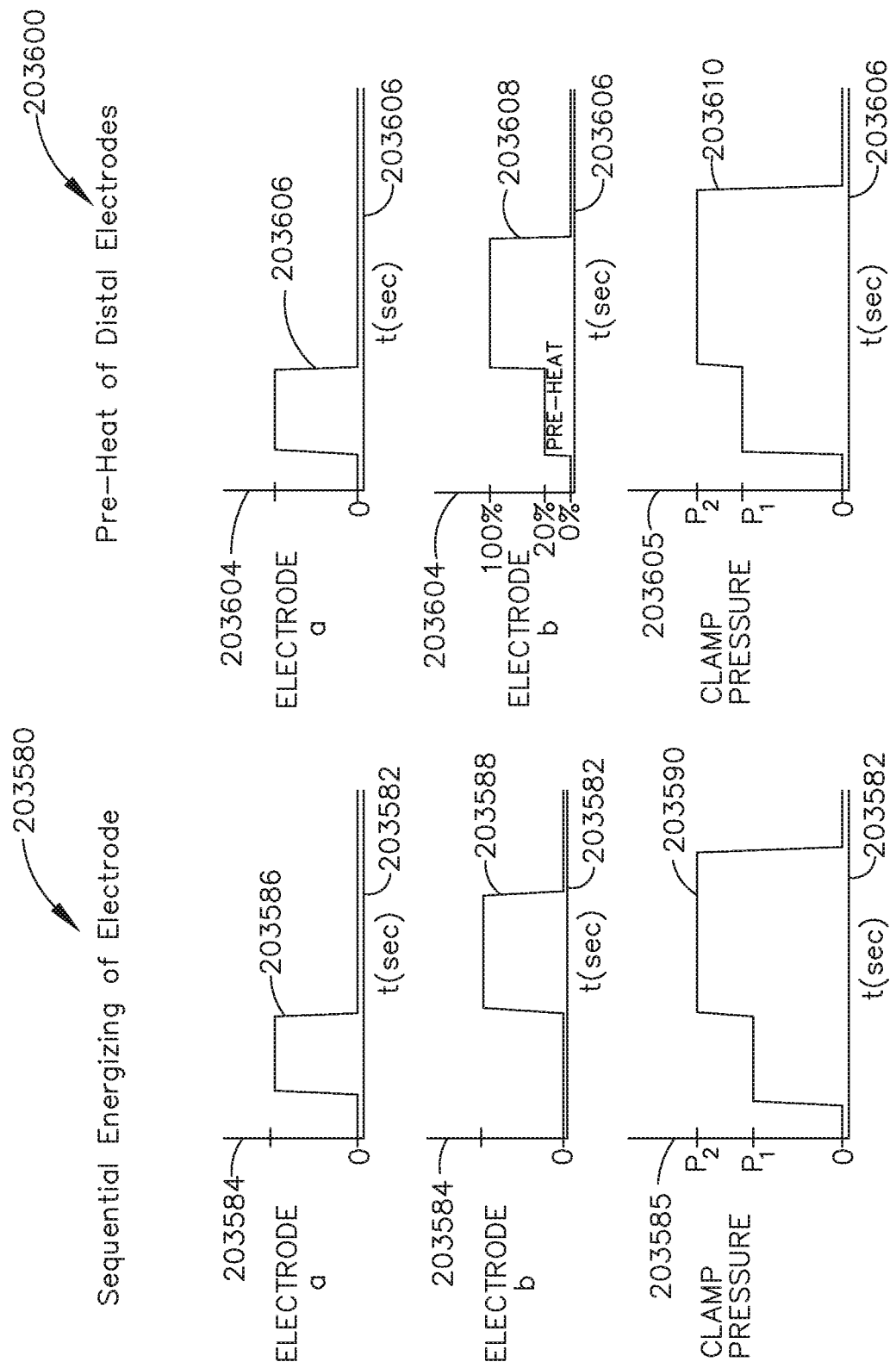

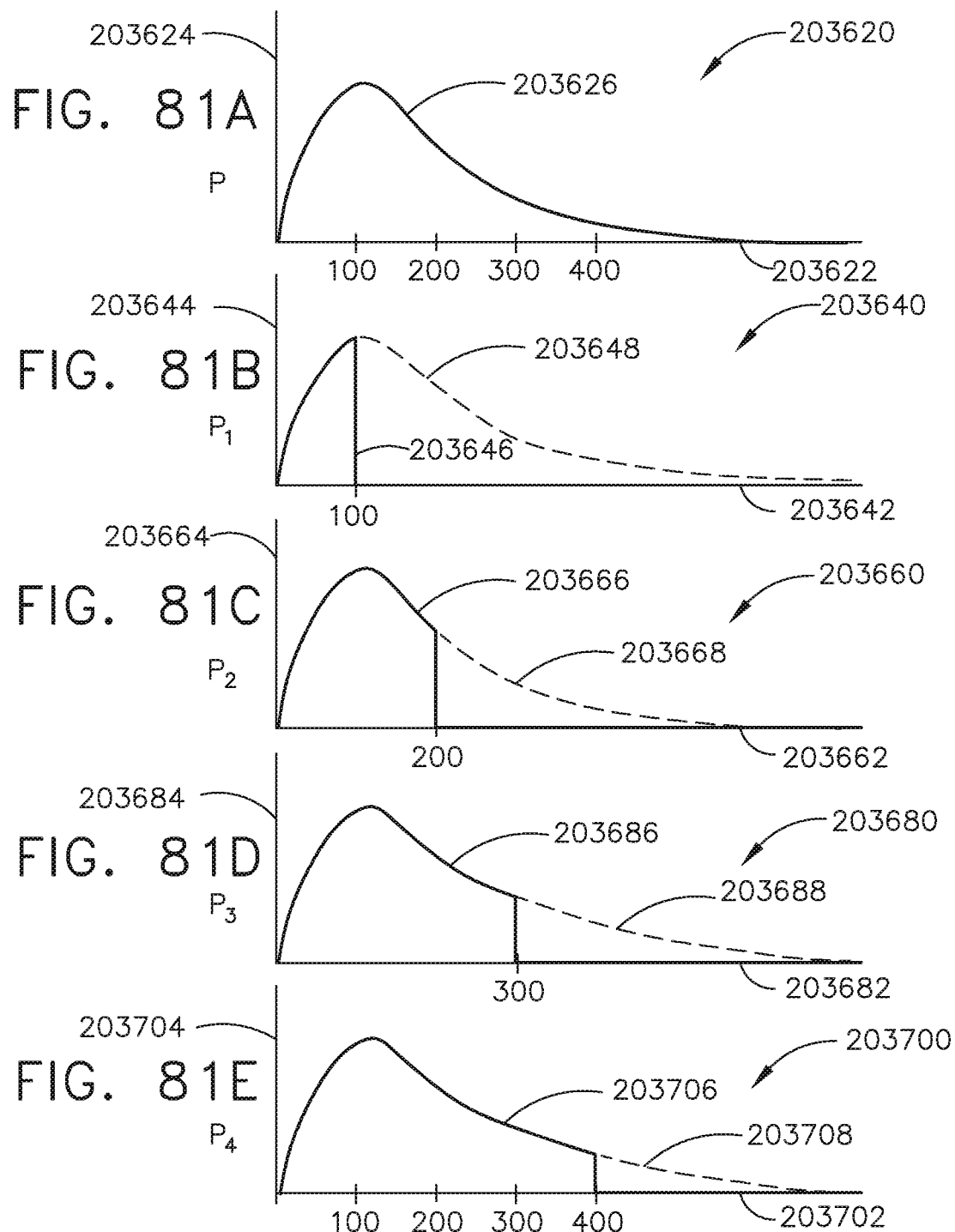

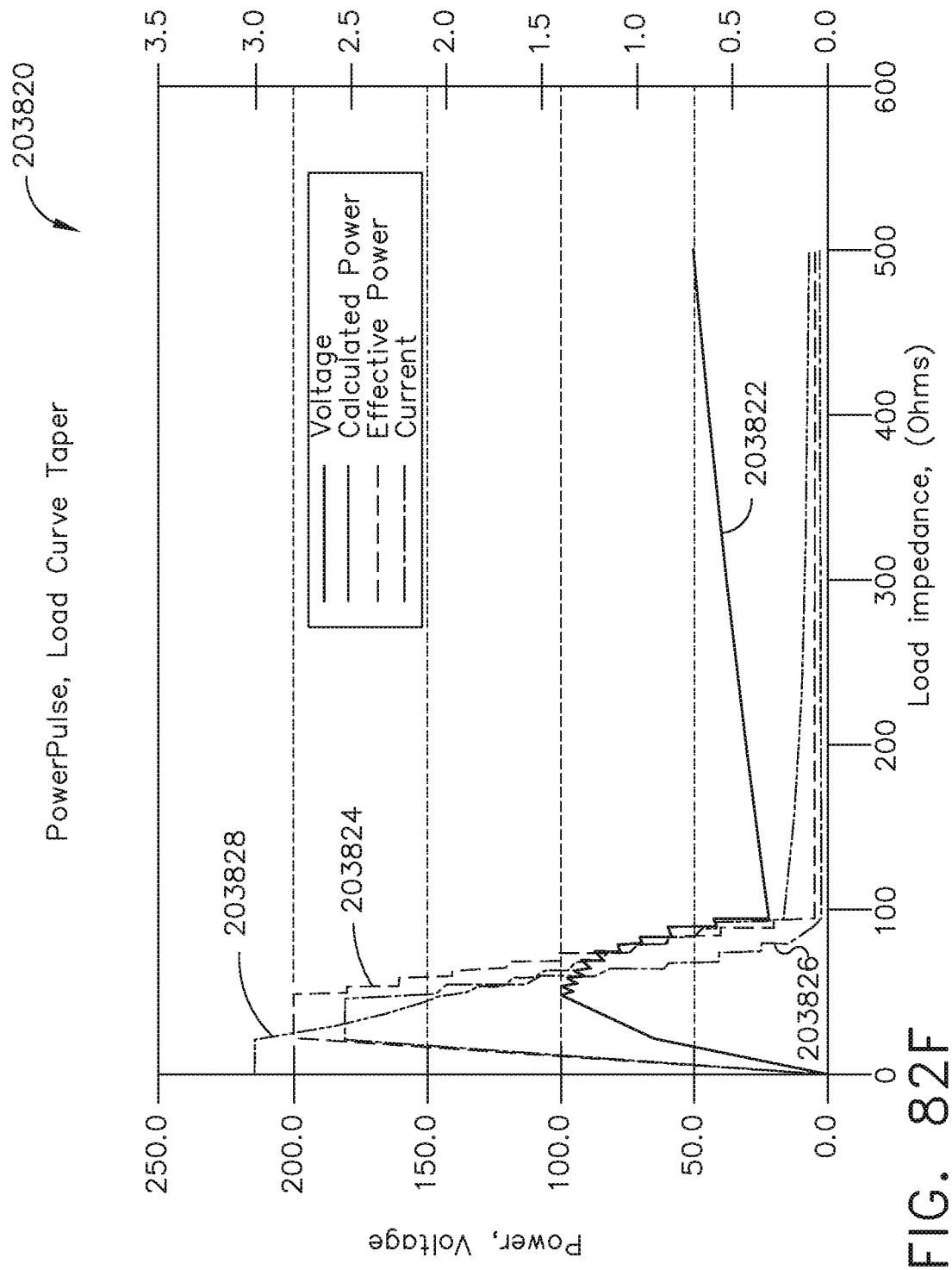

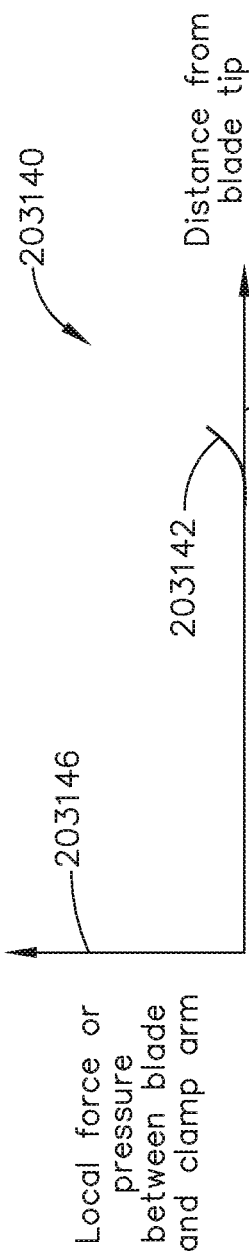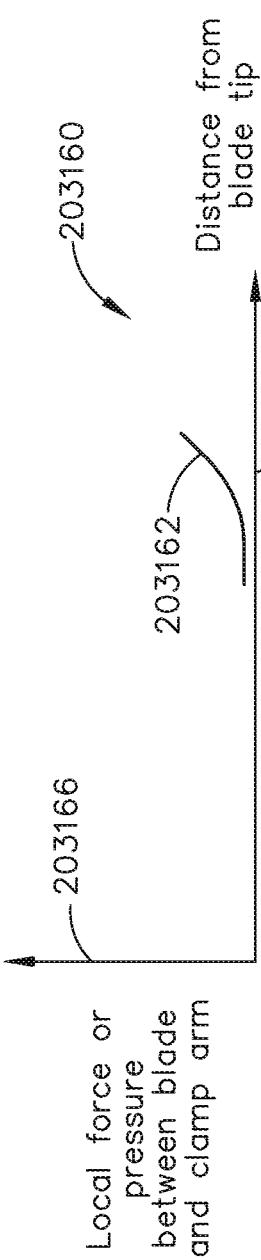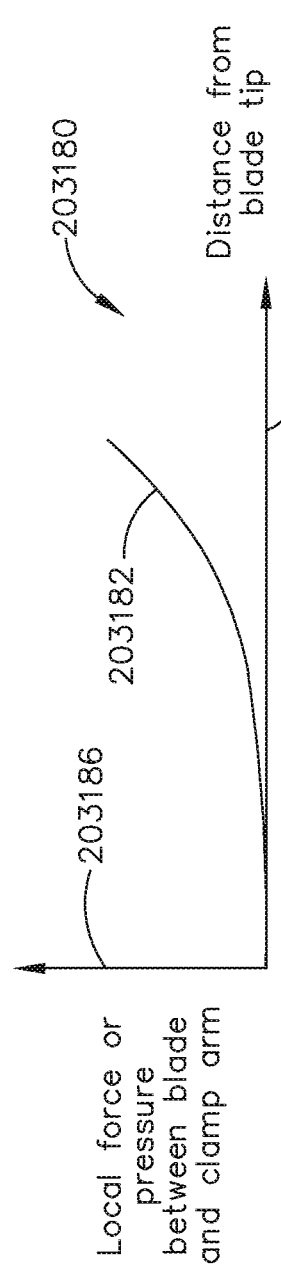

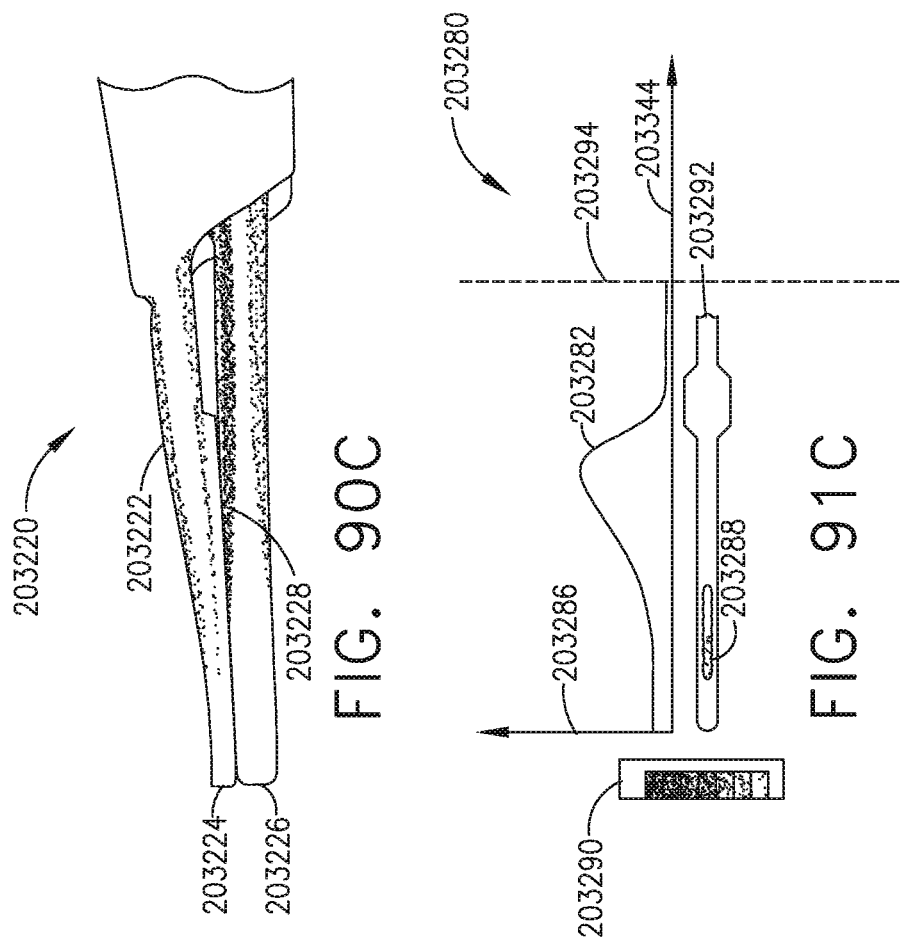

METHOD FOR CIRCULAR STAPLER CONTROL ALGORITHM ADJUSTMENT BASED ON SITUATIONAL AWARENESS

CROSS-REFERENCE TO RELATED APPLICATIONS

The present application claims priority under 35 U.S.C. § 119(e) to U.S. Provisional Patent Application No. 62/773,778, titled METHOD FOR ADAPTIVE CONTROL SCHEMES FOR SURGICAL NETWORK CONTROL AND INTERACTION, filed Nov. 30, 2018, to U.S. Provisional Patent Application No. 62/773,728, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Nov. 30, 2018, to U.S. Provisional Patent Application No. 62/773,741, titled METHOD FOR FACILITY DATA COLLECTION AND INTERPRETATION, filed Nov. 30, 2018, and to U.S. Provisional Patent Application No. 62/773,742, titled METHOD FOR CIRCULAR STAPLER CONTROL ALGORITHM ADJUSTMENT BASED ON SITUATIONAL AWARENESS, filed Nov. 30, 2018, the disclosure of each of which is herein incorporated by reference in its entirety.

The present application claims priority under 35 U.S.C. § 119(e) to U.S. Provisional Patent Application No. 62/750,529, titled METHOD FOR OPERATING A POWERED ARTICULATING MULTI-CLIP APPLIER, filed Oct. 25, 2018, to U.S. Provisional Patent Application No. 62/750,539, titled SURGICAL CLIP APPLIER, filed Oct. 25, 2018, and to U.S. Provisional Patent Application No. 62/750,555, titled SURGICAL CLIP APPLIER, filed Oct. 25, 2018, the disclosure of each of which is herein incorporated by reference in its entirety.

The present application also claims priority under 35 U.S.C. § 119(e) to U.S. Provisional Patent Application No. 62/729,183, titled CONTROL FOR A SURGICAL NETWORK OR SURGICAL NETWORK CONNECTED DEVICE THAT ADJUSTS ITS FUNCTION BASED ON A SENSED SITUATION OR USAGE, filed Sep. 10, 2018, to U.S. Provisional Patent Application No. 62/729,177, titled AUTOMATED DATA SCALING, ALIGNMENT, AND ORGANIZING BASED ON PREDEFINED PARAMETERS WITHIN A SURGICAL NETWORK BEFORE TRANSMISSION, filed Sep. 10, 2018, to U.S. Provisional Patent Application No. 62/729,176, titled INDIRECT COMMAND AND CONTROL OF A FIRST OPERATING ROOM SYSTEM THROUGH THE USE OF A SECOND OPERATING ROOM SYSTEM WITHIN A STERILE FIELD WHERE THE SECOND OPERATING ROOM SYSTEM HAS PRIMARY AND SECONDARY OPERATING MODES, filed Sep. 10, 2018, to U.S. Provisional Patent Application No. 62/729,185, titled POWERED STAPLING DEVICE THAT IS CAPABLE OF ADJUSTING FORCE, ADVANCEMENT SPEED, AND OVERALL STROKE OF CUTTING MEMBER OF THE DEVICE BASED ON SENSED PARAMETER OF FIRING OR CLAMPING, filed Sep. 10, 2018, to U.S. Provisional Patent Application No. 62/729,184, titled POWERED SURGICAL TOOL WITH A PREDEFINED ADJUSTABLE CONTROL ALGORITHM FOR CONTROLLING AT LEAST ONE END EFFECTOR PARAMETER AND A MEANS FOR LIMITING THE ADJUSTMENT, filed Sep. 10, 2018, to U.S. Provisional Patent Application No. 62/729,182, titled SENSING THE PATIENT POSITION AND CONTACT UTILIZING THE MONO-POLAR RETURN PAD ELECTRODE TO PROVIDE SITUATIONAL AWARENESS TO THE HUB, filed Sep. 10, 2018, to U.S. Provisional Patent Application No. 62/729,191, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, filed Sep. 10, 2018, to U.S. Provisional Patent Application No. 62/729,195, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Sep. 10, 2018, and to U.S. Provisional Patent Application No. 62/729,186, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES, filed Sep. 10, 2018, the disclosure of each of which is herein incorporated by reference in its entirety.

The present application also claims priority under 35 U.S.C. § 119(e) to U.S. Provisional Patent Application No. 62/721,995, titled CONTROLLING AN ULTRASONIC SURGICAL INSTRUMENT ACCORDING TO TISSUE LOCATION, filed Aug. 23, 2018, to U.S. Provisional Patent Application No. 62/721,998, titled SITUATIONAL AWARENESS OF ELECTROSURGICAL SYSTEMS, filed Aug. 23, 2018, to U.S. Provisional Patent Application No. 62/721,999, titled INTERRUPTION OF ENERGY DUE TO INADVERTENT CAPACITIVE COUPLING, filed Aug. 23, 2018, to U.S. Provisional Patent Application No. 62/721,994, titled BIPOLAR COMBINATION DEVICE THAT AUTOMATICALLY ADJUSTS PRESSURE BASED ON ENERGY MODALITY, filed Aug. 23, 2018, and to U.S. Provisional Patent Application No. 62/721,996, titled RADIO FREQUENCY ENERGY DEVICE FOR DELIVERING COMBINED ELECTRICAL SIGNALS, filed Aug. 23, 2018, the disclosure of each of which is herein incorporated by reference in its entirety.

The present application also claims priority under 35 U.S.C. § 119(e) to U.S. Provisional Patent Application No. 62/692,747, titled SMART ACTIVATION OF AN ENERGY DEVICE BY ANOTHER DEVICE, filed on Jun. 30, 2018, to U.S. Provisional Patent Application No. 62/692,748, titled SMART ENERGY ARCHITECTURE, filed on Jun. 30, 2018, and to U.S. Provisional Patent Application No. 62/692,768, titled SMART ENERGY DEVICES, filed on Jun. 30, 2018, the disclosure of each of which is herein incorporated by reference in its entirety.

The present application also claims priority under 35 U.S.C. § 119(e) to U.S. Provisional Patent Application No. 62/691,228, titled METHOD OF USING REINFORCED FLEX CIRCUITS WITH MULTIPLE SENSORS WITH ELECTROSURGICAL DEVICES, filed Jun. 28, 2018, to U.S. Provisional Patent Application No. 62/691,227, titled CONTROLLING A SURGICAL INSTRUMENT ACCORDING TO SENSED CLOSURE PARAMETERS, filed Jun. 28, 2018, to U.S. Provisional Patent Application No. 62/691,230, titled SURGICAL INSTRUMENT HAVING A FLEXIBLE ELECTRODE, filed Jun. 28, 2018, to U.S. Provisional Patent Application No. 62/691,219, titled SURGICAL EVACUATION SENSING AND MOTOR CONTROL, filed Jun. 28, 2018, to U.S. Provisional Patent Application No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM, filed Jun.

28, 2018, to U.S. Provisional Patent Application No. 62/691,262, titled SURGICAL EVACUATION SYSTEM WITH A COMMUNICATION CIRCUIT FOR COMMUNICATION BETWEEN A FILTER AND A SMOKE EVACUATION DEVICE, filed Jun. 28, 2018, and to U.S. Provisional Patent Application No. 62/691,251, titled DUAL IN-SERIES LARGE AND SMALL DROPLET FILTERS, filed Jun. 28, 2018, the disclosure of each of which is herein incorporated by reference in its entirety.

The present application claims priority under 35 U.S.C. § 119(e) to U.S. Provisional Patent Application No. 62/665,129, titled SURGICAL SUTURING SYSTEMS, filed May 1, 2018, to U.S. Provisional Patent Application No. 62/665,139, titled SURGICAL INSTRUMENTS COMPRISING CONTROL SYSTEMS, filed May 1, 2018, to U.S. Provisional Patent Application No. 62/665,177, titled SURGICAL INSTRUMENTS COMPRISING HANDLE ARRANGEMENTS, filed May 1, 2018, to U.S. Provisional Patent Application No. 62/665,128, titled MODULAR SURGICAL INSTRUMENTS, filed May 1, 2018, to U.S. Provisional Patent Application No. 62/665,192, titled SURGICAL DISSECTORS, filed May 1, 2018, and to U.S. Provisional Patent Application No. 62/665,134, titled SURGICAL CLIP APPLIER, filed May 1, 2018, the disclosure of each of which is herein incorporated by reference in its entirety.

The present application also claims priority under 35 U.S.C. § 119(e) to U.S. Provisional Patent Application No. 62/659,900, titled METHOD OF HUB COMMUNICATION, filed on Apr. 19, 2018, the disclosure of which is herein incorporated by reference in its entirety.

The present application also claims priority under 35 U.S.C. § 119(e) to U.S. Provisional Patent Application No. 62/650,898, filed on Mar. 30, 2018, titled CAPACITIVE COUPLED RETURN PATH PAD WITH SEPARABLE ARRAY ELEMENTS, to U.S. Provisional Patent Application No. 62/650,887, titled SURGICAL SYSTEMS WITH OPTIMIZED SENSING CAPABILITIES, filed Mar. 30, 2018, to U.S. Provisional Patent Application No. 62/650,882, titled SMOKE EVACUATION MODULE FOR INTERACTIVE SURGICAL PLATFORM, filed Mar. 30, 2018, and to U.S. Provisional Patent Application No. 62/650,877, titled SURGICAL SMOKE EVACUATION SENSING AND CONTROLS, filed Mar. 30, 2018, the disclosure of each of which is herein incorporated by reference in its entirety.

This application also claims the benefit of priority under 35 U.S.C. § 119(e) to U.S. Provisional Patent Application No. 62/649,302, titled INTERACTIVE SURGICAL SYSTEMS WITH ENCRYPTED COMMUNICATION CAPABILITIES, filed Mar. 28, 2018, to U.S. Provisional Patent Application No. 62/649,294, titled DATA STRIPPING METHOD TO INTERROGATE PATIENT RECORDS AND CREATE ANONYMIZED RECORD, filed Mar. 28, 2018, to U.S. Provisional Patent Application No. 62/649,300, titled SURGICAL HUB SITUATIONAL AWARENESS, filed Mar. 28, 2018, to U.S. Provisional Patent Application No. 62/649,309, titled SURGICAL HUB SPATIAL AWARENESS TO DETERMINE DEVICES IN OPERATING THEATER, filed Mar. 28, 2018, to U.S. Provisional Patent Application No. 62/649,310, titled COMPUTER IMPLEMENTED INTERACTIVE SURGICAL SYSTEMS, filed Mar. 28, 2018, to U.S. Provisional Patent Application No. 62/649,291, titled USE OF LASER LIGHT AND RED-GREEN-BLUE COLORATION TO DETERMINE PROPERTIES OF BACK SCATTERED LIGHT, filed Mar. 28, 2018, to U.S. Provisional Patent Application No. 62/649,296, titled ADAPTIVE CONTROL PROGRAM UPDATES FOR SURGICAL DEVICES, filed Mar. 28, 2018, to U.S. Provisional Patent Application No. 62/649,333, titled CLOUD-BASED MEDICAL ANALYTICS FOR CUSTOMIZATION AND RECOMMENDATIONS TO A USER, filed Mar. 28, 2018, to U.S. Provisional Patent Application No. 62/649,327, titled CLOUD-BASED MEDICAL ANALYTICS FOR SECURITY AND AUTHENTICATION TRENDS AND REACTIVE MEASURES, filed Mar. 28, 2018, to U.S. Provisional Patent Application No. 62/649,315, titled DATA HANDLING AND PRIORITIZATION IN A CLOUD ANALYTICS NETWORK, filed Mar. 28, 2018, to U.S. Provisional Patent Application No. 62/649,313, titled CLOUD INTERFACE FOR COUPLED SURGICAL DEVICES, filed Mar. 28, 2018, to U.S. Provisional Patent Application No. 62/649,320, titled DRIVE ARRANGEMENTS FOR ROBOT-ASSISTED SURGICAL PLATFORMS, filed Mar. 28, 2018, to U.S. Provisional Patent Application No. 62/649,307, titled AUTOMATIC TOOL ADJUSTMENTS FOR ROBOT-ASSISTED SURGICAL PLATFORMS, filed Mar. 28, 2018, and to U.S. Provisional Patent Application No. 62/649,323, titled SENSING ARRANGEMENTS FOR ROBOT-ASSISTED SURGICAL PLATFORMS, filed Mar. 28, 2018, the disclosure of each of which is herein incorporated by reference in its entirety.

This application also claims the benefit of priority under 35 U.S.C. § 119(e) to U.S. Provisional Patent Application No. 62/611,341, titled INTERACTIVE SURGICAL PLATFORM, filed Dec. 28, 2017, to U.S. Provisional Patent Application No. 62/611,340, titled CLOUD-BASED MEDICAL ANALYTICS, filed Dec. 28, 2017, and to U.S. Provisional Patent Application No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to various surgical systems. Surgical procedures are typically performed in surgical operating theaters or rooms in a healthcare facility such as, for example, a hospital. A sterile field is typically created around the patient. The sterile field may include the scrubbed team members, who are properly attired, and all furniture and fixtures in the area. Various surgical devices and systems are utilized in performance of a surgical procedure.

SUMMARY

In one aspect the present disclosure provides a method of adjusting a staple parameter of a surgical stapling instrument. The method comprising: determining, by a control circuit of the surgical stapling instrument, a first stroke length for a first staple driver of the surgical stapling instrument to drive a first row of staples of a circular stapling head assembly of the surgical stapling instrument; detecting, by the control circuit, a malformed staple in the first row of staples; adjusting, by the control circuit, the staple parameter, based on the detection of the malformed staple; and determining, by the control circuit, a second stroke length for a second staple driver of the surgical stapling instrument to drive a second row of staples of the circular stapling head assembly.

In another aspect the present disclosure provides a method of adjusting a cutting parameter of a surgical stapling instrument. The method comprising: receiving, by a control circuit of the surgical stapling instrument, a sensor output signal from a sensor of the surgical stapling instrument; determining, by the control circuit, a parameter associated with clamping of an end effector of the surgical stapling instrument, based on the sensor output signal; and controlling, by the control circuit, a torque applied to a cutting member of the surgical stapling instrument, wherein the motor moves the cutting member between first position and a second position by applying the torque to the cutting member.

In another aspect the present disclosure provides a method of controlling a surgical stapling instrument. The method comprising: receiving, by a control circuit of the surgical stapling instrument, a sensor output signal from a first sensor of the surgical stapling instrument; determining, by the control circuit, a parameter associated with operation of the surgical stapling instrument, based on the sensor output signal; determining, by the control circuit, an anvil gap of an anvil of the surgical stapling instrument, wherein the anvil clamps tissue; comparing, by the control circuit, the anvil gap to a predetermined gap; and executing, by the control circuit, an electronic lockout to prevent actuation of the surgical stapling instrument based on the comparison and the determined parameter.

FIGURES

The various aspects described herein, both as to organization and methods of operation, together with further objects and advantages thereof, may best be understood by reference to the following description, taken in conjunction with the accompanying drawings as follows.

FIG. 26 depicts a cross sectional view of the handle assembly of the instrument of FIG. 24, in accordance with at least one aspect of the present disclosure.

FIG. 27 depicts an enlarged, partial cross sectional view of the motor and battery assemblies of FIG. 24, in accordance with at least one aspect of the present disclosure.

24 showing an anvil in an open position, in accordance with at least one aspect of the present disclosure.

Figure 29A:
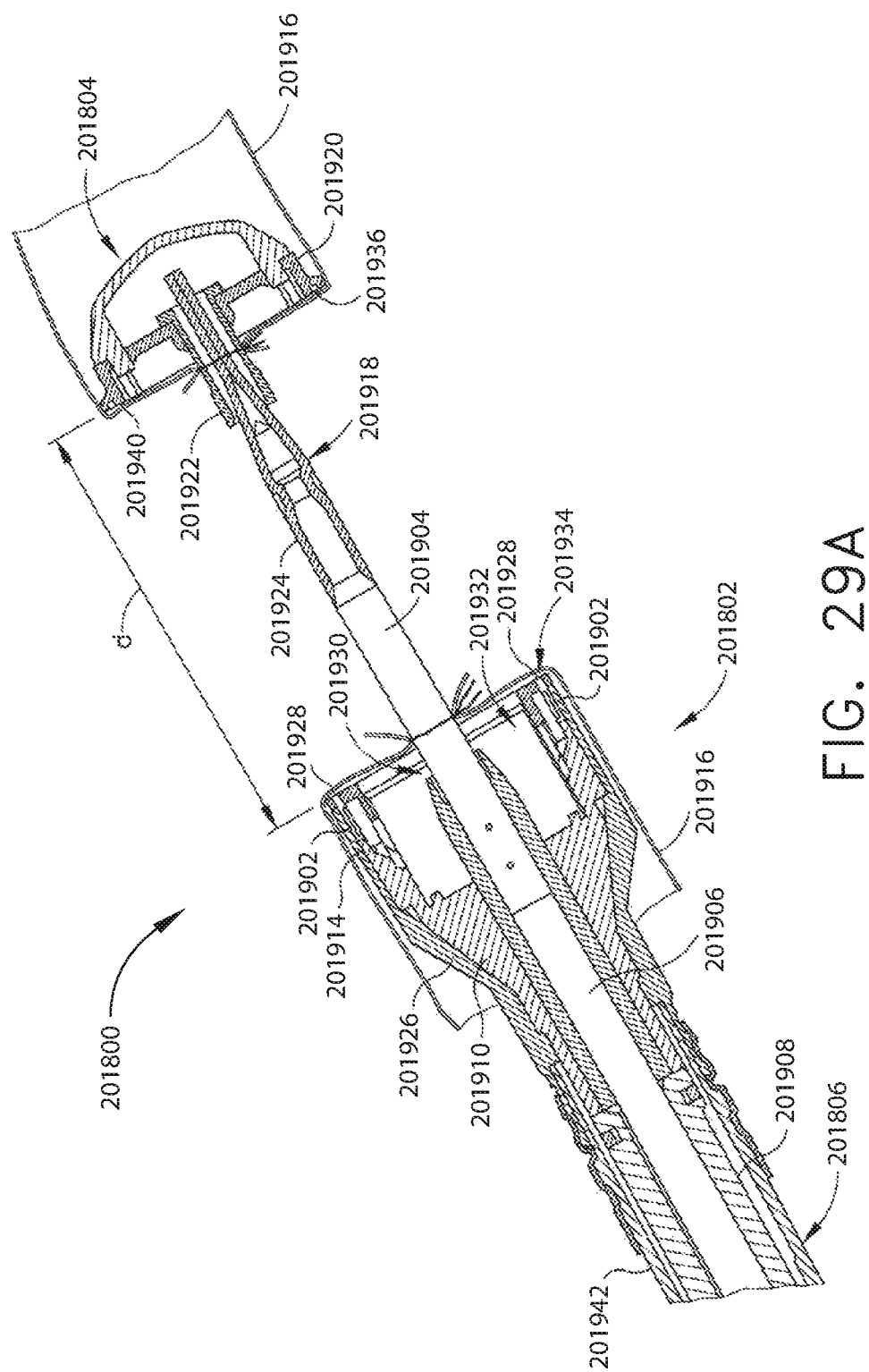
FIG. 29A depicts an enlarged longitudinal cross-section view of a stapling head assembly of the instrument of FIG.
Figure 29B:
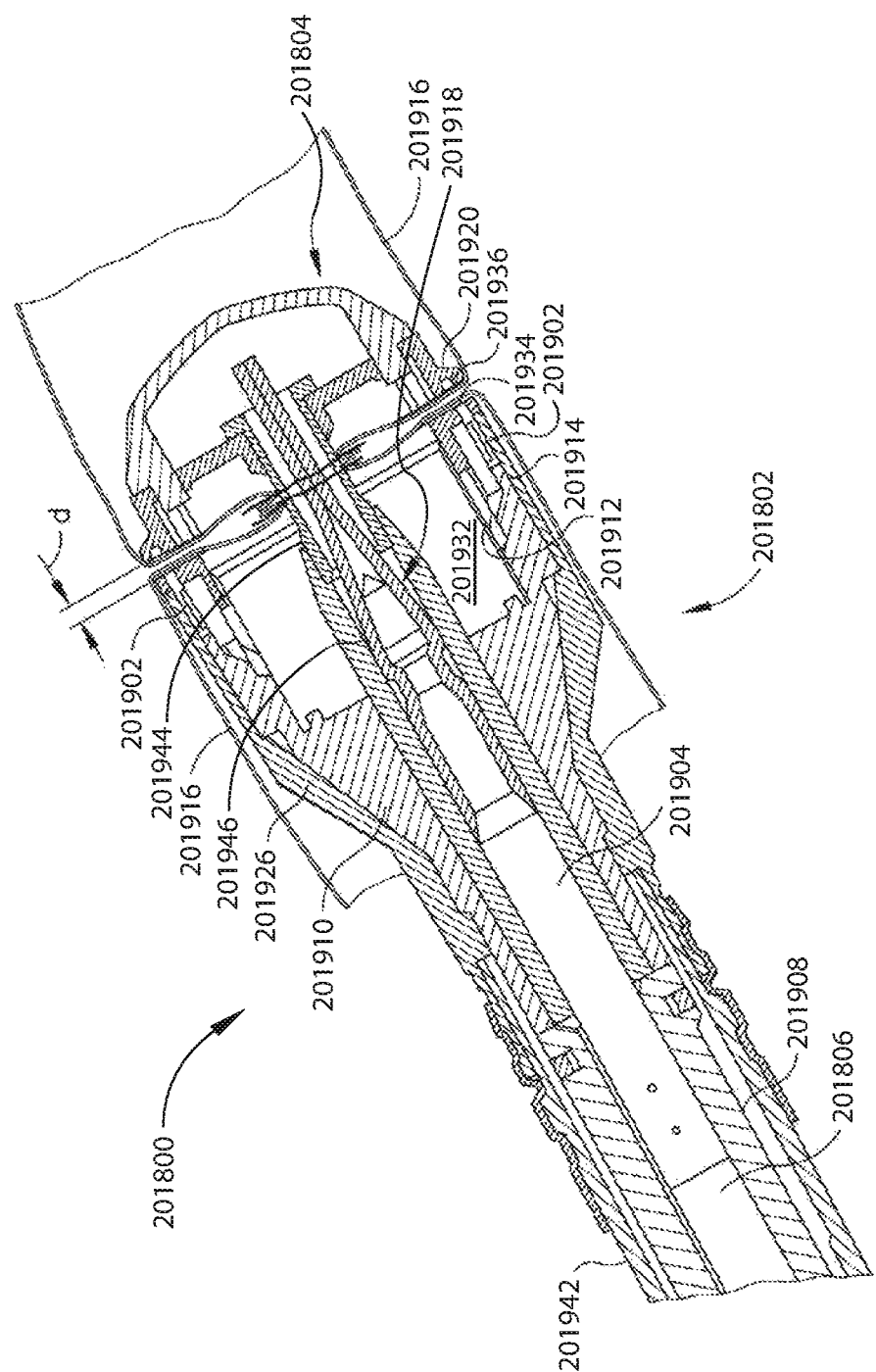

FIG. 29B depicts an enlarged longitudinal cross-sectional view of the stapling head assembly of FIG. 29A showing the anvil in a closed position, in accordance with at least one aspect of the present disclosure.

FIG. 29C depicts an enlarged longitudinal cross-sectional view of the stapling head assembly of FIG. 29A showing a staple driver and blade in a fired position, in accordance with at least one aspect of the present disclosure.

FIG. 30 depicts an enlarged partial cross-sectional view of a staple formed against the anvil, in accordance with at least one aspect of the present disclosure.

Figure 31:
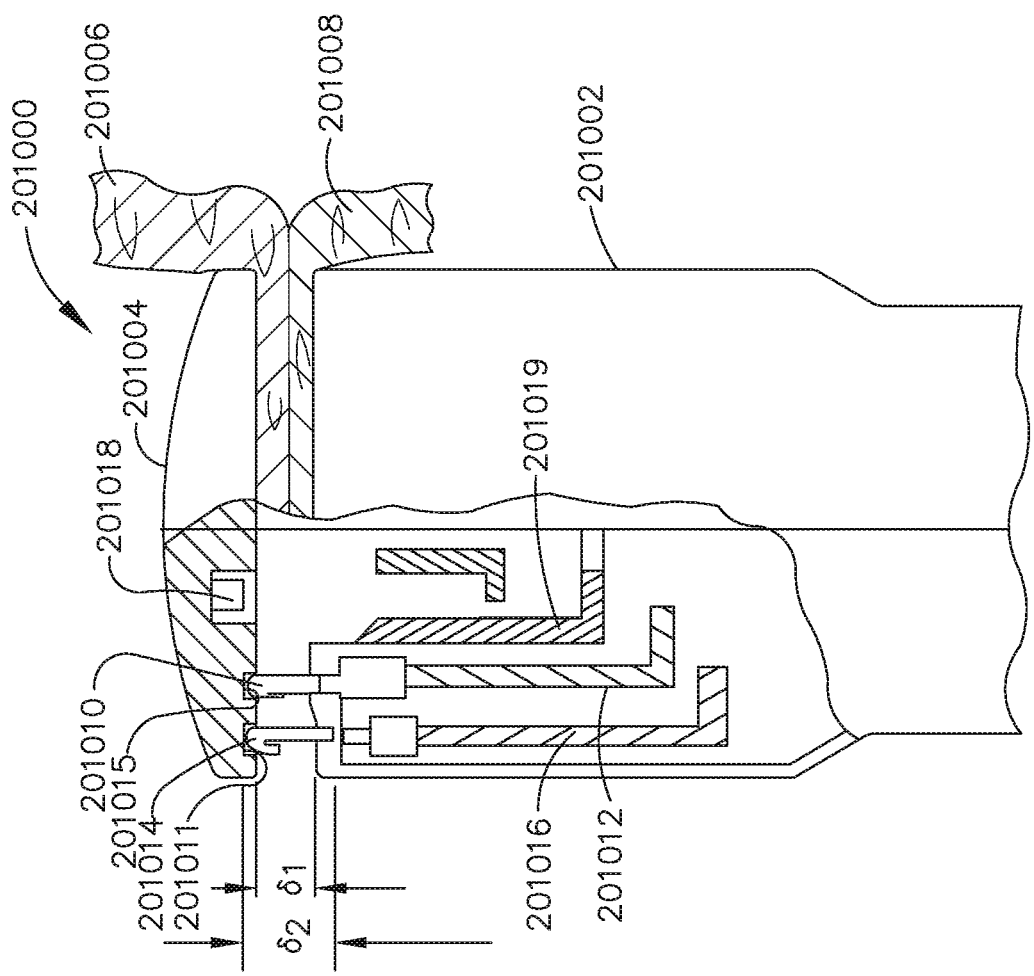

FIG. 31 is a partial cutaway view of a powered circular stapling device comprising a circular stapling head assembly and an anvil, in accordance with at least one aspect of the present disclosure.

Figure 32:
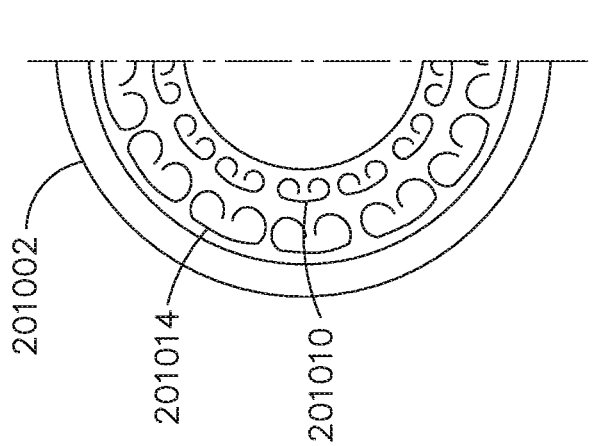

FIG. 32 is a partial top view of the circular stapling head assembly shown in FIG. 31 showing a first row of staples (inner staples) and a second row of staples (outer staples), in accordance with at least one aspect of the present disclosure.

FIG. 33 is a graph of the stroke of the staple drivers when the actual stroke of the first staple driver is less than the upper limit of the stroke length, in accordance with at least one aspect of the present disclosure.

FIG. 34 is a graph of the stroke of the staple drivers when the actual stroke of the first staple driver is equal to the upper limit of the stroke length, in accordance with at least one aspect of the present disclosure.

FIG. 35 is a diagram illustrating stroke length limit and algorithm adjustments based on staple formation, in accordance with at least one aspect of the present disclosure.

Figure 36:
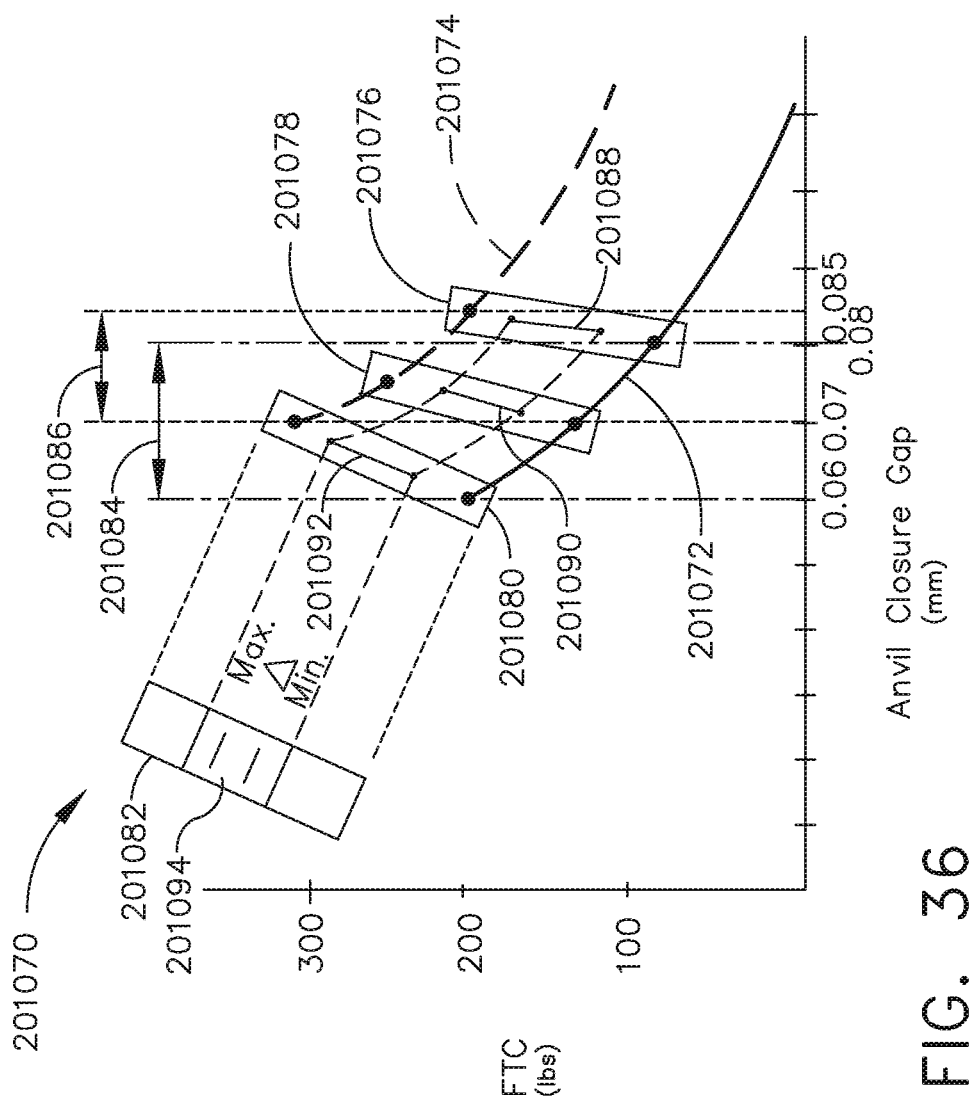

FIG. 36 is a graphical representation of viable staple firing range as indicated by usable staple height windows based on the tissue gap, closure force (FTC), or tissue creep stabilization sensed by the device or combinations thereof, in accordance with at least one aspect of the present disclosure.

Figure 37:
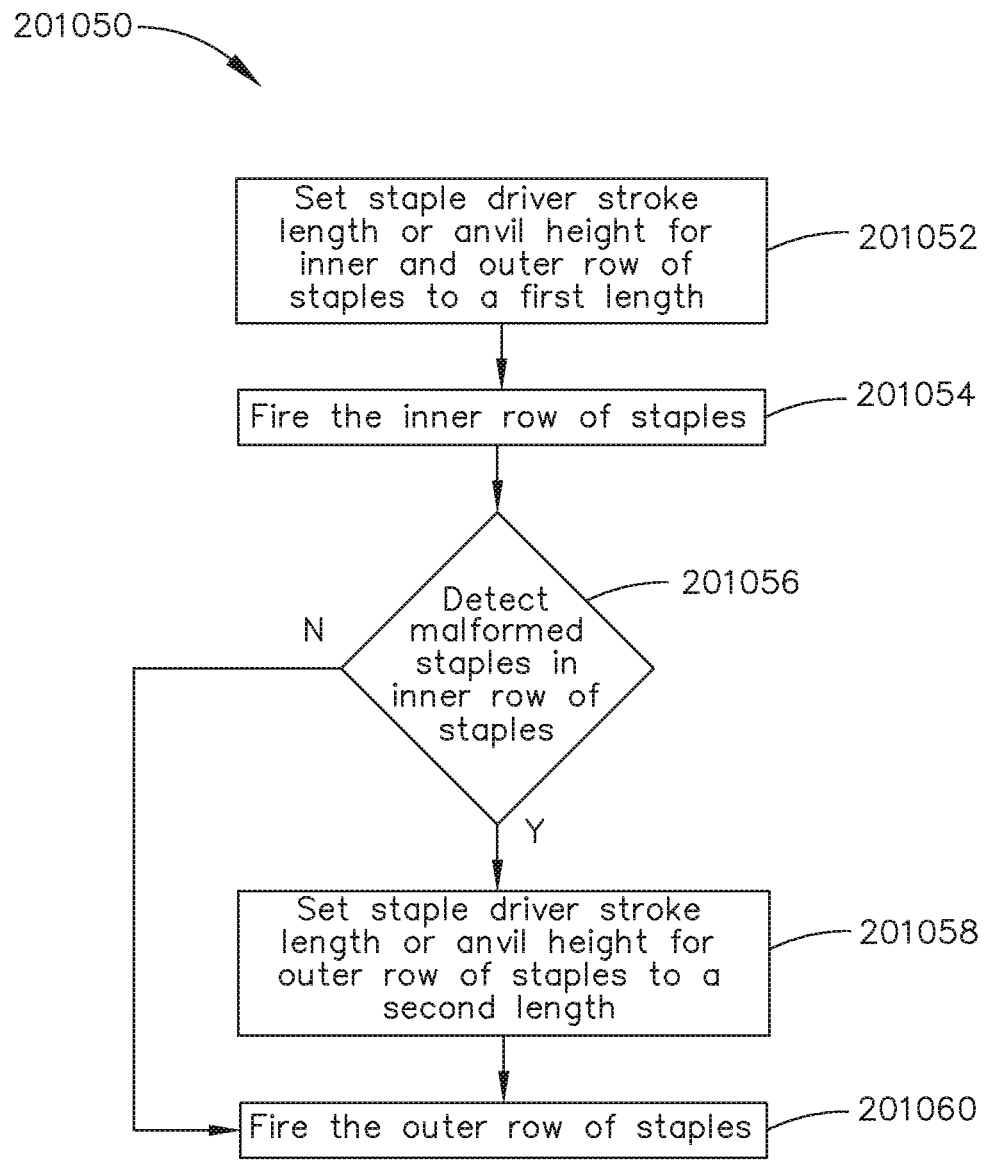

FIG. 37 is a logic flow diagram of a process depicting a control program or a logic configuration to adjust the stroke of the outer row of staple heights based on the force, tissue gap, or tissue creep during firing of the first row of staples, in accordance with at least one aspect of the present disclosure.

Figure 38:
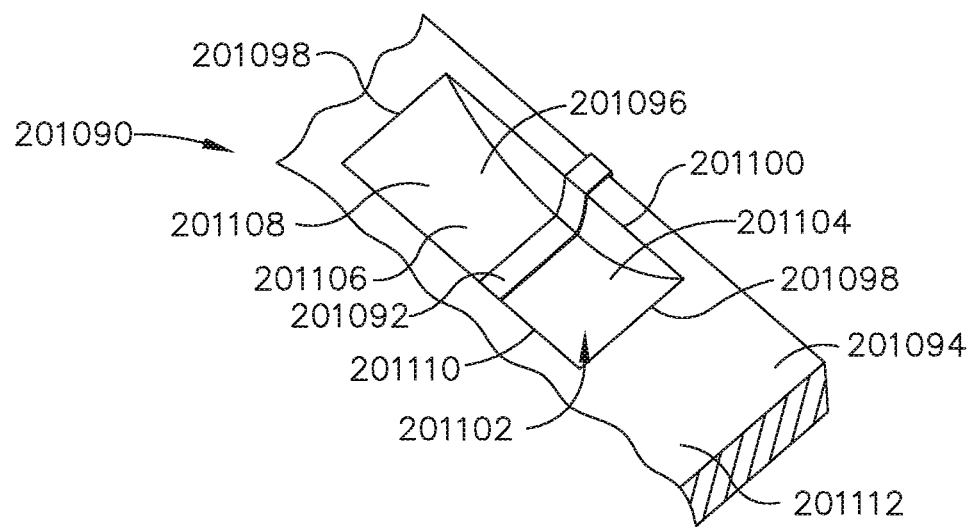

FIG. 38 illustrates a perspective view of a staple-forming pocket of the anvil of FIG. 31 including an electrically conductive circuit element, in accordance with at least one aspect of the present disclosure.

Figure 39:
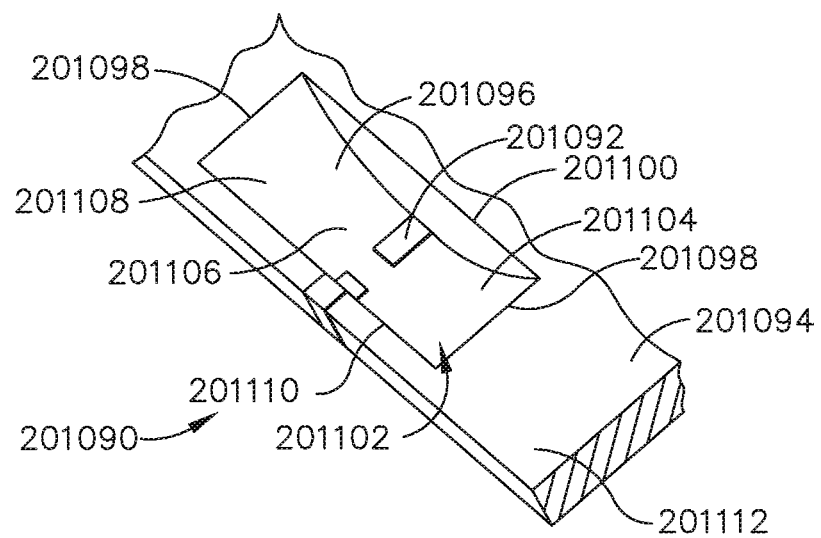

FIG. 39 illustrates a perspective view of the staple-forming pocket of FIG. 38 after the electrically conductive circuit element has been severed by a staple leg during proper formation of the staple leg, in accordance with at least one aspect of the present disclosure.

Figure 40:
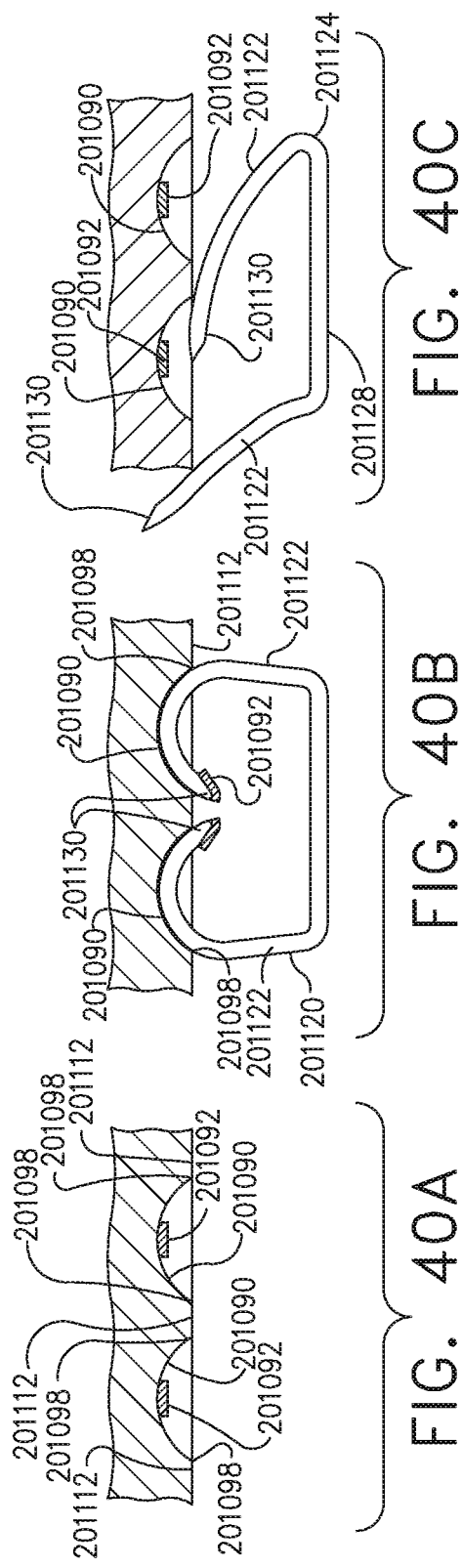

FIG. 40A illustrates a cross-sectional view of two adjacent staple-forming pockets in a row of staple-forming pockets of the anvil of FIG. 39, in accordance with at least one aspect of the present disclosure.

FIG. 40B illustrates a cross-sectional view of the staple-forming pockets of FIG. 40A being engaged with a properly forming staple that includes two staple legs that severed the electrically conductive circuit elements of the staple-forming pockets, in accordance with at least one aspect of the present disclosure.

FIG. 40C illustrates a cross-sectional view of the staple-forming pockets of FIG. 40A being engaged with an improperly forming staple that includes staple legs that failed to sever or missed the electrically conductive circuit elements of the staple-forming pockets, in accordance with at least one aspect of the present disclosure.

Figure 41:
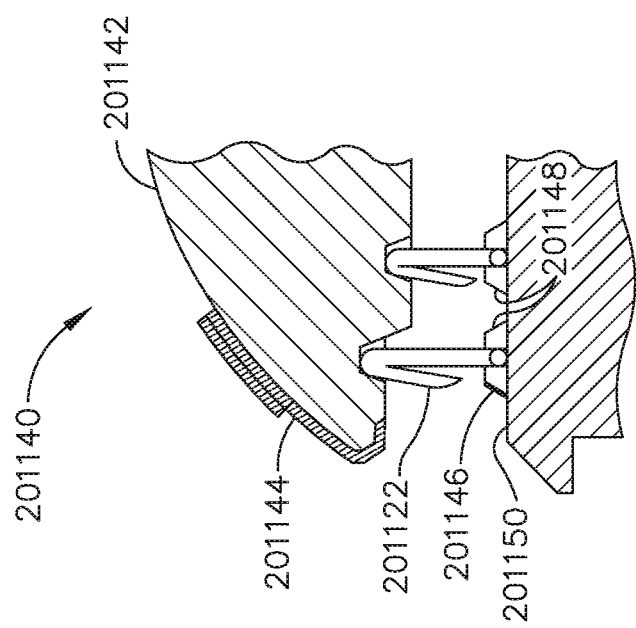

FIG. 41 illustrates a partial cross-sectional view of an anvil being pressed against staples of a staple cartridge, in accordance with at least one aspect of the present disclosure.

Figure 42:
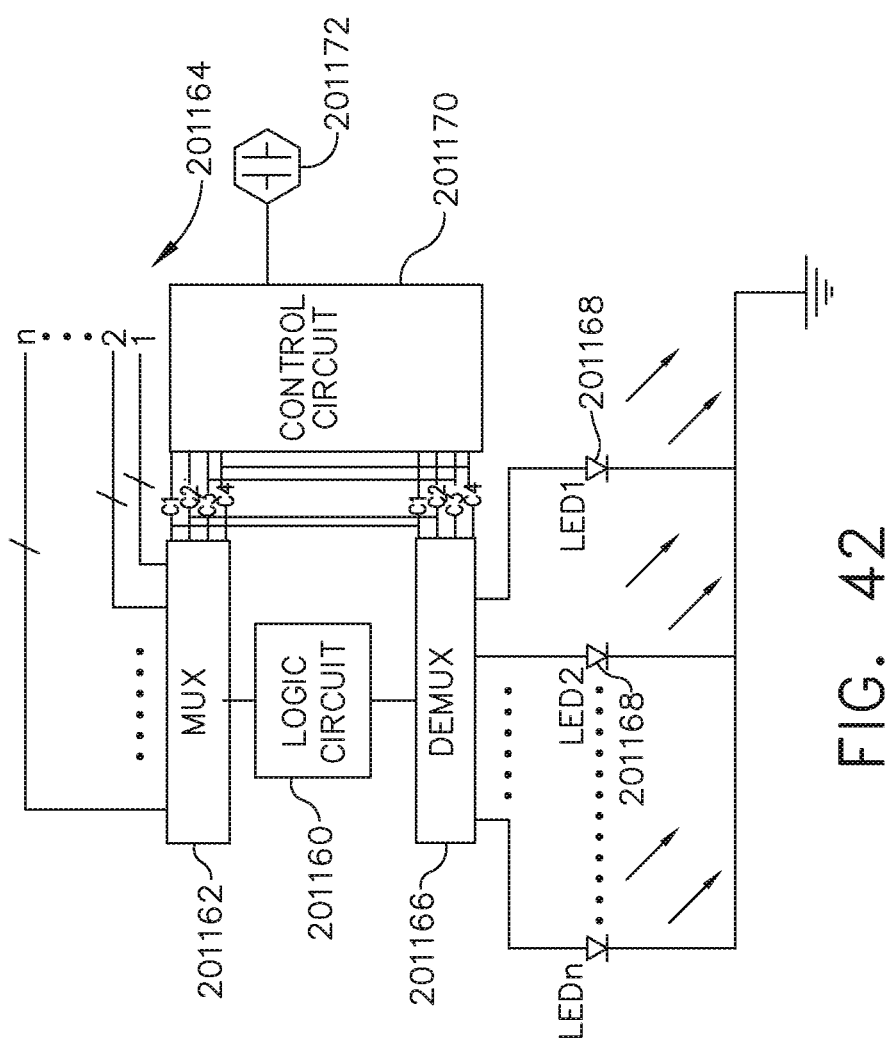

FIG. 42 is a circuit diagram, in accordance with at least one aspect of the present disclosure.

Figure 43:
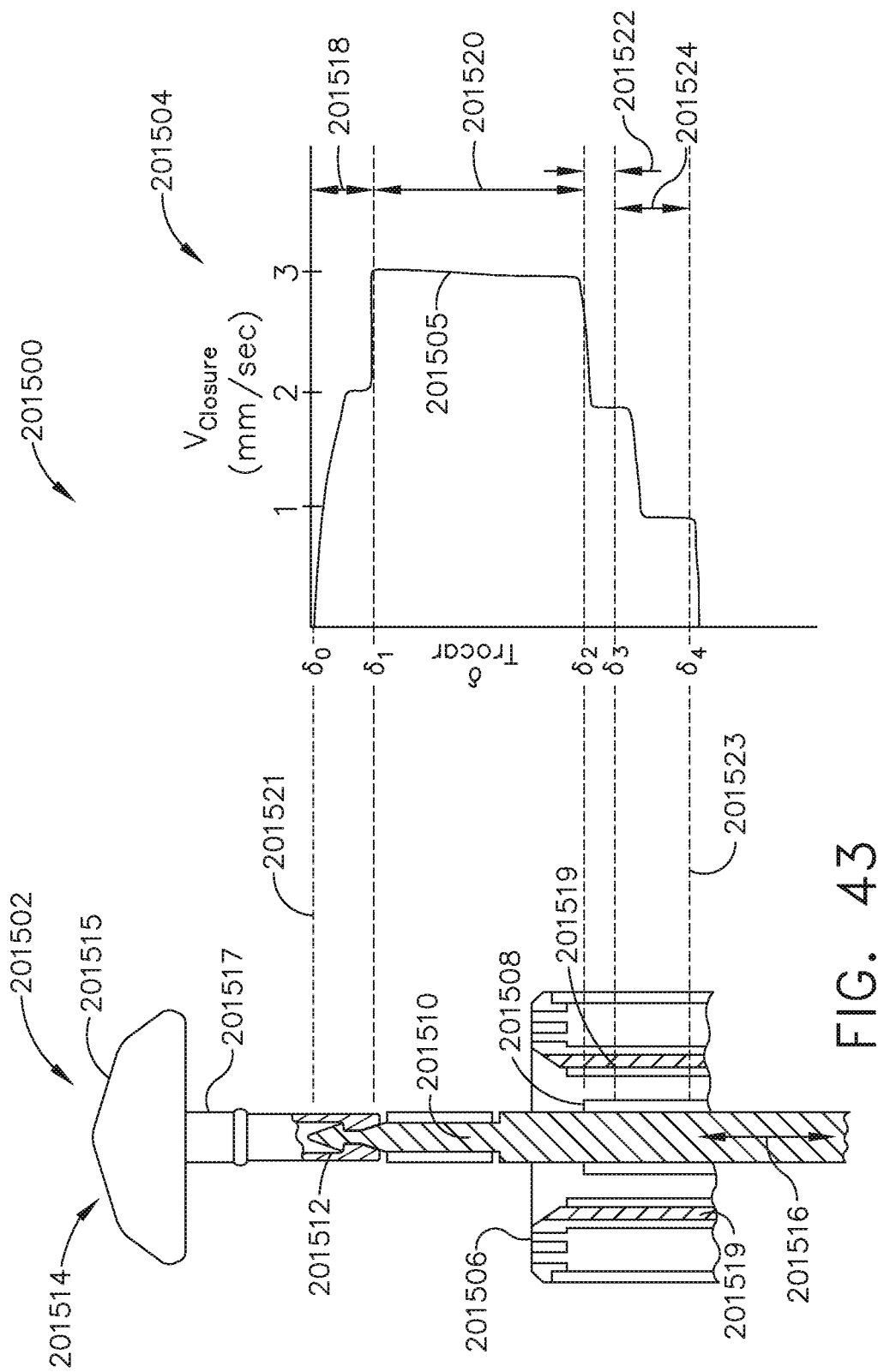

FIG. 43 is a diagram of graph and associated powered stapling device illustrating anvil closure rate adjustment at certain key points along a trocar's retraction stroke, in accordance with at least one aspect of the present disclosure.

Figure 44:
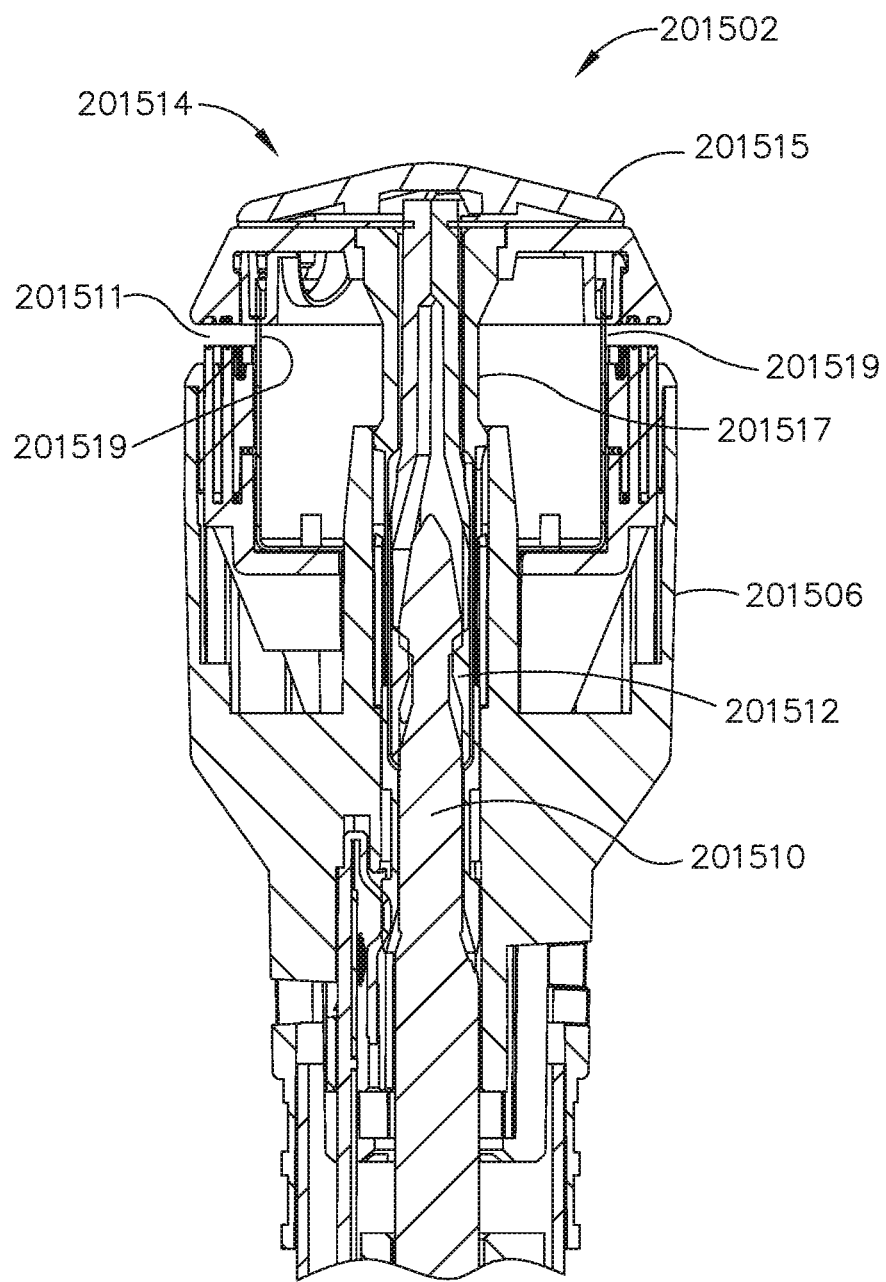

FIG. 44 is a view of a circular stapler, in accordance with at least one aspect of the present disclosure.

Figure 45:
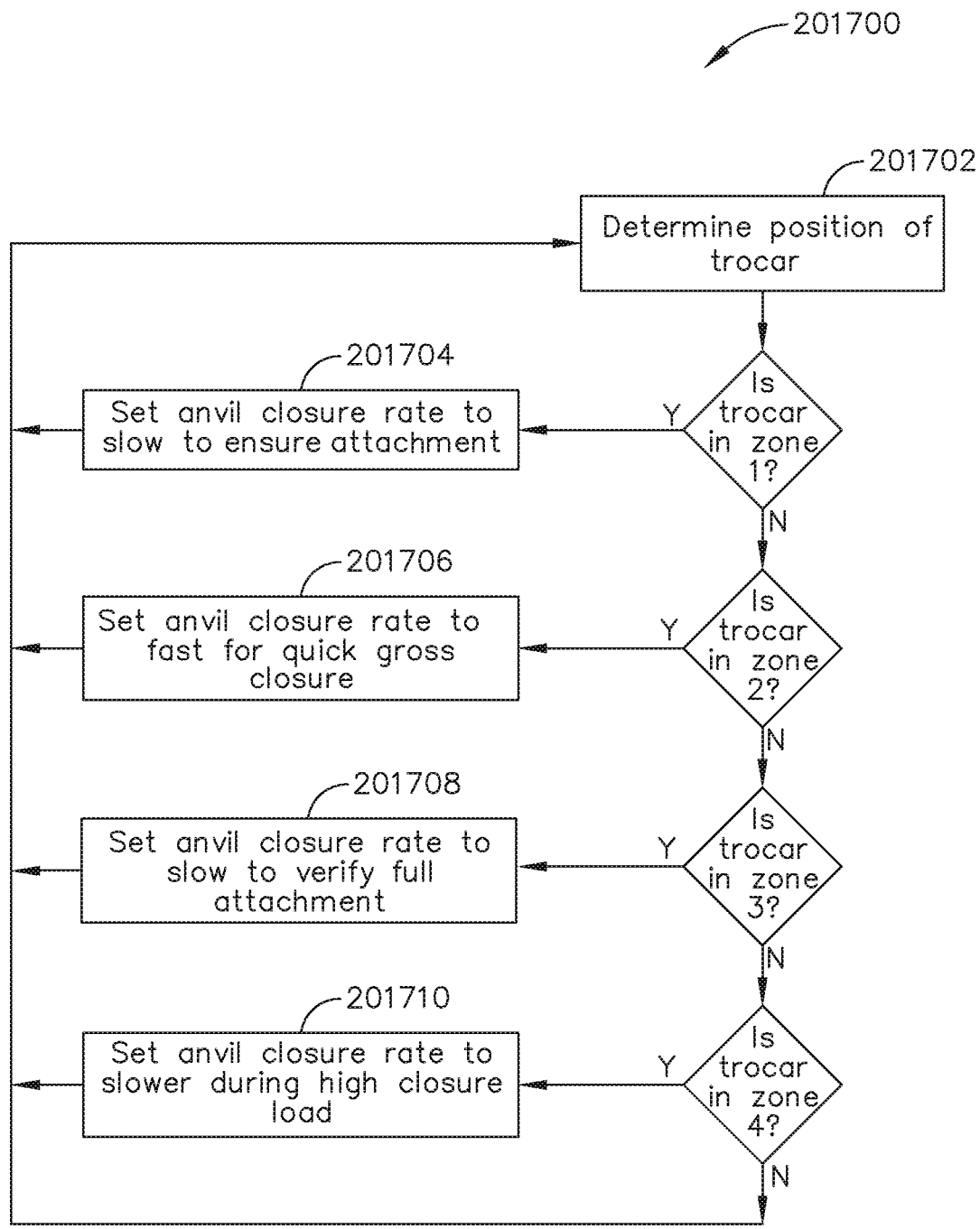

FIG. 45 is a logic flow diagram of a process depicting a control program or a logic configuration to adjust a closure rate of the anvil portion of the powered stapling device at certain key points along the retraction stroke of a trocar, in accordance with at least one aspect of the present disclosure.

Figure 46:
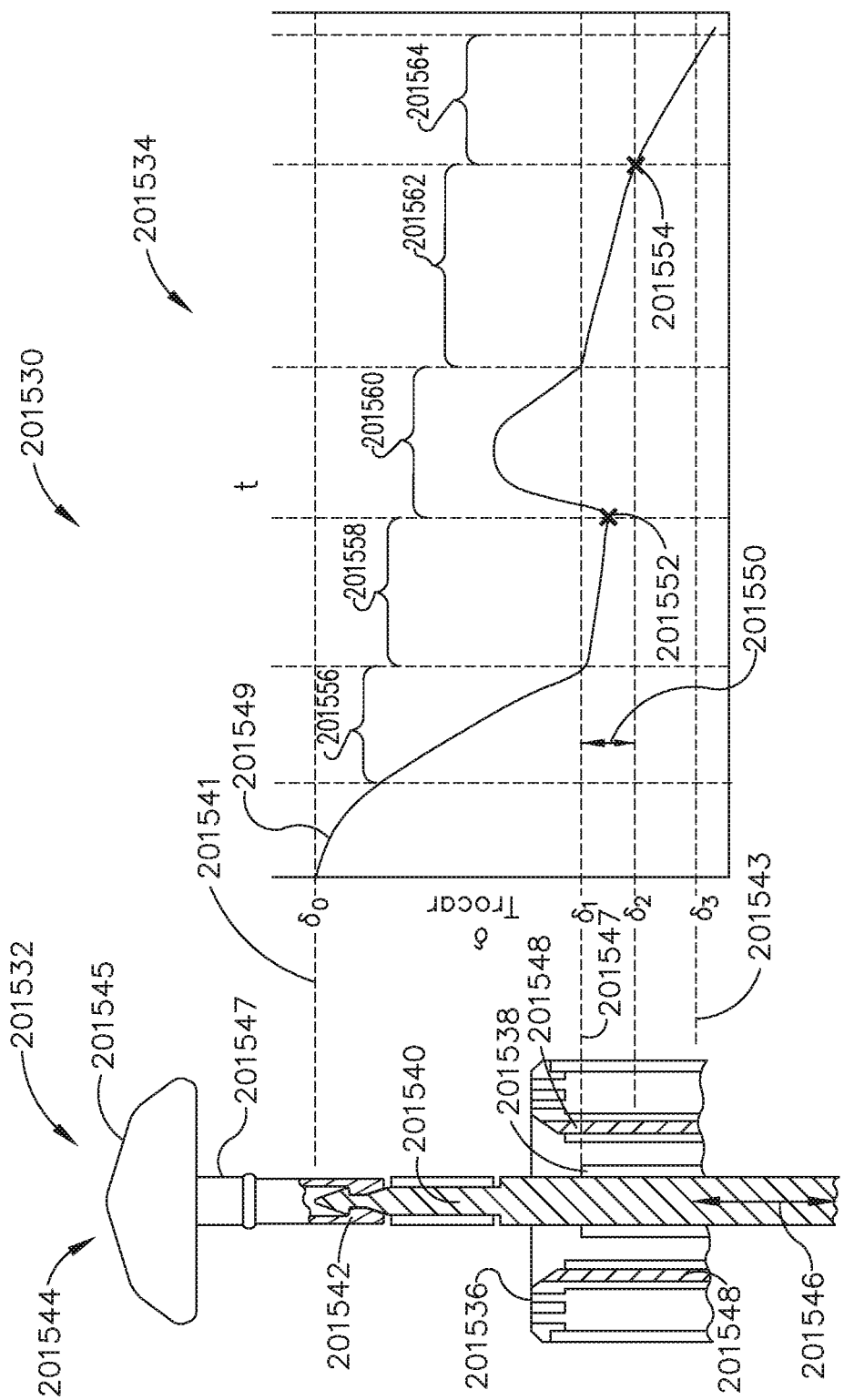

FIG. 46 is a diagram of graph and associated power stapling device diagram illustrating trocar position over time, in accordance with at least one aspect of the present disclosure.

Figure 47:
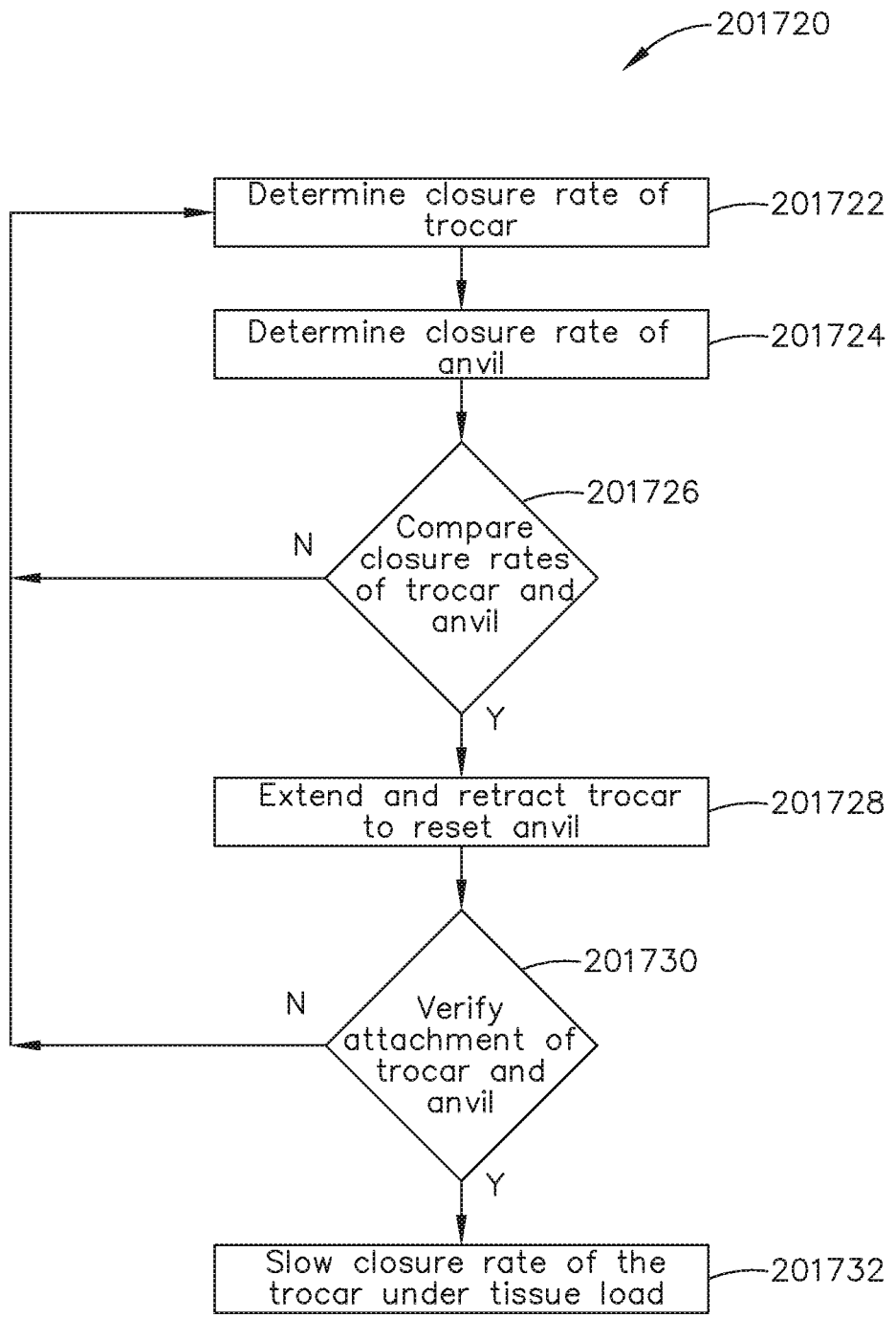

FIG. 47 is a logic flow diagram of a process depicting a control program or a logic configuration to detect multi-directional seating motions on the trocar to drive the anvil into proper seating, in accordance with at least one aspect of the present disclosure.

Figure 48:
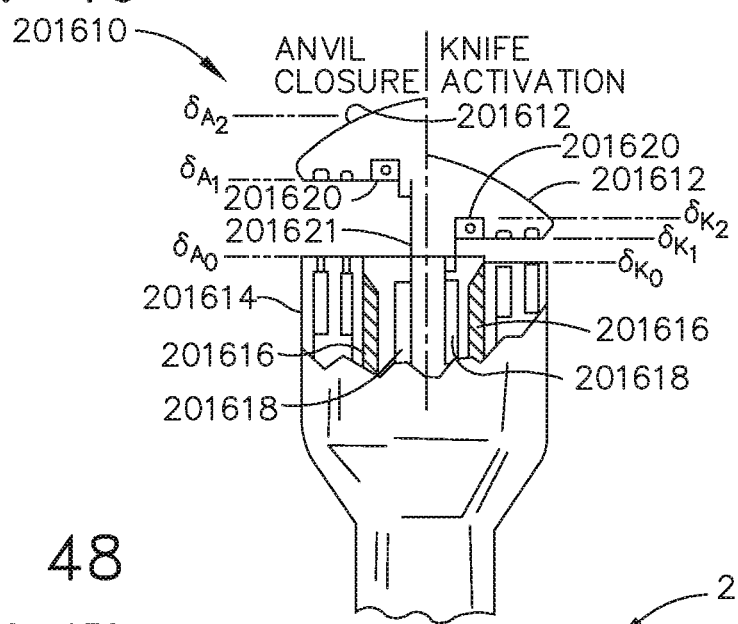

FIG. 48 is a partial schematic diagram of a circular powered stapling device showing anvil closure on the left side and knife actuation on the right side, in accordance with at least one aspect of the present disclosure.

Figure 49:
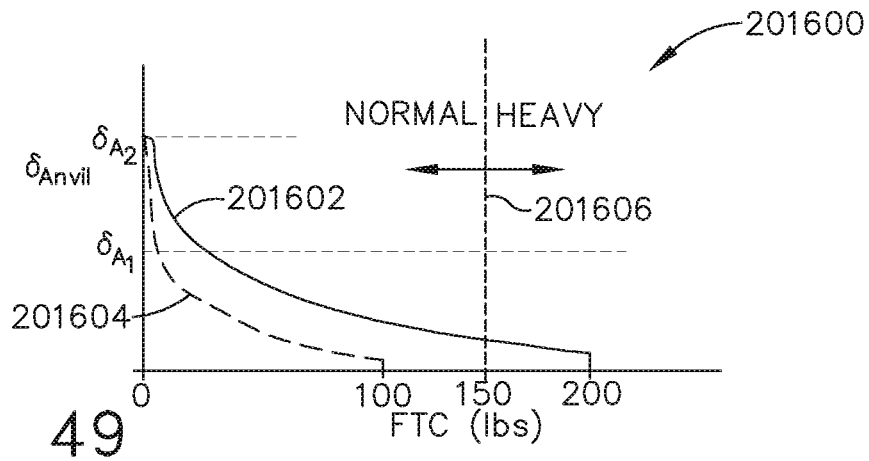

FIG. 49 is a graphical representation of anvil displacement ($\delta_{Anvil}$) along the vertical axis as a function of force to close (FTC) a clamp along the horizontal axis, in accordance with at least one aspect of the present disclosure.

Figure 50:
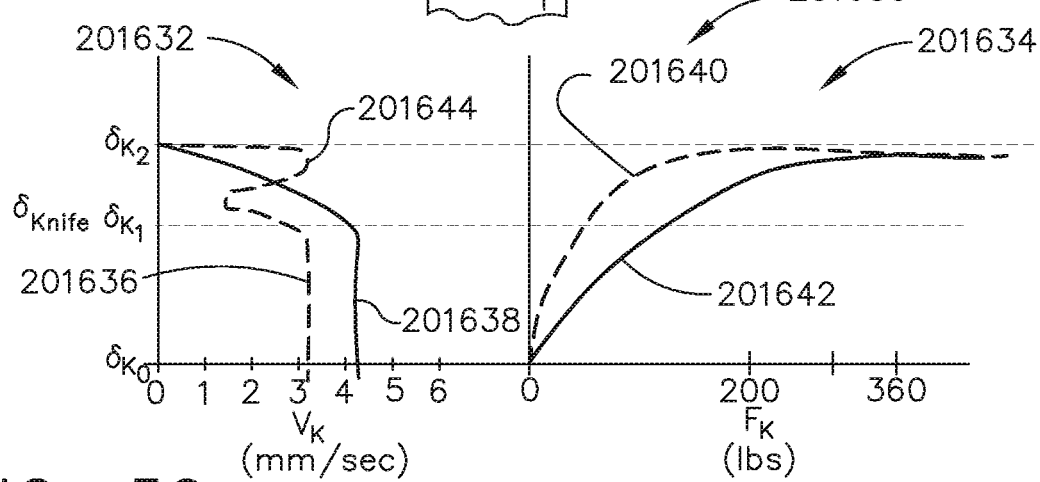

FIG. 50 is a graphical representation of knife displacement ($\delta_{Knife}$) along the vertical axis as a function of knife velocity ($V_K$ mm/sec) along the horizontal axis on the left and also as a function of knife force ($F_K$ lbs) along the horizontal axis on the right, in accordance with at least one aspect of the present disclosure.

Figure 51:
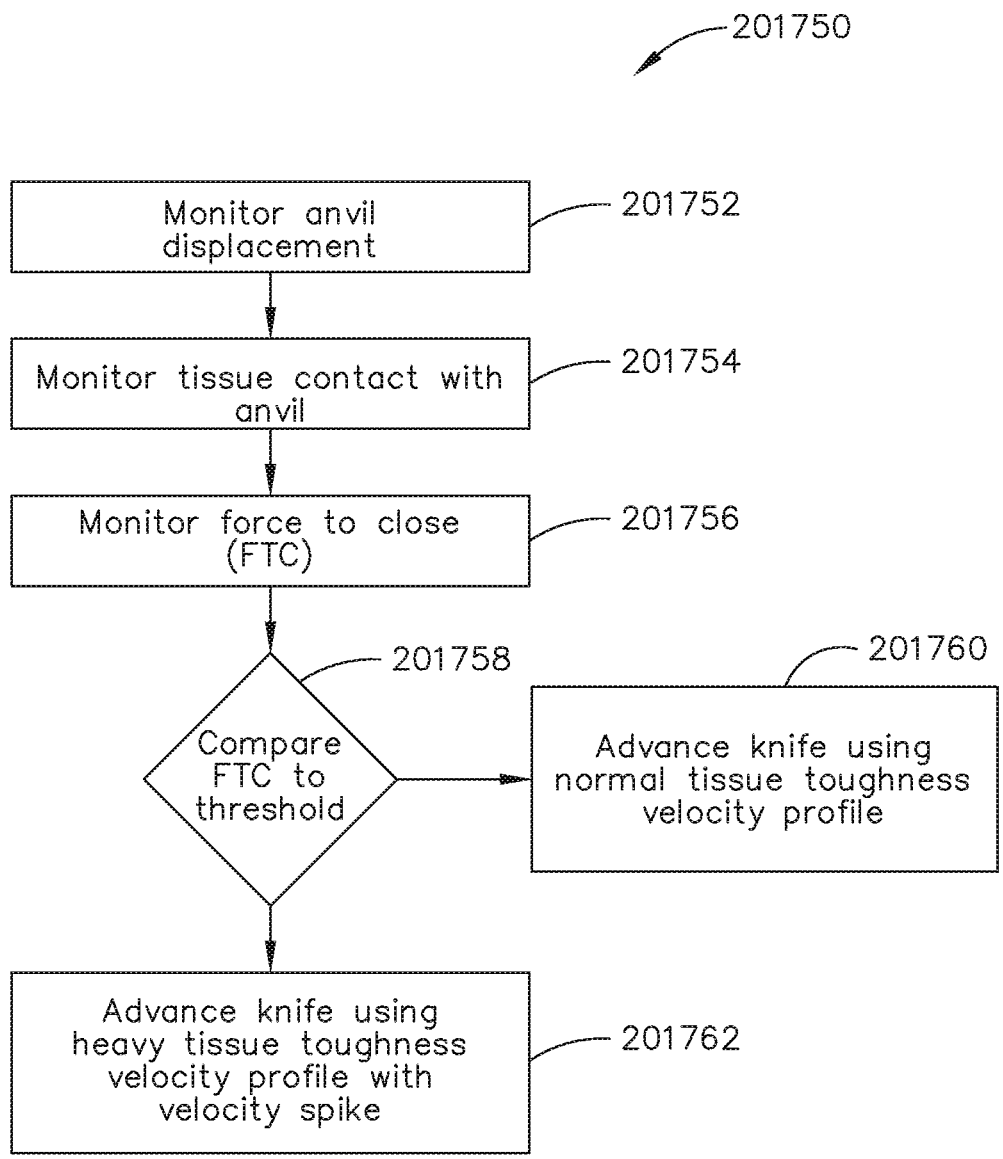

FIG. 51 is a logic flow diagram of a process depicting a control program or a logic configuration to detect the tissue gap and force-to-fire to adjust the knife stroke and speed, in accordance with at least one aspect of the present disclosure.

Figure 52:
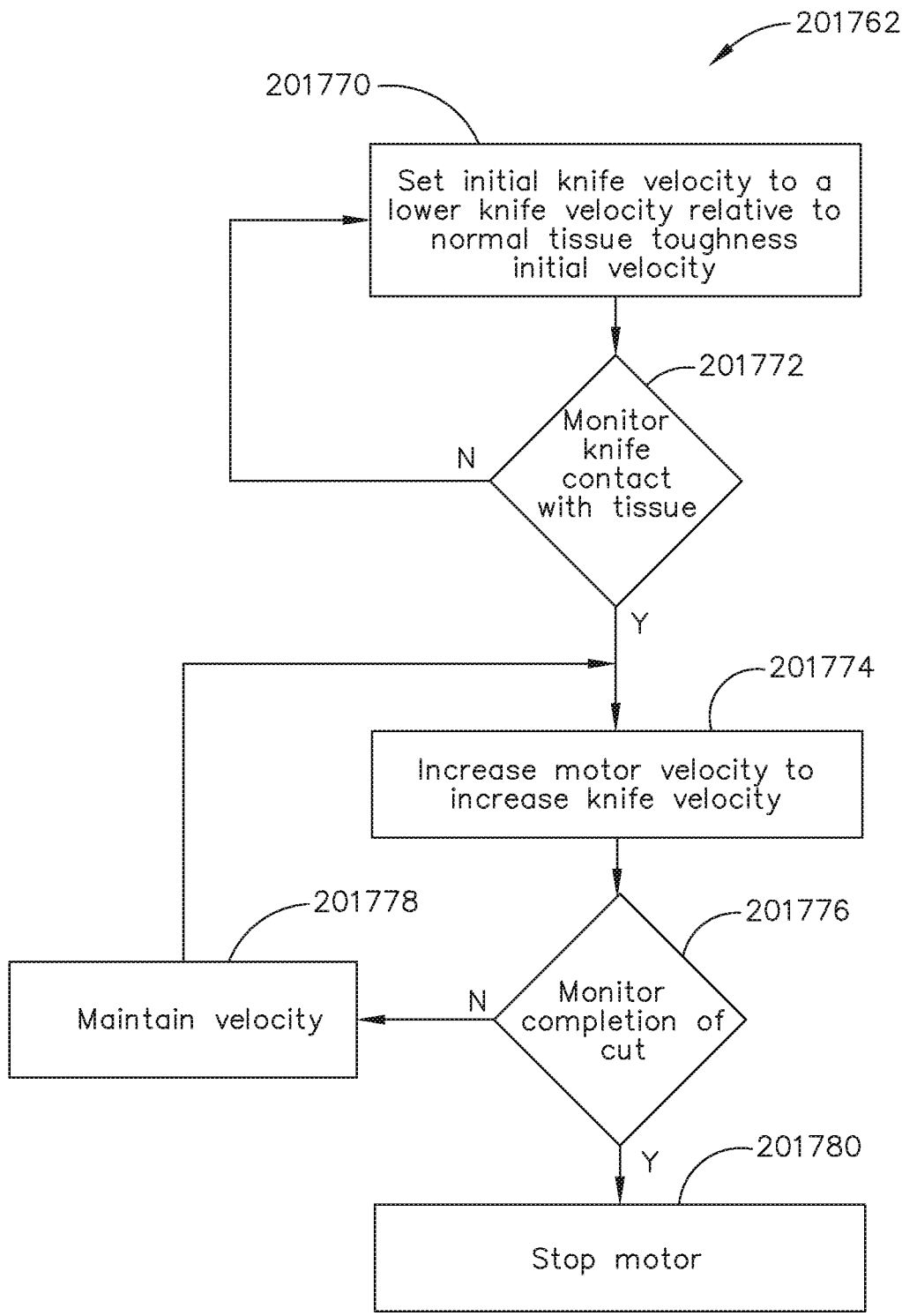

FIG. 52 is a logic flow diagram of a process depicting a control program or a logic configuration to advance the knife under a heavy tissue toughness velocity profile with a velocity spike as shown in FIG. 50, in accordance with at least one aspect of the present disclosure.

Figure 53:
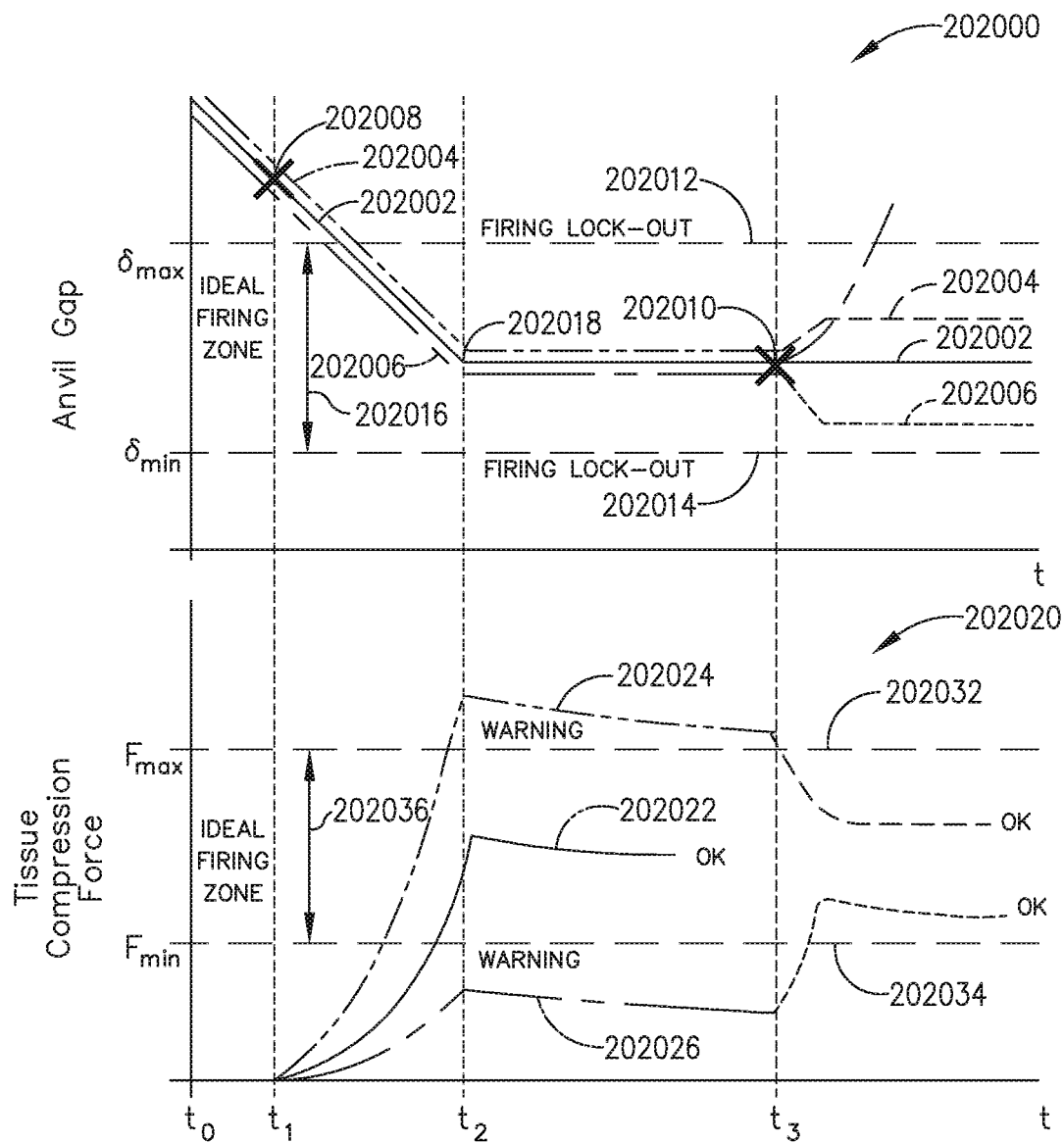

FIG. 53 is a graphical representation of a first pair of graphs depicting anvil gap and tissue compression force verse time for illustrative firings of a stapling instrument, in accordance with at least one aspect of the present disclosure.

Figure 54:
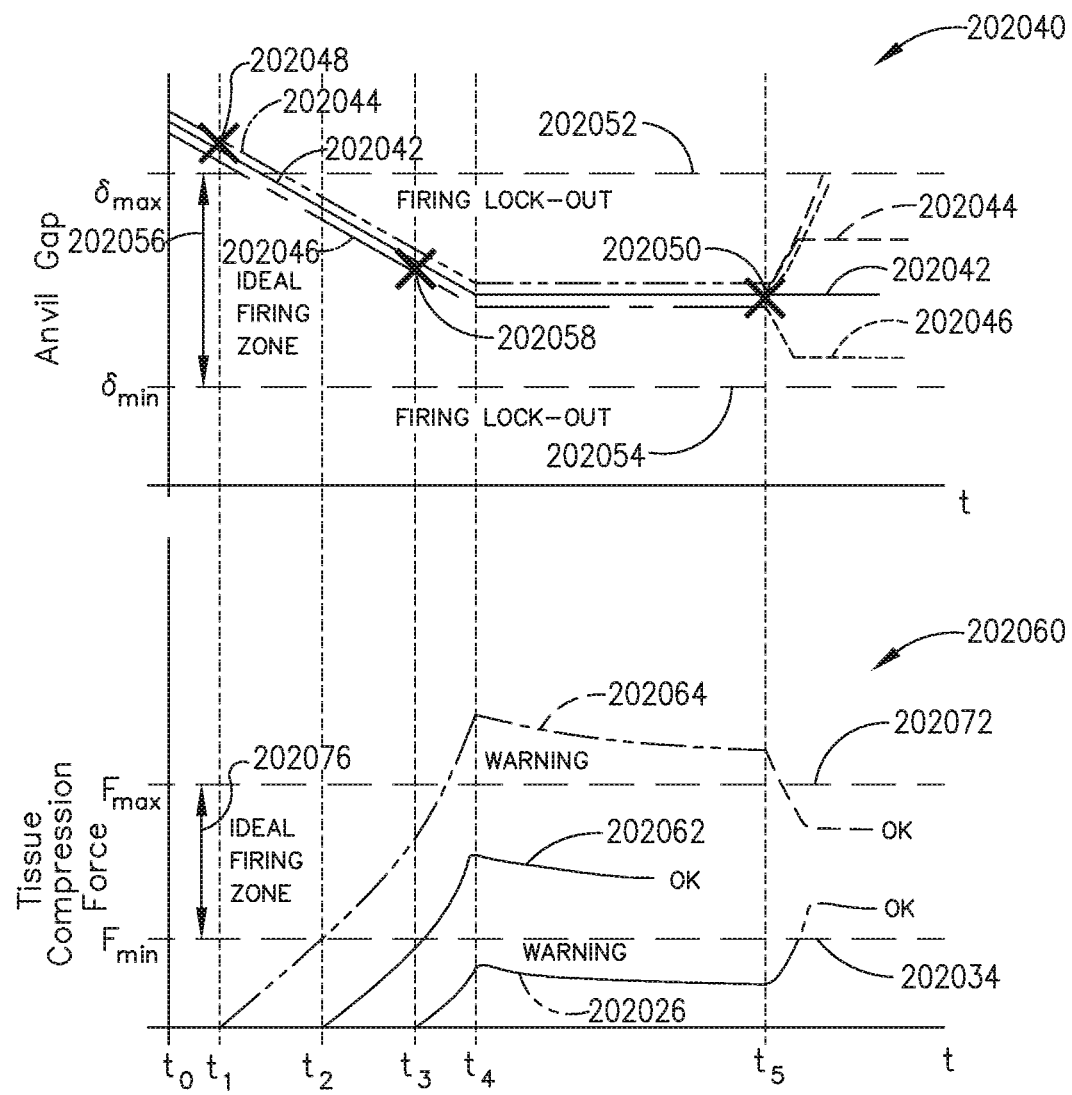

FIG. 54 is a graphical representation of a second pair of graphs depicting anvil gap and tissue compression force verse time for illustrative firings of a stapling instrument, in accordance with at least one aspect of the present disclosure.

FIG. 55 is a schematic diagram of a powered circular stapling device illustrating valid tissue gap, actual gap, normal range gap, and out of range gap, in accordance with at least one aspect of the present disclosure.

FIG. 56 is a logic flow diagram of a process depicting a control program or a logic configuration to provide discretionary or compulsory lockouts according to sensed parameters compared to thresholds, in accordance with at least one aspect of the present disclosure.

FIG. 57 is a diagram illustrating a range of tissue gaps and resulting staple forms, in accordance with at least one aspect of the present disclosure.

Figure 58:
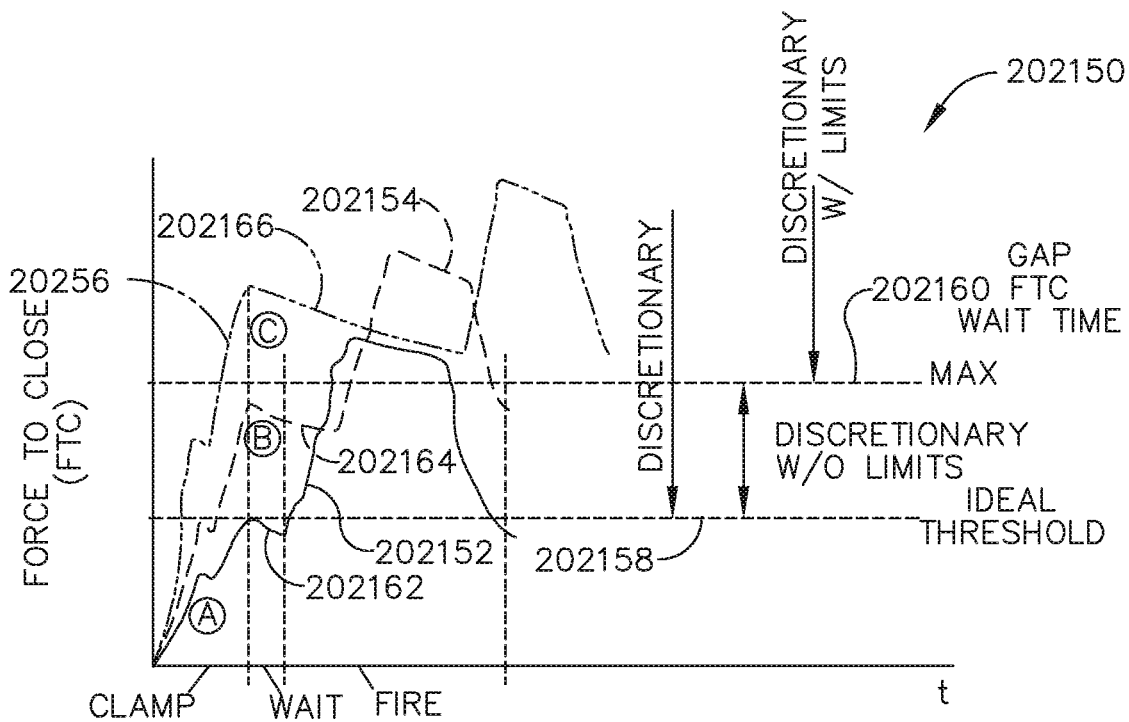

FIG. 58 is a graphical representation of three force to close (FTC) curves verse time, in accordance with at least one aspect of the present disclosure.

Figure 59:
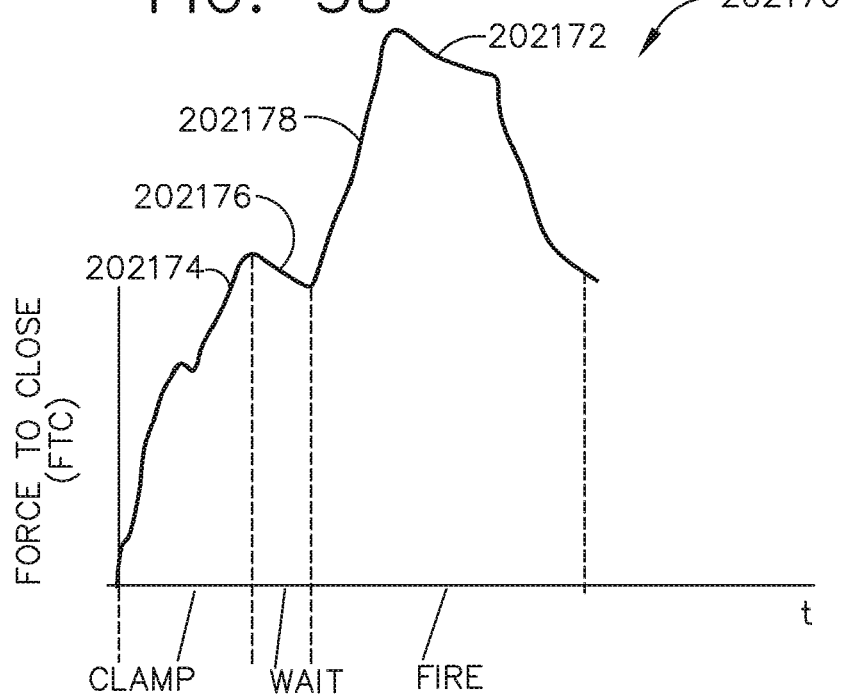

FIG. 59 is a detail graphical representation of a force to close (FTC) curve verse time, in accordance with at least one aspect of the present disclosure.

Figure 60:
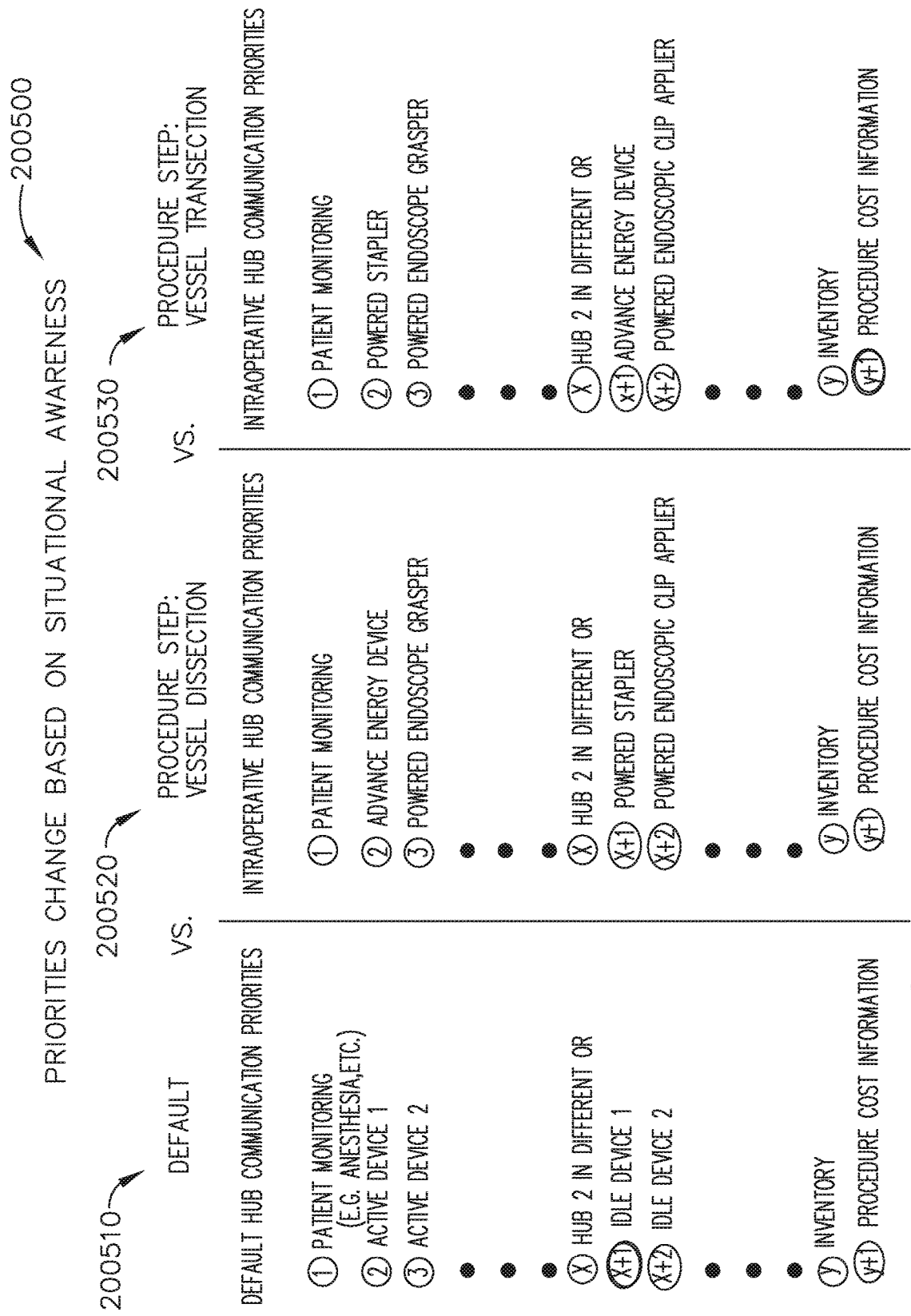

FIG. 60 is a chart indicating hub communication priorities according to procedure step, in accordance with at least one aspect of the present disclosure.

Figure 61:
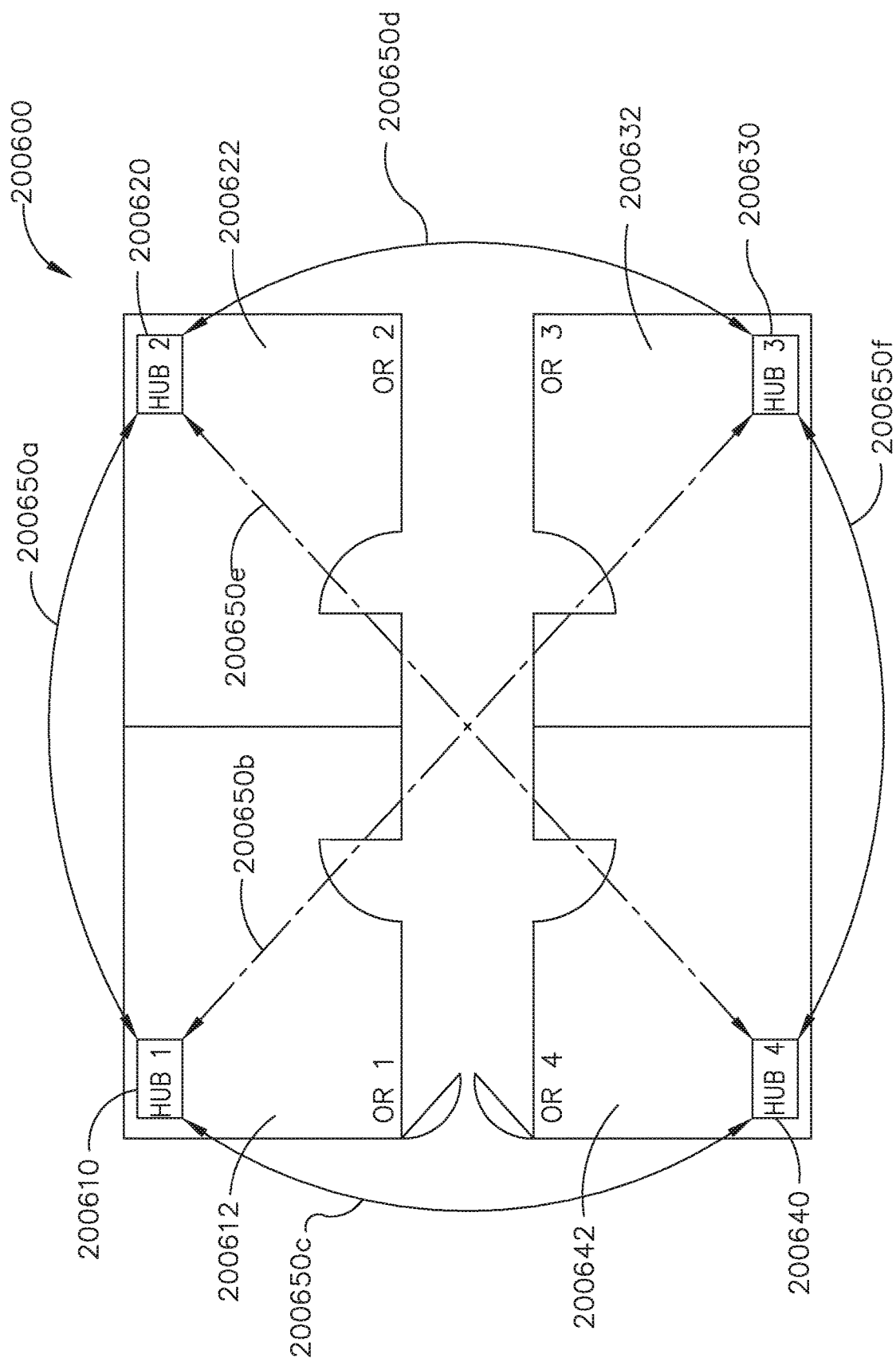

FIG. 61 is a diagram of a network of surgical hubs executing a distributed processing system, in accordance with at least one aspect of the present disclosure.

Figure 62:
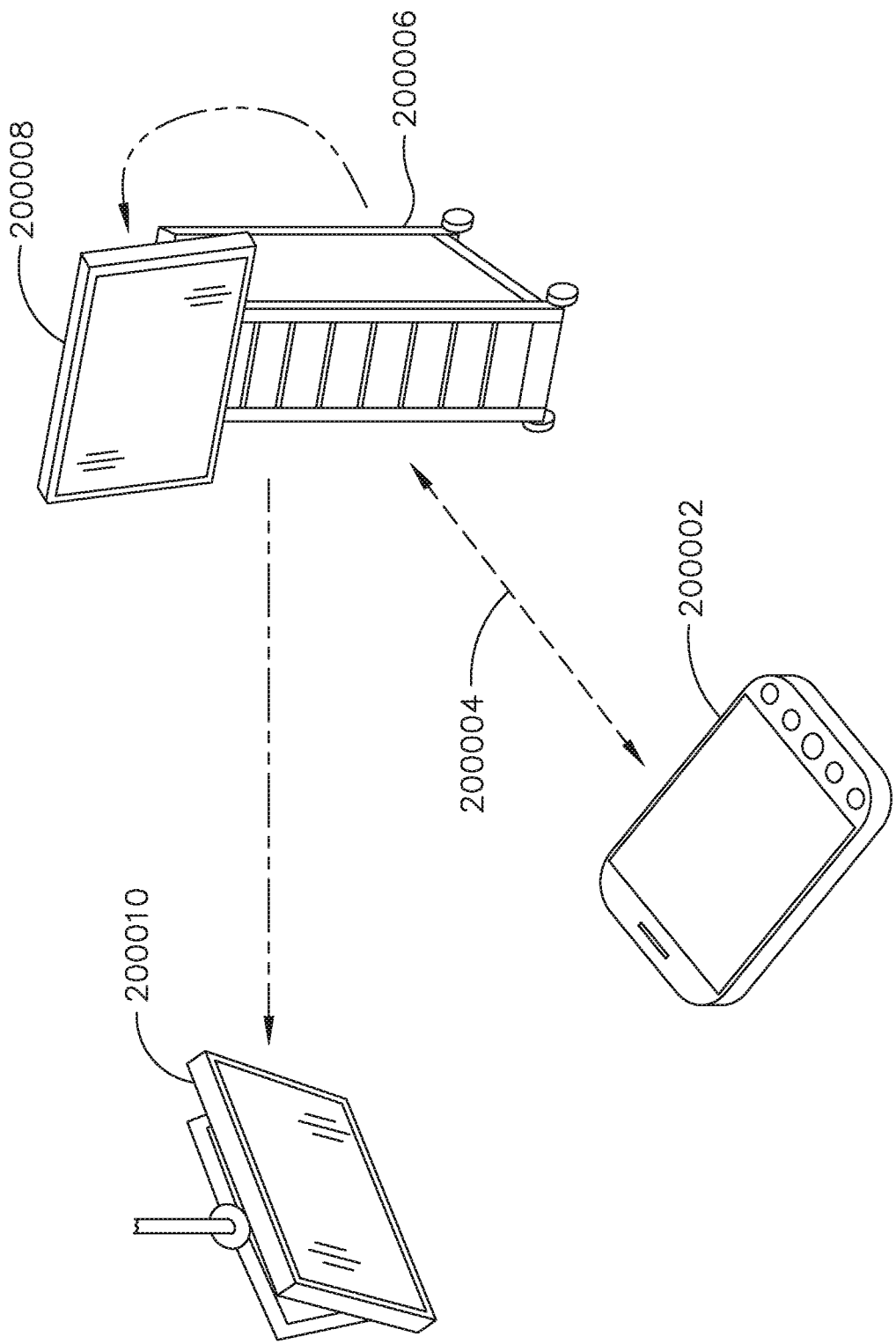

FIG. 62 is a diagram of a pairing of a personally owned wireless device with a surgical hub, in accordance with at least one aspect of the present disclosure.

FIG. 63 is a diagram of a cartridge configured to wirelessly communicate with a surgical hub, in accordance with at least one aspect of the present disclosure.

FIG. 63A depicts inductive power coupling between adjacent coils, in accordance with at least one aspect of the present disclosure.

Figure 64:
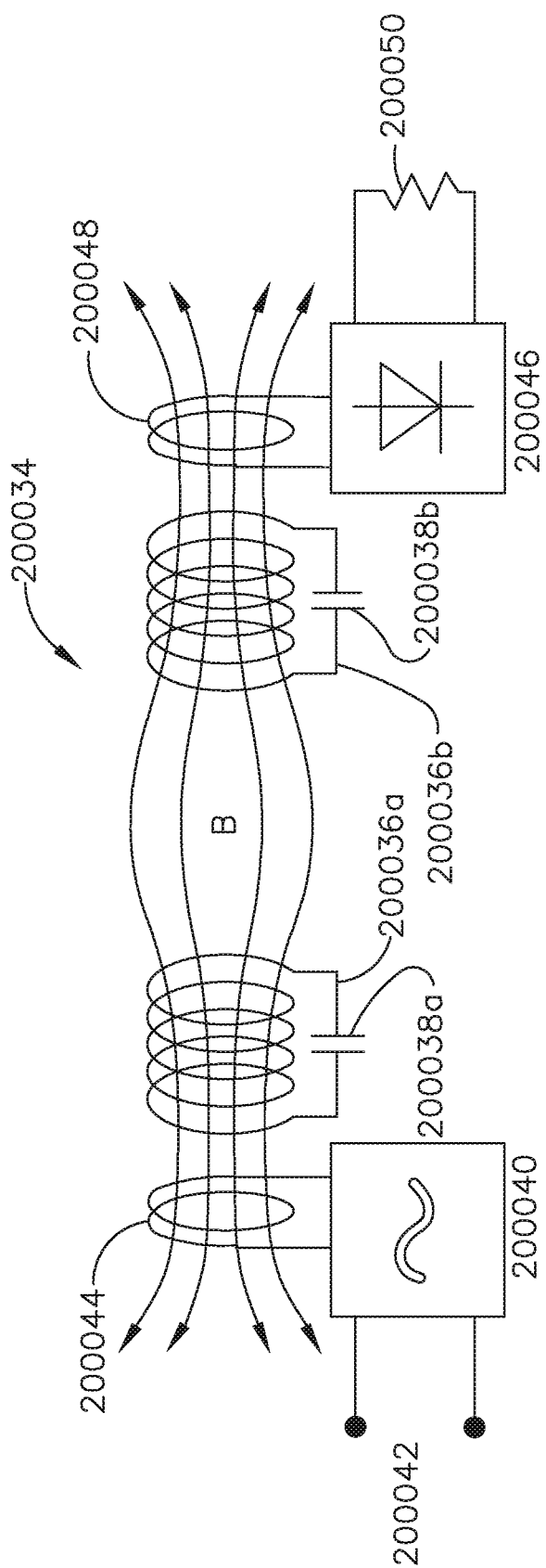

FIG. 64 is a block diagram of a resonant inductive wireless power system, in accordance with at least one aspect of the present disclosure.

Figures 65A, 65B:
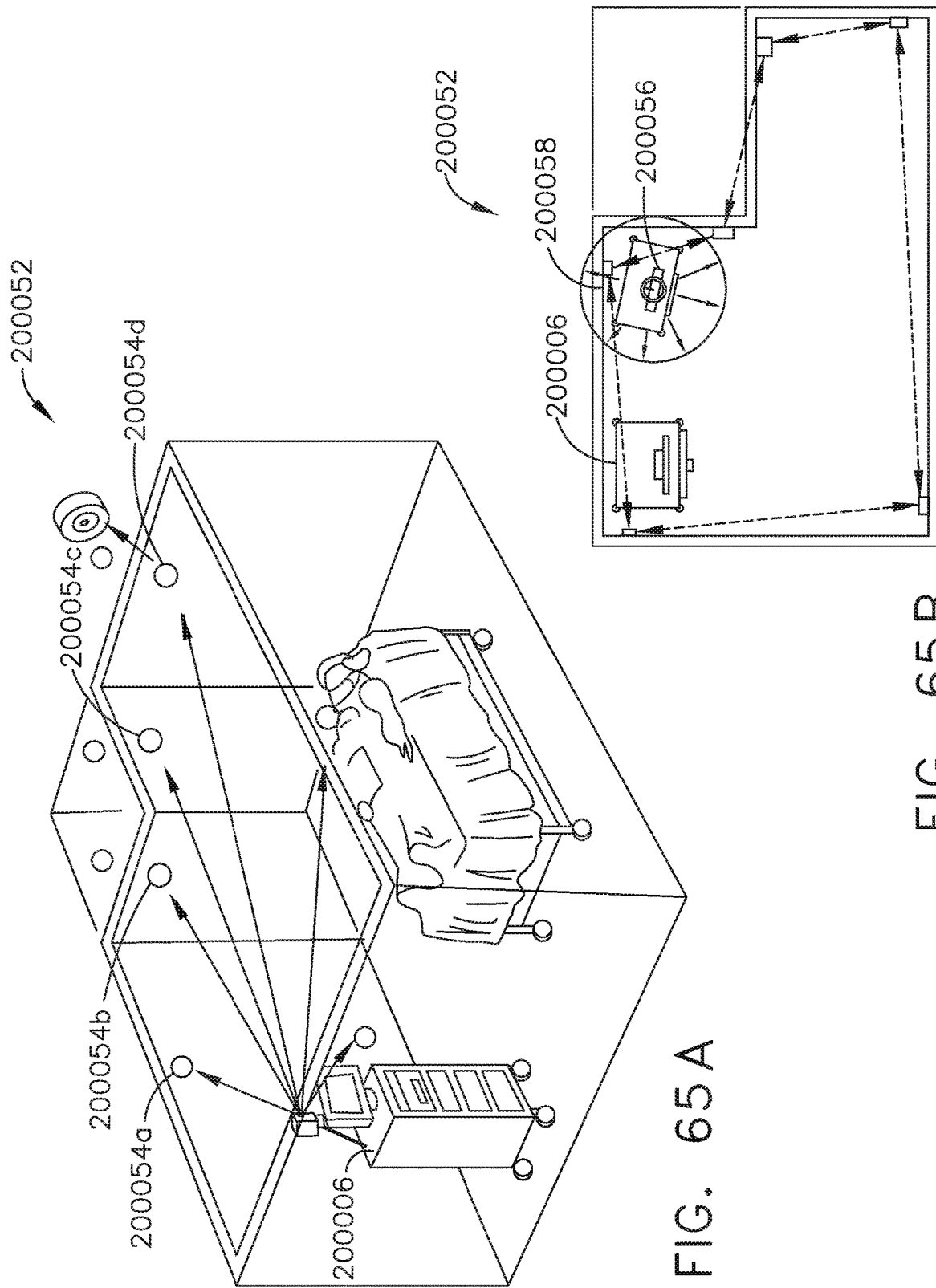

FIG. 65A is a diagram of a surgical hub detecting a room perimeter, in accordance with at least one aspect of the present disclosure.

FIG. 65B is a diagram of a room perimeter including one or more jamming beacons, in accordance with at least one aspect of the present disclosure.

Figure 66:
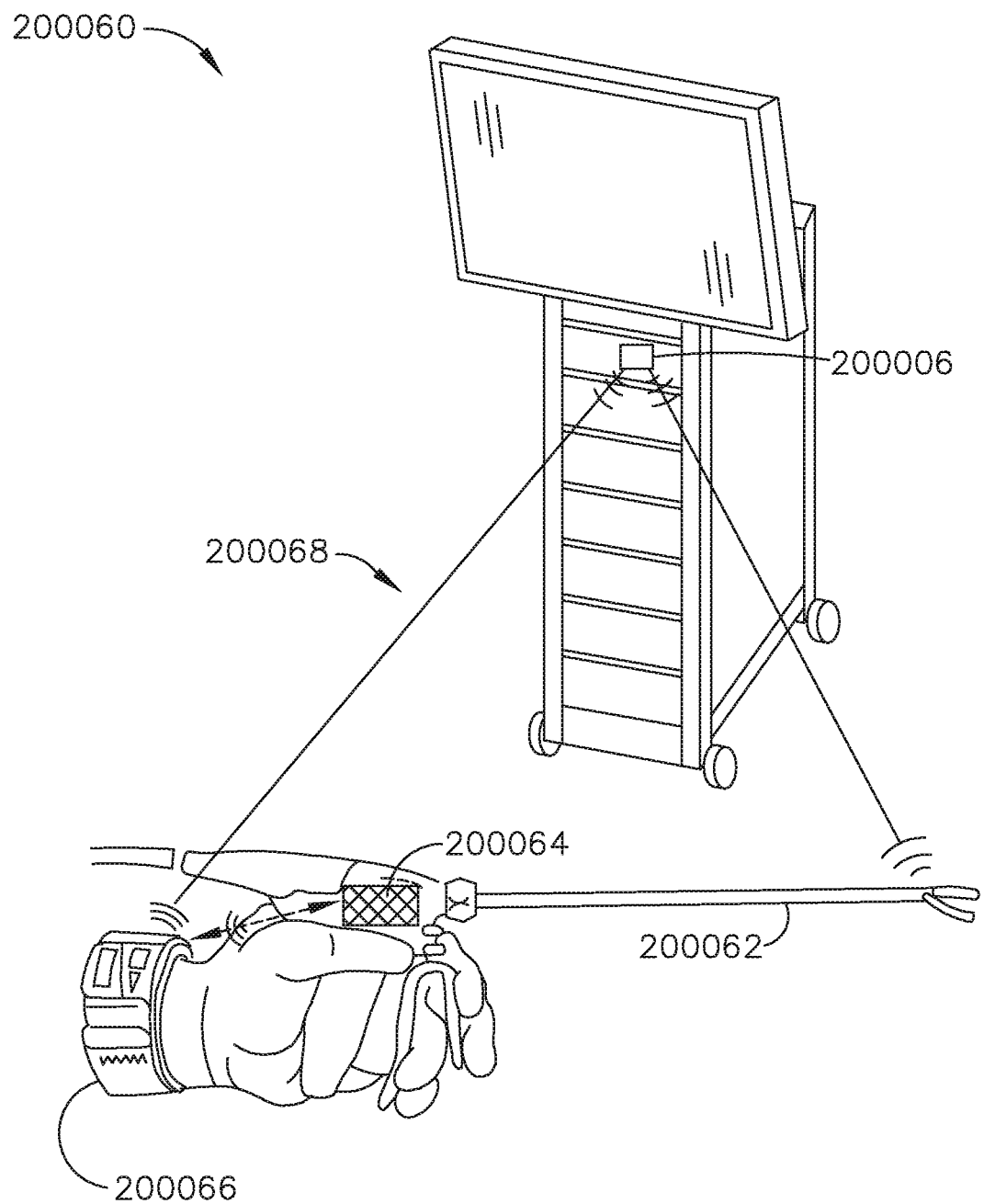

FIG. 66 is a diagram of interaction between a user-worn identifier and a surgical instrument, in accordance with at least one aspect of the present disclosure.

Figure 67:
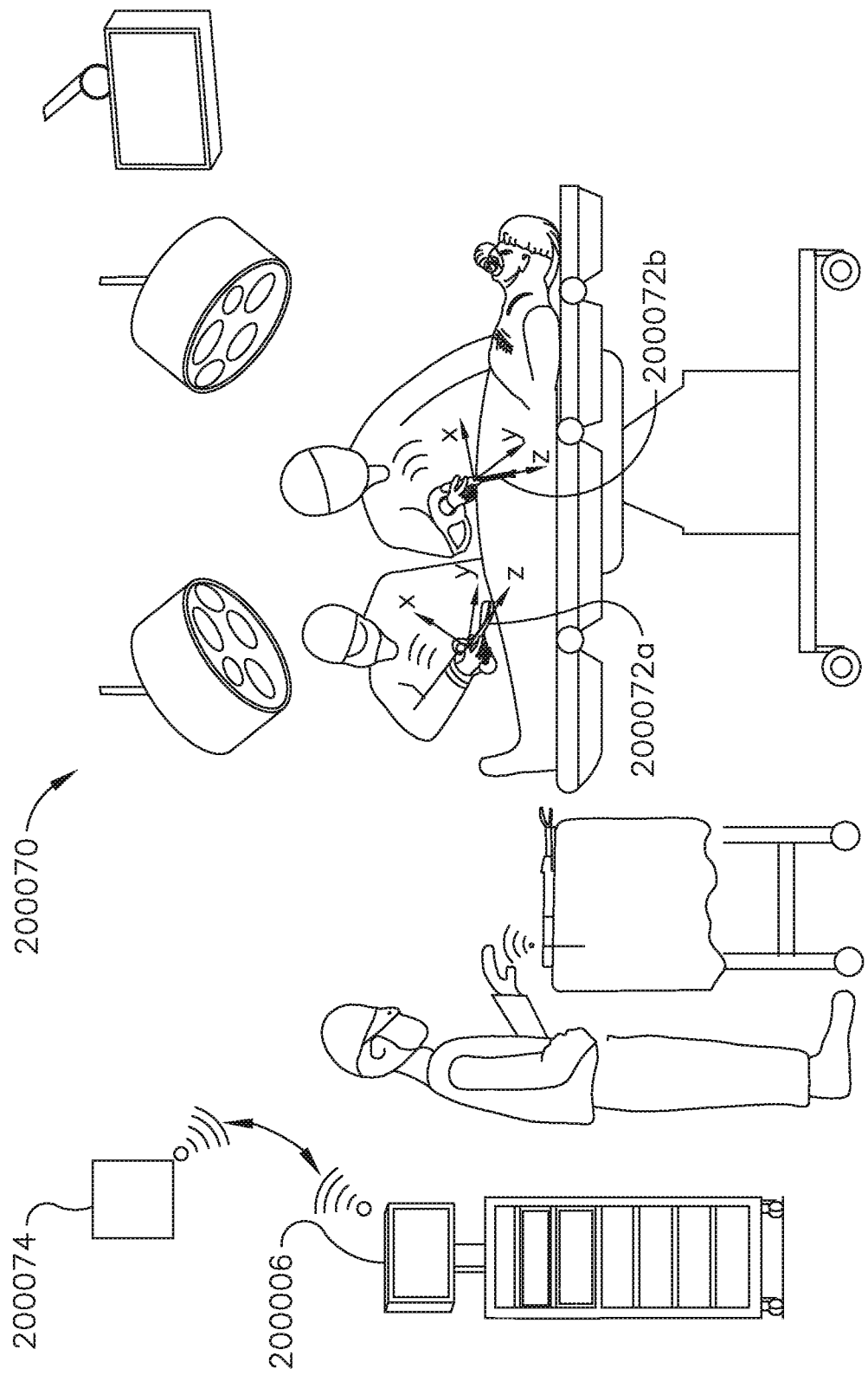

FIG. 67 is a diagram of a surgical system including a magnetic field generator for detecting the position and orientation of surgical devices relative thereto, in accordance with at least one aspect of the present disclosure.

Figure 68:
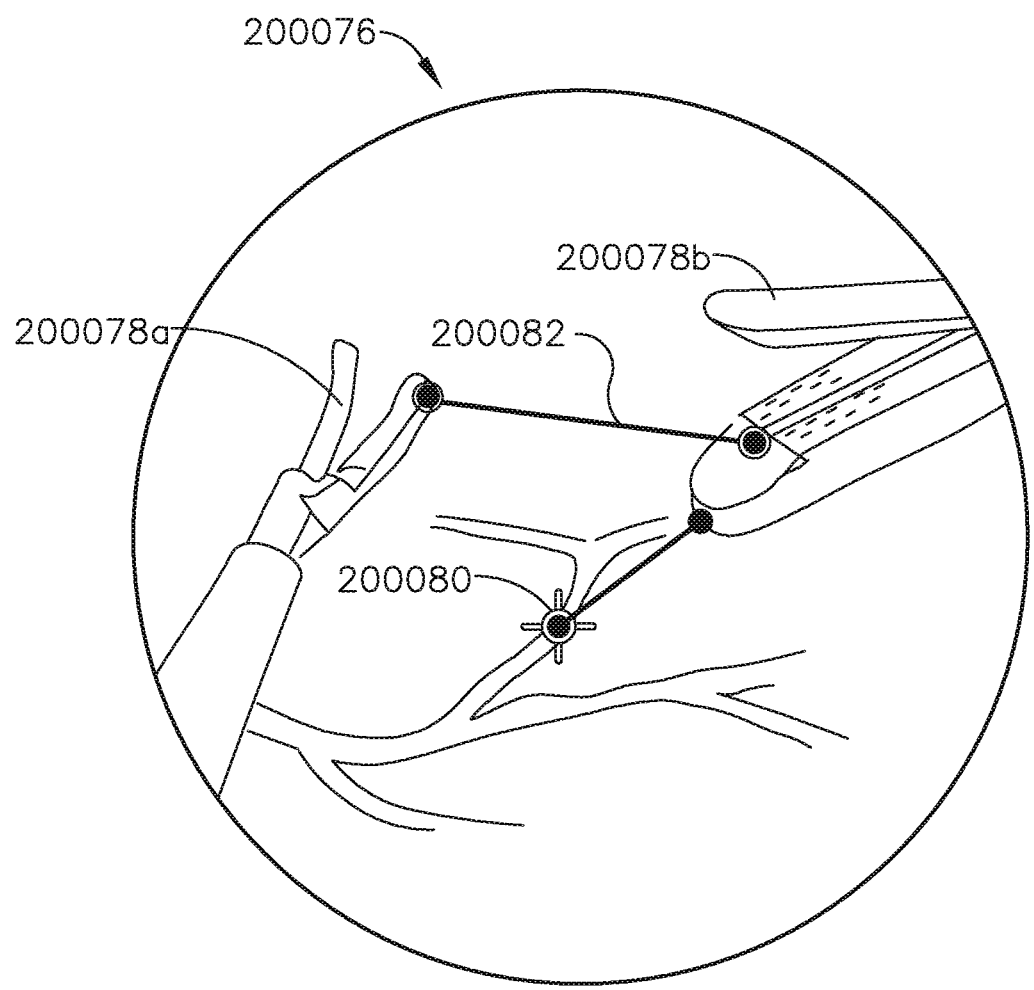

FIG. 68 is a diagram depicting a system for utilizing lidar to determine the positions of devices relative to a user-selected measurement site, in accordance with at least one aspect of the present disclosure.

Figure 69:
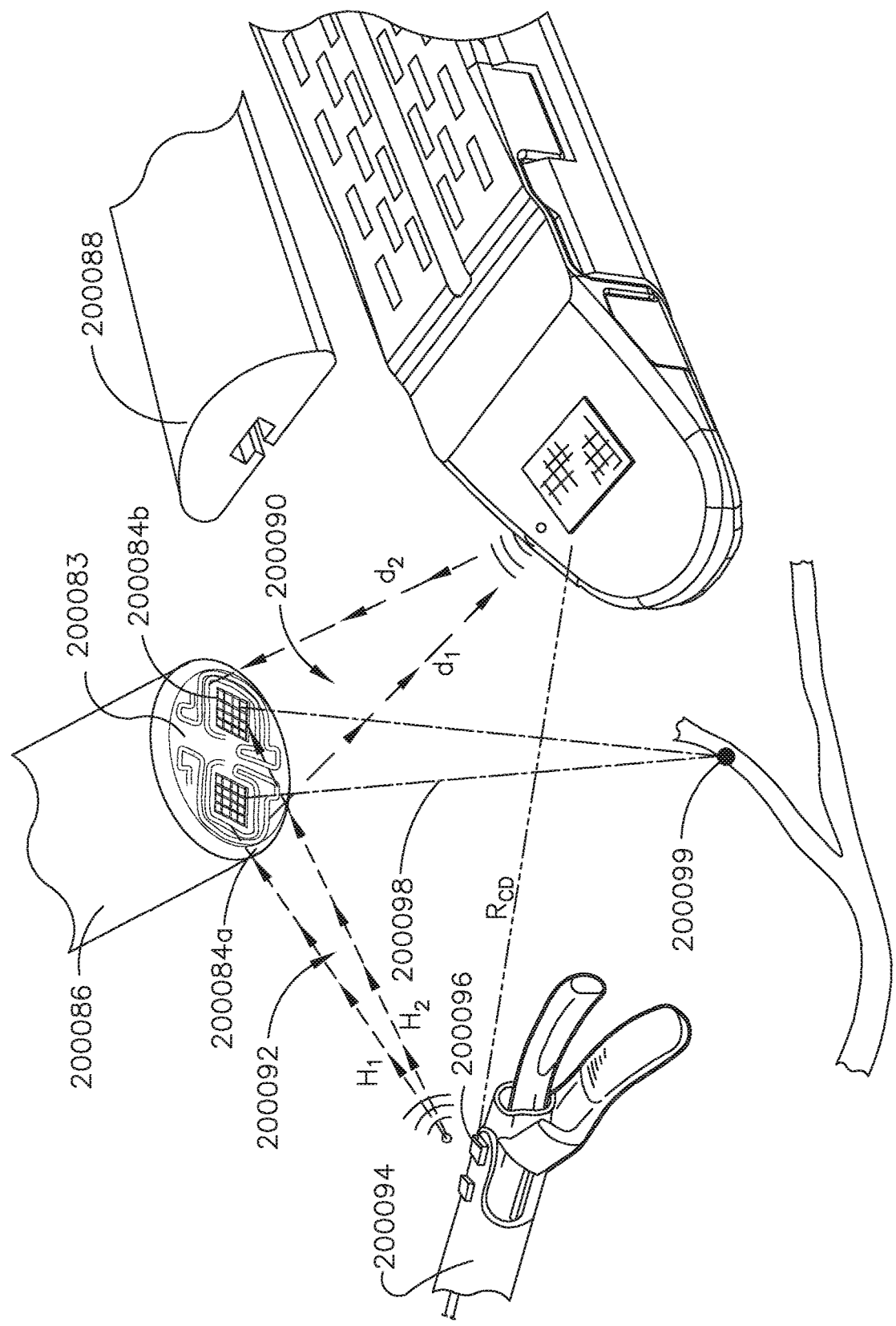

FIG. 69 is a diagram of a system for determining the relative position of devices via a dual-antenna receiver, in accordance with at least one aspect of the present disclosure.

Figure 70:
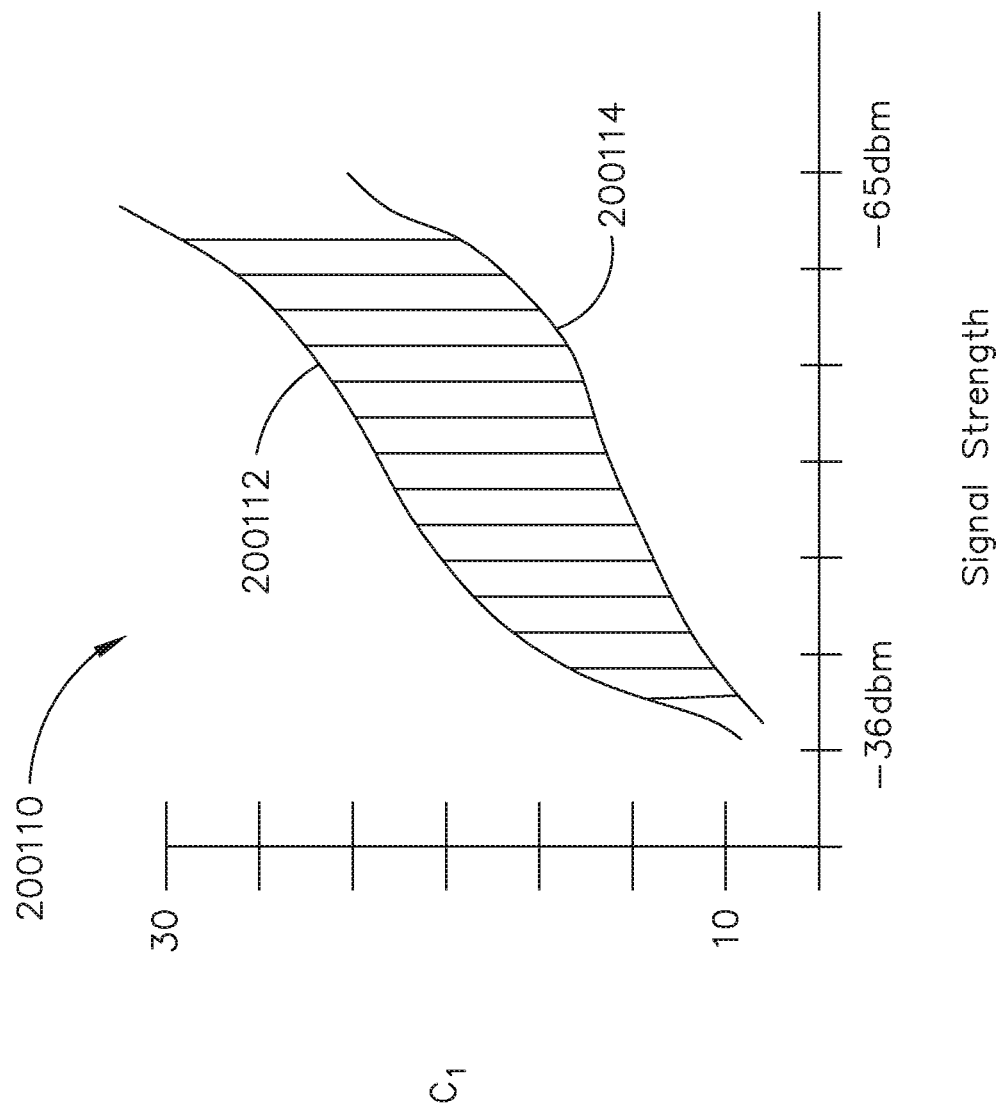

FIG. 70 is a graph depicting viable detected signal strength, in accordance with at least one aspect of the present disclosure.

Figure 71:
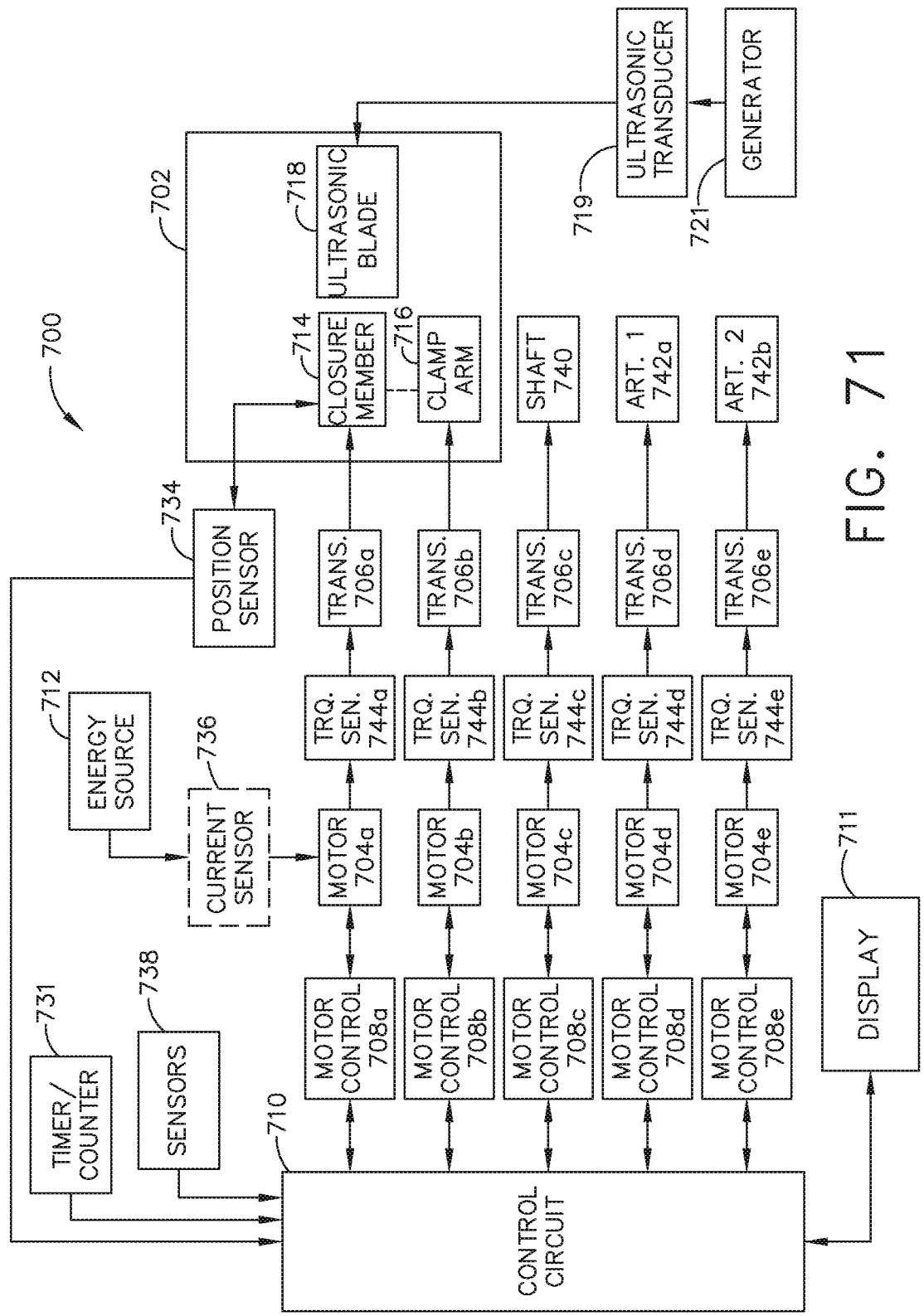

FIG. 71 is a schematic diagram of a robotic surgical instrument configured to operate a surgical tool described herein, in accordance with at least one aspect of the present disclosure.

Figure 72:
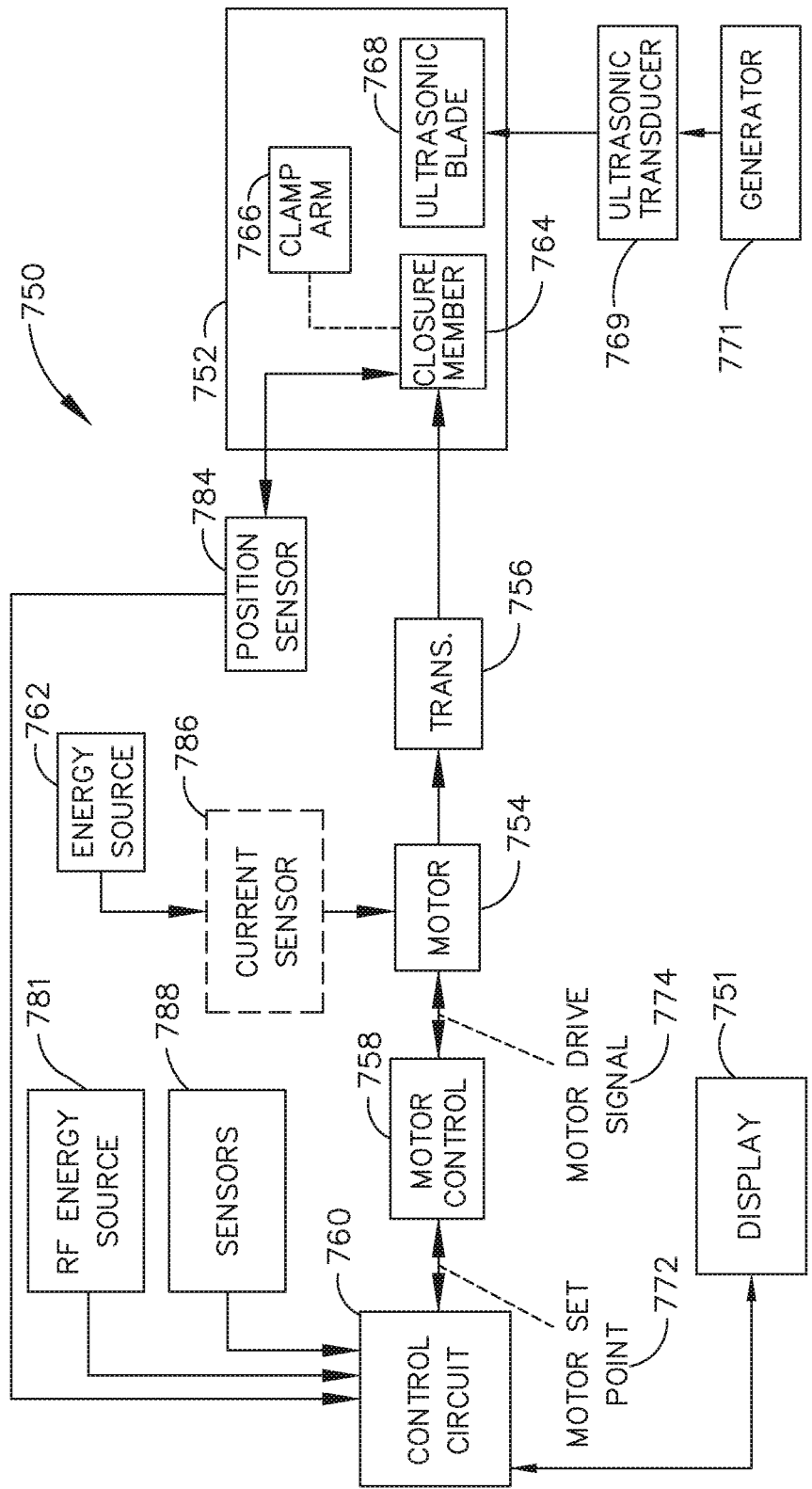

FIG. 72 illustrates a block diagram of a surgical instrument programmed to control the distal translation of a displacement member, in accordance with at least one aspect of the present disclosure.

Figure 73:
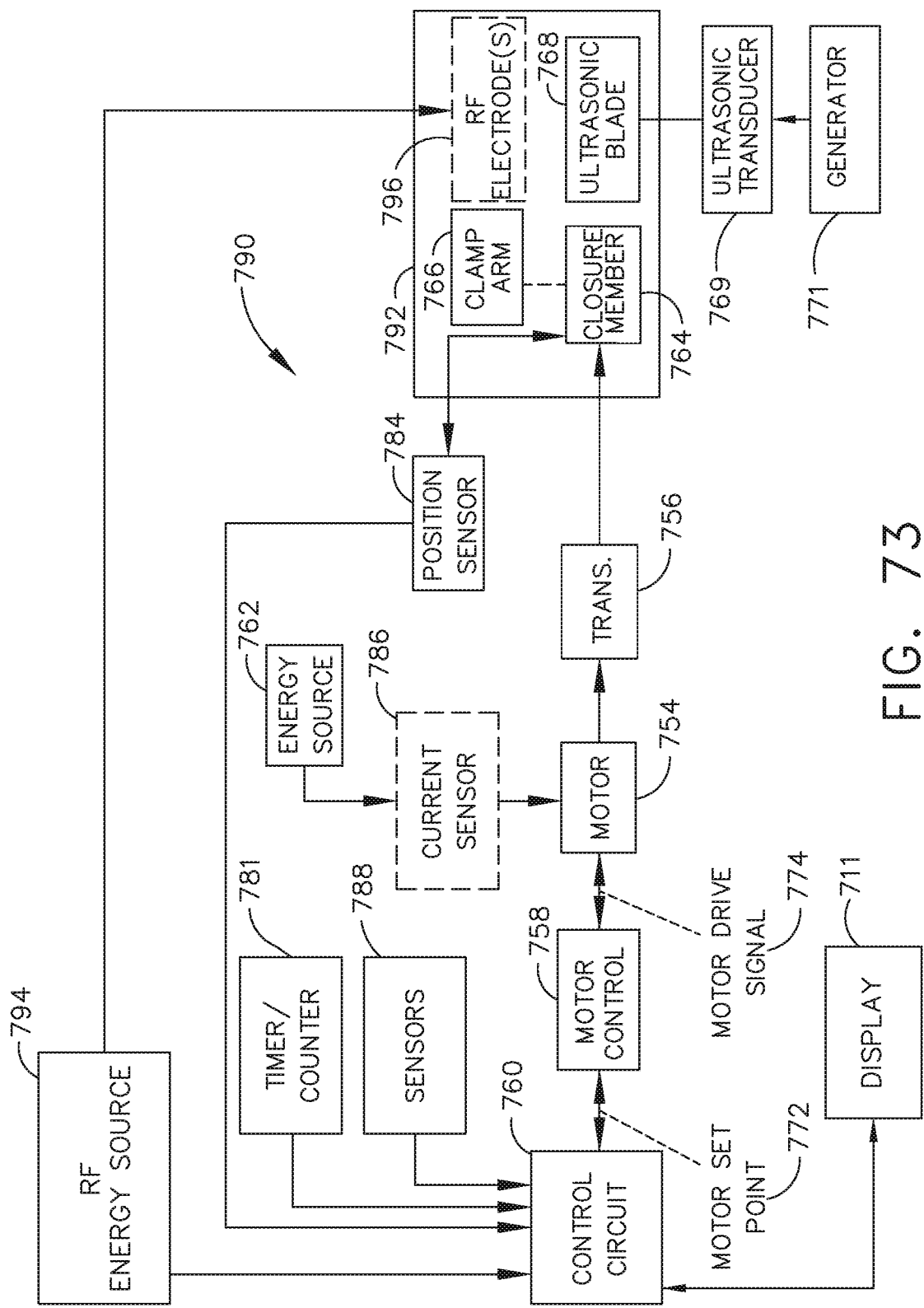

FIG. 73 is a schematic diagram of a surgical instrument configured to control various functions, in accordance with at least one aspect of the present disclosure.

Figure 74:
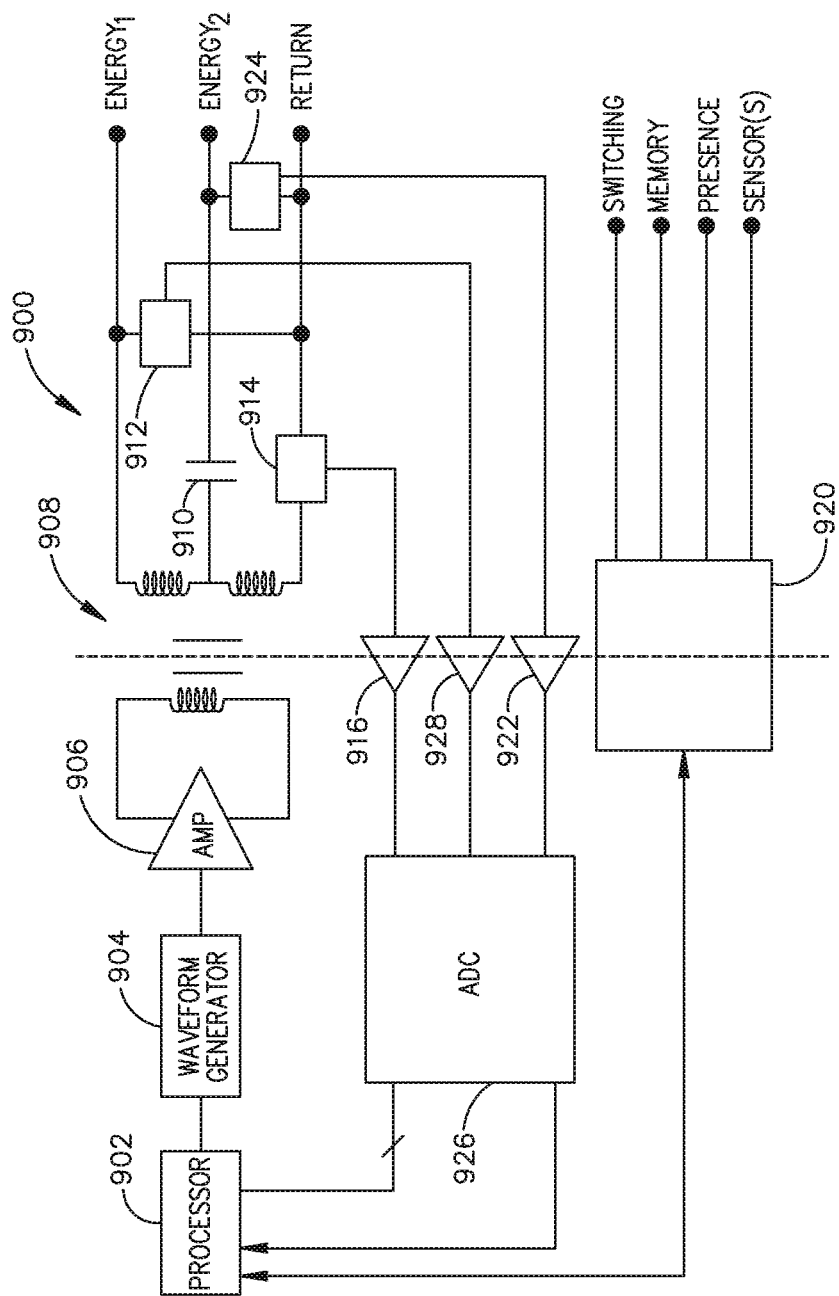

FIG. 74 illustrates an example of a generator, in accordance with at least one aspect of the present disclosure.

Figure 75:
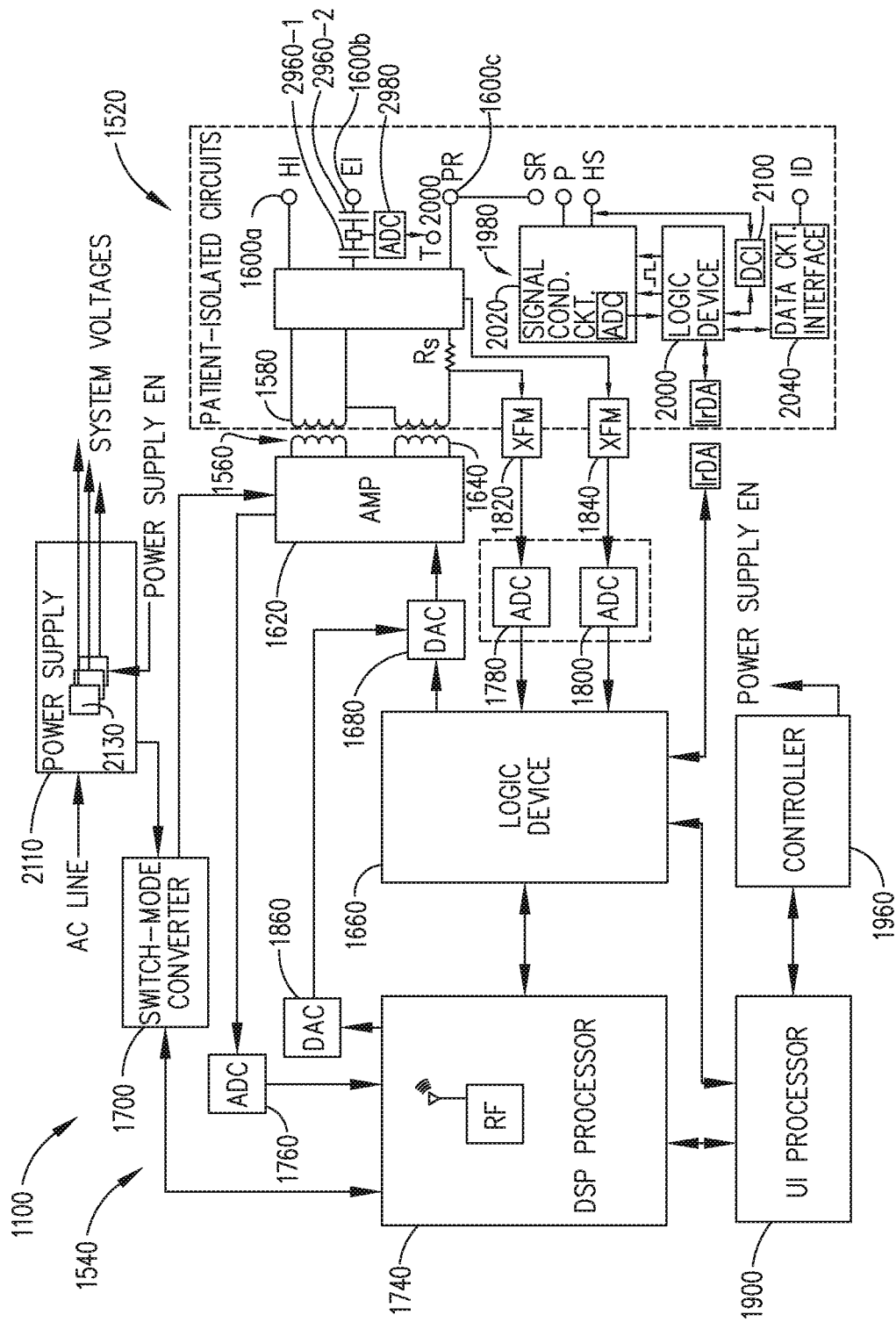

FIG. 75 is a structural view of a generator architecture, in accordance with at least one aspect of the present disclosure.

Figure 76:
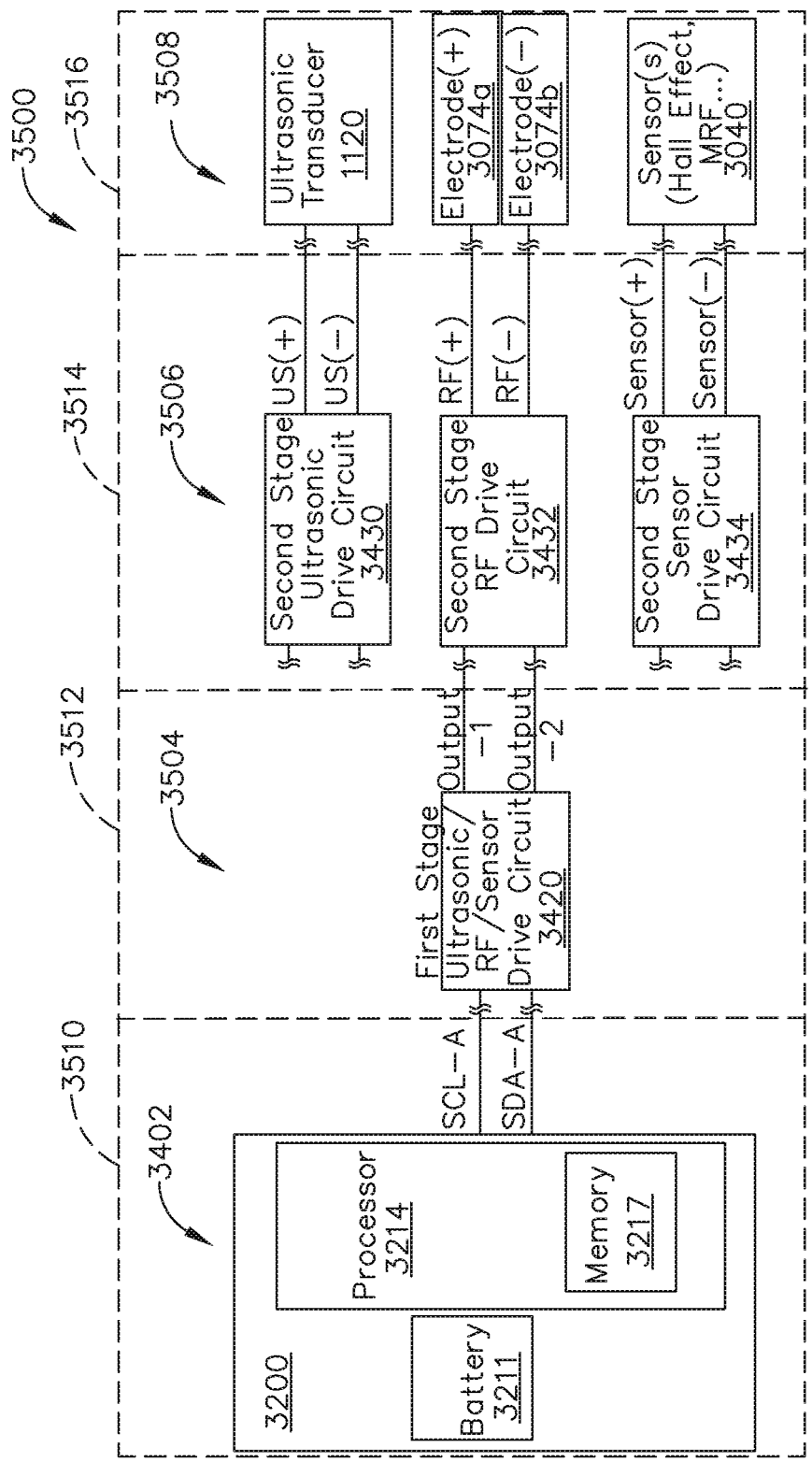

FIG. 76 illustrates a generator circuit partitioned into multiple stages where a first stage circuit is common to the second stage circuit, in accordance with at least one aspect of the present disclosure.

Figure 77:
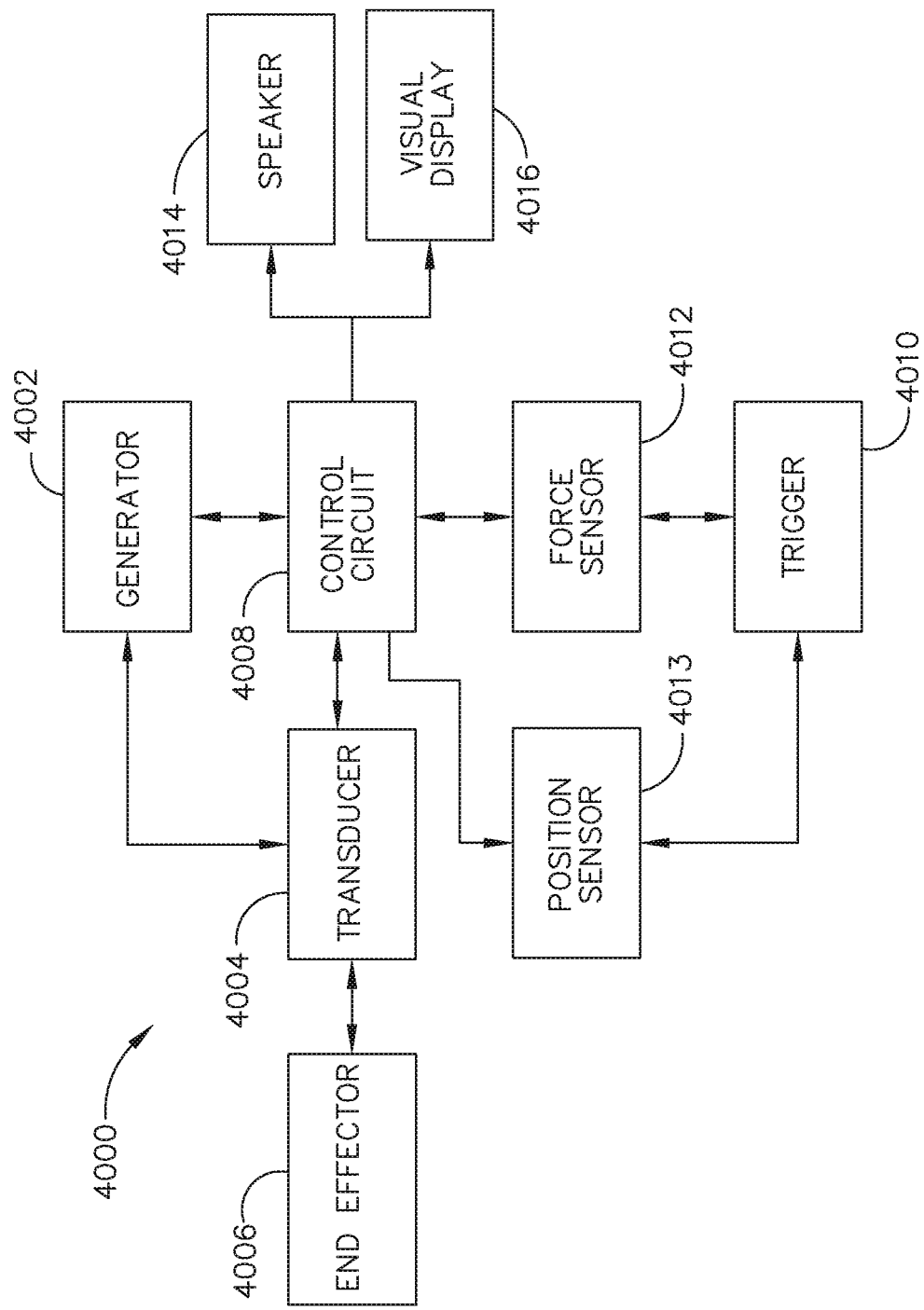

FIG. 77 illustrates a diagram of one aspect of a surgical instrument comprising a feedback system for use with a surgical instrument, according to one aspect of the present disclosure.

Figure 78A:
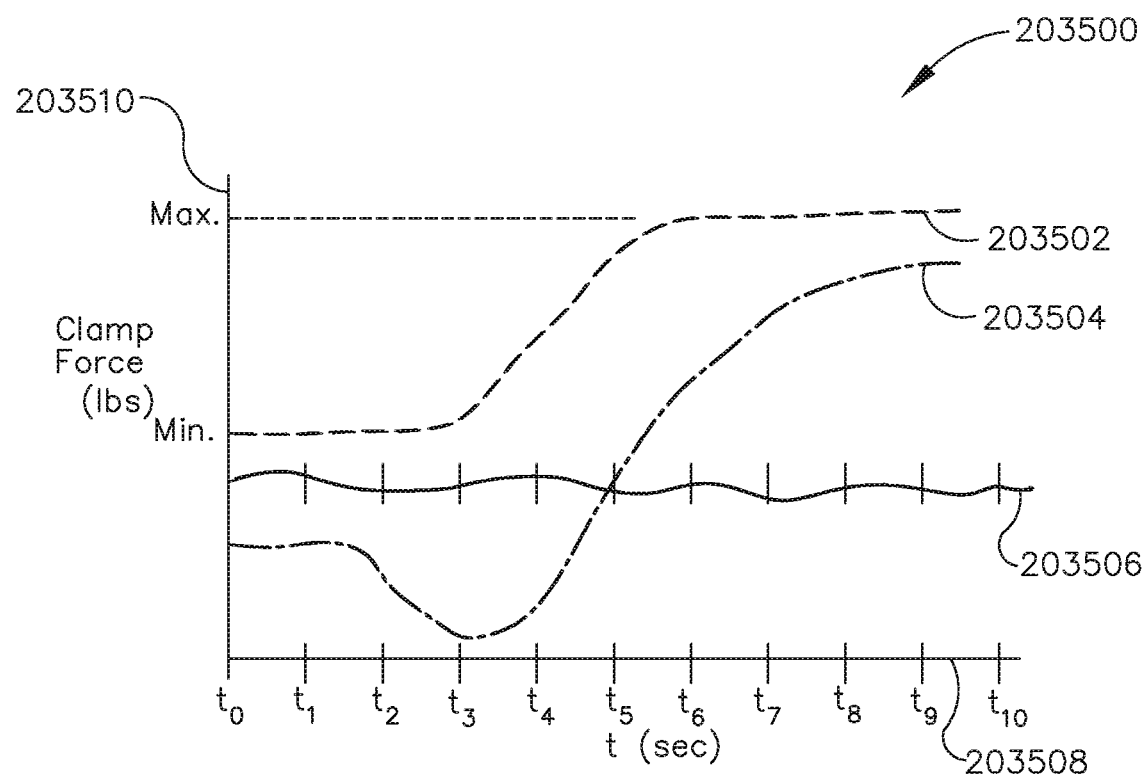
Figure 78B:
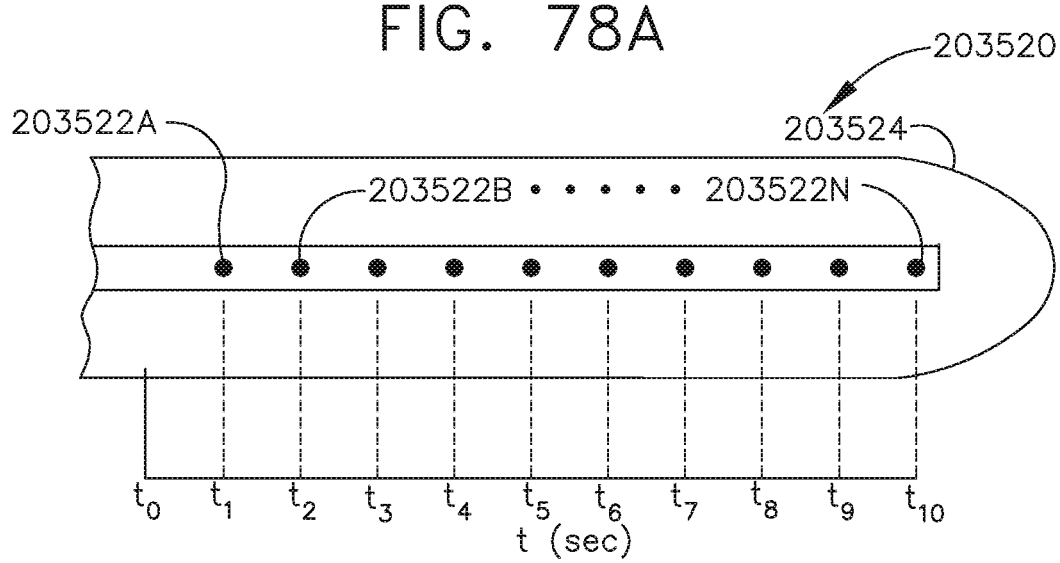

FIGS. 78A-78B are graphs including a graph of clamp force as a function of time and an associated graph indicating the shift in the location of coagulation and cutting along the length of the blade as a function time, in accordance with at least one aspect of the present disclosure.

Figure 79A:
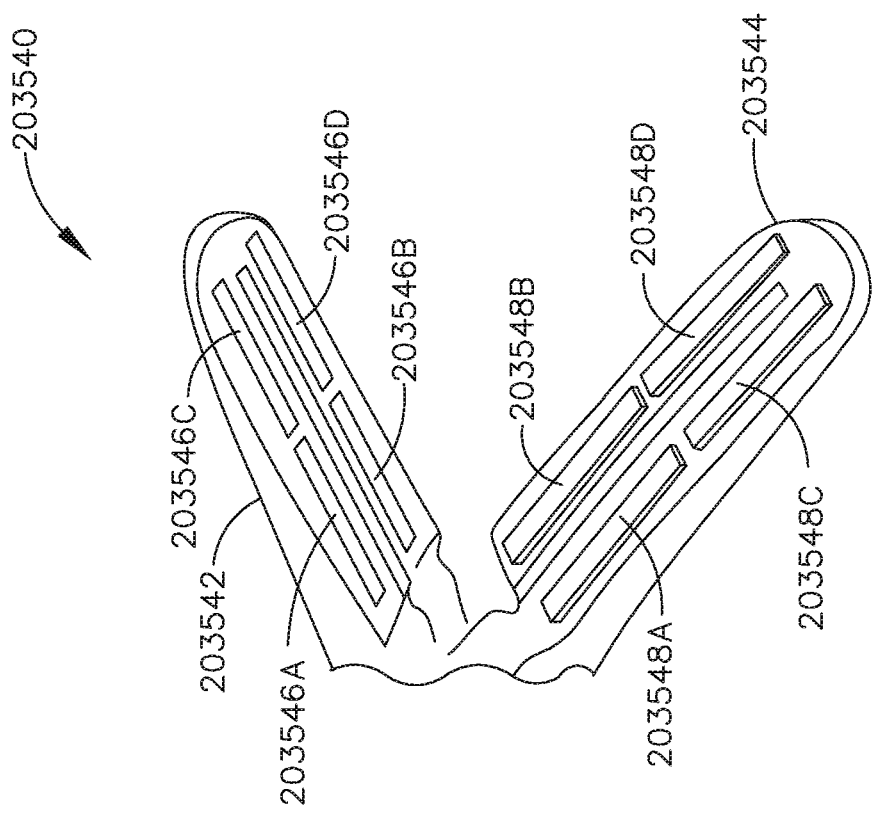
Figure 79B:
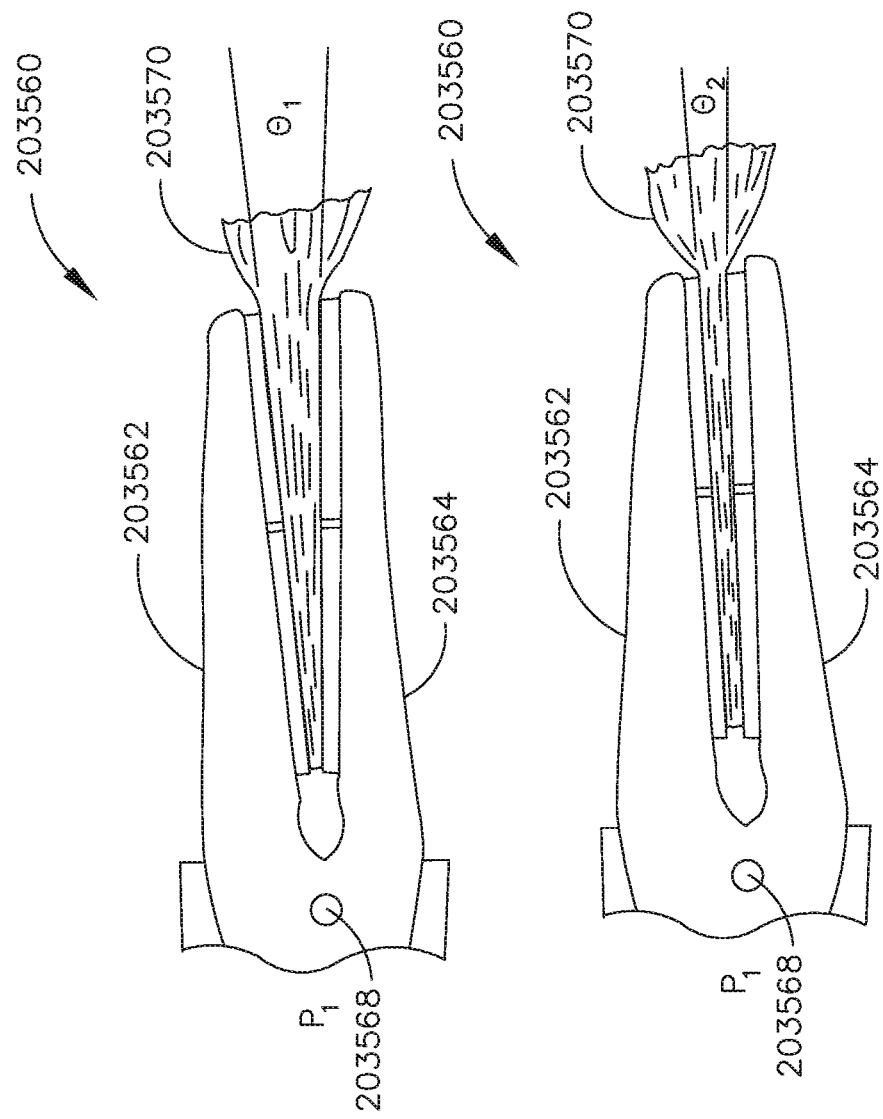

FIGS. 79A-79B depict segments of end effector electrodes and an illustration of controlling applied clamp force and delivered electrosurgical energy by the end effector, in accordance with at least one aspect of the present disclosure.

FIGS. 80A-80B are graphs illustrating controlling the energization or powering of the electrosurgical electrodes, in accordance with at least one aspect of the present disclosure.

FIGS. 81A-81E are a series of graphs illustrating the adjustment of power level to achieve a predictable sealing time, in accordance with at least one aspect of the present disclosure.

FIGS. 82A-82F are graphs and flow charts illustrating approaches to delivering energy according to power curves, in accordance with at least one aspect of the present disclosure.

Figure 83A:
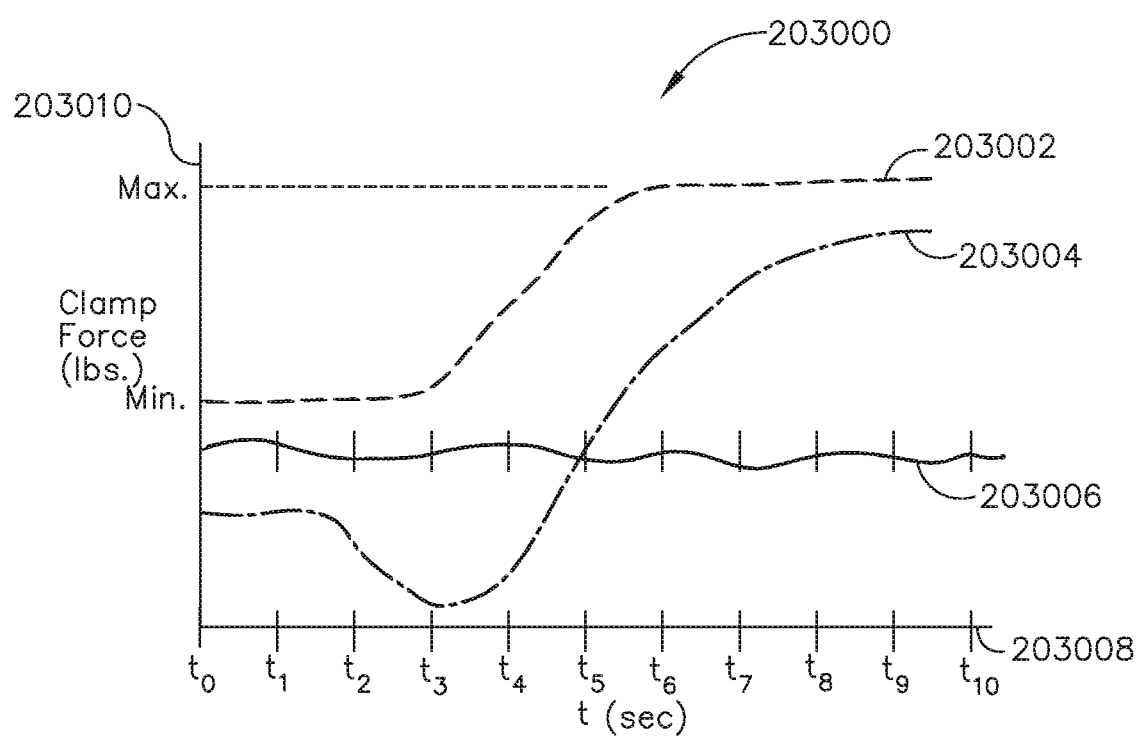
Figure 83B:
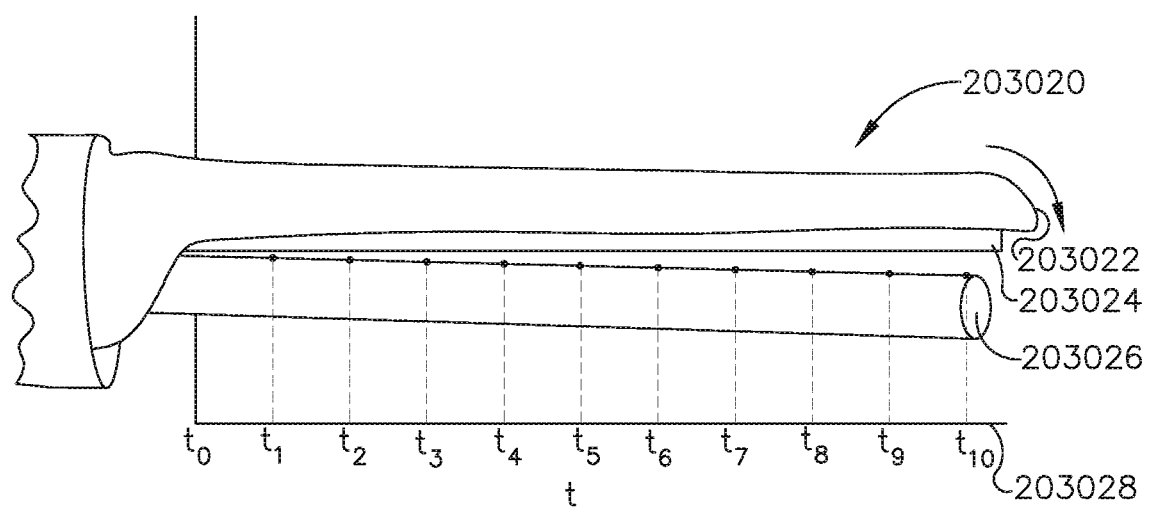

FIG. 83A-83B are graphs including a graph of clamp force as a function of time and an associated graph of a coagulation/cut focal point, in accordance with at least one aspect of the present disclosure.

Figure 84B:
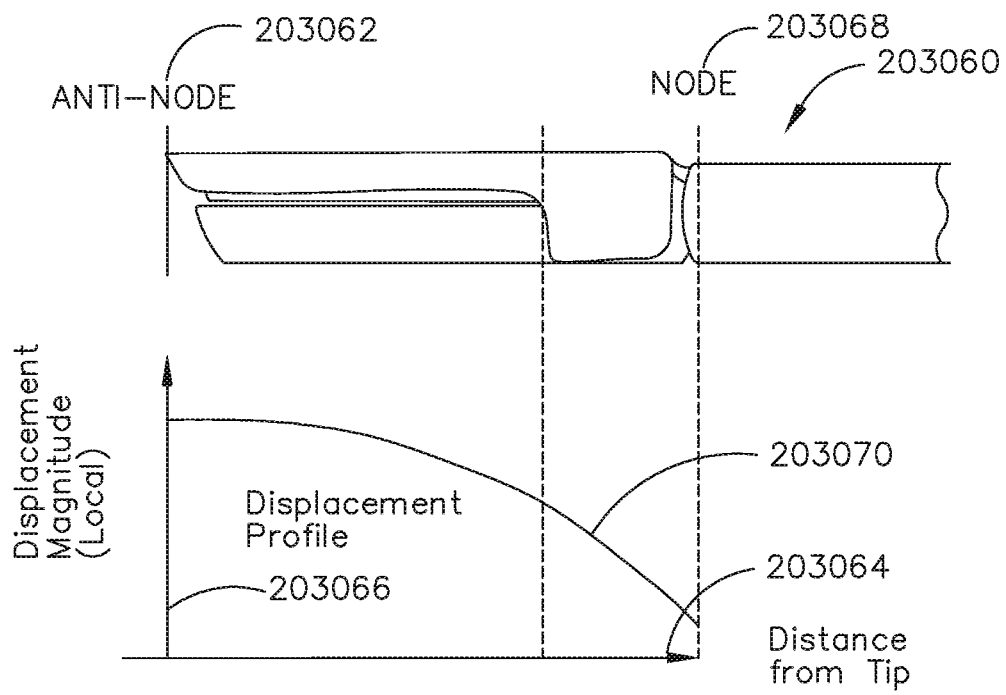
Figure 84A:
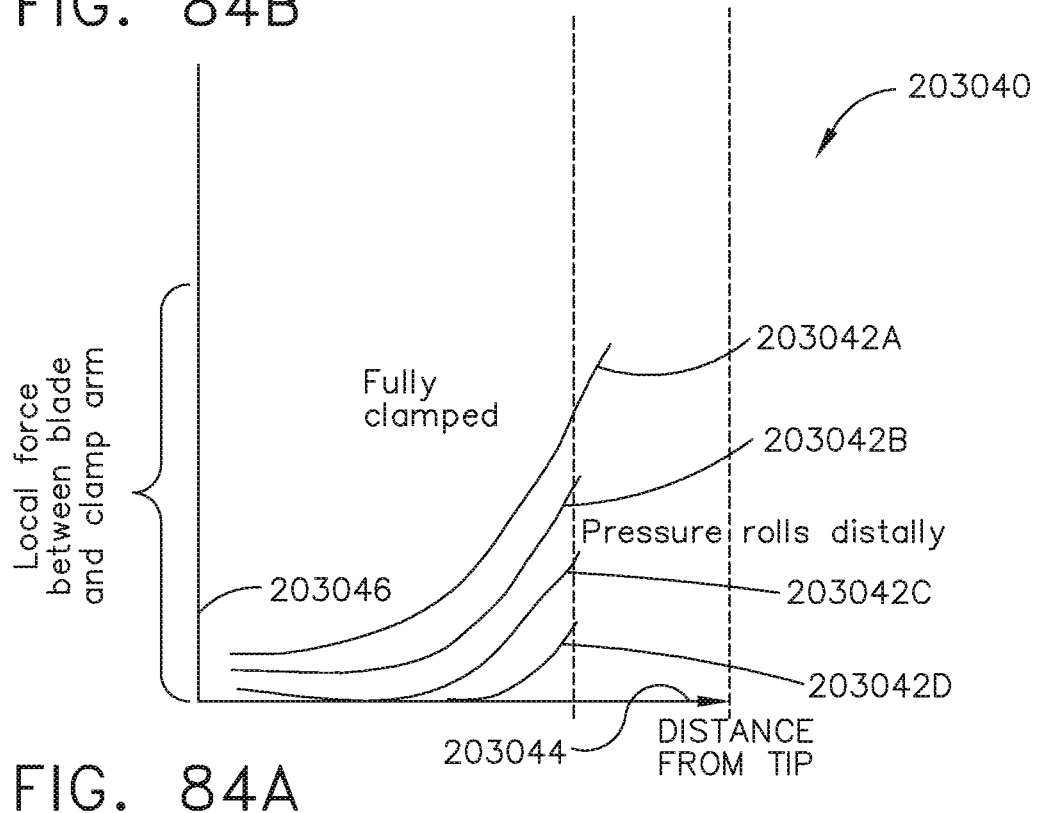

FIGS. 84A-84B are graphs including a graph of clamp force as a function of distance from the distal tip of the end effector and a graph of blade displacement as a function of distance from the distal tip, in accordance with at least one aspect of the present disclosure.

Figure 85:
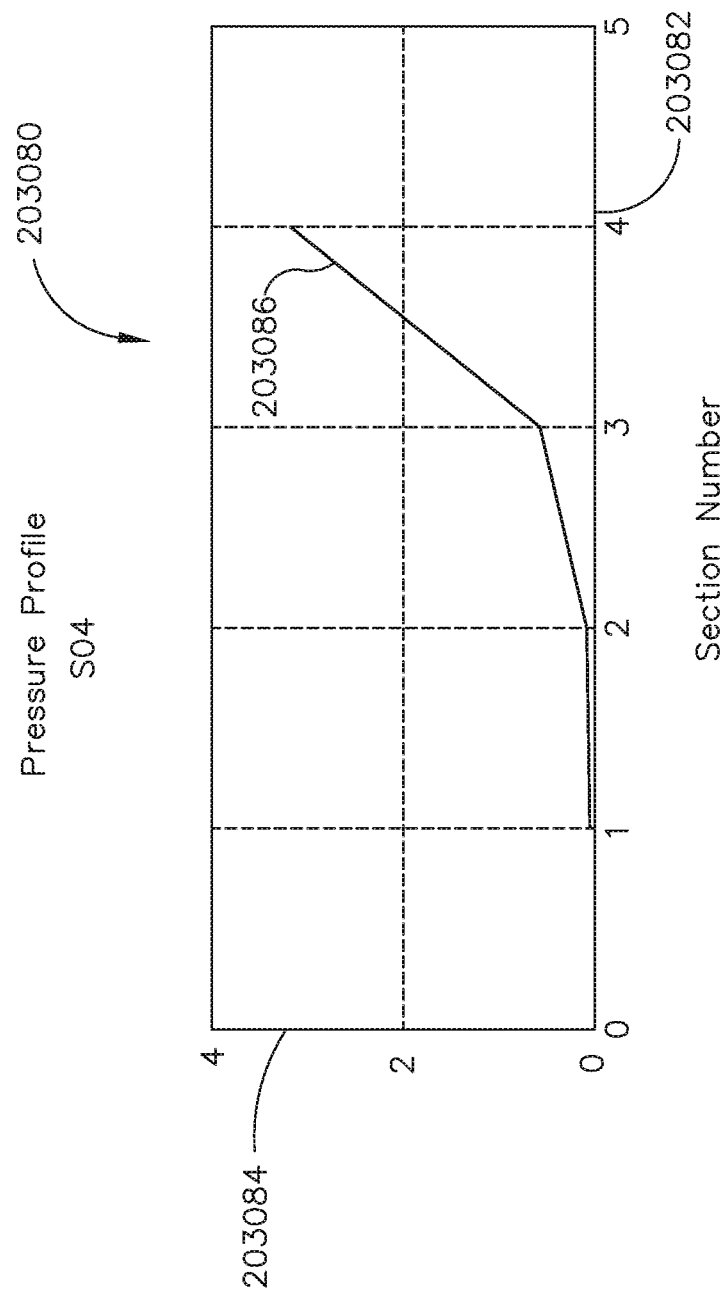

FIG. 85 is a graph of a clamp force distribution as a function of various sections along the length of the end effector, in accordance with at least one aspect of the present disclosure.

Figure 86:
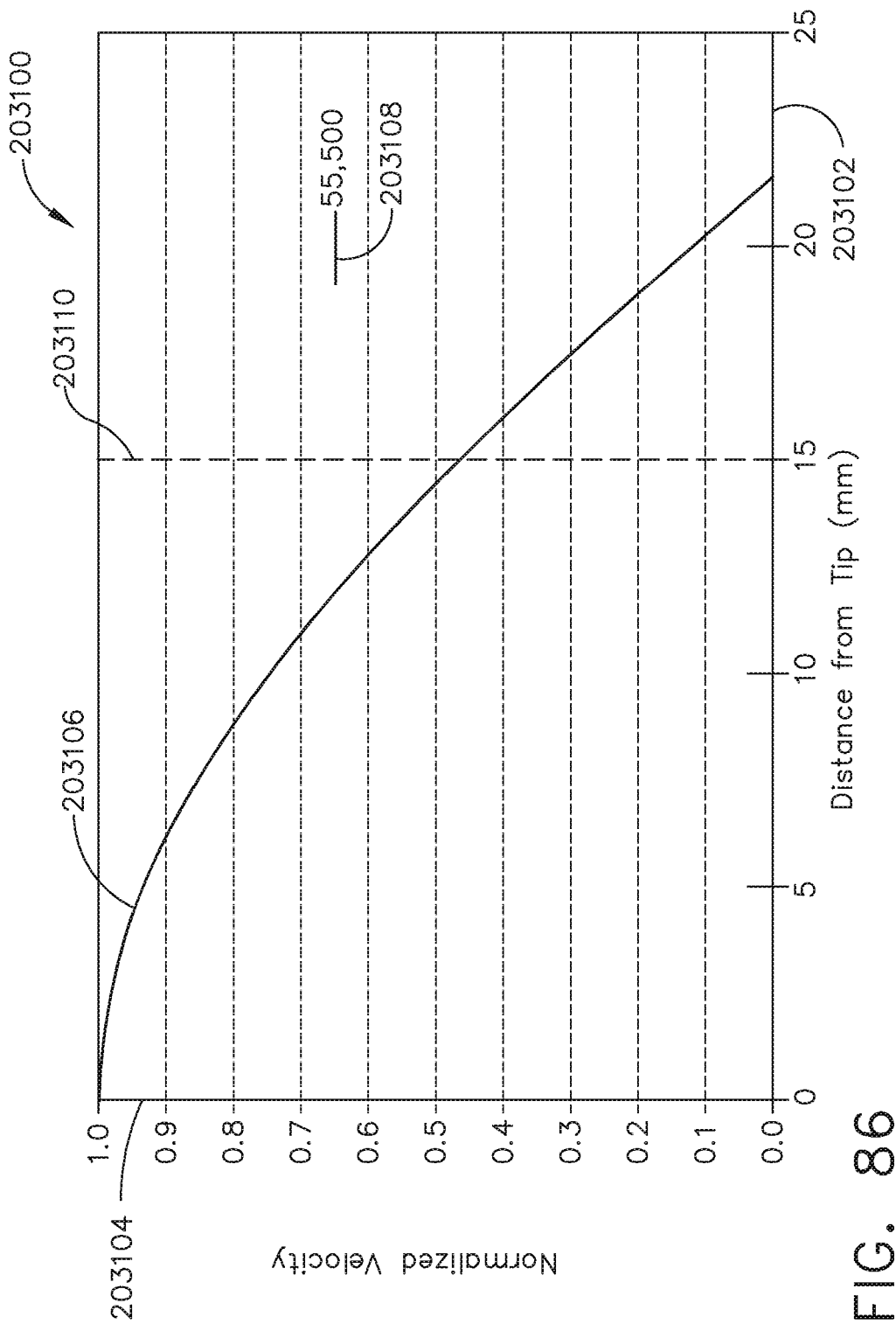

FIG. 86 is a graph of blade displacement profile as a function of distance from the distal tip of the end effector, in accordance with at least one aspect of the present disclosure.

Figure 87A:
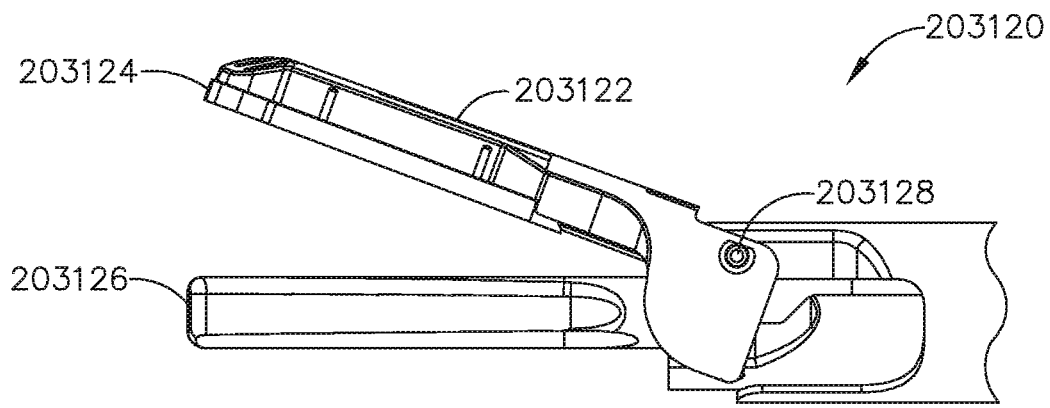
Figure 87B:
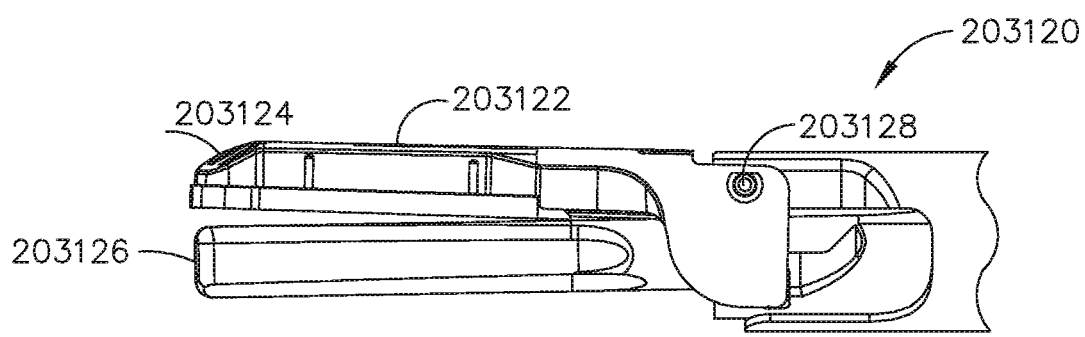
Figure 87C:
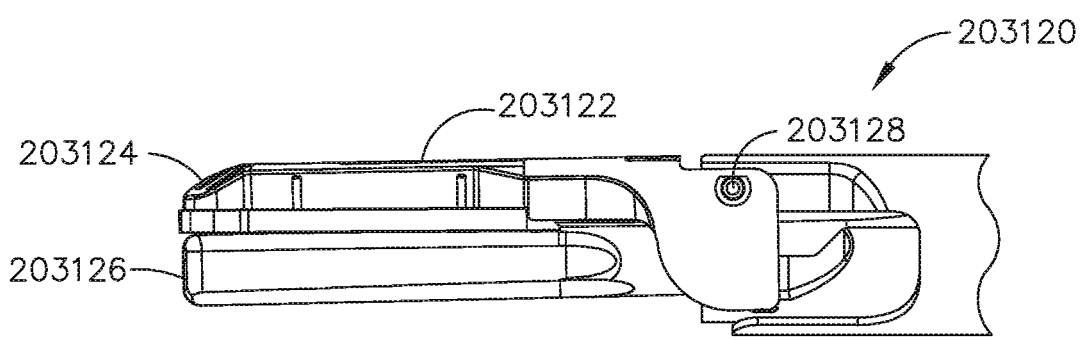

FIGS. 87A-87C are sectional views of end effector that illustrate a closure stroke of the end effector, in accordance with at least one aspect of the present disclosure.

FIGS. 88A-88C are graphs of clamp force applied between the blade and clamp arm as a function of distance from the distal tip of the end effector corresponding to the sectional views of FIGS. 87A-87C, in accordance with at least one aspect of the present disclosure.

Figure 89A:
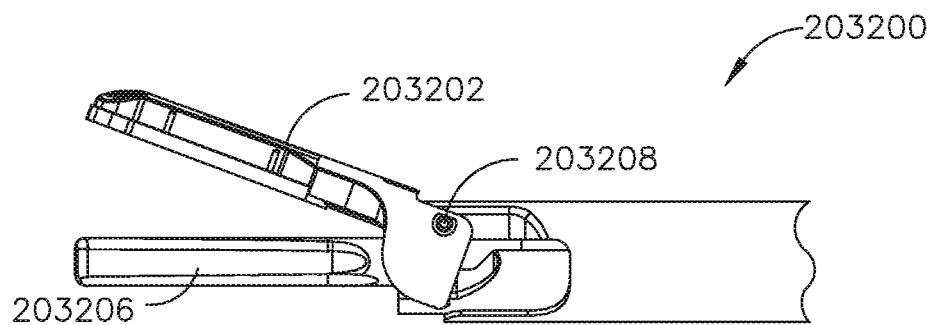
Figure 89B:
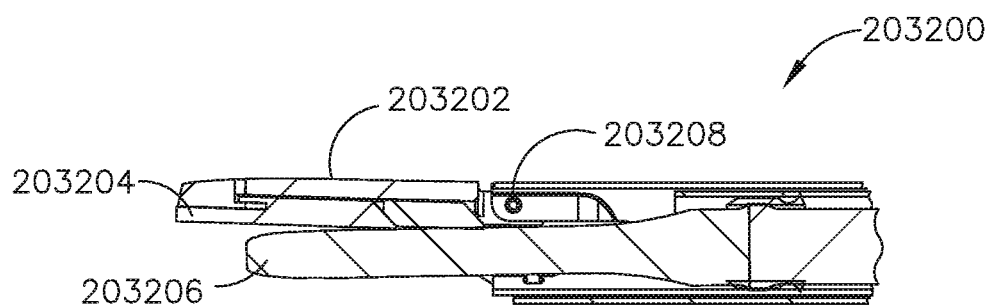
Figure 89C:
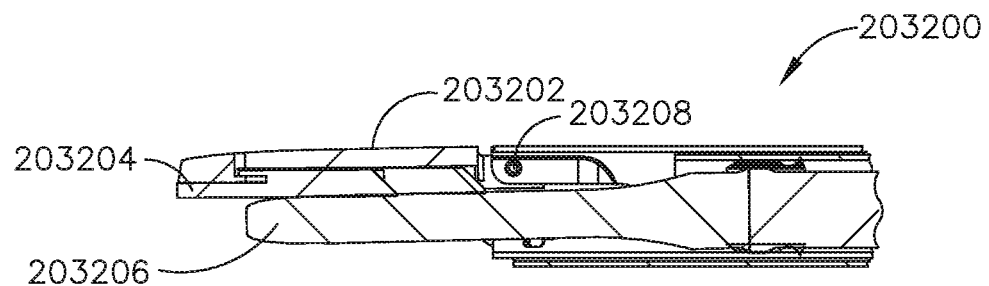

FIGS. 89A-89C are sectional views of the end effector that illustrate a proximal start closure stroke configuration, in accordance with at least one aspect of the present disclosure.

FIGS. 90A-90D are sectional views of the end effector that illustrate a distal start closure stroke configuration and indicate associated part stresses, in accordance with at least one aspect of the present disclosure.

FIGS. 91A-91D are graphs of clamp force applied between the ultrasonic blade and clamp arm as a function of distance from the distal tip of the end effector corresponding to the sectional views of FIGS. 90A-90D, in accordance with at least one aspect of the present disclosure.

FIGS. 92A-92E are sectional views of the end effector that illustrate a distal start closure stroke configuration and indicate associated part stresses, in accordance with at least one aspect of the present disclosure.

DESCRIPTION

Applicant of the present application owns the following U.S. patent applications, filed on Dec. 4, 2018, the disclosure of each of which is herein incorporated by reference in its entirety:

U.S. patent application Ser. No. 16/209,385, titled METHOD OF HUB COMMUNICATION, PROCESSING, STORAGE AND DISPLAY, now U.S. Patent Application Publication No. 2019/0200844;

U.S. patent application Ser. No. 16/209,395, titled METHOD OF HUB COMMUNICATION, now U.S. Patent Application Publication No. 2019/0201136;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,407, titled METHOD OF ROBOTIC HUB COMMUNICATION, DETECTION, AND CONTROL;

Attorney Docket No. END8505USNP/170772M, titled METHOD OF HUB COMMUNICATION, PROCESSING, DISPLAY, AND CLOUD ANALYTICS, now U.S. Patent Application Publication No. 2019/0201137;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;

U.S. patent application Ser. No. 16/209,447, titled METHOD FOR SMOKE EVACUATION FOR SURGICAL HUB, now U.S. Patent Application Publication No. 2019/0201045;

U.S. patent application Ser. No. 16/209,453, titled METHOD FOR CONTROLLING SMART ENERGY DEVICES, now U.S. Patent Application Publication No. 2019/0201046;

U.S. patent application Ser. No. 16/209,458, titled METHOD FOR SMART ENERGY DEVICE INFRASTRUCTURE, now U.S. Patent Application Publication No. 2019/0201047;

U.S. patent application Ser. No. 16/209,465, titled METHOD FOR ADAPTIVE CONTROL SCHEMES FOR SURGICAL NETWORK CONTROL AND INTERACTION, now U.S. Patent Application Publication No. 2019/0206563;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019/0104919; and U.S. patent application Ser. No. 16/209,490, titled METHOD FOR FACILITY DATA COLLECTION AND INTERPRETATION, now U.S. Patent Application Publication No. 2019/0206564.

Applicant of the present application owns the following U.S. patent applications, filed on Nov. 6, 2018, the disclosure of each of which is herein incorporated by reference in its entirety:

U.S. patent application Ser. No. 16/182,224, titled SURGICAL NETWORK, INSTRUMENT, AND CLOUD RESPONSES BASED ON VALIDATION OF RECEIVED DATASET AND AUTHENTICATION OF ITS SOURCE AND INTEGRITY;

U.S. patent application Ser. No. 16/182,230, titled SURGICAL SYSTEM FOR PRESENTING INFORMATION INTERPRETED FROM EXTERNAL DATA;

U.S. patent application Ser. No. 16/182,233, titled SURGICAL SYSTEMS WITH AUTONOMOUSLY ADJUSTABLE CONTROL PROGRAMS;

U.S. patent application Ser. No. 16/182,239, titled ADJUSTMENT OF DEVICE CONTROL PROGRAMS BASED ON STRATIFIED CONTEXTUAL DATA IN ADDITION TO THE DATA;

U.S. patent application Ser. No. 16/182,243, titled SURGICAL HUB AND MODULAR DEVICE RESPONSE ADJUSTMENT BASED ON SITUATIONAL AWARENESS;

U.S. patent application Ser. No. 16/182,248, titled DETECTION AND ESCALATION OF SECURITY RESPONSES OF SURGICAL INSTRUMENTS TO INCREASING SEVERITY THREATS;

U.S. patent application Ser. No. 16/182,251, titled INTERACTIVE SURGICAL SYSTEM;

U.S. patent application Ser. No. 16/182,260, titled AUTOMATED DATA SCALING, ALIGNMENT, AND ORGANIZING BASED ON PREDEFINED PARAMETERS WITHIN SURGICAL NETWORKS;

U.S. patent application Ser. No. 16/182,267, titled SENSING THE PATIENT POSITION AND CONTACT UTILIZING THE MONO-POLAR RETURN PAD ELECTRODE TO PROVIDE SITUATIONAL AWARENESS TO THE HUB;

U.S. patent application Ser. No. 16/182,249, titled POWERED SURGICAL TOOL WITH PREDEFINED ADJUSTABLE CONTROL ALGORITHM FOR CONTROLLING END EFFECTOR PARAMETER;

U.S. patent application Ser. No. 16/182,246, titled ADJUSTMENTS BASED ON AIRBORNE PARTICLE PROPERTIES;

U.S. patent application Ser. No. 16/182,256, titled ADJUSTMENT OF A SURGICAL DEVICE FUNCTION BASED ON SITUATIONAL AWARENESS;

U.S. patent application Ser. No. 16/182,242, titled REAL-TIME ANALYSIS OF COMPREHENSIVE COST OF ALL INSTRUMENTATION USED IN SURGERY UTILIZING DATA FLUIDITY TO TRACK INSTRUMENTS THROUGH STOCKING AND IN-HOUSE PROCESSES;

U.S. patent application Ser. No. 16/182,255, titled USAGE AND TECHNIQUE ANALYSIS OF SURGEON/STAFF PERFORMANCE AGAINST A BASELINE TO OPTIMIZE DEVICE UTILIZATION AND

PERFORMANCE FOR BOTH CURRENT AND FUTURE PROCEDURES;

U.S. patent application Ser. No. 16/182,269, titled IMAGE CAPTURING OF THE AREAS OUTSIDE THE ABDOMEN TO IMPROVE PLACEMENT AND CONTROL OF A SURGICAL DEVICE IN USE;

U.S. patent application Ser. No. 16/182,278, titled COMMUNICATION OF DATA WHERE A SURGICAL NETWORK IS USING CONTEXT OF THE DATA AND REQUIREMENTS OF A RECEIVING SYSTEM/USER TO INFLUENCE INCLUSION OR LINKAGE OF DATA AND METADATA TO ESTABLISH CONTINUITY;

U.S. patent application Ser. No. 16/182,290, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION;

U.S. patent application Ser. No. 16/182,232, titled CONTROL OF A SURGICAL SYSTEM THROUGH A SURGICAL BARRIER;

U.S. patent application Ser. No. 16/182,227, titled SURGICAL NETWORK DETERMINATION OF PRIORITIZATION OF COMMUNICATION, INTERACTION, OR PROCESSING BASED ON SYSTEM OR DEVICE NEEDS;

U.S. patent application Ser. No. 16/182,231, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES;

U.S. patent application Ser. No. 16/182,229, titled ADJUSTMENT OF STAPLE HEIGHT OF AT LEAST ONE ROW OF STAPLES BASED ON THE SENSED TISSUE THICKNESS OR FORCE IN CLOSING;

U.S. patent application Ser. No. 16/182,234, titled STAPLING DEVICE WITH BOTH COMPULSORY AND DISCRETIONARY LOCKOUTS BASED ON SENSED PARAMETERS;

U.S. patent application Ser. No. 16/182,240, titled POWERED STAPLING DEVICE CONFIGURED TO ADJUST FORCE, ADVANCEMENT SPEED, AND OVERALL STROKE OF CUTTING MEMBER BASED ON SENSED PARAMETER OF FIRING OR CLAMPING;

U.S. patent application Ser. No. 16/182,235, titled VARIATION OF RADIO FREQUENCY AND ULTRASONIC POWER LEVEL IN COOPERATION WITH VARYING CLAMP ARM PRESSURE TO ACHIEVE PREDEFINED HEAT FLUX OR POWER APPLIED TO TISSUE; and U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION.

Applicant of the present application owns the following U.S. patent applications that were filed on Oct. 26, 2018, the disclosure of each of which is herein incorporated by reference in its entirety:

U.S. patent application Ser. No. 16/172,303, titled METHOD FOR OPERATING A POWERED ARTICULATING MULTI-CLIP APPLIER;

U.S. patent application Ser. No. 16/172,130, titled CLIP APPLIER COMPRISING INTERCHANGEABLE CLIP RELOADS;

U.S. patent application Ser. No. 16/172,066, titled CLIP APPLIER COMPRISING A MOVABLE CLIP MAGAZINE;

U.S. patent application Ser. No. 16/172,078, titled CLIP APPLIER COMPRISING A ROTATABLE CLIP MAGAZINE;

U.S. patent application Ser. No. 16/172,087, titled CLIP APPLIER COMPRISING CLIP ADVANCING SYSTEMS;

U.S. patent application Ser. No. 16/172,094, titled CLIP APPLIER COMPRISING A CLIP CRIMPING SYSTEM;

U.S. patent application Ser. No. 16/172,128, titled CLIP APPLIER COMPRISING A RECIPROCATING CLIP ADVANCING MEMBER;

U.S. patent application Ser. No. 16/172,168, titled CLIP APPLIER COMPRISING A MOTOR CONTROLLER;

U.S. patent application Ser. No. 16/172,164, titled SURGICAL SYSTEM COMPRISING A SURGICAL TOOL AND A SURGICAL HUB;

U.S. patent application Ser. No. 16/172,328, titled METHOD OF HUB COMMUNICATION WITH SURGICAL INSTRUMENT SYSTEMS;

U.S. patent application Ser. No. 16/172,280, titled METHOD FOR PRODUCING A SURGICAL INSTRUMENT COMPRISING A SMART ELECTRICAL SYSTEM;

U.S. patent application Ser. No. 16/172,219, titled METHOD OF HUB COMMUNICATION WITH SURGICAL INSTRUMENT SYSTEMS;

U.S. patent application Ser. No. 16/172,248, titled METHOD OF HUB COMMUNICATION WITH SURGICAL INSTRUMENT SYSTEMS;

U.S. patent application Ser. No. 16/172,198, titled METHOD OF HUB COMMUNICATION WITH SURGICAL INSTRUMENT SYSTEMS; and U.S. patent application Ser. No. 16/172,155, titled METHOD OF HUB COMMUNICATION WITH SURGICAL INSTRUMENT SYSTEMS.

Applicant of the present application owns the following U.S. patent applications, filed on Aug. 28, 2018, the disclosure of each of which is herein incorporated by reference in its entirety:

U.S. patent application Ser. No. 16/115,214, titled ESTIMATING STATE OF ULTRASONIC END EFFECTOR AND CONTROL SYSTEM THEREFOR;

U.S. patent application Ser. No. 16/115,205, titled TEMPERATURE CONTROL OF ULTRASONIC END EFFECTOR AND CONTROL SYSTEM THEREFOR;

U.S. patent application Ser. No. 16/115,233, titled RADIO FREQUENCY ENERGY DEVICE FOR DELIVERING COMBINED ELECTRICAL SIGNALS;

U.S. patent application Ser. No. 16/115,208, titled CONTROLLING AN ULTRASONIC SURGICAL INSTRUMENT ACCORDING TO TISSUE LOCATION;

U.S. patent application Ser. No. 16/115,220, titled CONTROLLING ACTIVATION OF AN ULTRASONIC SURGICAL INSTRUMENT ACCORDING TO THE PRESENCE OF TISSUE;

U.S. patent application Ser. No. 16/115,232, titled DETERMINING TISSUE COMPOSITION VIA AN ULTRASONIC SYSTEM;

U.S. patent application Ser. No. 16/115,239, titled DETERMINING THE STATE OF AN ULTRASONIC ELECTROMECHANICAL SYSTEM ACCORDING TO FREQUENCY SHIFT;

U.S. patent application Ser. No. 16/115,247, titled DETERMINING THE STATE OF AN ULTRASONIC END EFFECTOR;

U.S. patent application Ser. No. 16/115,211, titled SITUATIONAL AWARENESS OF ELECTROSURGICAL SYSTEMS;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT;

U.S. patent application Ser. No. 16/115,240, titled DETECTION OF END EFFECTOR EMERSION IN LIQUID;

U.S. patent application Ser. No. 16/115,249, titled INTERRUPTION OF ENERGY DUE TO INADVERTENT CAPACITIVE COUPLING;

U.S. patent application Ser. No. 16/115,256, titled INCREASING RADIO FREQUENCY TO CREATE PAD-LESS MONOPOLAR LOOP;

U.S. patent application Ser. No. 16/115,223, titled BIPOLAR COMBINATION DEVICE THAT AUTOMATICALLY ADJUSTS PRESSURE BASED ON ENERGY MODALITY; and U.S. patent application Ser. No. 16/115,238, titled ACTIVATION OF ENERGY DEVICES.

Applicant of the present application owns the following U.S. patent applications, filed on Aug. 24, 2018, the disclosure of each of which is herein incorporated by reference in its entirety:

U.S. patent application Ser. No. 16/112,129, titled SURGICAL SUTURING INSTRUMENT CONFIGURED TO MANIPULATE TISSUE USING MECHANICAL AND ELECTRICAL POWER;

U.S. patent application Ser. No. 16/112,155, titled SURGICAL SUTURING INSTRUMENT COMPRISING A CAPTURE WIDTH WHICH IS LARGER THAN TROCAR DIAMETER;

U.S. patent application Ser. No. 16/112,168, titled SURGICAL SUTURING INSTRUMENT COMPRISING A NON-CIRCULAR NEEDLE;

U.S. patent application Ser. No. 16/112,180, titled ELECTRICAL POWER OUTPUT CONTROL BASED ON MECHANICAL FORCES;

U.S. patent application Ser. No. 16/112,193, titled REACTIVE ALGORITHM FOR SURGICAL SYSTEM;

U.S. patent application Ser. No. 16/112,099, titled SURGICAL INSTRUMENT COMPRISING AN ADAPTIVE ELECTRICAL SYSTEM;

U.S. patent application Ser. No. 16/112,112, titled CONTROL SYSTEM ARRANGEMENTS FOR A MODULAR SURGICAL INSTRUMENT;

U.S. patent application Ser. No. 16/112,119, titled ADAPTIVE CONTROL PROGRAMS FOR A SURGICAL SYSTEM COMPRISING MORE THAN ONE TYPE OF CARTRIDGE;

U.S. patent application Ser. No. 16/112,097, titled SURGICAL INSTRUMENT SYSTEMS COMPRISING BATTERY ARRANGEMENTS;

U.S. patent application Ser. No. 16/112,109, titled SURGICAL INSTRUMENT SYSTEMS COMPRISING HANDLE ARRANGEMENTS;

U.S. patent application Ser. No. 16/112,114, titled SURGICAL INSTRUMENT SYSTEMS COMPRISING FEEDBACK MECHANISMS;

U.S. patent application Ser. No. 16/112,117, titled SURGICAL INSTRUMENT SYSTEMS COMPRISING LOCKOUT MECHANISMS;

U.S. patent application Ser. No. 16/112,095, titled SURGICAL INSTRUMENTS COMPRISING A LOCKABLE END EFFECTOR SOCKET;

U.S. patent application Ser. No. 16/112,121, titled SURGICAL INSTRUMENTS COMPRISING A SHIFTING MECHANISM;

U.S. patent application Ser. No. 16/112,151, titled SURGICAL INSTRUMENTS COMPRISING A SYSTEM FOR ARTICULATION AND ROTATION COMPENSATION;

U.S. patent application Ser. No. 16/112,154, titled SURGICAL INSTRUMENTS COMPRISING A BIASED SHIFTING MECHANISM;

U.S. patent application Ser. No. 16/112,226, titled SURGICAL INSTRUMENTS COMPRISING AN ARTICULATION DRIVE THAT PROVIDES FOR HIGH ARTICULATION ANGLES;

U.S. patent application Ser. No. 16/112,062, titled SURGICAL DISSECTORS AND MANUFACTURING TECHNIQUES;

U.S. patent application Ser. No. 16/112,098, titled SURGICAL DISSECTORS CONFIGURED TO APPLY MECHANICAL AND ELECTRICAL ENERGY;

U.S. patent application Ser. No. 16/112,237, titled SURGICAL CLIP APPLIER CONFIGURED TO STORE CLIPS IN A STORED STATE;

U.S. patent application Ser. No. 16/112,245, titled SURGICAL CLIP APPLIER COMPRISING AN EMPTY CLIP CARTRIDGE LOCKOUT;

U.S. patent application Ser. No. 16/112,249, titled SURGICAL CLIP APPLIER COMPRISING AN AUTOMATIC CLIP FEEDING SYSTEM;

U.S. patent application Ser. No. 16/112,253, titled SURGICAL CLIP APPLIER COMPRISING ADAPTIVE FIRING CONTROL; and U.S. patent application Ser. No. 16/112,257, titled SURGICAL CLIP APPLIER COMPRISING ADAPTIVE CONTROL IN RESPONSE TO A STRAIN GAUGE CIRCUIT.

Applicant of the present application owns the following U.S. patent applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS;

U.S. patent application Ser. No. 16/024,057, titled CONTROLLING A SURGICAL INSTRUMENT ACCORDING TO SENSED CLOSURE PARAMETERS;

U.S. patent application Ser. No. 16/024,067, titled SYSTEMS FOR ADJUSTING END EFFECTOR PARAMETERS BASED ON PERIOPERATIVE INFORMATION;

U.S. patent application Ser. No. 16/024,075, titled SAFETY SYSTEMS FOR SMART POWERED SURGICAL STAPLING;

U.S. patent application Ser. No. 16/024,083, titled SAFETY SYSTEMS FOR SMART POWERED SURGICAL STAPLING;

U.S. patent application Ser. No. 16/024,094, titled SURGICAL SYSTEMS FOR DETECTING END EFFECTOR TISSUE DISTRIBUTION IRREGULARITIES;

U.S. patent application Ser. No. 16/024,138, titled SYSTEMS FOR DEFECTING PROXIMITY OF SURGICAL END EFFECTOR TO CANCEROUS TISSUE;

U.S. patent application Ser. No. 16/024,150, titled SURGICAL INSTRUMENT CARTRIDGE SENSOR ASSEMBLIES;

U.S. patent application Ser. No. 16/024,160, titled VARIABLE OUTPUT CARTRIDGE SENSOR ASSEMBLY;

U.S. patent application Ser. No. 16/024,124, titled SURGICAL INSTRUMENT HAVING A FLEXIBLE ELECTRODE;

U.S. patent application Ser. No. 16/024,132, titled SURGICAL INSTRUMENT HAVING A FLEXIBLE CIRCUIT;

U.S. patent application Ser. No. 16/024,141, titled SURGICAL INSTRUMENT WITH A TISSUE MARKING ASSEMBLY;

U.S. patent application Ser. No. 16/024,162, titled SURGICAL SYSTEMS WITH PRIORITIZED DATA TRANSMISSION CAPABILITIES;

U.S. patent application Ser. No. 16/024,066, titled SURGICAL EVACUATION SENSING AND MOTOR CONTROL;

U.S. patent application Ser. No. 16/024,096, titled SURGICAL EVACUATION SENSOR ARRANGEMENTS;

U.S. patent application Ser. No. 16/024,116, titled SURGICAL EVACUATION FLOW PATHS;

U.S. patent application Ser. No. 16/024,149, titled SURGICAL EVACUATION SENSING AND GENERATOR CONTROL;

U.S. patent application Ser. No. 16/024,180, titled SURGICAL EVACUATION SENSING AND DISPLAY;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM;

U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE; and U.S. patent application Ser. No. 16/024,273, titled DUAL IN-SERIES LARGE AND SMALL DROPLET FILTERS.

Applicant of the present application owns the following U.S. patent applications, filed on Mar. 29, 2018, the disclosure of each of which is herein incorporated by reference in its entirety:

U.S. patent application Ser. No. 15/940,641, titled INTERACTIVE SURGICAL SYSTEMS WITH ENCRYPTED COMMUNICATION CAPABILITIES;

U.S. patent application Ser. No. 15/940,648, titled INTERACTIVE SURGICAL SYSTEMS WITH CONDITION HANDLING OF DEVICES AND DATA CAPABILITIES;

U.S. patent application Ser. No. 15/940,656, titled SURGICAL HUB COORDINATION OF CONTROL AND COMMUNICATION OF OPERATING ROOM DEVICES;

U.S. patent application Ser. No. 15/940,666, titled SPATIAL AWARENESS OF SURGICAL HUBS IN OPERATING ROOMS;

U.S. patent application Ser. No. 15/940,670, titled COOPERATIVE UTILIZATION OF DATA DERIVED FROM SECONDARY SOURCES BY INTELLIGENT SURGICAL HUBS;

U.S. patent application Ser. No. 15/940,677, titled SURGICAL HUB CONTROL ARRANGEMENTS;

U.S. patent application Ser. No. 15/940,632, titled DATA STRIPPING METHOD TO INTERROGATE PATIENT RECORDS AND CREATE ANONYMIZED RECORD;

U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, titled SELF DESCRIBING DATA PACKETS GENERATED AT AN ISSUING INSTRUMENT;

U.S. patent application Ser. No. 15/940,649, titled DATA PAIRING TO INTERCONNECT A DEVICE MEASURED PARAMETER WITH AN OUTCOME;

U.S. patent application Ser. No. 15/940,654, titled SURGICAL HUB SITUATIONAL AWARENESS;

U.S. patent application Ser. No. 15/940,663, titled SURGICAL SYSTEM DISTRIBUTED PROCESSING;

U.S. patent application Ser. No. 15/940,668, titled AGGREGATION AND REPORTING OF SURGICAL HUB DATA;

U.S. patent application Ser. No. 15/940,671, titled SURGICAL HUB SPATIAL AWARENESS TO DETERMINE DEVICES IN OPERATING THEATER;

U.S. patent application Ser. No. 15/940,686, titled DISPLAY OF ALIGNMENT OF STAPLE CARTRIDGE TO PRIOR LINEAR STAPLE LINE;

U.S. patent application Ser. No. 15/940,700, titled STERILE FIELD INTERACTIVE CONTROL DISPLAYS;

U.S. patent application Ser. No. 15/940,629, titled COMPUTER IMPLEMENTED INTERACTIVE SURGICAL SYSTEMS;

U.S. patent application Ser. No. 15/940,704, titled USE OF LASER LIGHT AND RED-GREEN-BLUE COLORATION TO DETERMINE PROPERTIES OF BACK SCATTERED LIGHT;

U.S. patent application Ser. No. 15/940,722, titled CHARACTERIZATION OF TISSUE IRREGULARITIES THROUGH THE USE OF MONO-CHROMATIC LIGHT REFRACTIVITY;

U.S. patent application Ser. No. 15/940,742, titled DUAL CMOS ARRAY IMAGING;

U.S. patent application Ser. No. 15/940,636, titled ADAPTIVE CONTROL PROGRAM UPDATES FOR SURGICAL DEVICES;

U.S. patent application Ser. No. 15/940,653, titled ADAPTIVE CONTROL PROGRAM UPDATES FOR SURGICAL HUBS;

U.S. patent application Ser. No. 15/940,660, titled CLOUD-BASED MEDICAL ANALYTICS FOR CUSTOMIZATION AND RECOMMENDATIONS TO A USER;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, titled CLOUD-BASED MEDICAL ANALYTICS FOR SECURITY AND AUTHENTICATION TRENDS AND REACTIVE MEASURES;

U.S. patent application Ser. No. 15/940,706, titled DATA HANDLING AND PRIORITIZATION IN A CLOUD ANALYTICS NETWORK;

U.S. patent application Ser. No. 15/940,675, titled CLOUD INTERFACE FOR COUPLED SURGICAL DEVICES;

U.S. patent application Ser. No. 15/940,627, titled DRIVE ARRANGEMENTS FOR ROBOT-ASSISTED SURGICAL PLATFORMS;

U.S. patent application Ser. No. 15/940,637, titled COMMUNICATION ARRANGEMENTS FOR ROBOT-ASSISTED SURGICAL PLATFORMS;

U.S. patent application Ser. No. 15/940,642, titled CONTROLS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,680, titled CONTROLLERS FOR ROBOT-ASSISTED SURGICAL PLATFORMS;

U.S. patent application Ser. No. 15/940,683, titled COOPERATIVE SURGICAL ACTIONS FOR ROBOT-ASSISTED SURGICAL PLATFORMS;

U.S. patent application Ser. No. 15/940,690, titled DISPLAY ARRANGEMENTS FOR ROBOT-ASSISTED SURGICAL PLATFORMS; and U.S. patent application Ser. No. 15/940,711, titled SENSING ARRANGEMENTS FOR ROBOT-ASSISTED SURGICAL PLATFORMS.

Applicant of the present application owns the following U.S. Provisional patent applications, filed on Mar. 8, 2018, the disclosure of each of which is herein incorporated by reference in its entirety:

U.S. Provisional Patent Application No. 62/640,417, titled TEMPERATURE CONTROL IN ULTRASONIC DEVICE AND CONTROL SYSTEM THEREFOR; and U.S. Provisional Patent Application No. 62/640,415, titled ESTIMATING STATE OF ULTRASONIC END EFFECTOR AND CONTROL SYSTEM THEREFOR.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Surgical Hubs

Figure 1:
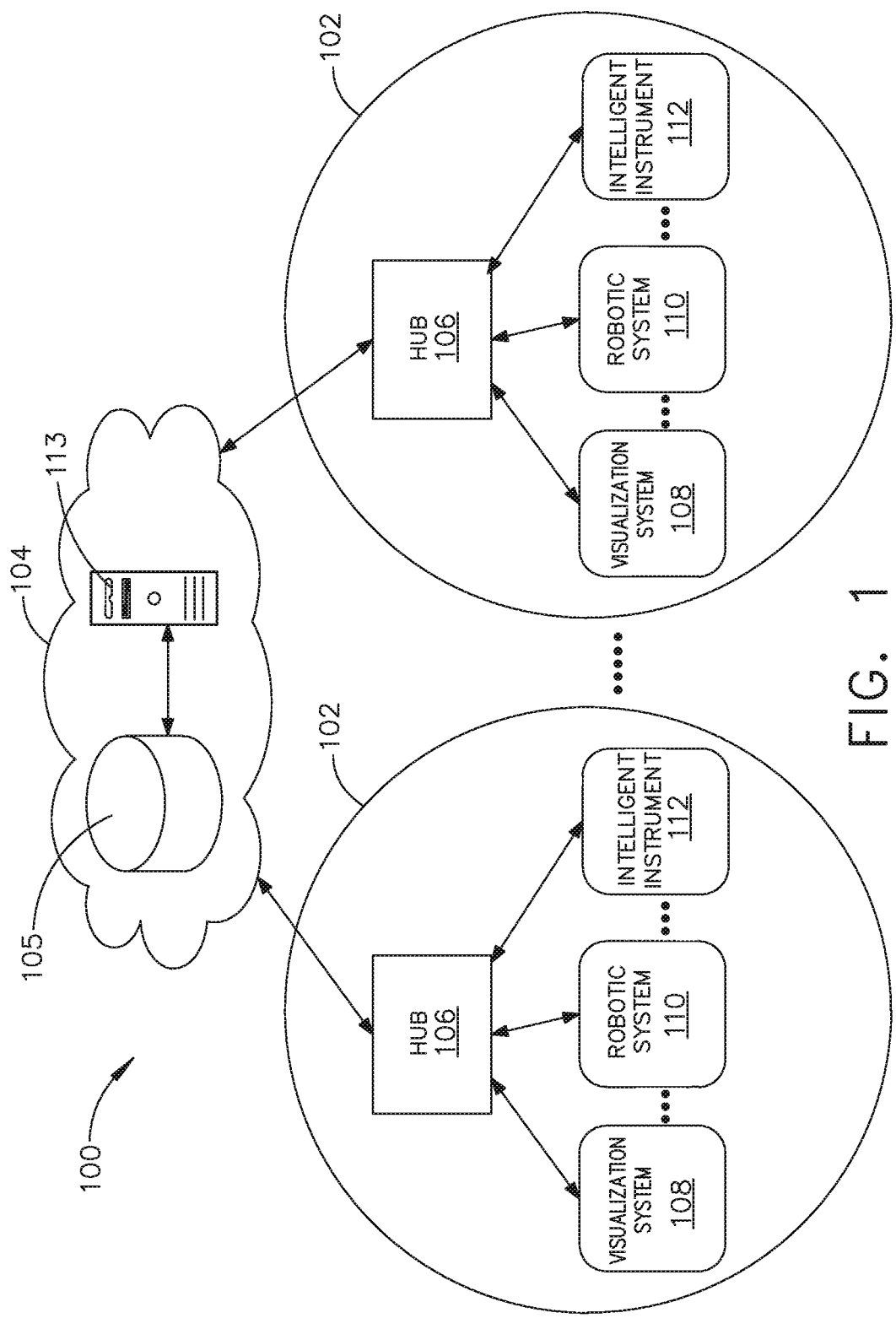
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

In various aspects, the intelligent instruments 112 as described herein with reference to FIGS. 1-7 may be implemented as a powered circular stapling device 201800 (FIGS. 24-30) and 201000 (FIGS. 31-32). The intelligent instruments 112 (e.g., devices $1_a$-$1_n$) such as the powered circular stapling device 201800 (FIGS. 24-30) and 201000 (FIGS. 31-32) are configured to operate in a surgical data network 201 as described with reference to FIG. 8.

Figure 2:
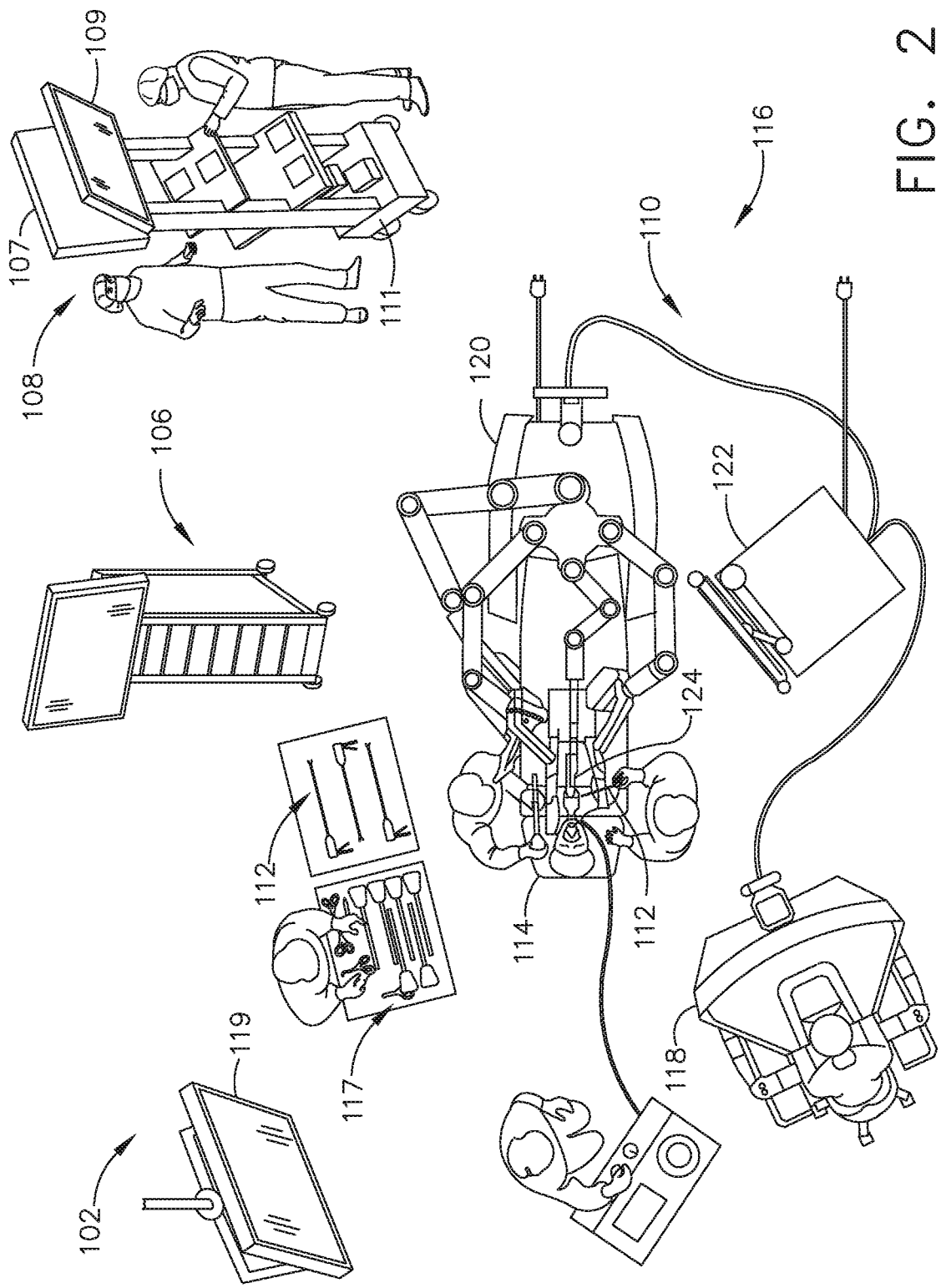
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, coordinate information flow is further described in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
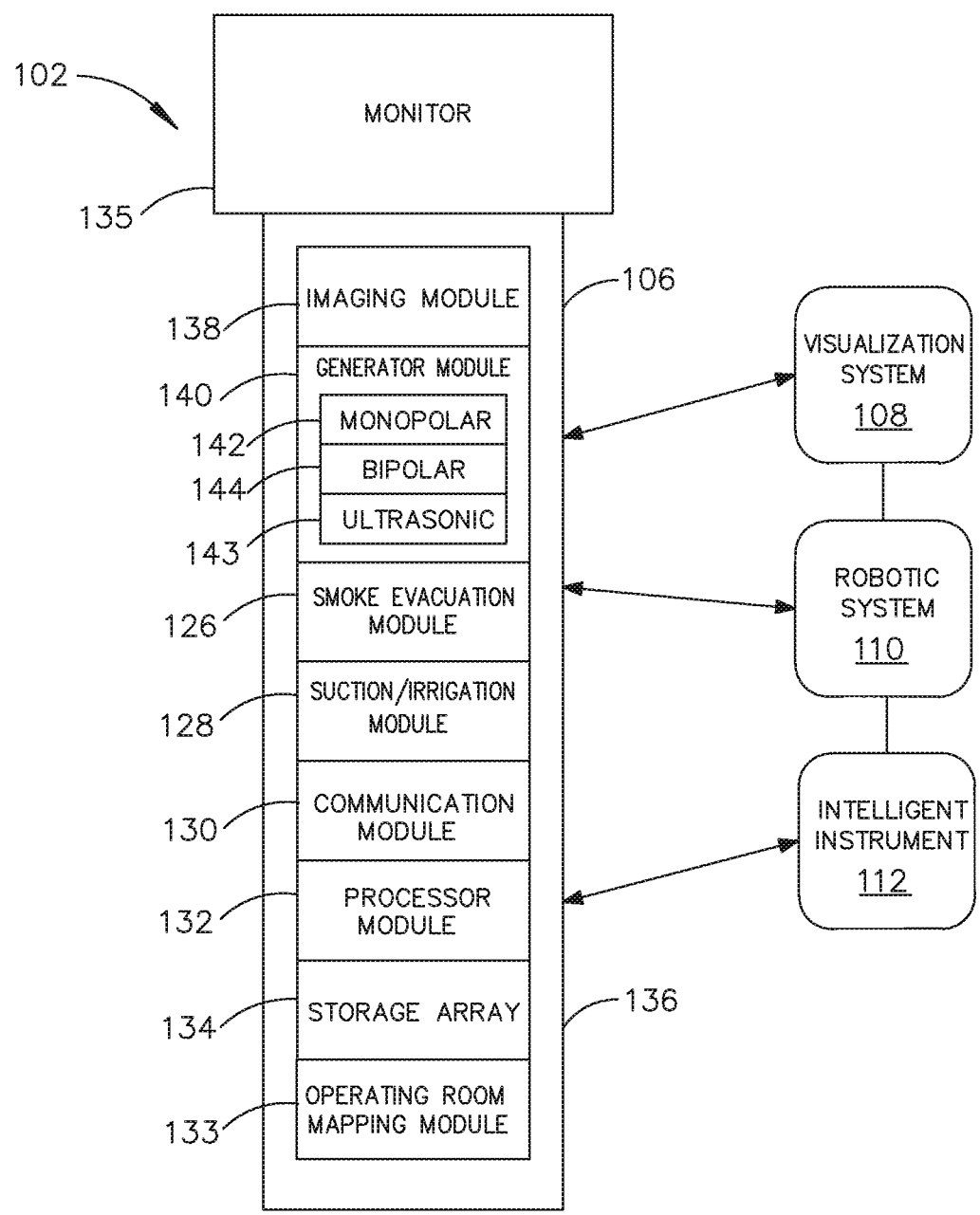
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts.

Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
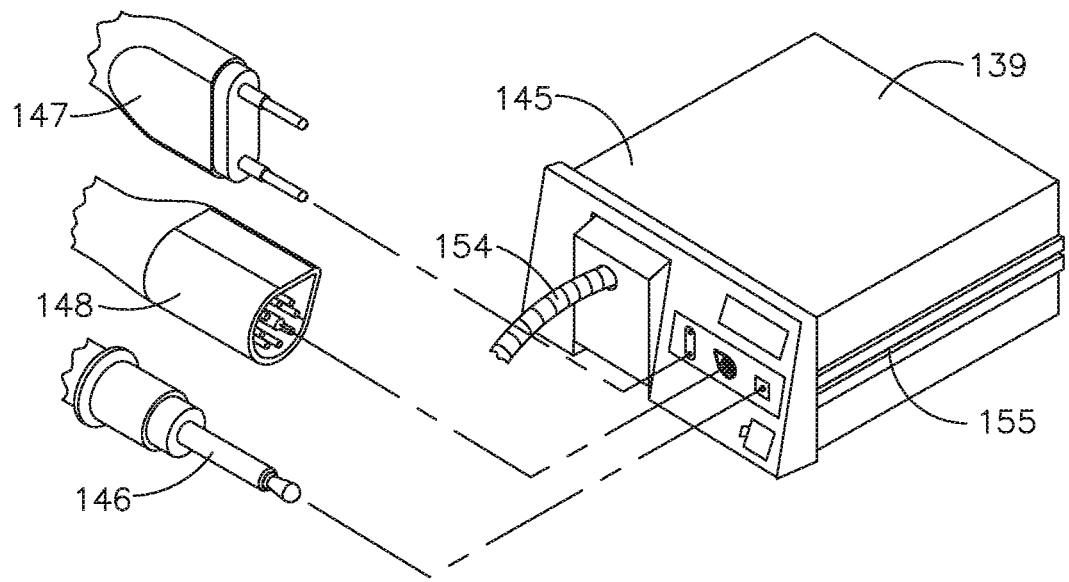
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
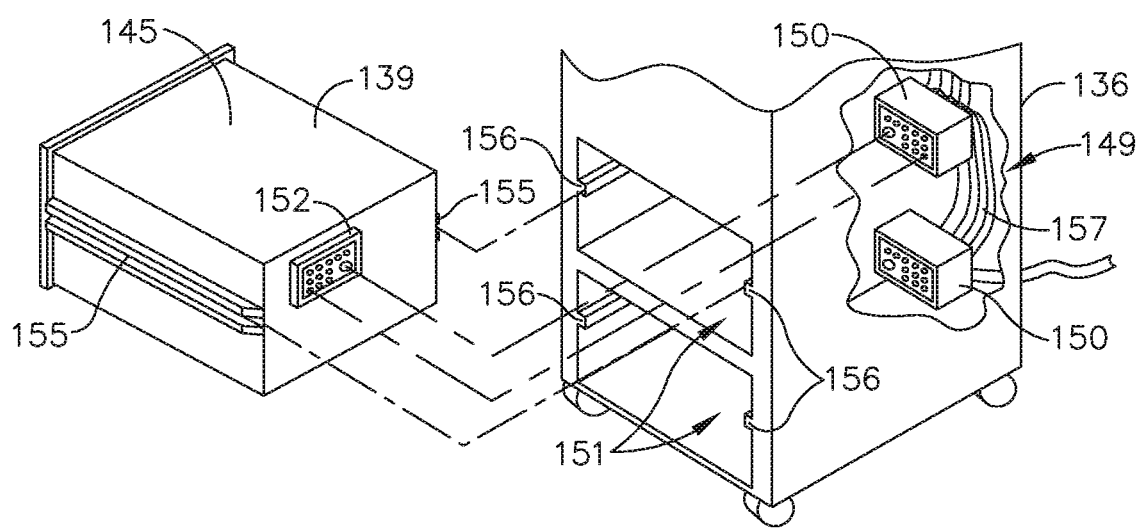
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
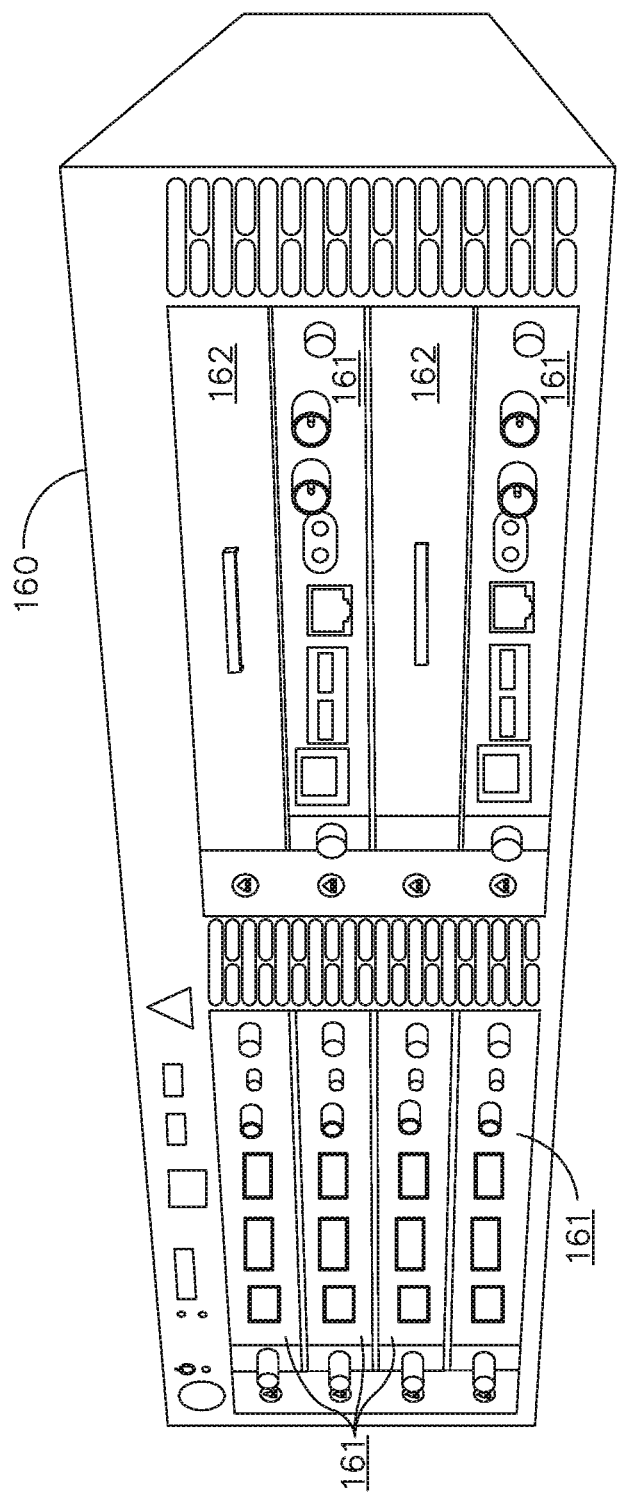
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
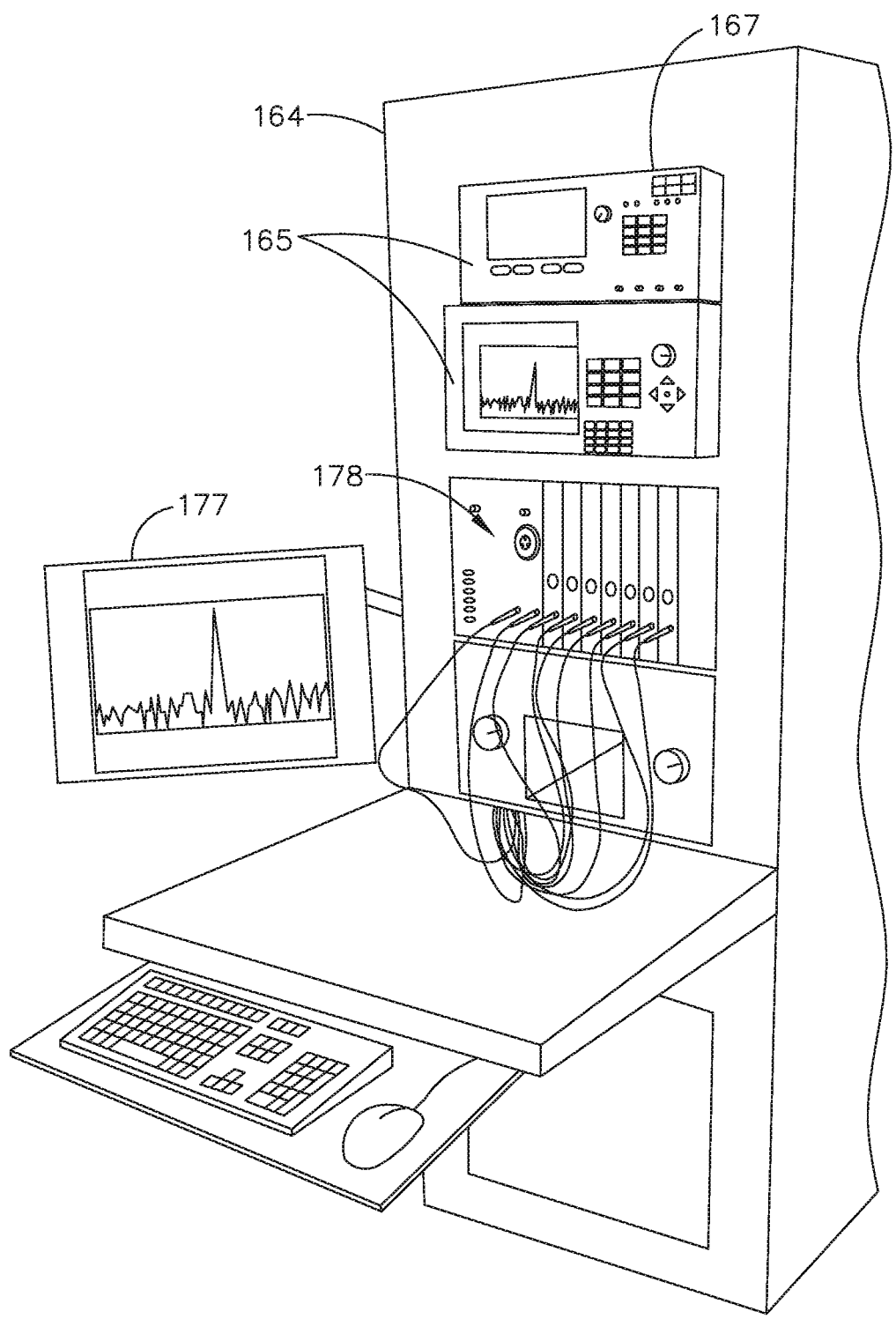
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVEN- TIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
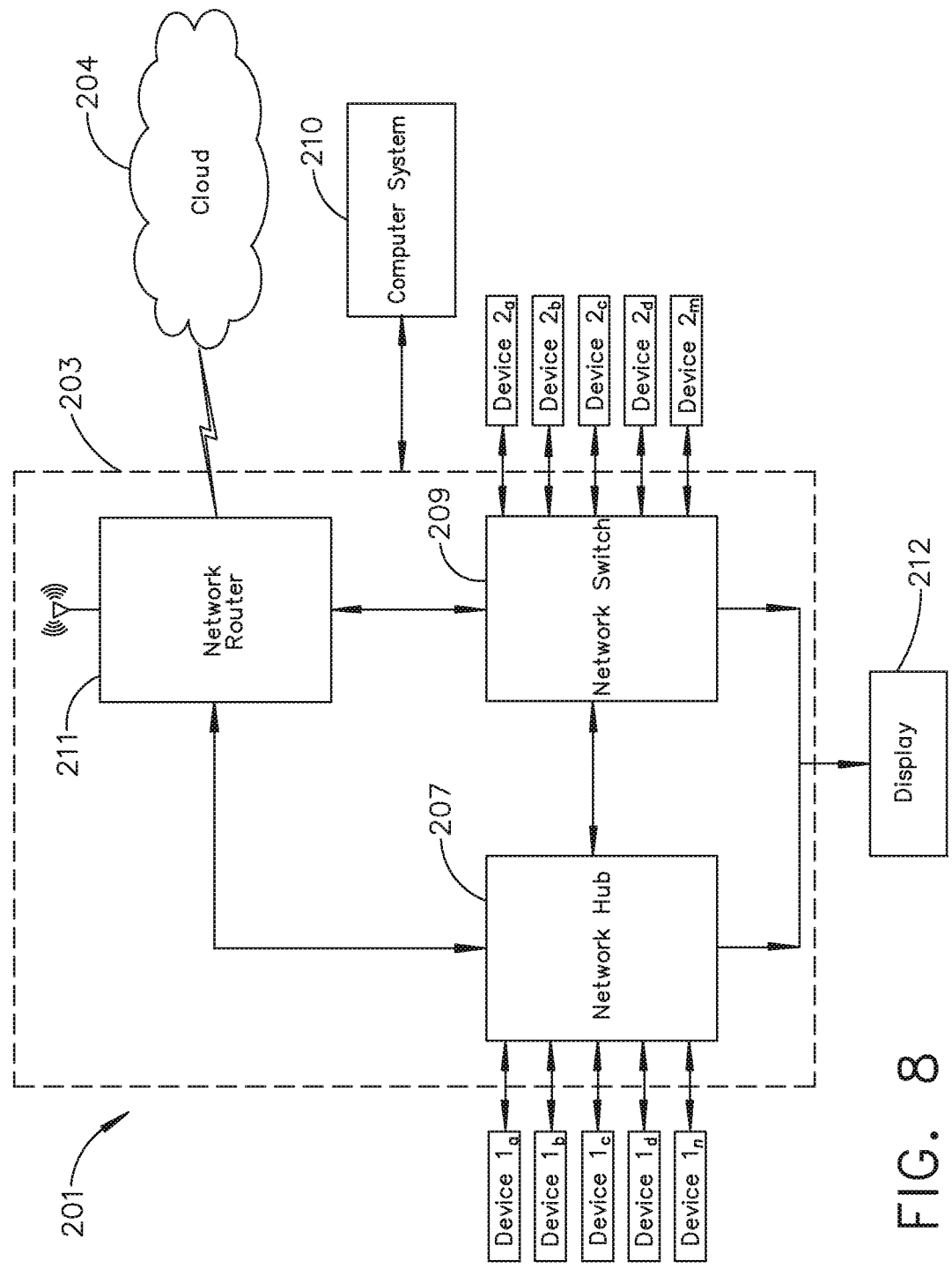
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LIE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
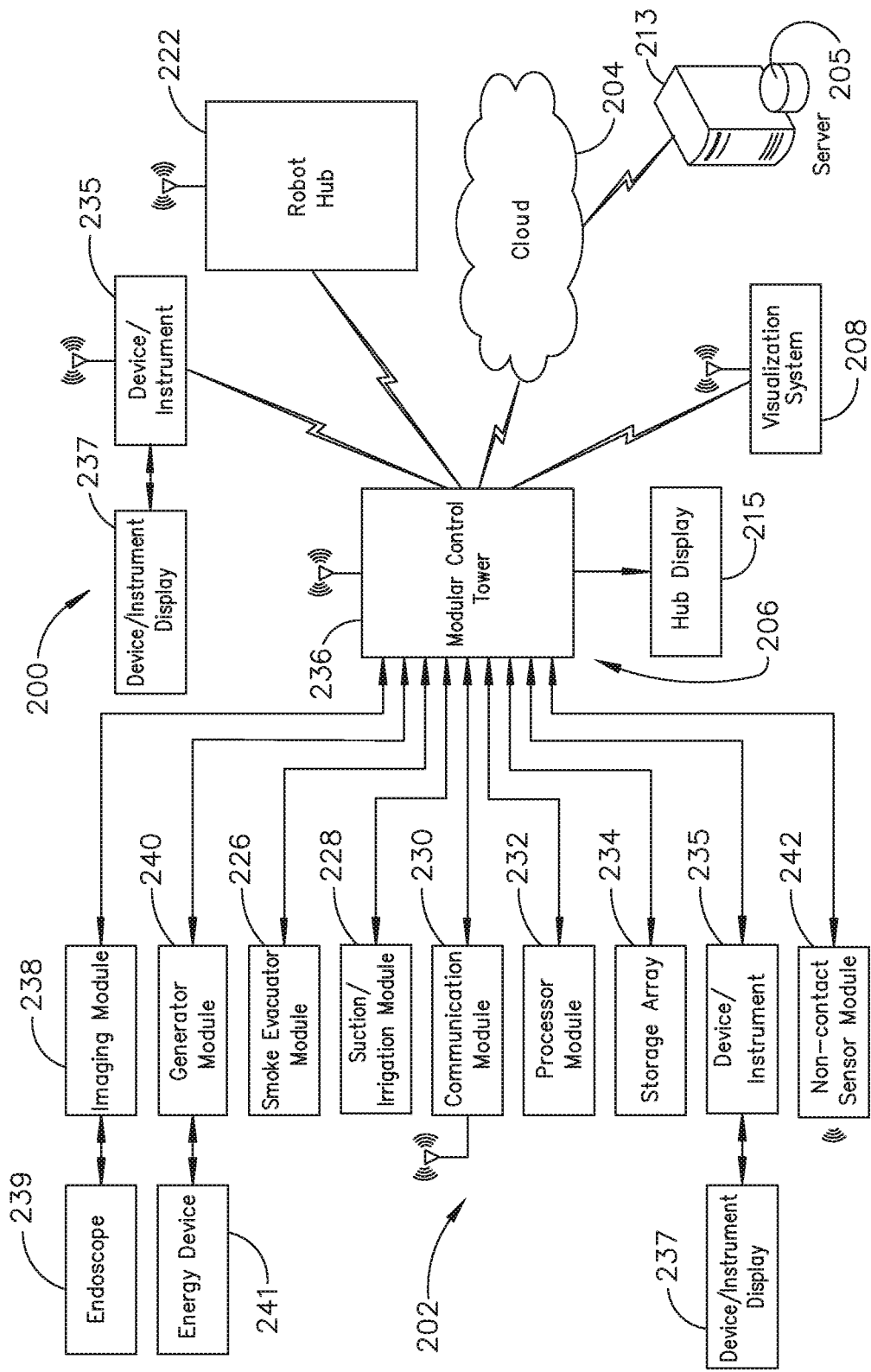
FIG. 9 illustrates a computer-implemented interactive surgical system, in accordance with at least one aspect of the present disclosure.
Figure 10:
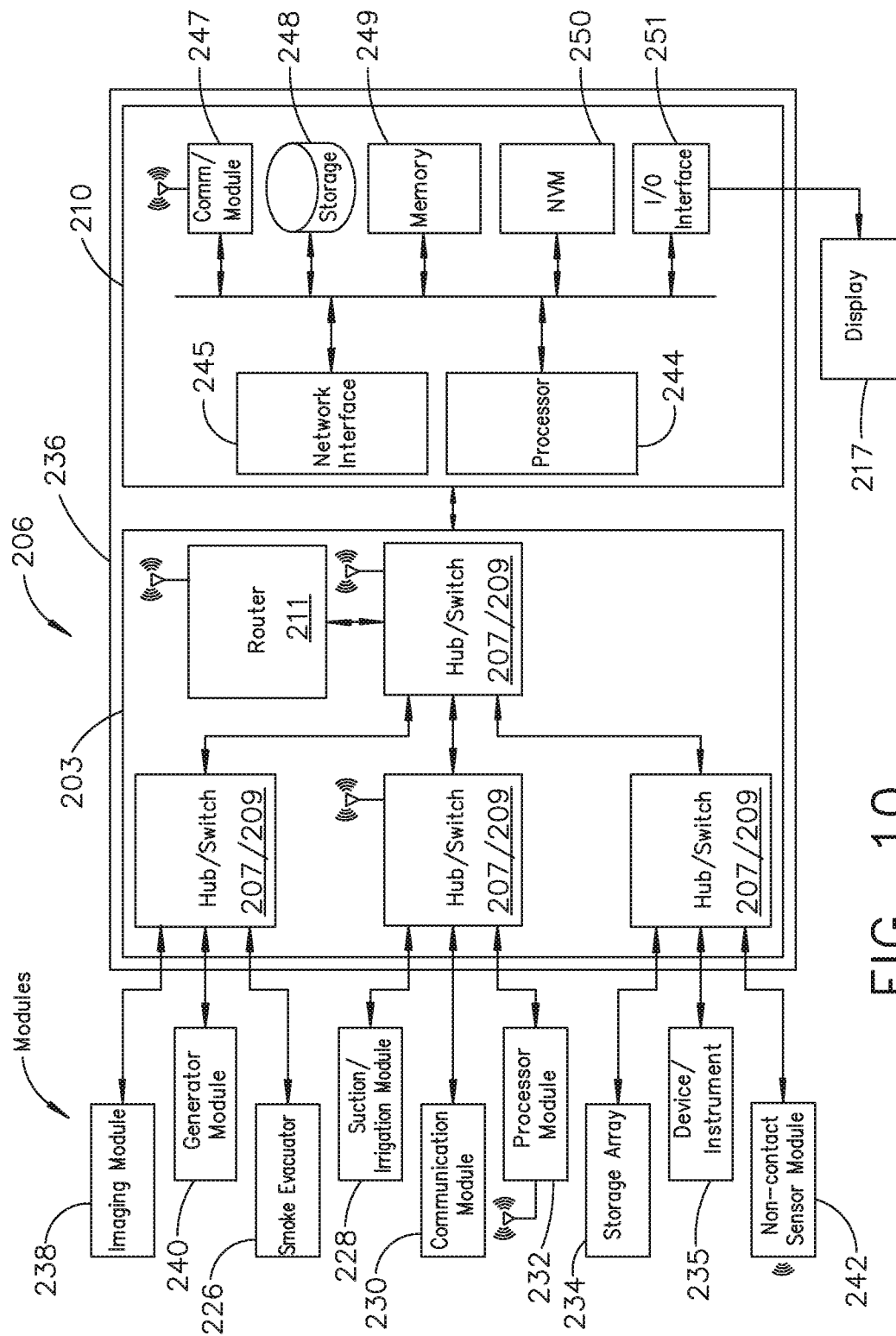
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

In various aspects, the devices/instruments 235 described with reference to FIGS. 9-10, may be implemented as a powered circular stapling device 201800 (FIGS. 24-30) and 201000 (FIGS. 31-32). Accordingly, the powered circular stapling device 201800 (FIGS. 24-30) and 201000 (FIGS. 31-32) is configured to interface with the modular control tower 236 ant the surgical hub 206. Once connected to the surgical hub 206 the powered circular stapling device 201800 (FIGS. 24-30) and 201000 (FIGS. 31-32) is configured to interface with the cloud 204, the server 213, other hub connected instruments, the hub display 215, or the visualization system 209, or combinations thereof. Further, once connected to hub 206, the powered circular stapling device 201800 (FIGS. 24-30) and 201000 (FIGS. 31-32) may utilize the processing circuits available in the hub local computer system 210.

Figure 11:
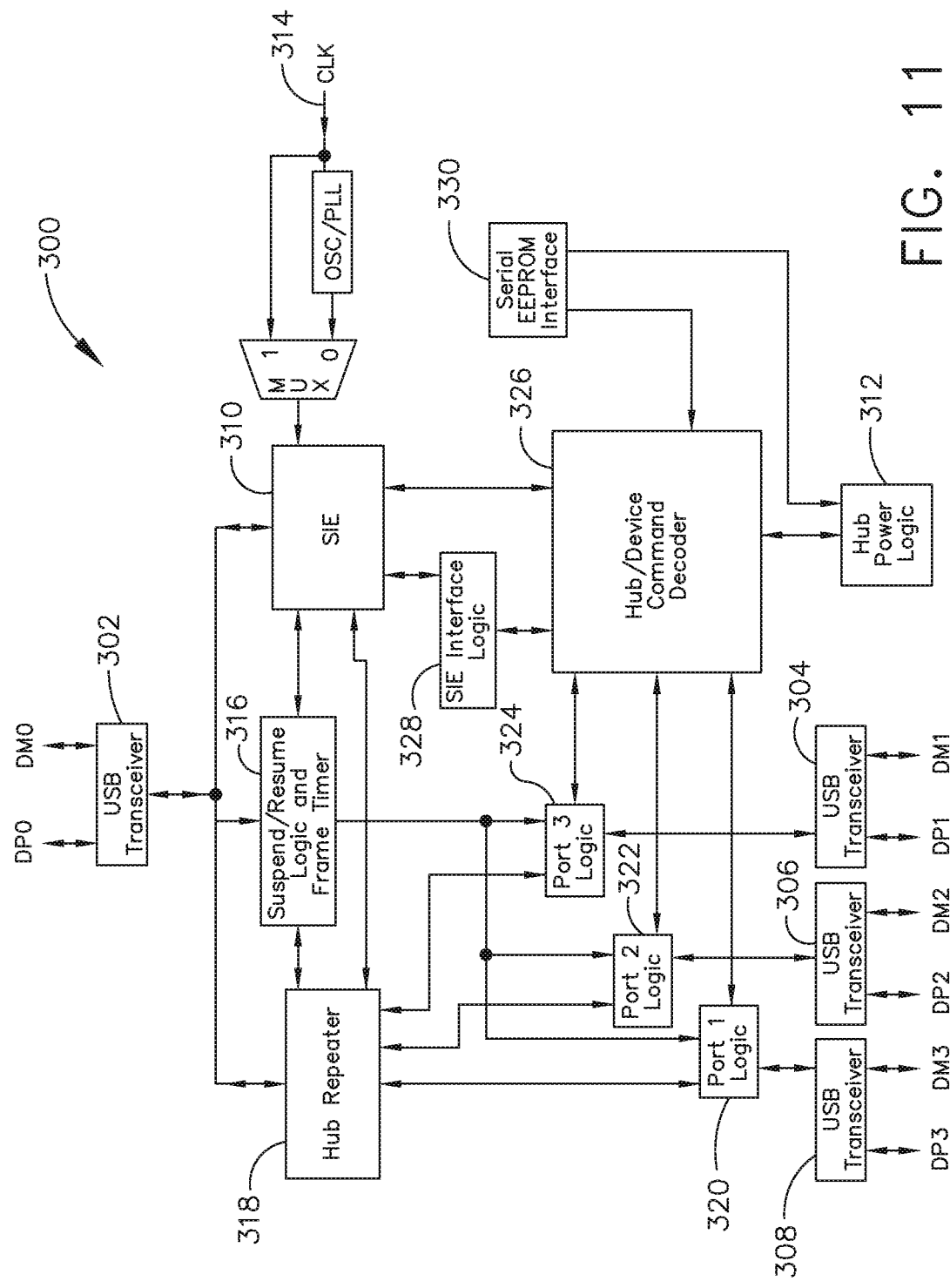
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Additional details regarding the structure and function of the surgical hub and/or surgical hub networks can be found in U.S. Provisional Patent Application No. 62/659,900, titled METHOD OF HUB COMMUNICATION, filed Apr. 19, 2018, which is hereby incorporated by reference herein in its entirety.

Cloud System Hardware and Functional Modules

Figure 12:
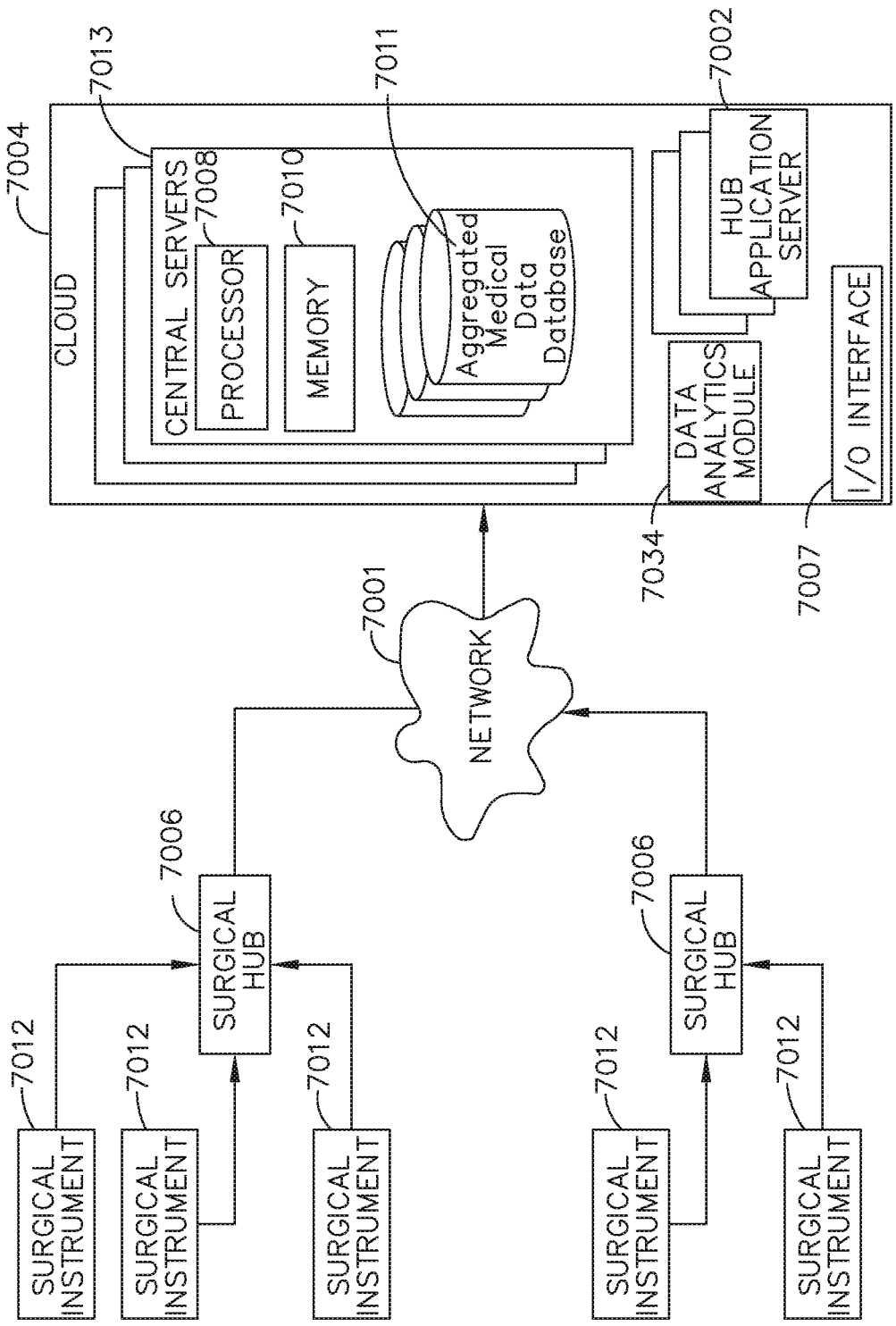
FIG. 12 is a block diagram of a cloud computing system comprising a plurality of smart surgical instruments coupled to surgical hubs that may connect to the cloud component of the cloud computing system, in accordance with at least one aspect of the present disclosure.

FIG. 12 is a block diagram of the computer-implemented interactive surgical system, in accordance with at least one aspect of the present disclosure. In one aspect, the computer-implemented interactive surgical system is configured to monitor and analyze data related to the operation of various surgical systems that include surgical hubs, surgical instruments, robotic devices and operating theaters or healthcare facilities. The computer-implemented interactive surgical system comprises a cloud-based analytics system. Although the cloud-based analytics system is described as a surgical system, it is not necessarily limited as such and could be a cloud-based medical system generally. As illustrated in FIG. 12, the cloud-based analytics system comprises a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 is communicatively coupled to one or more surgical instruments 7012. The hubs 7006 are also communicatively coupled to the cloud 7004 of the computer-implemented interactive surgical system via the network 7001. The cloud 7004 is a remote centralized source of hardware and software for storing, manipulating, and communicating data generated based on the operation of various surgical systems. As shown in FIG. 12, access to the cloud 7004 is achieved via the network 7001, which may be the Internet or some other suitable computer network. Surgical hubs 7006 that are coupled to the cloud 7004 can be considered the client side of the cloud computing system (i.e., cloud-based analytics system). Surgical instruments 7012 are paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 12, the cloud 7004 comprises central servers 7013 (which may be same or similar to remote server 113 in FIG. 1 and/or remote server 213 in FIG. 9), hub application servers 7002, data analytics modules 7034, and an input/output ("I/O") interface 7007. The central servers 7013 of the cloud 7004 collectively administer the cloud computing system, which includes monitoring requests by client surgical hubs 7006 and managing the processing capacity of the cloud 7004 for executing the requests. Each of the central servers 7013 comprises one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7011 of the cloud 7004. In particular, the cloud 7004 may advantageously perform data analysis and operations on the aggregated data to yield insights and/or perform functions that individual hubs 7006 could not achieve on their own. To this end, as shown in FIG. 12, the cloud 7004 and the surgical hubs 7006 are communicatively coupled to transmit and receive information. The I/O interface 7007 is connected to the plurality of surgical hubs 7006 via the network 7001. In this way, the I/O interface 7007 can be configured to transfer information between the surgical hubs 7006 and the aggregated medical data databases 7012. Accordingly, the I/O interface 7007 may facilitate read/write operations of the cloud-based analytics system. Such read/write operations may be executed in response to requests from hubs 7006. These requests could be transmitted to the hubs 7006 through the hub applications. The I/O interface 7007 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 are configured to host and supply shared capabilities to software applications (e.g. hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 13.

The particular cloud computing system configuration described in the present disclosure is specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch controlled user interfaces such that clinicians may control aspects of interaction between the surgical instruments 7012 and the cloud 7004. Other suitable user interfaces for control such as auditory controlled user interfaces can also be used.

Figure 13:
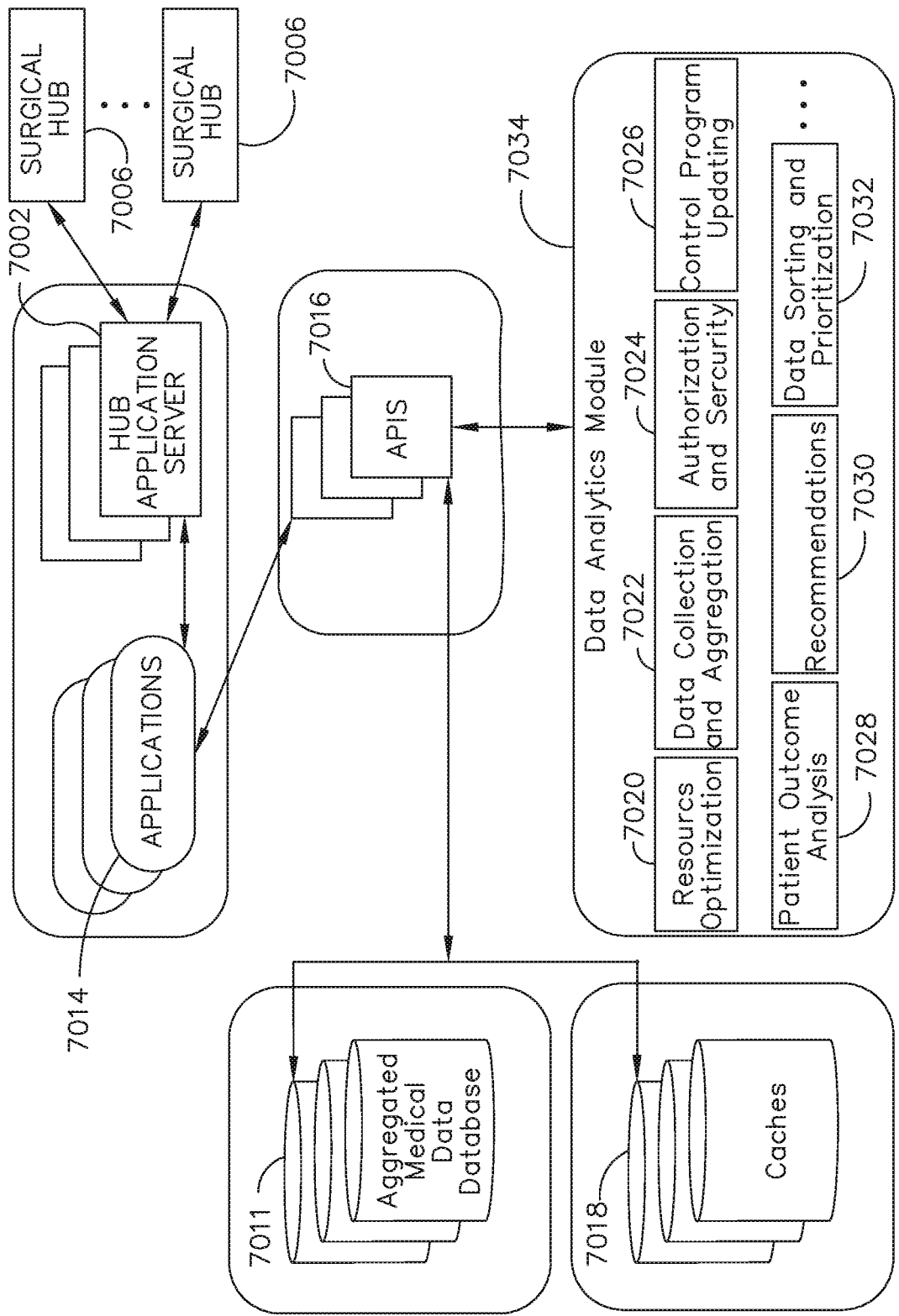
FIG. 13 is a functional module architecture of a cloud computing system, in accordance with at least one aspect of the present disclosure.

FIG. 13 is a block diagram which illustrates the functional architecture of the computer-implemented interactive surgical system, in accordance with at least one aspect of the present disclosure. The cloud-based analytics system includes a plurality of data analytics modules 7034 that may be executed by the processors 7008 of the cloud 7004 for providing data analytic solutions to problems specifically arising in the medical field. As shown in FIG. 13, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 define the set of protocols and routines corresponding to the hub applications 7014. Additionally, the APIs 7016 manage the storing and retrieval of data into and from the aggregated medical data databases 7011 for the operations of the applications 7014. The caches 7018 also store data (e.g., temporarily) and are coupled to the APIs 7016 for more efficient retrieval of data used by the applications 7014. The data analytics modules 7034 in FIG. 13 include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules are used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical hub 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently.

The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that are transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004.

Furthermore, for security purposes, the cloud could maintain a database of hubs 7006, instruments 7012, and other devices that may comprise a "black list" of prohibited devices. In particular, a surgical hub 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local zone of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described above to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g. a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been compromised, for example.

In various aspects, the surgical instrument(s) 7012 described above with reference to FIGS. 12 and 13, may be implemented as a powered circular stapling device 201800 (FIGS. 24-30) and 201000 (FIGS. 31-32). Accordingly, the powered circular stapling device 201800 (FIGS. 24-30) and 201000 (FIGS. 31-32) is configured to interface with the surgical hub 7006 and the network 2001, which is configured to interface with cloud 7004. Accordingly, the processing power provided by the central servers 7013 and the data analytics module 7034 are configured to process information (e.g., data and control) from the powered circular stapling device 201800 (FIGS. 24-30) and 201000 (FIGS. 31-32). Additional details regarding the cloud analysis system can be found in U.S. Provisional Patent Application No. 62/659,900, titled METHOD OF HUB COMMUNICATION, filed Apr. 19, 2018, which is hereby incorporated by reference herein in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 14:
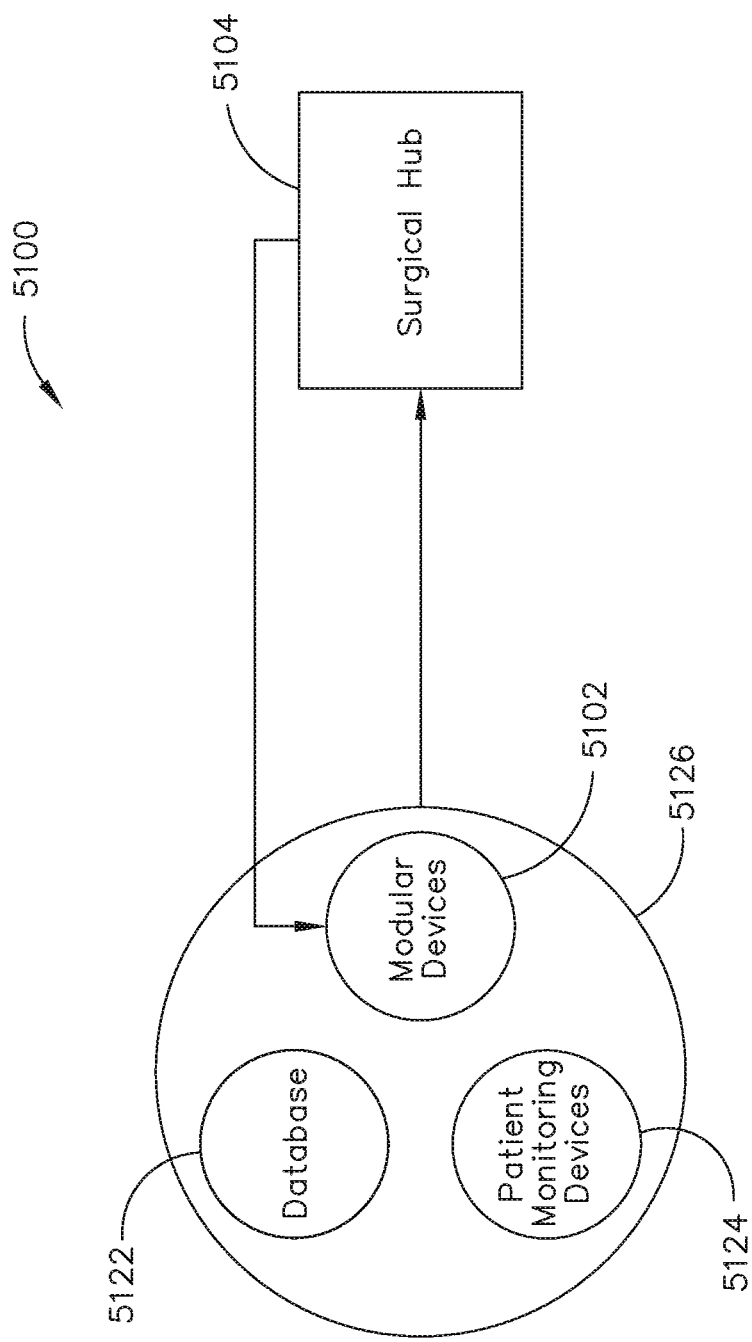
FIG. 14 illustrates a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 14 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor).

A surgical hub 5104, which may be similar to the hub 106 in many respects, can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure scanned by a suitable scanner for example and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

In one aspect, as described hereinbelow with reference to FIGS. 24-40, the modular device 5102 is implemented as a powered circular stapling device 201800 (FIGS. 24-30) and 201000 (FIGS. 31-32). Accordingly, the modular device 5102 implemented as a powered circular stapling device 201800 (FIGS. 24-30) and 201000 (FIGS. 31-32) is configured to operate as a data source 5126 and to interact with the database 5122 and patient monitoring devices 5124. The modular device 5102 implemented as a powered circular stapling device 201800 (FIGS. 24-30) and 201000 (FIGS. 31-32) is further configured to interact with the surgical hub 5104 to provide information (e.g., data and control) to the surgical hub 5104 and receive information (e.g., data and control) from the surgical hub 5104.

Figure 15:
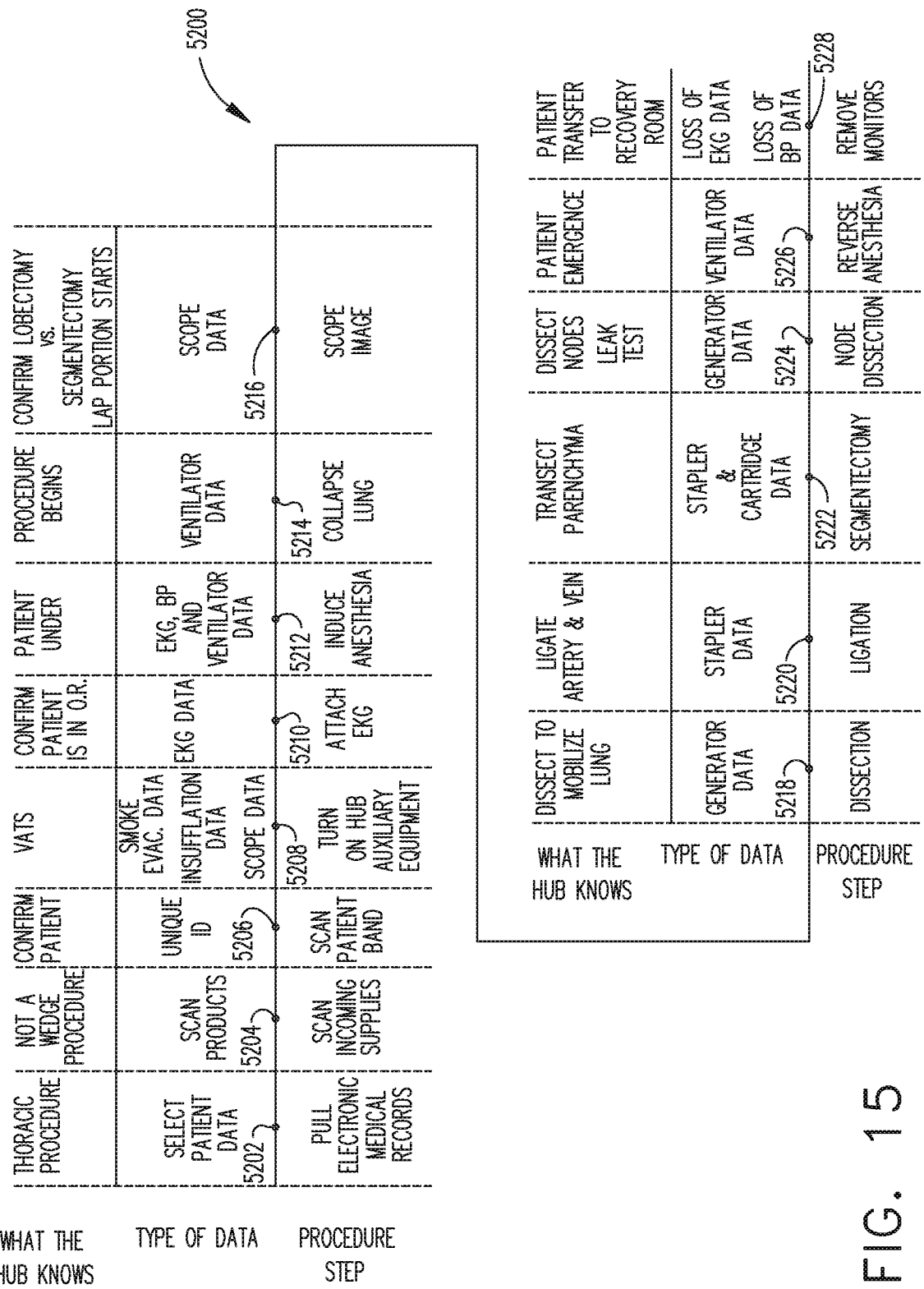
FIG. 15 is a timeline depicting situational awareness of a surgical hub, in accordance with at least one aspect of the present disclosure.

Referring now to FIG. 15, a timeline 5200 depicting situational awareness of a hub, such as the surgical hub 106 or 206 (FIGS. 1-11), for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 5202 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step 5204, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 5206, the medical personnel scan the patient band via a scanner that is communicably connected to the surgical hub 106, 206. The surgical hub 106, 206 can then confirm the patient's identity based on the scanned data.

Fourth step 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 5210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 5212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step 5212, the pre-operative portion of the lung segmentectomy procedure is completed and the operative portion begins.

Seventh step 5214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 5216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 5218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 5220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 5222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 5224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 5224, the incisions are closed up and the post-operative portion of the procedure begins.

Thirteenth step 5226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 5228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

In various aspects, the powered circular stapling device 201800 (FIGS. 24-30) and 201000 (FIGS. 31-32) is configured to operate in a situational awareness in a hub environment, such as the surgical hub 106 or 206 (FIGS. 1-11), for example, as depicted by the timeline 5200. Situational awareness is further described in U.S. Provisional Patent Application Ser. No. 62/659,900, titled METHOD OF HUB COMMUNICATION, filed Apr. 19, 2018, which is herein incorporated by reference in its entirety. In certain instances, operation of a robotic surgical system, including the various robotic surgical systems disclosed herein, for example, can be controlled by the hub 106, 206 based on its situational awareness and/or feedback from the components thereof and/or based on information from the cloud 104.

Surgical Instrument Hardware

Figure 16:
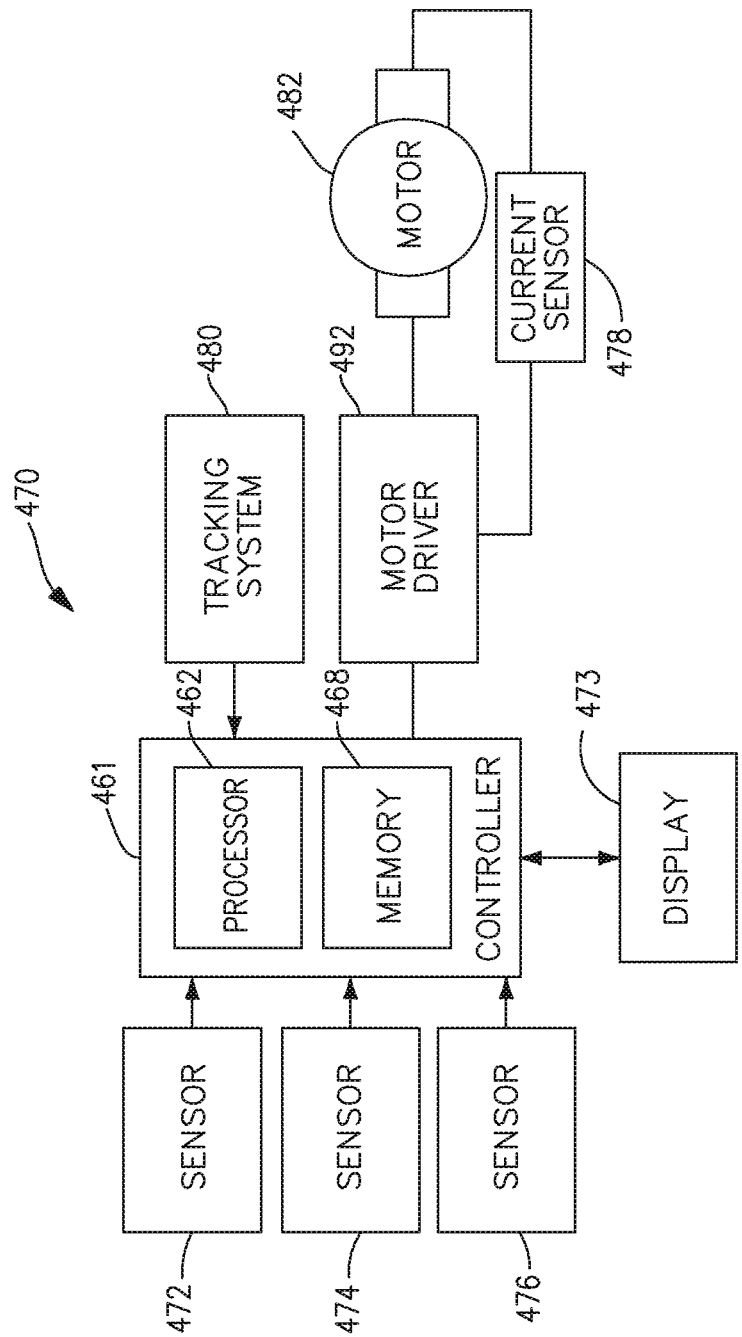
FIG. 16 illustrates a logic diagram of a control system of a surgical instrument or tool, in accordance with at least one aspect of the present disclosure.

FIG. 16 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the knife element, trocar, or anvil of a powered circular stapling device. A tracking system 480 is configured to determine the position of the longitudinally movable displacement member. The position information is provided to the processor 462, which can be programmed or configured to determine the position of the longitudinally movable drive member as well as the position of a firing member, firing bar, and knife element. Additional motors may be provided at the tool driver interface to control knife firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the knife, each of which can be adapted and configured to include a rack of drive teeth. Accordingly, as used herein, the term displacement member is used generically to refer to any movable member of the surgical instrument or tool such as the drive member, the firing member, the firing bar, the knife, trocar or anvil of a powered circular stapling device, or any element that can be displaced. In one aspect, the longitudinally movable drive member is coupled to the firing member, the firing bar, and the knife. Accordingly, the absolute positioning system can, in effect, track the linear displacement of the knife by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the knife, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, knife, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to a knife in a firing stroke of the surgical instrument or tool. The knife is configured to engage a wedge sled, which is configured to upwardly cam staple drivers to force out staples into deforming contact with an anvil. The knife also includes a sharpened cutting edge that can be used to sever tissue as the knife is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 1-14. The control system 470 may be employed by the motorized circular stapling instrument 201800 (FIGS. 24-30), 201000 (FIGS. 31-32) to control aspects of the motorized circular stapling instruments 201800, 201000. Aspects of the control system 470 may be employed by the motorized circular stapling instruments 201800, 201000 to sense the position of the anvil, tissue compression forces, among others, by employing 472, 474, 476, the tracking system 480, and current sensor 478 to provide feedback to the controller 461.

Figure 17:
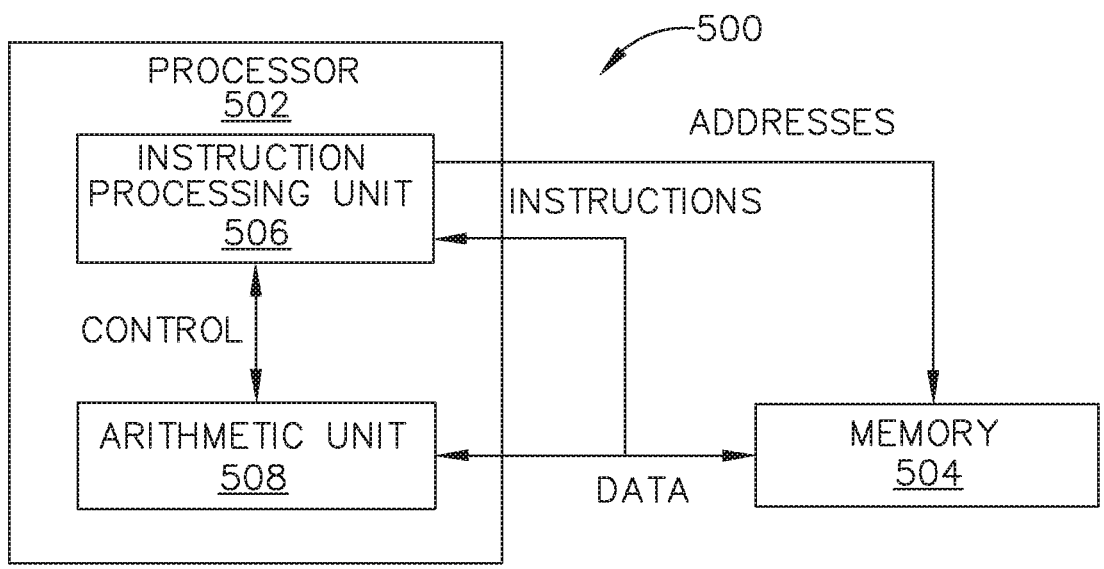
FIG. 17 illustrates a control circuit configured to control aspects of the surgical instrument or tool, in accordance with at least one aspect of the present disclosure.

FIG. 17 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 18:
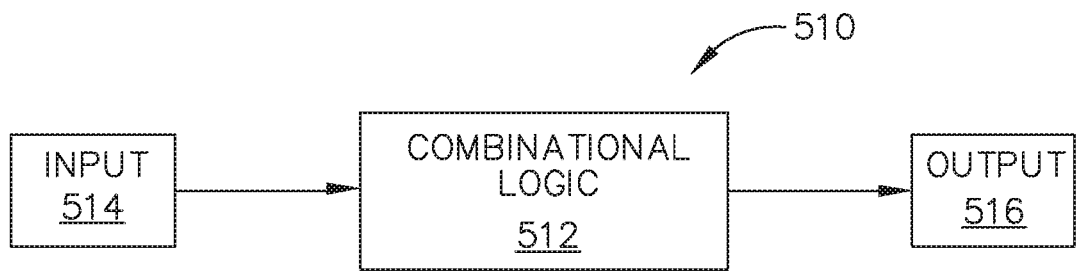
FIG. 18 illustrates a combinational logic circuit configured to control aspects of the surgical instrument or tool, in accordance with at least one aspect of the present disclosure.

FIG. 18 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 19:
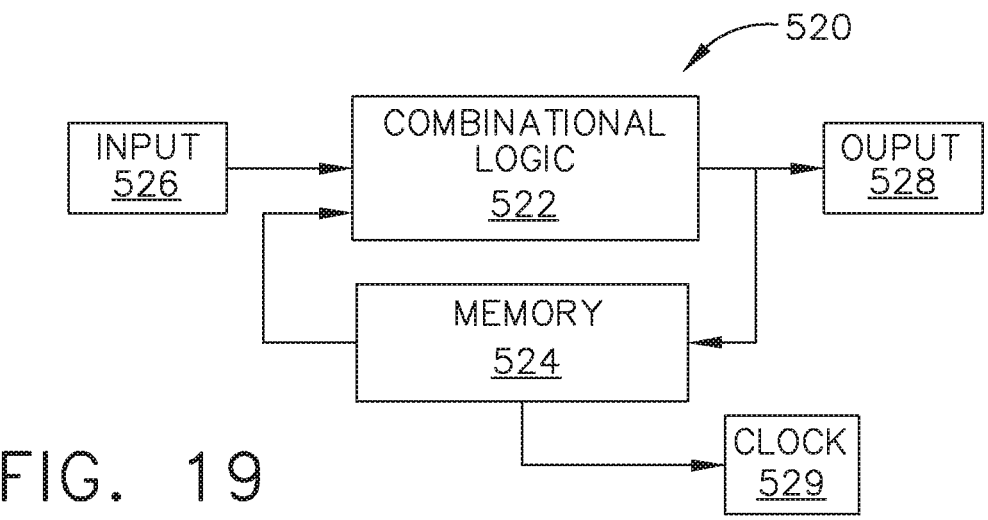
FIG. 19 illustrates a sequential logic circuit configured to control aspects of the surgical instrument or tool, in accordance with at least one aspect of the present disclosure.

FIG. 19 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 17) and a finite state machine to implement various processes herein. In other aspects, the finite state machine may comprise a combination of a combinational logic circuit (e.g., combinational logic circuit 510, FIG. 18) and the sequential logic circuit 520.

Figure 20:
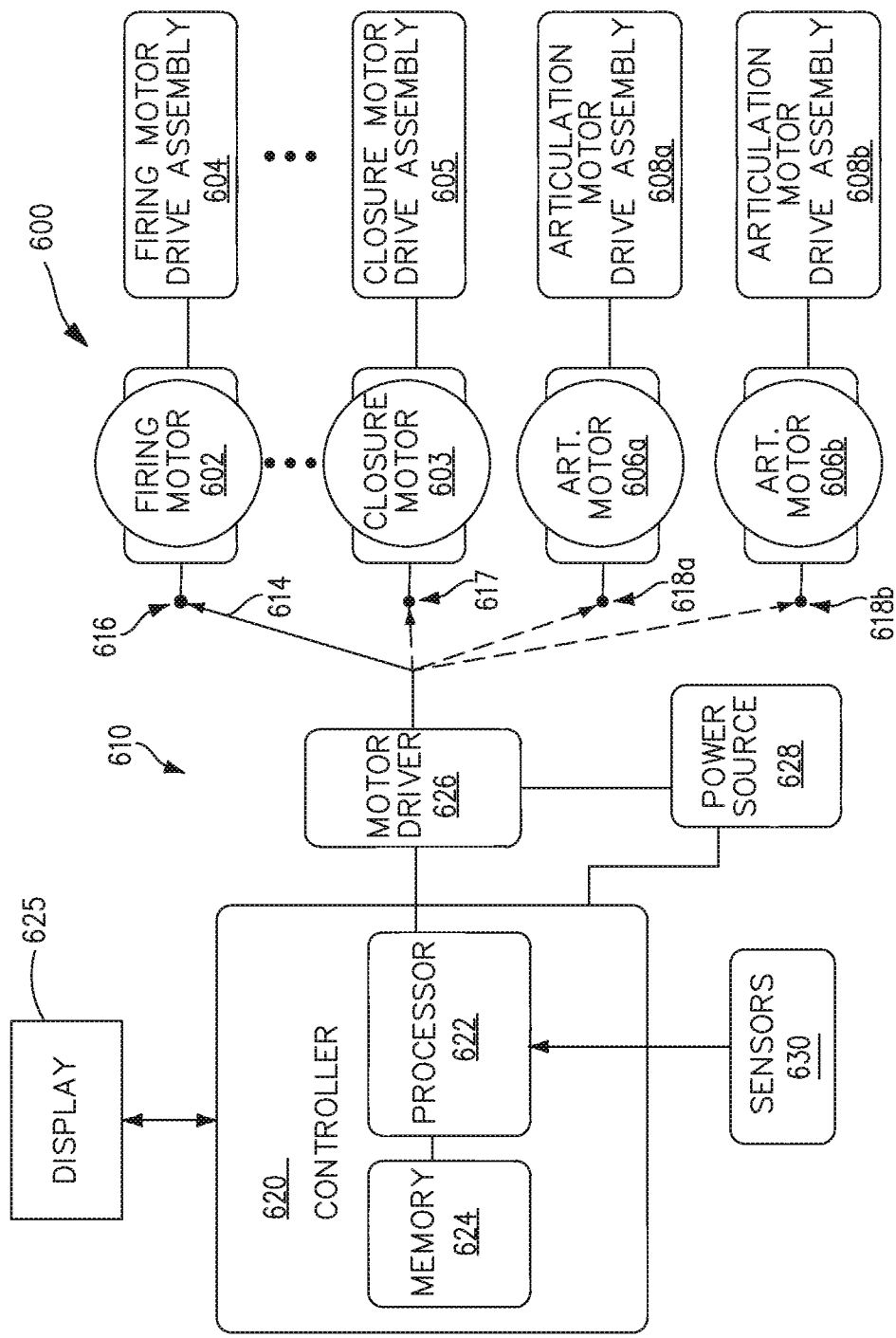
FIG. 20 illustrates a surgical instrument or tool comprising a plurality of motors which can be activated to perform various functions, in accordance with at least one aspect of the present disclosure.

FIG. 20 illustrates a surgical instrument 600 or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of the surgical instrument 600 can be individually activated to cause firing, closure, and/or articulation motions in the end effector. The firing, closure, and/or articulation motions can be transmitted to the end effector through a shaft assembly, for example. In one aspect, the surgical instrument 600 is representative of a hand held surgical instrument. In another aspect, the surgical instrument 600 is representative of a robotic surgical instrument. In other aspects, the surgical instrument 600 is representative of a combination of a hand held and robotic surgical instrument. In various aspects, the surgical stapler 600 may be representative of a linear stapler or a circular stapler.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the knife element. In certain instances, the firing motions generated by the motor 602 may cause the staples to be deployed from the staple cartridge into tissue captured by the end effector and/or the cutting edge of the knife element to be advanced to cut the captured tissue, for example. The knife element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603. In a circular stapler implementation, the motor 603 may be coupled to a trocar portion of a circular stapler portion of a powered stapling device. The motor 603 can be employed to advance and retract the trocar.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the knife element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 20, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 20, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the knife of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

The surgical instrument 600 may comprise wired or wireless communication circuits to communicate with the modular communication hub as shown in FIGS. 1-14. The surgical instrument 600 may be the motorized circular stapling instrument 201800 (FIGS. 24-30), 201000 (FIGS. 31-32).

Figure 21:
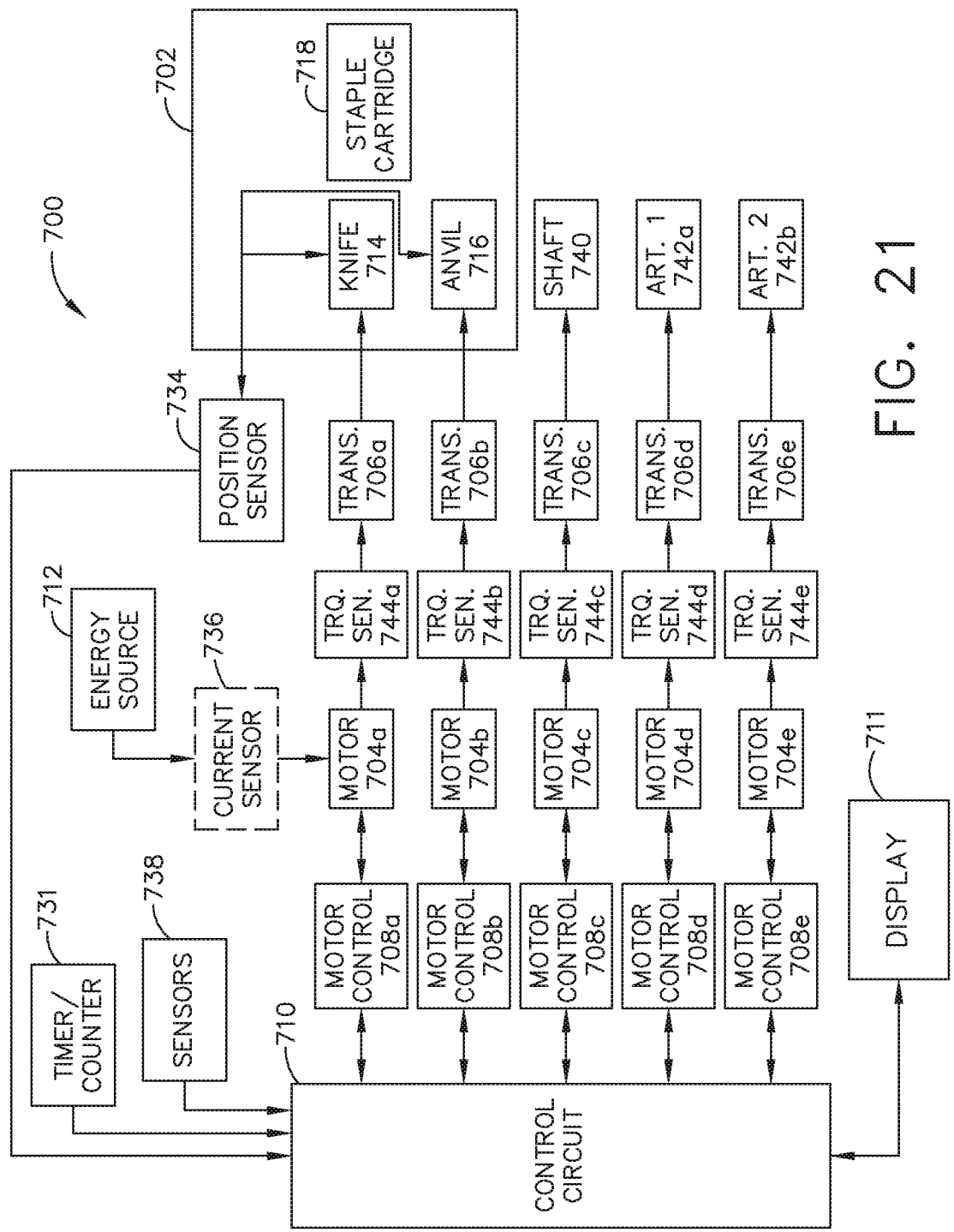
FIG. 21 is a schematic diagram of a surgical instrument configured to operate a surgical tool described herein, in accordance with at least one aspect of the present disclosure.

FIG. 21 is a schematic diagram of a surgical instrument 700 configured to operate a surgical tool described herein according to one aspect of this disclosure. The surgical instrument 700 may be programmed or configured to control distal/proximal translation of a displacement member, distal/proximal displacement of a closure tube, shaft rotation, and articulation, either with single or multiple articulation drive links In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members. In one aspect, the surgical instrument 700 is representative of a hand held surgical instrument. In another aspect, the surgical instrument 700 is representative of a robotic surgical instrument. In other aspects, the surgical instrument 700 is representative of a combination of a hand held and robotic surgical instrument. In various aspects, the surgical stapler 700 may be representative of a linear stapler or a circular stapler.

In one aspect, the surgical instrument 700 comprises a control circuit 710 configured to control an anvil 716 and a knife 714 (or cutting element including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the knife 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the knife 714 as determined by the position sensor 734 with the output of the timer/counter 731 such that the control circuit 710 can determine the position of the knife 714 at a specific time (t) relative to a starting position or the time (t) when the knife 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the knife 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the knife 714. The position sensor 734 may be or include any type of sensor that is capable of generating position data that indicate a position of the knife 714. In some examples, the position sensor 734 may include an encoder configured to provide a series of pulses to the control circuit 710 as the knife 714 translates distally and proximally. The control circuit 710 may track the pulses to determine the position of the knife 714. Other suitable position sensors may be used, including, for example, a proximity sensor. Other types of position sensors may provide other signals indicating motion of the knife 714. Also, in some examples, the position sensor 734 may be omitted. Where any of the motors 704a-704e is a stepper motor, the control circuit 710 may track the position of the knife 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the knife 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the knife 714. The transmission 706a comprises movable mechanical elements such as rotating elements and a firing member to control the movement of the knife 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the knife 714. A position sensor 734 may be configured to provide the position of the knife 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, a knife 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In a circular stapler implementation, the transmission 706c element is coupled to the trocar to advance or retract the trocar. In one aspect, the shaft 740 is part of a closure system that comprises a trocar 201904 and a trocar actuator 201906 as discussed in more detail with reference to FIGS. 29A-29 hereinbelow. Accordingly, the control circuit 710 controls the motor control circuit 708c to control the motor 704c to advance or retract the trocar. A torque sensor 744c is provided to measure the torque applied by the shaft of the motor 704c to the transmission components 706c employed in advancing and retracting the trocar. The position sensor 734 may include a variety of sensors to track the position of the trocar, the anvil 716, or the knife 714, or any combination thereof. Other sensors 738 may be employed to measure a variety of parameters including position or velocity of the trocar, the anvil 716, or the knife 714, or any combination thereof. The torque sensor 744c, the position sensor 734, and the sensors 738 are coupled to the control circuit 710 as inputs to various processes for controlling the operation of the surgical instrument 700 in a desired manner.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements such as the knife 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move a knife 714 in the end effector 702 at or near a target velocity. The surgical instrument 700 can include a feedback controller, which can be one of any feedback controllers, including, but not limited to a PID, a state feedback, a linear-quadratic (LQR), and/or an adaptive controller, for example. The surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

The surgical instrument 700 may comprise wired or wireless communication circuits to communicate with the modular communication hub as shown in FIGS. 1-14. The surgical instrument 700 may be the motorized circular stapling instrument 201800 (FIGS. 24-30), 201000 (FIGS. 31-32).

Figure 22:
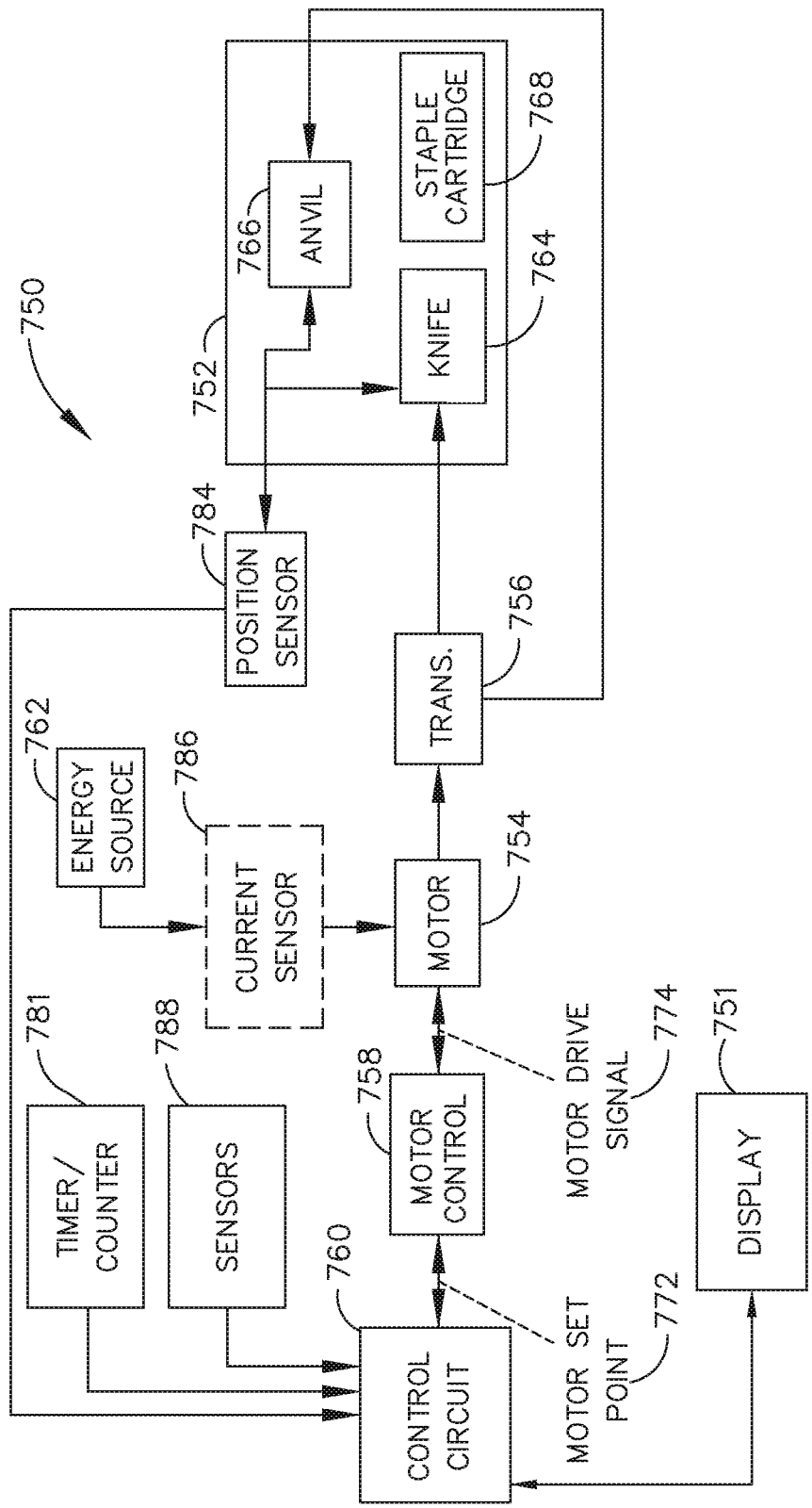
FIG. 22 illustrates a block diagram of a surgical instrument configured to control various functions, in accordance with at least one aspect of the present disclosure.

FIG. 22 illustrates a block diagram of a surgical instrument 750 configured to control various functions, according to one aspect of this disclosure. In one aspect, the surgical instrument 750 is programmed to control the distal translation of a displacement member such as the knife 764, or other suitable cutting element. The surgical instrument 750 comprises an end effector 752 that may comprise an anvil 766, a knife 764 (including a sharp cutting edge), and a removable staple cartridge 768.

The position, movement, displacement, and/or translation of a linear displacement member, such as the knife 764, can be measured by an absolute positioning system, sensor arrangement, and position sensor 784. Because the knife 764 is coupled to a longitudinally movable drive member, the position of the knife 764 can be determined by measuring the position of the longitudinally movable drive member employing the position sensor 784. Accordingly, in the following description, the position, displacement, and/or translation of the knife 764 can be achieved by the position sensor 784 as described herein. A control circuit 760 may be programmed to control the translation of the displacement member, such as the knife 764. The control circuit 760, in some examples, may comprise one or more microcontrollers, microprocessors, or other suitable processors for executing instructions that cause the processor or processors to control the displacement member, e.g., the knife 764, in the manner described. In one aspect, a timer/counter 781 provides an output signal, such as the elapsed time or a digital count, to the control circuit 760 to correlate the position of the knife 764 as determined by the position sensor 784 with the output of the timer/counter 781 such that the control circuit 760 can determine the position of the knife 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the knife 764 via a transmission 756. The transmission 756 may include one or more gears or other linkage components to couple the motor 754 to the knife 764. In one aspect, the transmission is coupled to a trocar actuator of a circular stapler to advance or retract the trocar. A position sensor 784 may sense a position of the knife 764, the trocar, or the anvil 766, or a combination thereof. The position sensor 784 may be or include any type of sensor that is capable of generating position data that indicate a position of the knife 764. In some examples, the position sensor 784 may include an encoder configured to provide a series of pulses to the control circuit 760 as the knife 764 translates distally and proximally. The control circuit 760 may track the pulses to determine the position of the knife 764. Other suitable position sensors may be used, including, for example, a proximity sensor. Other types of position sensors may provide other signals indicating motion of the knife 764. Also, in some examples, the position sensor 784 may be omitted. Where the motor 754 is a stepper motor, the control circuit 760 may track the position of the knife 764 by aggregating the number and direction of steps that the motor 754 has been instructed to execute. The position sensor 784 may be located in the end effector 752 or at any other portion of the instrument.

In a circular stapler implementation, the transmission 756 element may be coupled to the trocar to advance or retract the trocar, to the knife 764 to advance or retract the knife 764, or the anvil 766 to advance or retract the anvil 766. These functions may be implemented with a single motor using suitable clutching mechanism or may be implemented using separate motors as shown with reference to FIG. 21, for example. In one aspect, the transmission 756 is part of a closure system that comprises a trocar 201904 and a trocar actuator 201906 as discussed in more detail with reference to FIGS. 29A-29C hereinbelow. Accordingly, the control circuit 760 controls the motor control circuit 758 to control the motor 754 to advance or retract the trocar. Similarly, the motor 754 may be configured to advance or retract the knife 764 and advance or retract the anvil 766. A torque sensor may be provided to measure the torque applied by the shaft of the motor 754 to the transmission components 756 employed in advancing and retracting the trocar, the knife 764, or the anvil 766, or combinations thereof. The position sensor 784 may include a variety of sensors to track the position of the trocar, the knife 764, or the anvil 766, or any combination thereof. Other sensors 788 may be employed to measure a variety of parameters including position or velocity of the trocar, the knife 764, or the anvil 766, or any combination thereof. The torque sensor, the position sensor 784, and the sensors 788 are coupled to the control circuit 760 as inputs to various processes for controlling the operation of the surgical instrument 750 in a desired manner.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors. In one aspect, the sensors 788 may be configured to determine the position of a trocar of a circular stapler.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the knife 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a knife 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or knife 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, a knife 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the knife 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

The surgical instrument 750 may comprise wired or wireless communication circuits to communicate with the modular communication hub as shown in FIGS. 1-14. The surgical instrument 750 may be the motorized circular stapling instrument 201800 (FIGS. 24-30), 201000 (FIGS. 31-32).

Figure 23:
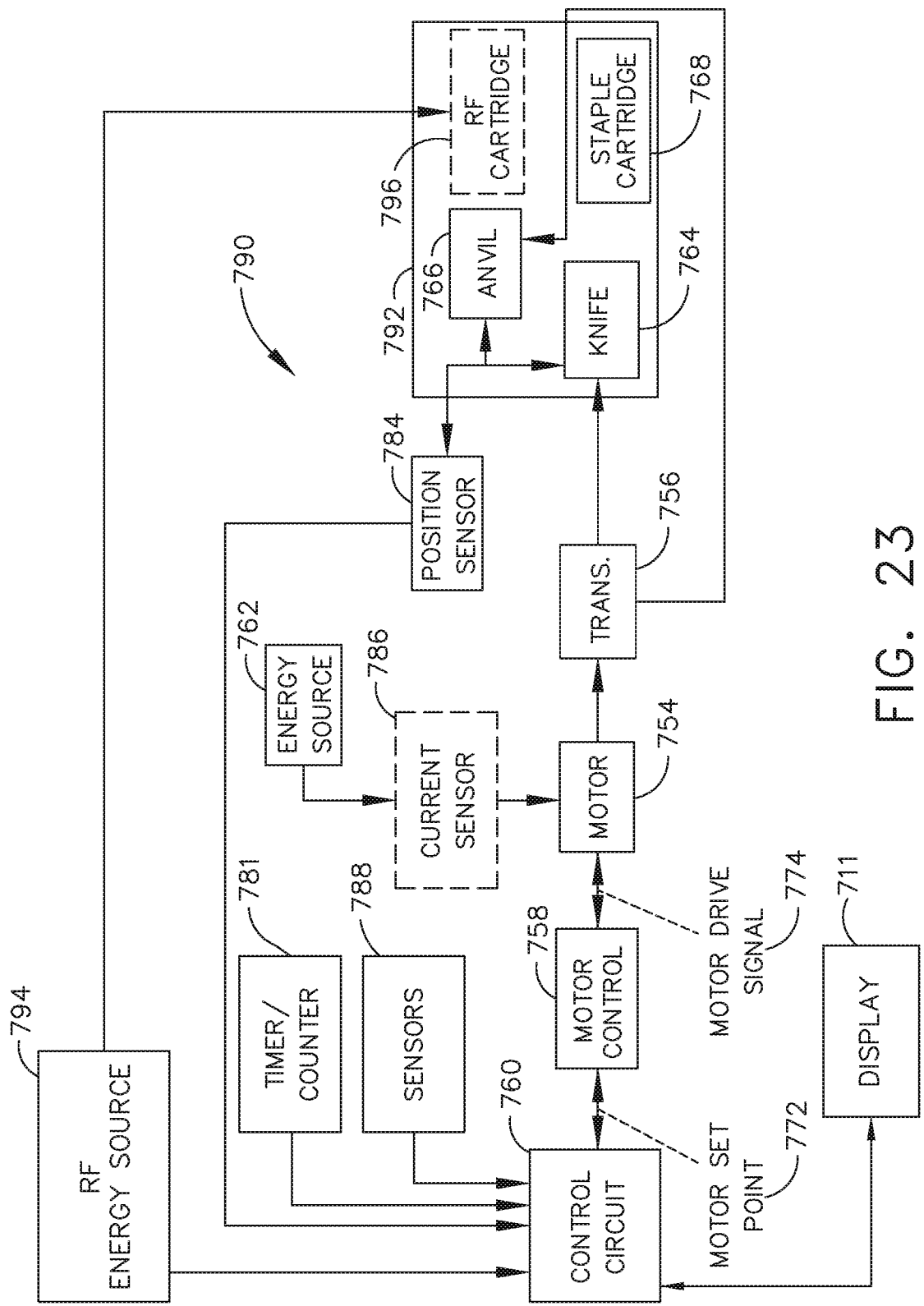
FIG. 23 is a schematic diagram of a surgical instrument configured to control various functions, in accordance with at least one aspect of the present disclosure.

FIG. 23 is a schematic diagram of a surgical instrument 790 configured to control various functions according to one aspect of this disclosure. In one aspect, the surgical instrument 790 is programmed to control distal translation of a displacement member such as the knife 764. The surgical instrument 790 comprises an end effector 792 that may comprise an anvil 766, a knife 764, and a removable staple cartridge 768 which may be interchanged with an RF cartridge 796 (shown in dashed line).

With reference to FIGS. 21-23, in various aspects, sensors 738, 788 may be implemented as a limit switch, electromechanical device, solid-state switches, Hall-effect devices, MR devices, GMR devices, magnetometers, among others. In other implementations, the sensors 738, 788 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738, 788 may include electrical conductorless switches, ultrasonic switches, accelerometers, and inertial sensors, among others.

In one aspect, the position sensor 734, 784 may be implemented as an absolute positioning system comprising a magnetic rotary absolute positioning system implemented as an AS5055EQFT single-chip magnetic rotary position sensor available from Austria Microsystems, AG. The position sensor 734, 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the knife 714, 764 may be implemented as a knife member comprising a knife body that operably supports a tissue cutting blade thereon and may further include anvil engagement tabs or features and channel engagement features or a foot. In one aspect, the staple cartridge 718, 768 may be implemented as a standard (mechanical) surgical fastener cartridge, which may be a linear staple cartridge or a circular staple cartridge. In one aspect, the RF cartridge 796 (FIG. 23) may be implemented as an RF cartridge. These and other sensors arrangements are described in commonly owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety.

The position, movement, displacement, and/or translation of a linear displacement member, such as the trocar, the knife 714, 764, or the anvil 716, 766 can be measured by an absolute positioning system, sensor arrangement, and position sensor represented as position sensor 734, 784. Because the knife 714, 764 is coupled to the longitudinally movable drive member, the position of the trocar, the knife 714, 764, or the anvil 716, 766 can be determined by measuring the position of the longitudinally movable drive member employing the position sensor 734, 784. Accordingly, in the following description, the position, displacement, and/or translation of the trocar, the knife 764, or the anvil 716, 766 can be achieved by the position sensor 734, 784 as described herein. A control circuit 710, 760 may be programmed to control the translation of the displacement member, such as the trocar, the knife 764, or the anvil 716, 766 as described herein. The control circuit 710, 760, in some examples, may comprise one or more microcontrollers, microprocessors, or other suitable processors for executing instructions that cause the processor or processors to control the displacement member, e.g., the trocar, the knife 764, or the anvil 716, 766 in the manner described. In one aspect, a timer/counter 731, 781 provides an output signal, such as the elapsed time or a digital count, to the control circuit 710, 760 to correlate the position of trocar, the knife 714, 764, or the anvil 716, 766 as determined by the position sensor 734, 784 with the output of the timer/counter 731, 781 such that the control circuit 710, 760 can determine the position of the trocar, the knife 714, 764, or the anvil 716, 766 at a specific time (t) relative to a starting position. The timer/counter 731, 781 may be configured to measure elapsed time, count external events, or time external events.

The control circuit 710, 760 may generate a motor set point signal 772. The motor set point signal 772 (to each motor when multiple motors are used) may be provided to a motor controller 708*a-e*, 758. The motor controller 708*a-e*, 758 may comprise one or more circuits configured to provide a motor drive signal 774 to the motor 704*a-e*, 754 to drive the motor 704*a-e*, 754 as described herein. In some examples, the motor 704*a-e*, 754 may be a brushed DC electric motor. For example, the velocity of the motor 704*a-e*, 754 may be proportional to the motor drive signal 774. In some examples, the motor 704*a-e*, 754 may be a brushless DC electric motor and the motor drive signal 774 may comprise a PWM signal provided to one or more stator windings of the motor 704*a-e*, 754. Also, in some examples, the motor controller 708*a-e*, 758 may be omitted, and the control circuit 710, 760 may generate the motor drive signal 774 directly.

The motor 704*a-e*, a battery, a super capacitor, or any other suitable energy source. The motor 704*a-e*, 754 may be mechanically coupled to the trocar, the knife 764, or the anvil 716, 766 via a transmission 706*a-e*, 756. The transmission 706*a-e*, 756 may include one or more gears or other linkage components to couple the motor 704*a-e*, 754 to the trocar, the knife 764, or the anvil 716, 766. A position sensor 734, 784 may sense a position of the trocar, the knife 714, 764, or the anvil 716, 766. The position sensor 734, 784 may be or include any type of sensor that is capable of generating position data that indicate a position of the trocar, the knife 764, or the anvil 716, 766. In some examples, the position sensor 734, 784 may include an encoder configured to provide a series of pulses to the control circuit 710, 760 as the trocar, the knife 764, or the anvil 716, 766 translates distally and proximally. The control circuit 710, 760 may track the pulses to determine the position of the trocar, the knife 714, 764, or the anvil 716, 766. Other suitable position sensors may be used, including, for example, a proximity sensor. Other types of position sensors may provide other signals indicating motion of the trocar, the knife 764, or the anvil 716, 766. Also, in some examples, the position sensor 734, 784 may be omitted. Where the motor 704*a-e*, 754 is a stepper motor, the control circuit 710, 760 may track the position of the trocar, the knife 714, 764, or the anvil 716, 766 by aggregating the number and direction of steps that the motor 704*a-e*, 754 has been instructed to execute. The position sensor 734, 784 may be located in the end effector 702, 752, 792 or at any other portion of the instrument.

The control circuit 710, 760 may be in communication with one or more sensors 738, 788. The sensors 738, 788 may be positioned on the end effector 702, 752, 792 and adapted to operate with the surgical instrument 700, 750, 790 to measure the various derived parameters such as gap distance versus time, tissue compression versus time, and anvil strain versus time. The sensors 738, 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 702, 752, 792. The sensors 738, 788 may include one or more sensors.

The one or more sensors 738, 788 may comprise a strain gauge, such as a micro-strain gauge, configured to measure the magnitude of the strain in the anvil 716, 766 during a clamped condition. The strain gauge provides an electrical signal whose amplitude varies with the magnitude of the strain. The sensor 738, 788 may comprise a pressure sensor configured to detect a pressure generated by the presence of compressed tissue between the anvil 716, 766 and the staple cartridge 718, 768. The sensors 738, 788 may be configured to detect impedance of a tissue section located between the anvil 716, 766 and the staple cartridge 718, 768 that is indicative of the thickness and/or fullness of tissue located therebetween.

The sensors 738, 788 may be is configured to measure forces exerted on the anvil 716, 766 by the closure drive system. For example, one or more sensors 738, 788 can be at an interaction point between a closure tube and the anvil 716, 766 to detect the closure forces applied by a closure tube to the anvil 716, 766. The forces exerted on the anvil 716, 766 can be representative of the tissue compression experienced by the tissue section captured between the anvil 716, 766 and the staple cartridge 738, 768. The one or more sensors 738, 788 can be positioned at various interaction points along the closure drive system to detect the closure forces applied to the anvil 716, 766 by the closure drive system. The one or more sensors 738, 788 may be sampled in real time during a clamping operation by a processor portion of the control circuit 710, 760. The control circuit 760 receives real-time sample measurements to provide and analyze time-based information and assess, in real time, closure forces applied to the anvil 716, 766.

A current sensor 736, 786 can be employed to measure the current drawn by the motor 704*a-e*, 754. The force required to advance the trocar, the knife 714, 764, or the anvil 716, 766 corresponds to the current drawn by the motor 704*a-e*, 754. The force is converted to a digital signal and provided to the control circuit 710, 760.

With reference to FIG. 23, an RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

The surgical instrument 790 may comprise wired or wireless communication circuits to communicate with the modular communication hub as shown in FIGS. 1-14. The surgical instrument 790 may be the motorized circular stapling instrument 201800 (FIGS. 24-30), 201000 (FIGS. 31-32).

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Motorized Circular Stapling Surgical Instrument

Figure 24:
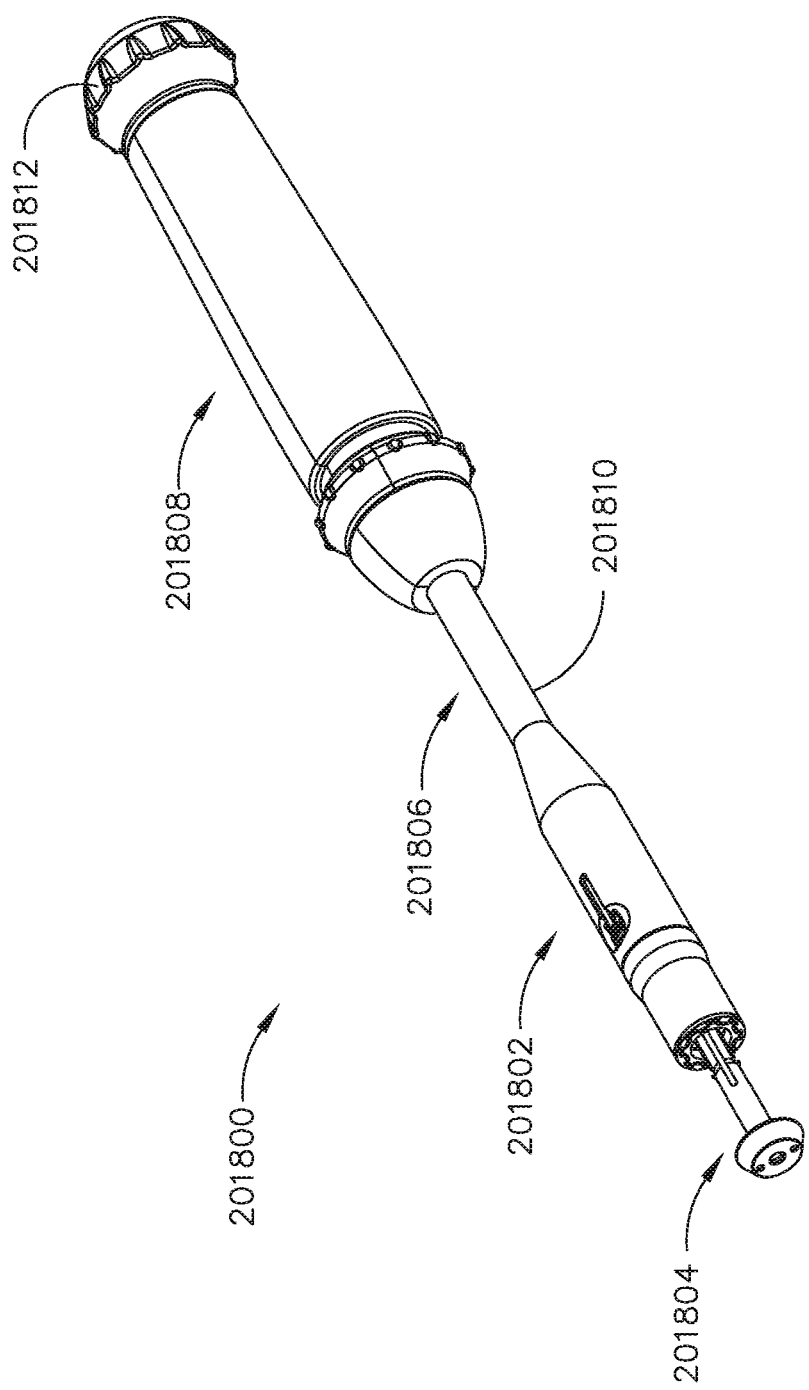
FIG. 24 depicts a perspective view of a circular stapling surgical instrument, in accordance with at least one aspect of the present disclosure.

In some instances, it may be desirable to provide motorized control of a circular stapling instrument. The examples below include merely an illustrative version of a circular stapling instrument where a single motor can be used to control both clamping and cutting/stapling of tissue via a single rotary drive. FIG. 24 shows an example motorized circular stapling instrument 201800. The Instrument 201800 of this example comprises a stapling head assembly 201802, an anvil 201804, a shaft assembly 201806, a handle assembly 201808, and a rotation knob 201812. The stapling head assembly 201802 selectively couples with the anvil 201804. The stapling head assembly 201802 is operable to clamp tissue between staple pockets and staple forming pockets of the anvil 201804. The stapling head assembly 201802 comprises a cylindrical knife that is operable to sever tissue captured between stapling head assembly 201802 and the anvil 201804. The stapling head assembly 201802 drives staples through the tissue captured between stapling head assembly 201802 and the anvil 201804. The stapling instrument 201800 may be used to create a secure anastomosis (e.g., an end-to-end anastomosis) within a gastro-intestinal tract of a patient or elsewhere. An outer tubular member 201810 is coupled to the actuator handle assembly 201808. The outer tubular member 201810 provides a mechanical ground between the stapling head assembly 201802 and the handle assembly 201808.

The stapling head assembly 201802 is operable to clamp tissue, sever tissue, and staple tissue all in response to a single rotary input communicated via the shaft assembly 201806. Accordingly, actuation inputs translated linearly through shaft assembly 201806 are not required for the stapling head assembly 201802, though the stapling head assembly 201802 may comprise a translating clutch feature. By way of example only, at least part of stapling head assembly 201802 may be configured in accordance with at least some of the teachings of U.S. patent application Ser. No. 13/716,318, entitled "Motor Driven Rotary Input Circular Stapler with Modular End Effector," filed on Dec. 17, 2012, and published as U.S. Pat. Pub. No. 2014/0166728 on Jun. 19, 2014, the disclosure of which is incorporated by reference herein. Other suitable configurations for the stapling head assembly 201802 will be apparent to those of ordinary skill in the art in view of the teachings herein.

The shaft assembly 201806 couples the handle assembly 201808 with the stapling head assembly 201802. The shaft assembly 201806 comprises a single actuation feature, rotary driver actuator 201814 shown in FIG. 25. The driver actuator 201814 is operable to drive the stapling head assembly 201802 to clamp tissue, sever tissue, and staple tissue. Accordingly, linear actuation through the shaft assembly 201806 is not required, though the rotary driver actuator 201814 may translate longitudinally to shift between a tissue clamping mode and a tissue cutting/stapling mode. For instance, the driver actuator 201814 may translate from a first longitudinal position, in which rotation of the driver actuator 201814 provides clamping of tissue at the stapling head assembly 201802, to a second longitudinal position, in which rotation of driver actuator 210814 provides cutting and stapling of tissue at the stapling head assembly 201802. Some versions of the shaft assembly 201806 may include one or more flexible sections. An example of a shaft assembly that is configured with flexible sections and that may be incorporated into shaft assembly 201806 is disclosed in U.S. patent application Ser. No. 13/716,323, entitled "Motor Driven Rotary Input Circular Stapler with Lockable Flexible Shaft," filed on Dec. 17, 2012, and published as U.S. Pat. Pub. No. 2014/0166718 on Jun. 19, 2014, the disclosure of which is incorporated by reference herein. Alternatively, the shaft assembly 201806 may be rigid along the length of the shaft assembly 201806 or have one or more flexible sections configured in some other fashion.

Figure 25:
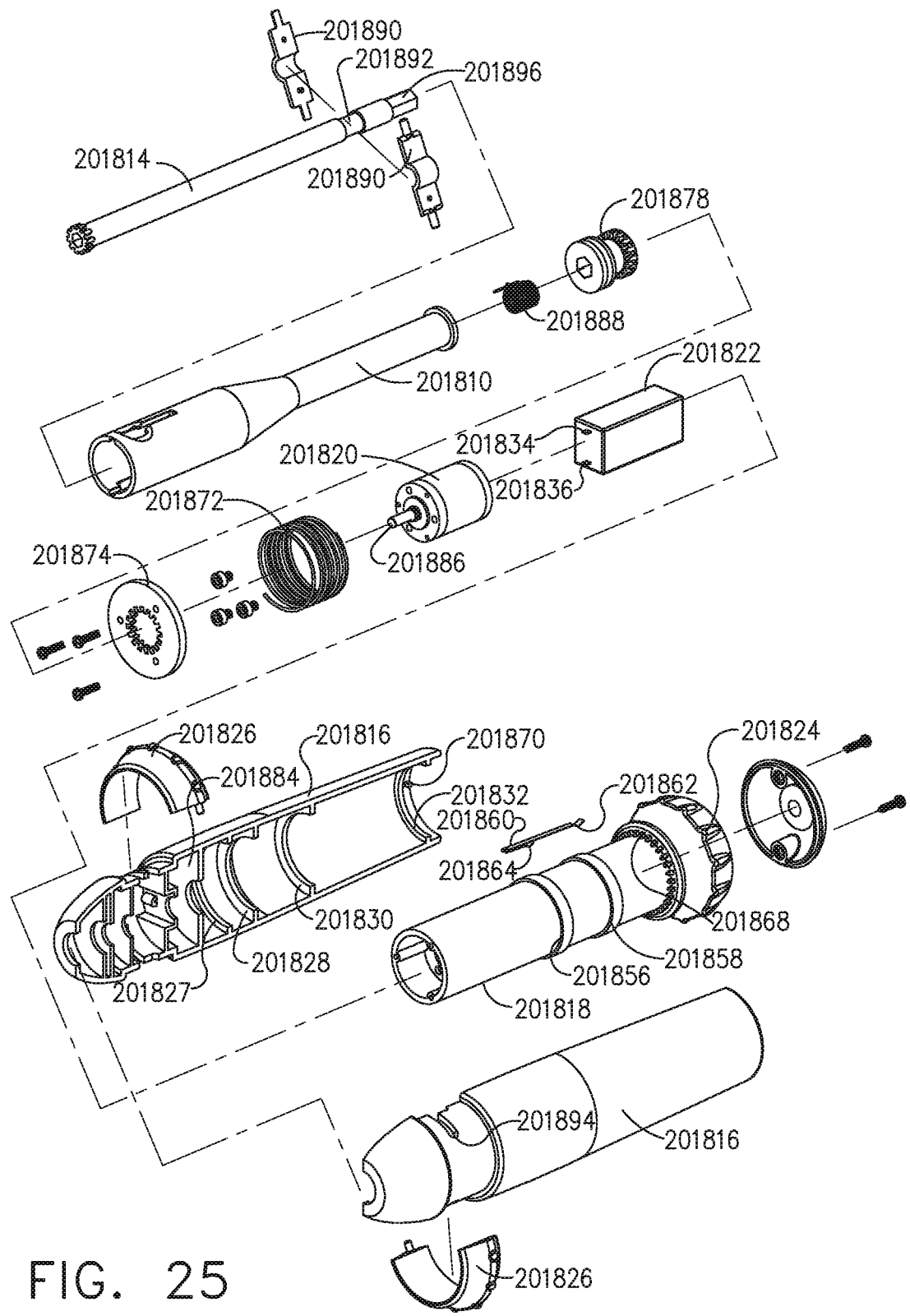
FIG. 25 depicts an exploded view of the handle and shaft assemblies of the instrument of FIG. 24, in accordance with at least one aspect of the present disclosure.

The handle assembly 201808 is shown in FIGS. 25-27. The handle assembly 201808 comprises a handle housing 201816, a motor housing 201818, a motor 201820, a battery 201822, a rotation knob 201812, and a firing ring 201826. The motor housing 201818 is positioned within the handle housing 201816. The handle housing 201816 comprises ribs (201827, 201828, 201830, 201832) extending inwardly into the handle housing 201816 to support the motor housing 201818, as shown in FIG. 26. The battery 201822 is positioned proximal to the motor 201820 within the motor housing 201818. The battery 201822 may be removed from the motor housing 201818 to be replaced, discarded, or recharged. As best seen in FIG. 27, the battery 201822 comprises electrical contacts 201834, 201836 extending distally from the battery 201822. The motor 201820 comprises electrical contacts 201838, 201840 extending proximally from the motor 201820. The battery electrical contact 201836 and the motor electrical contact 201840 are coupled via a conductive metal band 201842. A screw 201844 couples the band 201842 to the motor housing 201818 to fix the position of the band 201842 relative to the motor housing 201818. Accordingly, the band 201842 is configured to constantly couple the battery electrical contact 201836 and the motor electrical contact 201840.

As shown in FIG. 27, a battery electrical contact 201846 is coupled to a conductive metal band 201848. The metal band 201848 is secured to the motor housing 201818 via a conductive screw 201854. The motor electrical contact 201838 is coupled to a conductive metal band 201852. The metal band 201852 is secured to the motor housing 201818 via a conductive screw 201850. The motor housing 201818 is formed of an electrically insulative material (e.g., plastic) and comprises annular contacts 201856, 201858 wrapped around the motor housing 201818. Screws 201850, 201854 are each coupled with a respective annular contact 201856, 201858 to electrically couple the battery electrical contact 201834 and the motor electrical contact 201838 to the annular contacts 201856, 201858, respectively.

Another conductive metal band 201860 is secured to the handle housing 201816. Each end of the metal band 201860 forms a respective spring contact 201862, 201864. The motor housing 201818 translates proximally and/or distally relative to handle housing 201816 to selectively couple and/or decouple the spring contacts 201862, 201864 with annular contacts 201856, 201858. In particular, when the motor housing 201818 is in a distal position, the spring contact 201862 engages the annular contact 201856 and the spring contact 201864 engages the annular contact 201858 to couple the battery 201822 with the motor 201820 and supply power to the motor 201820. It should be understood that, since the spring contacts 201862, 201864 are part of the same conductive metal band 201860, and since the contacts 201836, 201840 are already coupled via a band 201866, the engagement between the spring contacts 201862, 201864 and the annular contacts 201856, 201858 completes a circuit between the battery 201822 and the motor 201820. This positioning is used to provide motorized actuation of the stapling head assembly 201802. When the motor housing 201818 is in a proximal position, the spring contacts 201862, 201864 are decoupled from the annular contacts 201856, 201858, such that the battery 201822 is decoupled from the motor 201820 and the motor 201820 does not receive power. This positioning is used to provide manual actuation of stapling head assembly 201802. The annular shape of the annular contacts 201856, 201858 enables proper contact between the spring contacts 201862, 201864 and the annular contacts 201856, 201858 regardless of the angular position of the motor housing 201818 within the handle housing 201816. In some versions, the band 201860 may include a break that is coupled with an external switch, such that a user may actuate the external switch in order to complete the coupling between the battery 201822 and the motor 201820 after the motor housing 201818 is in the distal position.

A proximal end of motor housing 201818 is fixedly secured to rotation knob 201812, as shown in FIG. 25. In one aspect, rotation knob 201812 may be coupled to a motor to rotate the rotation knob 201812. Rotation knob 201812 protrudes proximally from handle housing 201816 and comprises splines 201868 extending distally from rotation knob 201812. Handle housing 201816 comprises corresponding teeth 201870 to selectively engage splines 201868. Rotation knob 201812 is pulled and/or pushed to translate motor housing 201818 within handle housing 201816. When rotation knob 201812 is in a proximal position, splines 201868 are disengaged from handle housing 201816 such that rotation knob 201812 and motor housing 201818 are free to rotate relative to handle housing 201816. This positioning is used to provide manual actuation of stapling head assembly 201802. When rotation knob 201812 is in a distal position, splines 201868 engage corresponding teeth 201870 in handle housing 201816 to lock rotation knob 201812 and motor housing 201818 from rotating relative to handle housing 201816. Splines 201868 and teeth 201870 thus provide a mechanical ground for motor housing 201818 relative to handle housing 201816. This positioning is used to provide motorized actuation of stapling head assembly 201802 as will be described in greater detail below. Rotation knob 201812 is biased to the distal position by a resilient member 201872 in handle housing 201816. In particular, resilient member 201872 extends distally from rib 201828 of handle housing 201816 to a first gear 201874, which is unitarily secured to the distal end of motor housing 201818. When rotation knob 201812 is in the proximal position, resilient member 201872 compresses between first gear 201874 and rib 201828 to resiliently bias handle housing 201816 to the distal position.

Figure 28A:
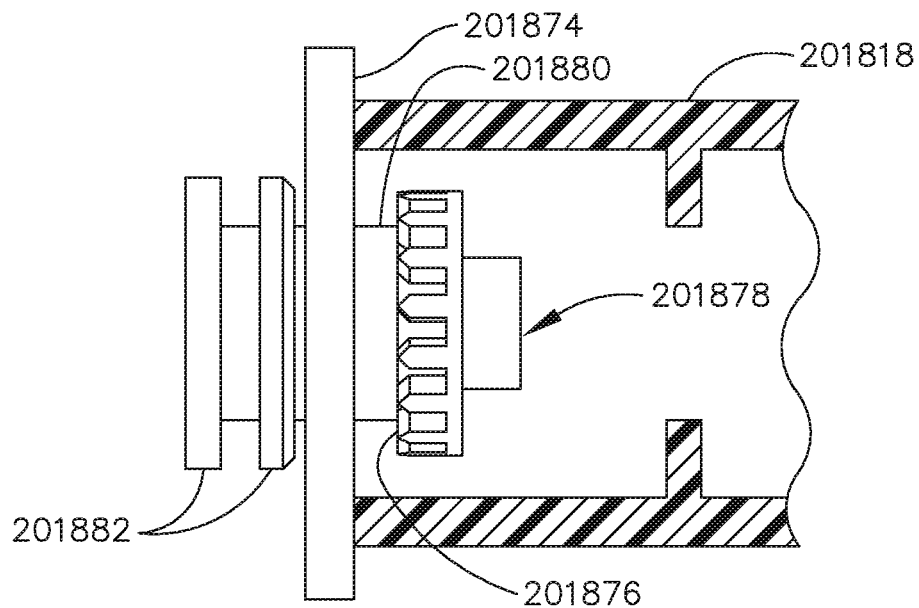
FIG. 28A depicts a side elevational view of an operational mode selection assembly of the instrument of FIG. 24, with a first gear disengaged from a second gear, in accordance with at least one aspect of the present disclosure.
Figure 28B:
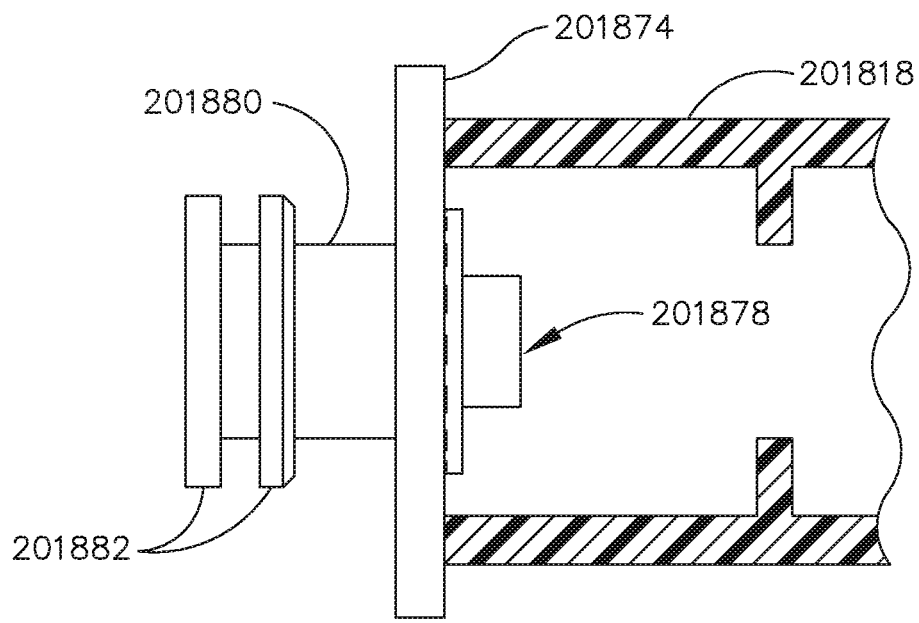
FIG. 28B depicts a side elevational view of the operational mode selection assembly of FIG. 28A, with the first gear engaged with the second gear, in accordance with at least one aspect of the present disclosure.

An operational mode selection assembly is positioned distal to motor housing 201818 within handle housing 201816. As shown in FIGS. 28A-28B, the operational mode selection assembly comprises a first gear 201874 and a second gear 201878, with first gear 201874 being coaxially and slidably disposed about second gear 201878. First gear 201874 comprises square teeth aligned around an inner opening of first gear 201874. The square teeth define a circumferentially spaced array of recesses. Second gear 201878 comprises a shaft 201880, splines 201876, and annular flanges 201882, as shown in FIGS. 28A-28B. Shaft 201880 has a distally presented opening. Distally presented opening is hexagonal to receive proximal end 201896 of driver actuator 201814, which is also hexagonal (FIG. 25). Shaft 201880 also has a proximally presented opening (not shown) that is semi-circular to complement and receive drive shaft 201886 extending distally from motor 201820. Other suitable shapes and configurations of shafts 201896, 201886 may used to couple second gear 201878 with shafts 201896, 201886.

As shown in FIG. 28A, splines 201876 of second gear 201878 are positioned on a proximal end of shaft 201880 and extend distally. Splines 201876 correspond to teeth of first gear 201874, such that splines 201876 are configured to fit within the recesses defined between the teeth. A pair of annular flanges 201882 are positioned at a distal end of shaft 201880 and extend outwardly to engage an inwardly extending annular rib 201884 of handle housing 201816, thereby fixing the longitudinal position of second gear 201878 within handle housing 201816. While annular rib 201884 fixes the longitudinal position of second gear 201878 within handle housing 2001816, annular rib 201884 nevertheless allows second gear 201878 to rotate relative to handle housing 201816. Other suitable engagement features to longitudinally fix second gear 201878 will be apparent to one with ordinary skill in the art based on the teachings herein.

First gear 201874 is positioned around second gear 201878, as shown in FIGS. 28A-28B. First gear 201874 is fixedly coupled to a distal end of motor housing 201818 such that first gear 201874 translates and rotates unitarily with motor housing 201818. When motor housing 201818 is in a proximal position, as shown in FIG. 28B, motor 201820 and first gear 201874 are also in a proximal position. In this position, drive shaft 201886 of motor 201820 is disengaged from second gear 201878 and teeth of first gear 201874 engage splines of second gear 201878. Thus, when rotation knob 201812 rotates, motor housing 201818 and first gear 201874 also rotate. This positioning thereby provides manual actuation of stapling head assembly 201802. With teeth of first gear 2018784 engaged with splines 201876, rotation knob 201812 thereby rotates second gear 201878 relative to motor housing 201818. When motor housing 201818 is in a distal position, as shown in FIG. 28A, motor 201820 and first gear 291874 are also in a distal position. Motor 201820 is engaged with second gear 201878 via shafts 201886, 201880. First gear 201874 slides over shaft 201880 of second gear 201878 to disengage splines 201876. Thus, the rotation of drive shaft 201886 of motor 201820 thereby rotates second gear 201878. This positioning thereby provides motorized actuation of stapling head assembly 201802. In other words, when knob 201812 and motor housing 201818 are in a distal position as shown in FIG. 28A, motor 201820 rotates second gear 201878. When knob 201812 and motor housing 201818 are in a proximal position as shown in FIG. 28B, knob 201812 rotates second gear 201878.

Referring back to FIGS. 25-26, a distal end of second gear 201878 is coupled to driver actuator 201814, such that rotation of second gear 201878 rotates driver actuator 201814. Accordingly, when second gear 201878 is rotated, driver actuator 201814 is rotated to adjust the gap distance d between anvil 201804 and stapling head assembly 201802. Handle housing 201816 further comprises firing ring 201826 and coupling member 201890. Coupling member 201890 is secured around recess 201892 of driver actuator 201814, as shown in FIG. 25. Accordingly, coupling member 201890 translates with driver actuator 201814, but driver actuator 201814 is free to rotate within coupling member 201890. Coupling member 201890 comprises protrusions extending outwardly that connect coupling member 201890 to firing ring 201826. The protrusions of coupling member 201890 extends through slot 201894 of housing assembly

201816, as shown in FIG. 25. Slot 201894 extends circumferentially about part of handle assembly 201816. Firing ring 201826 is wrapped around handle housing 201816 and is rotatable and translatable relative to handle housing 201816 to manually drive the protrusions of coupling member 201890 through slot 201894.

When firing ring 201826 is in a distal position, protrusions of coupling member 201890 are positioned within slot 201894 of handle housing 201816. When coupling member 201890 is positioned within slot 201894, coupling member 201890 couples driver actuator 201814 with features in stapling head assembly 201802 operable to adjust the gap distance d between anvil 201804 and stapling head assembly 201802. For instance, if coupling member 201890 is rotated clockwise within slot 201894, the gap distance d is decreased to close anvil 201804 relative to stapling head assembly 201802. If coupling member 201890 is rotated counterclockwise within slot 201894, the gap distance d is increased to open anvil 201804 relative to stapling head assembly 201802. A resilient member 201888 is positioned proximal to coupling member 201890 to bias coupling member 201890 distally (FIG. 25). Coupling member 201890 of firing ring 201826 may then be translated proximally through slots. When firing ring 201826 is in the proximal position, protrusions of coupling member 201890 are positioned within a slot. When coupling member 201890 is positioned within a slot, coupling member 201890 couples driver actuator 201814 with features in stapling head assembly 201802 that drive a knife and staples in response to rotation of driver actuator 201814. For instance, if coupling member 201890 is rotated clockwise within a slot, stapling head assembly 201802 drives a knife and staples. The configuration of the slot prevents coupling member 201890 from being rotated counterclockwise. Other suitable coupling member 201890 rotation configurations will be apparent to one with ordinary skill in view of the teachings herein.

As shown in FIG. 26, a switch 201898 is positioned in handle housing 201816 to align with coupling member 201890. When the motorized operational mode is selected, switch 201898 is configured to electrically couple motor 201820 and battery 201822 when switch 201898 is depressed, and switch 201898 is configured to electrically decouple motor 201820 and battery 201822 when switch 201898 is not depressed. Coupling member 201890 is configured to engage and depress switch 201898 when coupling member 201890 is rotated.

Referring now to FIGS. 29A-29C, in the present example, instrument 201800 comprises a closure system and a firing system. The closure system comprises a trocar 201904, a trocar actuator 201906, and a rotating knob 201812 (FIG. 24). As previously discussed, the rotation knob 201812 may be coupled to a motor to rotate the rotation knob 201812 in a clockwise or counterclockwise direction. An anvil 201804 may be coupled to a distal end of trocar 201904. Rotating knob 201812 is operable to longitudinally translate trocar 201904 relative to stapling head assembly 201802, thereby translating anvil 201804 when anvil 201804 is coupled to trocar 201904, to clamp tissue between anvil 201804 and stapling head assembly 201804. The firing system comprises a trigger, a trigger actuation assembly, a driver actuator 201908, and a staple driver 201910. Staple driver 201910 includes a cutting element, such as a knife 201912, configured to sever tissue when staple driver 201910 is actuated longitudinally. In addition, staples 201902 are positioned distal to a plurality of staple driving members 201914 of staple driver 201910 such that staple driver 201910 also drives staples 201902 distally when staple driver 201910 is actuated longitudinally. Thus, when staple driver 201910 is actuated via driver actuator 201908, knife 201912 members 201914 substantially simultaneously sever tissue 201916 and drive staples 201902 distally relative to stapling head assembly 201802 into tissue. The components and functionalities of the closure system and firing system will now be described in greater detail.

As shown in FIGS. 29A-29C, anvil 201804 is selectively coupleable to instrument 201800 to provide a surface against which staples 201902 may be bent to staple material contained between stapling head assembly 201802 and anvil 201804. Anvil 201804 of the present example is selectively coupleable to a trocar or pointed rod 201904 that extends distally relative to stapling head assembly 201802. Referring to FIGS. 29A-29C, anvil 201804 is selectively coupleable via the coupling of a proximal shaft 201918 of anvil 201904 to a distal tip of trocar 201904. Anvil 201804 comprises a generally circular anvil head 201920 and a proximal shaft 201918 extending proximally from anvil head 201920. In the example shown, proximal shaft 201918 comprises a tubular member 201922 having resiliently biased retaining clips 201924 to selectively couple anvil 201804 to trocar 201904, though this is merely optional, and it should be understood that other retention features for coupling anvil 201804 to trocar 201904 may be used as well. For example, C-clips, clamps, threading, pins, adhesives, etc. may be employed to couple anvil 201804 to trocar 201904. In addition, while anvil 201804 is described as selectively coupleable to trocar 201904, in some versions proximal shaft 201918 may include a one-way coupling feature such that anvil 201804 cannot be removed from trocar 201904 once anvil 201804 is attached. By way of example one-way features include barbs, one way snaps, collets, collars, tabs, bands, etc. Of course still other configurations for coupling anvil 201804 to trocar 201904 will be apparent to one of ordinary skill in the art in view of the teachings herein. For instance, trocar 201904 may instead be a hollow shaft and proximal shaft 201918 may comprise a sharpened rod that is insertable into the hollow shaft.

Anvil head 201920 of the present example comprises a plurality of staple forming pockets 201936 formed in a proximal face 201940 of anvil head 201920. Accordingly, when anvil 201804 is in the closed position and staples 201902 are driven out of stapling head assembly 201802 into staple forming pockets 201936, as shown in FIG. 29C, legs 201938 of staples 201902 are bent to form completed staples.

With anvil 201804 as a separate component, it should be understood that anvil 201804 may be inserted and secured to a portion of tissue 201916 prior to being coupled to stapling head assembly 201802. By way of example only, anvil 201804 may be inserted into and secured to a first tubular portion of tissue 201916 while instrument 201800 is inserted into and secured to a second tubular portion of tissue 201916. For instance, the first tubular portion of tissue 201916 may be sutured to or about a portion of anvil 201804, and the second tubular portion of tissue 201916 may be sutured to or about trocar 201904.

As shown in FIG. 29A, anvil 201804 is then coupled to trocar 201904. Trocar 201904 of the present example is shown in a distal most actuated position. Such an extended position for trocar 201904 may provide a larger area to which tissue 201916 may be coupled prior to attachment of anvil 201804. In addition, the extended position of trocar 20190400 may also provide for easier attachment of anvil 201804 to trocar 201904. Trocar 201904 further includes a tapered distal tip. Such a tip may be capable of piercing through tissue and/or aiding the insertion of anvil 201804 on to trocar 201904, though the tapered distal tip is merely optional. For instance, in other versions trocar 201904 may have a blunt tip. In addition, or in the alternative, trocar 201904 may include a magnetic portion (not shown) which may attract anvil 201804 towards trocar 201904. Of course still further configurations and arrangements for anvil 201804 and trocar 201904 will be apparent to one of ordinary skill in the art in view of the teachings herein.

When anvil 201804 is coupled to trocar 201904, the distance between a proximal face of the anvil 201804 and a distal face of stapling head assembly 201802 defines a gap distance d. Trocar 201904 of the present example is translatable longitudinally relative to stapling head assembly 201802 via an adjusting knob 201812 (FIG. 24) located at a proximal end of actuator handle assembly 201808 (FIG. 24), as will be described in greater detail below. Accordingly, when anvil 201804 is coupled to trocar 201904, rotation of adjusting knob 201812 enlarges or reduces gap distance d by actuating anvil 201804 relative to stapling head assembly 201802. For instance, as shown sequentially in FIGS. 29A-29B, anvil 201804 is shown actuating proximally relative to actuator handle assembly 201808 from an initial, open position to a closed position, thereby reducing the gap distance d and the distance between the two portions of tissue 201916 to be joined. Once the gap distanced is brought within a predetermined range, stapling head assembly 201802 may be fired, as shown in FIG. 29C, to staple and sever tissue 201916 between anvil 201804 and stapling head assembly 201802. Stapling head assembly 201802 is operable to staple and sever tissue 201916 by a trigger of actuator handle assembly 201808, as will be described in greater detail below.

Still referring to FIGS. 29A-29C, a user sutures a portion of tissue 201916 about tubular member 201944 such that anvil head 201920 is located within a portion of the tissue 201916 to be stapled. When tissue 201916 is attached to anvil 201804, retaining clips 201924 and a portion of tubular member 201922 protrude out from tissue 201916 such that the user may couple anvil 201804 to trocar 201904. With tissue 201916 coupled to trocar 201904 and/or another portion of stapling head assembly 201802, the user attaches anvil 201804 to trocar 201904 and actuates anvil 201804 proximally towards stapling head assembly 201802 to reduce the gap distance d. Once instrument 201800 is within the operating range, the user then staples together the ends of tissue 201916, thereby forming a substantially contiguous tubular portion of tissue 201916.

Stapling head assembly 201802 of the present example is coupled to a distal end of shaft assembly 201806 and comprises a tubular casing 201926 housing a slidable staple driver 201910 and a plurality of staples 201902 contained within staple pockets 201928. Shaft assembly 201806 of the present example comprises an outer tubular member 201942 and a driver actuator 201908. Staples 201902 and staple pockets 201928 are disposed in a circular array about tubular casing 201926. In the present example, staples 201902 and staple pockets 201928 are disposed in a pair of concentric annular rows of staples 201902 and staple pockets 201928. Staple driver 201910 is operable to actuate longitudinally within tubular casing 201926 in response to rotation of actuator handle assembly 201808 (FIG. 24). As shown in FIGS. 29A-29C, staple driver 201910 comprises a flared cylindrical member having a trocar opening 201930, a central recess 201932, and a plurality of members 201914 disposed circumferentially about central recess 201932 and extending distally relative to shaft assembly 201806. Each member 201914 is configured to contact and engage a corresponding staple 201902 of the plurality of staples 201902 within staple pockets 201928. Accordingly, when staple driver 201910 is actuated distally relative to actuator handle assembly 201808, each member 201914 drives a corresponding staple 201902 out of its staple pocket 201928 through a staple aperture 201934 formed in a distal end of tubular casing 201926. Because each member 201914 extends from staple driver 201910, the plurality of staples 201902 is driven out of stapling head assembly 201802 at substantially the same time. When anvil 201804 is in the closed position, staples 201902 are driven into staple forming pockets 201936 to bend legs 201938 of the staples 201902, thereby stapling the material located between anvil 201804 and stapling head assembly 201808. FIG. 30 depicts by way of example staple 201902 driven by a member 201914 into a staple forming pocket 201928 of anvil 201804 to bend legs 201938.

The motorized circular stapling instruments 201800, 201000 described herein with reference to FIGS. 24-31 may be controlled using any of the control circuits described in connection with FIGS. 16-23. For example, the control system 470 described with reference to FIG. 16. Further, the motorized circular stapling instrument 201800 may be employed in a hub and cloud environment as described in connection with FIGS. 1-15.

Circular Stapler Control Algorithms

In various aspects the present disclosure provides a powered stapling device that is configured with circular stapler control algorithms to adjust independently actuatable staple rows based on the force-to-close (FTC) a clamp on the tissue or the tissue gap between the clamp and the stapler. Accordingly, the stroke of an outer row of staple heights can be adjusted based on the force, tissue gap, or tissue creep during firing the first row of staples, for example. Adjustment of staple height of at least one row of staples based on the sensed tissue thickness or force in closing focuses on the adjustment of a selection window based on tissue thickness/load in closing. In other aspects, the user adjustable range of selectable staple heights may be varied based on the tissue loading detected during the anvil retraction operation. As the tissue compression is increased or the tissue gap is decreased the nominal staple height for the center of the window may be adjusted. In other aspects, the adjustment of the window range of acceptable staples is displayed as the compression is increased or the tissue gap decreased. In other aspects, once the tissue compression is completed then stabilization of the tissue, can further adjust the acceptable range based on the rate of tissue creep and time waited.

Adjustment of Staple-Forming Parameters

In various aspects, staple-forming parameters of a powered circular stapler can be adjusted based on a sensed tissue property. In one aspect, a control algorithm can be configured to adjust staple height of at least one row of staples based on the sensed tissue thickness or force in closing or in firing a former staple row. In one aspect, the user-adjustable range of selectable staple heights is varied based on the tissue loading detected during the anvil retraction operation. As the tissue compression is increased or the tissue gap is decreased, the nominal staple height for the center of the window is adjusted. In one aspect, the adjustment of the window range of an acceptable staple is displayed as the compression is increased or the tissue gap decreased. In one aspect, once the tissue compression is completed and the tissue is stabilized, the control algorithm can further be configured to adjust the acceptable parameter ranges based on the rate of tissue creep and wait time.

FIG. 31 is a partial cutaway view of a powered circular stapling device 201000 comprising a circular stapling head assembly 201002 and an anvil 201004, in accordance with at least one aspect of the present disclosure. The powered circular stapling device 20100 is shown clamping a first portion of tissue 201006 and a second portion of tissue 201008 between the anvil 201004 and the circular stapling head assembly 201002. Compression of the tissue 201006, 201008 between the anvil 201004 and the circular stapling head assembly 201002 is measured with a sensor 201018, such as a strain gauge, for example. The circular stapling head assembly 201002 also includes a knife 201019 that can be advanced at different rates to cut through tissue 201006, 201008 clamped between the anvil 201004 and the circular stapling head assembly 201002 after the inner and outer rows of staples 201010, 201014 are fired and formed against corresponding staple forming pockets 201011, 201015 of the anvil 201004.

FIG. 32 is a partial top view of the circular stapling head assembly 201002 shown in FIG. 31 showing a first row of staples 201010 (inner staples) and a second row of staples 201014 (outer staples), in accordance with at least one aspect of the present disclosure. The inner row of staples 201010 and the second row of staples 201014 are independently actuatable by first and second staple drivers 201012, 201016.

With reference now to FIGS. 31 and 32, once the tissue 201006, 201008 is clamped between the anvil 201004 and the circular stapling head assembly 201002, a first gap $\delta_1$ is set for the inner row of staples 201010 and a second gap $\delta_2$ is set for the outer row of staples 201014. As the tissue compression is increased or the tissue gap $\delta_1$, $\delta_2$ is decreased, and the nominal staple height for the center of a window is adjusted. The first staple driver 201012 drives the inner row of staples 201010 through the tissue 201006, 201008 and the inner row of staples 201010 are formed against the anvil 201004. Subsequently, the second staple driver 201016 independently drives the outer row of staples 201010 through the tissue 201006, 201008 and the outer row of staples 201014 are formed against the anvil 201004.

The independently actuatable staple rows 201010, 201014 may be formed based on the FTC clamped by the anvil 201004 on the tissue 201006, 201008 or the tissue gap $\delta_1$, $\delta_2$ between the anvil 201004 clamp and the circular stapling head assembly 201002. Accordingly, the stroke of the outer row of staple 201014 heights can be adjusted based on the clamping FTC, tissue gap $\delta_1$, $\delta_2$, or tissue creep during firing of the first row of staples 201010, for example. Adjustment of the staple height of at least one row of staples based on the sensed tissue thickness or FTC focuses on the adjustment of a selection window based on tissue 201006, 201008 thickness/load in closing. In other aspects, the user adjustable range of selectable staple heights may be varied based on the tissue loading detected during an anvil 201004 retraction operation. As the tissue compression (e.g., FTC) is increased or the tissue gap $\delta_1$, $\delta_2$ is decreased the nominal staple height for the center of the window may be adjusted as described herein with reference to FIG. 37. In other aspects, the adjustment of the window range of acceptable staples is displayed as the compression is increased or the tissue gap decreased. In other aspects, once the tissue compression is completed then stabilization of the tissue, can further adjust the acceptable range based on the rate of tissue creep and time waited.

Adjustment of Staple Rows Based on FTC/Tissue Gap

FIGS. 33 and 34 illustrate a pair of graphs 201020, 201030 and FIG. 35 illustrates an associated diagram 201040 illustrating the adjustment of drive rate or height of a second row of staples according to formation of a first row of staples, in accordance with at least one aspect of the present disclosure. As depicted in FIGS. 34-35 and with reference also to FIGS. 31 and 32, a control algorithm of a powered circular stapler 201000 senses the number and location of malformed staples in the first or inner row of staples 201010 and then adjusts the anvil height, stroke length, or stroke rate, or a combination thereof accordingly for the subsequently driven second or outer row of staples 201014 in order to accommodate areas with poor staple formation.

FIG. 33 is a graph 201020 of the stroke of the staple drivers 201012, 201016 when the actual stroke of the first staple driver 201012 is less than the upper limit of the stroke length, in accordance with at least one aspect of the present disclosure. With reference also to FIGS. 31 and 32, the inner row of staples 201010 are driven at a first firing rate 201022 over a first stroke length by the first staple driver 201012. If there are no malformed staples detected in the inner row of staples 201010, the second stroke starts just at the end of the first stroke as shown by line 201026, and the outer row of staples 201014 are driven at a second firing rate 201024 by the second staple driver 201016 that is equal to the first firing rate 201022 over a second stroke length that is not necessarily equal to the first stroke length. With reference to the diagram 201040 of FIG. 35, when the stroke length is set to the upper limit as shown in row 201042 and the actual stroke is less than the upper limit, if there are no malformed staples in the inner row of staples 201010, then the algorithm does not adjust the stroke rate or the anvil 201004 height. If, however, a malformed staple is detected in the inner row of staples 201010, then the algorithm may adjust the stroke rate or may delay the firing start of the outer row of staples 201014 before driving the outer row of staples 201014 as shown in FIG. 34, for example.

FIG. 34 is a graph 201030 of the stroke of the staple drivers 201012, 201016 when the actual stroke of the first staple driver 201012 is equal to the upper limit of the stroke length, in accordance with at least one aspect of the present disclosure. With reference also to FIGS. 31 and 32, the inner row of staples 201010 are driven at a second firing rate 201031 over a second stroke length by the first staple driver 201012. If there are malformed staples detected in the inner row of staples 201010, the second stroke starts after a delay period at the end of the first stroke as shown by line 201032, and the outer row of staples 201014 are driven at a third firing rate 201034 over a third stroke length by the second staple driver 201016 that is lower than the second firing rate 201031. The second stroke ends at a displacement indicated by line 201036. With reference to the diagram 201040 of FIG. 35, when the stroke length is set to the upper limit as shown in the upper limit row 201042 and the actual stroke is equal to the upper limit, if there are malformed staples in the inner row of staples 201010, then the algorithm may lower the stroke rate or may delay the firing start of the outer row of staples 201014 or both before driving the outer row of staples 201014 as shown in FIG. 34, for example.

With reference to FIG. 35, and FIGS. 31-34, other conditions tested by the algorithm include when the stroke is set to the lower limit as shown in row 201044 or when the stroke is set to a median limit as shown in row 201046. When the stroke is set to the lower limit as shown in row 201044, no adjustment is taken by the algorithm when no malformed staples are detected in the inner row of staples 201010. If, however, a malformed staple is detected in the first row of staples 201010, the algorithm increases the lower limit to increase the gap between the anvil 201004 and the circular stapling head assembly 201002. When the stroke is set to the median limit as shown in row 201046, no adjustment is taken by the algorithm when no malformed staples are detected in the inner row of staples 201010. If, however, a malformed staple is detected in the first row of staples 201010, the algorithm increases the median limit to increase the gap between the anvil 201004 and the circular stapling head assembly 201002.

Adjustment of Staple Firing Range Based on Tissue Parameters

FIG. 36 is a graphical representation of viable staple firing range as indicated by usable staple height windows 201076, 201078, 201080, 201082 based on the tissue gap, closure force (FTC), or tissue creep stabilization sensed by the device or combinations thereof, in accordance with at least one aspect of the present disclosure. In one aspect, a stapler control algorithm can be configured to adjust the viable staple firing range as indicated by usable staple height windows 201076, 201078, 201080, 201082 in FIG. 36 based on the tissue gap, closure force (FTC), or tissue creep stabilization sensed by the device or combinations thereof. Accordingly, the control algorithm can adjust the usable staple height windows 201076, 201078, 201080, 201082 of the powered circular stapling device 201000 described with reference to FIGS. 31-35 based on a sensed parameter.

In one aspect, the control algorithm of the powered circular stapling device 201000 adjusts the height $\delta_1$, $\delta_2$ of the anvil 201004 to prevent creep below the lowest setting. FIG. 36 is a graph 201070 illustrating viable staple height windows 201076, 201078, 201080, 201082 according to FTC and anvil 201004 closure gap $\delta$ (or anvil 201004 height as previously described) for different tissue thicknesses, in accordance with at least one aspect of the present disclosure. As depicted in FIG. 36, the viable staple height windows 201076, 201078, 201080, 201082 for different tissue types vary according to anvil closure gap and/or FTC.

The graph 201070 depicts FTC (lbs), shown along the vertical axis, as a function of anvil 201004 closure gap $\delta_1$, $\delta_2$, shown along the horizontal axis, for thin tissue shown by a first curve 201072 and for thick tissue shown by a second curve 201074. Viable staple height windows 201076, 201078, 201080, 201082 are defined between the two curves 201072, 201074. A thin tissue zone 201084 is defined between a first anvil 201004 gap $\delta_a$ and a third anvil 201004 gap $\delta_c$. A thick tissue zone 201086 is defined between a second anvil 201004 gap $\delta_b$, and a fourth anvil 201004 gap $\delta_d$. By way of example, the first anvil 201004 gap $\delta_a$ is ~0.060 mm, the second anvil 201004 gap $\delta_b$ is ~0.070 mm, a third anvil 201004 gap $\delta_c$ is ~0.080 mm, and a fourth anvil 201004 gap $\delta_d$ is ~0.085 mm. Each viable staple height windows 201076, 201078, 201080, 201082 defines a viable staple firing range 201088, 201090, 201092. As shown by the window 201082, each of the viable staple height windows 201076, 201078, 201080, 201082 includes a window indicator 201092 that shows the maximum and minimum of the viable staple firing range 201088, 201090, 201092. Accordingly, the powered circular stapling device 201000 adjusts the height $\delta$ of the anvil 201004 to prevent creep below the lowest setting.

With reference to FIGS. 31-36, FIG. 37 is a logic flow diagram of a process 201050 depicting a control program or a logic configuration to adjust the stroke of the outer row of staple 201014 heights based on the force, tissue gap, or tissue creep during firing of the first row of staples 201010, in accordance with at least one aspect of the present disclosure. This process 201050 may be implemented with any of the control circuits described with reference to FIGS. 16-23. This process 201050 may be implemented in a hub or cloud computing environment described with reference to FIGS. 1-15, for example.

In particular, the process 201050 depicted in FIG. 37 will now be described with reference to the control circuit 760 of FIG. 22. The control circuit 760 sets 201502 the first and second staple drivers 201012, 201016 or anvil 201004 height $\delta_1$, $\delta_2$ for the inner and outer rows of staples 201010, 201014 to a first predetermined length. The first predetermined length may be an upper limit, lower limit, or median limit. Once the first and second staple drivers 201012, 201016 or anvil 201004 height $\delta_1$, $\delta_2$ for the inner and outer rows of staples 201010, 201014 is set to a first predetermined length, the control circuit 760 fires 201054 the inner row of staples 201010 by advancing the first staple driver 201012 by the first predetermined length. If the control circuit 760 detects 201056 a number and location of malformed staples in the inner staple row of staples 201010, the control circuit 760 sets 201058 the stroke length of the second staple driver 201016 or anvil 201004 height $\delta_1$, $\delta_2$ for the outer row of staples 201014 to a second length. In various aspects, the stroke length of the second staple driver 201016 may be more or less than the stroke length used for the first staple driver 201012. In other aspects, the control circuit 760 may set a stroke rate of the second staple driver 201016 may be adjusted to a stroke rate that is faster or slower than the stroke rate used for the first staple driver 201012. In other aspects, the control circuit 760 may set a delay period before firing the second staple driver 201016. Once the new stroke length of the second staple driver 201016 or anvil 201004 height $\delta_1$, $\delta_2$ for the outer row of staples 201014 is set 201058, the control circuit 760 fires 201060 the outer row of staples 201014.

Staple Formation Detection

The malformed staples may be detected using a variety of techniques. Among these, are the staple formation detection techniques described with reference to FIGS. 38-41. In one aspect, detection of staple formation may be implemented by way of anvil pocket contact. The staple formation technique can be employed to sense "good" staple form by sensing that the staple tips scraped across the bottom of individual anvil pockets. This can be implemented by providing small electrical circuits in each anvil pocket which will lose continuity if a staple leg passes through them. Layers of insulating/conductive/insulating ink can be applied to the anvil to form these circuits and isolate them from the conductive material of the anvil and the tissue. When a staple passes through the anvil pocket (predictor of good staple form), the circuit is broken and the device interprets this as good staple form. Single-use anvils can have the electrical circuits printed directly onto the anvil material. Reusable anvils would require that the circuits be repaired. This may be implemented by providing a film circuit that would apply as a pressure-sensitive applique between firings. A special fixture with the pressure sensitive adhesive circuit on it would allow alignment and transfer to the anvil. In order to minimize the amount of data to be collected, transmitted, and analyzed, the circuits could be only in the outer anvil pockets. Tissue flow generally affects the outer staple legs the most. Therefore, monitoring the success of the outer staples would be a good indicator of success of all the staples. In one aspect, the circuits can be printed with very small conductive traces because the current necessary for a conductivity check can be extremely small to prevent false "success" readings that would occur if the circuit was severed outside of the anvil pockets, the circuit outside of the anvil pockets can be armored with a tough protective outer layer and/or the circuits can be layered and run (sub-anvil deck) in thin channels in the anvil (too thin for a staple wire to penetrate).

In certain instances, an electrical circuit can be positioned in the path of a properly forming staple. In such instances, an interruption in electrical continuity of an electrical circuit can be construed as an indication that a staple was properly formed while persistence in the electrical continuity of the electrical circuit can be construed as an indication that the staple was improperly formed. In other instances, an electrical circuit can be positioned in a likely path of an improperly forming staple. In such other instances, an interruption in electrical continuity of the electrical circuit can be construed as an indication that a staple was improperly formed while persistence in the electrical continuity of the electrical circuit can be construed as an indication that the staple was properly formed.

Referring to FIG. 38 and FIGS. 40A-C, a staple forming pocket 201090, such as the staple forming pockets 201011, 201015 of the anvil 201004 shown in FIG. 31, may be coupled to an electrical circuit that includes one or more electrically conductive circuit elements 201092 that cause an interruption in the electrical circuit when severed by a staple leg 201122 of a staple 201120, such as the staple 201010, 201014 shown in FIG. 31, as the staple leg 210122 is formed. An electrically conductive circuit element 201092 of an electrical circuit can be positioned in the path of a properly forming staple leg 201122. A severance of the electrically conductive circuit element 201092 can be construed as an indication that a staple 201120 was properly formed. In other instances, an electrically conductive circuit element 201092 of an electrical circuit can be positioned in a likely path of an improperly forming staple 201124. In such instances, a severance of the electrically conductive circuit element 201092 can be construed as an indication that the staple was improperly formed.

To prevent false readings that would occur if a portion of the electric circuit other than the electrically conductive circuit element 201092 was severed, portions of the electric circuit, other than the electrically conductive circuit element 201092, can be armored with a tough protective outer layer. Alternatively, portions of the electric circuit, other than the electrically conductive circuit element 201092, can be layered and/or run below the tissue-contacting surface 210094 of the anvil such as the anvil 201004 shown in FIG. 31. Alternatively, portions of an electric circuit, other than the electrically conductive circuit element 201092, can be run in thin channels that are too thin for a staple leg 201122 to penetrate. Once the electrically conductive circuit elements 201092 are severed by the forming staples 201120, the anvil can be replaced. Alternatively, the electrically conductive circuit elements 201092 may be repaired prior to reusing the anvil.

The number of electrically conductive circuit elements 201092 can vary depending on the number of staple legs 201122 that are tracked. In at least one instance, every staple-forming pocket 201090 may include an electrically conductive circuit element 201092. Alternatively, the electrical circuits can be strategically positioned against staples with a relatively high likelihood of malformation. Since improper staple formation is more likely to occur in inner rows of staples than outer rows of staples during a firing sequence of the powered circular stapling device 201000, the electrically conductive circuit elements 201092 can be located at the inner and outer rows of the staple-forming pockets 201090 on both sides of the anvil.

All the pockets 201090 of an inner or outer row of staple-forming pockets 201090 can include electrically conductive circuit elements 201092. Accordingly, an anvil can include an electric circuit for each of the staple-forming pockets 201090 in an inner or outer row of staple-forming pockets 201090 of the anvil. Alternatively, to reduce the size of the anvil, the electrically conductive circuit elements 201092 can be concentrated at every other pocket 201090 in the inner or outer rows. In at least one example, only proximal staple legs 201122 of the staples 201120 in an inner row of staples 201120 can be tracked for malformation by the electrical circuits. Alternatively, only distal staple legs 210122 of the staples 201120 in an inner row of staples 201120 can be tracked for malformation by the electrical circuits.

The position of an electrically conductive circuit element 201092 of an electrical circuit with respect to a tissue-contacting surface 201094 of an anvil can dictate whether a change in the status of the electrical circuit can be construed as an indication of proper or improper formation of a staple leg 201122. An electrically conductive circuit element 201092 can be disposed adjacent a staple-forming pocket 201090. In one example, the electrically conductive circuit element 201092 can be disposed at an outer perimeter defined by the staple-forming pocket 201090. In another example, an electrically conductive circuit element 201092 can be disposed on an inner surface of a staple-forming pocket 201090.

As illustrated in FIG. 38 and FIGS. 40A-C, a staple-forming pocket 201090 comprises a concave surface 201096 that intersects the tissue-contacting surface 201094 at outer edges 201098. The electrically conductive circuit element 201092 can be positioned onto the concave surface 201096 in the path of a properly forming staple 201120. Side walls 201100 along with the concave surface 201096 define a forming track 201102 for a staple leg 210122. The concave surface 201096 includes a first contact portion 201104, a deep portion 201106, and an end portion 201108. The first contact portion 201104 is configured to make first contact with the tip of the staple leg 201122 as the staple leg 201120 enters the staple-forming pocket 201090. The staple leg 201120 is then curled as it follows the forming track 201102 passing along the deep portion 201106 and the end portion 201018 of the concave surface 201096. The end portion 201108 guides the staple leg 201122 toward the base of the staple 201126.

As illustrated in FIG. 38 and FIGS. 40A-C, the electrically conductive circuit element 201092 can be positioned across the forming track 201102. Since successful contact with the first contact portion 201104 increases the likelihood of proper formation of a staple leg 201122, placing the electrically conductive circuit element 201092 onto the forming track 201102 at a position beyond the first contact portion 201104 improves the accuracy of detecting proper staple 201120 or improper staple 201124 formation.

In at least one example, the electrically conductive circuit element 201092 is placed on the forming track 201102 between the first contact portion 201104 and the deep portion 201106. In at least one example, the electrically conductive circuit element 201092 is placed on the forming track 201102 between the deep portion 201106 and the end portion 201108. In at least one example, the electrically conductive circuit element 201092 is placed on the forming track 201102 within the deep portion 201106. In at least one example, the electrically conductive circuit element 201092 is placed on the forming track 201102 at the center, or substantially at the center, of the deep portion 201106. In at least one example, the electrically conductive circuit element 201092 is placed on the forming track 201102 at the deepest section of the forming track 201102. In at least one example, the electrically conductive circuit element 201092 is positioned onto the concave surface 201096 closer to the first contact portion 201104 than end portion 201108. In at least one example, the electrically conductive circuit element 201092 is positioned onto the concave surface 201096 closer the end portion 201108 than the first contact portion 201104.

As illustrated in FIG. 38 and FIGS. 40A-C, an electrically conductive circuit element 201092 can be disposed onto the concave surface 201096, and may extend between the side walls 201110. As illustrated in FIG. 39, the electrically conductive circuit element 201092 is severed by a staple leg 201122 during proper formation of the staple leg 201122. An electrical circuit may enter a staple-forming pocket 201090 by extending over a side wall 201110, as illustrated in FIG. 38. The electrical circuits may extend along an outer surface of the anvil.

FIG. 40A is a cross-sectional view of two adjacent staple-forming pockets 201090 that are configured to receive staple legs 201122 extending from a base 201126 of a staple 201120. With reference also to FIGS. 38-39, each of the two staple-forming pockets 201090 includes an electrically conductive circuit element 201092 disposed at a deep portion 201106 thereof. As illustrated in FIG. 40B, a properly forming staple 201120 will sever or break the electrically conductive circuit elements 201092. On the contrary, a malformed staple 201124 will not sever or break the electrically conductive circuit elements 201092, as illustrated in FIG. 40C. Accordingly, the electrical continuity of an electrical circuit is interrupted in the example of FIG. 40B while the electrical continuity of an electrical circuit remains intact in the example of FIG. 40C.

With reference to FIGS. 38-40C, notably, the tips 201130 of the staple legs 201122 of the malformed staple 201124 missed the initial contact portions 201104 and instead engaged the tissue-contacting surface 201094 outside the staple-forming pockets 201090, which caused the malformation. Accordingly, in certain instances, placing electrically conductive circuit elements 201092 onto the tissue-contacting surface 201094 in areas around the staple-forming pockets 201090 can be useful in detecting staple malformation. Such electrically conductive circuit elements 201092 are not severed when staples, like the staple 201124, are malformed by engaging the tissue-contacting surface 201094 around the staple-forming pockets 201090. In such instances, the breakage of the electrically conductive circuit elements 201092 indicates improper formation of the staples.

In various instances, the electrically conductive circuit elements 201092 are positioned between neighboring staple-forming pockets 201090. In at least one example, an electrically conductive circuit element 201092 is disposed onto a connecting surface 201112 extending between two outer edges 201098 of adjacent staple-forming pockets 201090. In one example, an electrically conductive circuit element 201092 may extend around a staple-forming pocket 201090.

Other likely paths of improperly forming staples legs 201122 transect outer edges of an anvil. Accordingly, staple malformation can be detected by placing one or more electrically conductive circuit elements on the outer edges of an anvil. Interruptions in the electrical continuity of electrical circuits that include such electrically conductive circuit elements indicates that staples nearing such outer edges were improperly formed while persistence in the electrical continuity of the electrical circuits indicates that the staples nearing such outer edges were properly formed, or at least did not engage the outer edges during formation.

Referring to FIG. 41 and FIGS. 38-40C, in an alternative aspect, an anvil 201142 portion of a powered circular stapling device 201140 includes electrically conductive circuit elements 201144 wrapped over an outer edge of the anvil 201142. For example, as illustrated in FIG. 41, an electrically conductive circuit element 201144 is wrapped over a beveled outer edge of the anvil 201142 to reduce trauma to treated tissue. At least a portion of the outer edge is depressed to create space for the electrically conductive circuit element 201144 so that the electrically conductive circuit element 201144 is flush with the tissue-contacting surface 201094 of the anvil 201142, as illustrated in FIG. 41.

Employing electrically conductive circuit elements to detect staple malformation need not be limited to anvils of the motorized circular stapling device 201000. In various instances, electrically conductive circuit elements can be disposed onto a staple cartridge 201152 of the motorized circular stapling device 201000. As illustrated in FIG. 41, a staple cartridge 201152 includes electrically conductive circuit elements 201146 that are disposed onto pocket extenders 201148 positioned on a tissue-contacting surface 201150 of the staple cartridge 201152. Pocket extenders 201148 are positioned onto staple cavities of the staple cartridge 201152 to guide the staple legs 201122 as staples 201120 are deployed into tissue clamped between the staple cartridge 201152 and the anvil 201142. In various instances, the pocket extenders 201148 are configured to conceal end portions or tips of the staple legs while the staple legs are in their initial or unfired positions.

Like the electrically conductive circuit elements 201144, the electrically conductive circuit elements 201146 are employed to assess proper formation of the staples 201120. As illustrated in FIG. 41, an electrically conductive circuit element 201146 can be disposed onto a pocket extender 201148. In certain instances, an electrically conductive circuit element 201146 can be positioned across a top portion of a pocket extender 201148. In such instances, an electrically conductive circuit element 201146 can be broken when a staple leg 201122 exits the pocket extender 201148 during a firing sequence of the staple cartridge 201152. The electrically conductive circuit element 201146 can also be positioned at various other locations on the tissue-contacting surface 201150 of the staple cartridge 201152.

FIG. 42 illustrates a schematic diagram of a logic circuit 201160. A multiplexer 201162 can be employed to provide an input for the logic circuit 201160 by selecting one of an "n" number of input bundles 201164. As illustrated in FIG. 42, "n" equals 10. With reference also to FIGS. 38-41, each input bundle 201164 includes twelve branches, for example, that include electrically conductive circuit elements 201092 disposed in staple-forming pockets 201090, as illustrated in FIGS. 38-40C. A demultiplexer 201166 is configured to receive the output of the logic circuit 201160. The demultiplexer 201166 is connected to an "n" number of optional indicators 201168 that is equal to the number of input bundles 201164.

A control circuit 201170 is electrically connected to the control lines of the multiplexer 201162 and the demultiplexer 201166. The control circuit 201170 is configured to synchronize the control lines of the multiplexer 201162 and the demultiplexer 201166 in order to simultaneously select an indicator 201168 and a corresponding input bundle 201164 based on input from a position sensor 201172. The position sensor 201172 communicates the position of the anvil 201142 as the anvil 201142 is retracted. As described above, the anvil 201142 receives the staple legs 201122 into the staple-forming pockets 201090 as the staple drivers deploy the staples 201120 into deforming contact with the anvil 201142. As the anvil 201142 is retracted, the control circuit 201170 employs the multiplexer 201162 and the demultiplexer 201166 to select an indicator 201168 and a corresponding input bundle 201164 that provides signal input from a treatment region represented by the indicator 201168. A different indicator 201168 and corresponding input bundle 201164 is sequentially selected for every treatment region as the anvil 201142 is retracted.

The control circuit 201170 detects or senses the number and location of malformed staples 201128 (FIG. 40C) in the inner row of staples 201010 or outer row of staples 201014 or a combination thereof (FIGS. 31-32). The information identifying the number and location of malformed staples 201128 (FIG. 40C) of an initially deployed staple row, e.g., the inner row of staples 201010, is provided to the control circuit 760 (FIG. 22), for example, to adjust the height of the anvil 201004 (FIG. 31) or stroke of the staple driver of a subsequently deployed staple row, e.g., adjusts the stroke of the staple driver 201016 of the outer row of staples 201014. This technique may be employed to accommodate areas with poor or malformed staples in the initially deployed staple row.

Adjustment of Closure Rate or Direction Based on Sensed Attachment

In various aspects, the closure rate or direction of a circular stapler, or a combination thereof, can be adjusted based on the sensed attachment, relative to the fully attached state, of the anvil. In one aspect, the present disclosure provides a digitally enabled circular stapler algorithm for determining the variation the closure rate of the anvil at key locations of the trocar to ensure proper seating of the anvil on the trocar. FIG. 43 is a diagram 201500 of a powered stapling device 201502 and a graph 201504 illustrating the closure rate adjustment of an anvil 201514 portion of the powered stapling device 201502 at certain key points along the retraction stroke of a trocar 201510, in accordance with at least one aspect of the present disclosure. The powered stapling device 201502 is similar to the motorized circular stapling instrument 201800 described herein with reference to FIGS. 24-30, may be controlled using any of the control circuits described in connection with FIGS. 16-23, and may be employed in a hub and cloud environment as described in connection with FIGS. 1-15. The anvil 201514 includes an anvil head 201515 and an anvil shank 201517. The trocar 201510 can be advanced and retracted in the direction indicated by arrow 201516. In one aspect, the closure rate of the anvil 210514 can be adjusted at certain key points along the retraction stroke of the trocar 201510 to improve the final seating of the anvil 201514 on the trocar 201510 if the trocar 201510 is marginally attached but not fully attached to the anvil 201514.

The powered stapling device 201502, shown on the left side of FIG. 43, includes a circular stapling head assembly 201506 with a seating collar 201508 that receives the trocar 201510 therethrough. The trocar 201510 engages the anvil 201514 via a locking feature 201512. The trocar 210510 is movable, e.g., advanced and retracted, in the directions indicated by arrow 201516. A cutting element, such as a knife 201519, severs tissue when the circular stapling head assembly 201506 is driven towards the anvil 201514. In one aspect, the closure rate of the anvil 201514 can be adjusted at certain key points along the retraction stroke of the anvil 201510 in order to, for example, improve the final seating of the anvil 201514 on the trocar 201510 if the trocar 210510 is marginally attached but not fully attached to the anvil 201514. Accordingly, the closure rate of the anvil 201514 can be varied at key locations to ensure proper seating. The position or displacement of the trocar 210510 as it is advanced or retracted by a trocar actuator coupled to a motor, as previously described with reference to FIGS. 24-30, may be detected by a plurality of proximity sensors disposed along the displacement path of the trocar 210510. In some aspects, the position or displacement of the trocar 210510 may be tracked using the tracking system 480 (FIG. 16) or the position sensors 734, 784 (FIGS. 21, 23).

On the right side of FIG. 43, the graph 201504 illustrates the closure rate of the anvil 201514 as a function of the position of the trocar 201510 at certain key points, labeled as "δ Trocar" along the vertical axis and "$V_{closure}$ mm/sec" along the horizontal axis, in accordance with at least one aspect of the present disclosure. An anvil 201514 closure rate velocity profile curve 201505 is plotted as a function of the position of the trocar 201510. The closure rate of the anvil 201514 can be slow at a first zone 201518 to ensure proper attachment of the trocar 210510 to the anvil 201514, faster at a second zone 201520 during closure, slower again at a third zone 201522 to verify attachment, and then even slower at a fourth zone 201524 during application of a high closure load.

The anvil 201514 closure rate adjustment at certain key points along the trocar's 201510 retraction stroke improves the final seating of the anvil 201514 on the trocar 201510 if it marginally attached but not fully attached. At trocar 201510 position $δ_0$ the anvil 201514 is in a fully open position 201521 and at trocar 201510 position $δ_4$ the anvil 201514 is in a fully closed position 201523. Between the trocar 201510 fully open position 201521 $δ_0$ and fully closed position $δ_4$ the closure rate of the anvil 201514 is adjusted based on the position of the trocar 201510. For example, at the first zone 201518, as the trocar 201510 moves from the fully opened position 201521 $δ_0$ to a first trocar 201510 position $δ_1$, the closure rate of the anvil 201514 is slow (between 0-2 mm/sec) to ensure proper attachment of the anvil 201514 to the trocar 201510. At the second zone 201520, when the trocar 201510 moves from $δ_1$ to $δ_2$, the anvil 201514 is closed at a constant quick closure rate (3 mm/sec). When the trocar 201510 moves from $δ_2$ to $δ_3$ position, in the third zone 201522, the closure rate of the anvil 201514 is slowed to verify full attachment of the anvil 201514 to the trocar 201510. Finally, when the trocar 201510 moves from $δ_3$ to $δ_4$ position, in the fourth zone 201524, the closure rate of the anvil 201514 is slowed once again during high closure loads.

FIG. 44 is a section view of the powered stapling device 201502 shown in FIG. 43 in a closed configuration, e.g., the circular stapling head assembly 201506 advanced towards the anvil 201514. As shown in FIG. 44, the circular stapling head assembly 201506 and the trocar 201510 are shown in an advanced configuration to grasp tissue in the tissue gap 210511 defined between the anvil 201514 and the circular stapling head assembly 201506. As described herein, the trocar 201510 may be advanced or retracted by a motor coupled to, for example, a trocar actuator, as previously described with reference to FIGS. 24-30. A knife 201519 is employed to sever tissue captured between the anvil 201514 and the trocar 201510. The knife 201519 is coupled to a motor, which is configured to advance and retract the knife 201519. A control circuit is employed to control the motor and to control the rate of advancement/retraction of the trocar 201510 or the knife 201519 or a combination thereof.

FIG. 45 is a logic flow diagram of a process 201700 depicting a control program or a logic configuration to adjust a closure rate of the anvil 201514 portion of the powered stapling device 201502 at certain key points along the retraction stroke of a trocar 201510, in accordance with at least one aspect of the present disclosure. This process 201700 may be implemented with any of the control circuits described with reference to FIGS. 16-23. This process 201700 may be implemented in a hub or cloud computing environment described with reference to FIGS. 1-15, for example.

In particular, the process 201700 depicted in FIG. 45 will now be described with reference to the control circuit 760 of FIG. 22. The control circuit 760 determines 201702 the position of the trocar 201510 based on information received from position sensor 784. Alternatively, the position of the trocar 201510 may be determined based on information received from the sensors 788 or the timer/counter 781 circuit or a combination thereof. Based on the position of the trocar 201510, the control circuit 760 controls the closure rate of the anvil 201514 ($V_{closure}$ mm/sec) as a function of the position of the trocar 201510 at certain key points, in accordance with at least one aspect of the present disclosure. Accordingly, when the position of the trocar 201510 is located in a first zone 201518, where the anvil 201514 is attached to the trocar 201510, the process 201700 continues along the yes (Y) branch and the control circuit 760 sets 201704 the closure rate of the anvil 201514 to slow to ensure proper attachment of the trocar 210510 to the anvil 201514. Otherwise the process 201700 continues along the no (N) branch. When the position of the trocar 201510 is located in a second zone 201520, referred to as a quick gross closure zone, the process 201700 continues along the yes (Y) branch and the control circuit 760 sets 201706 the closure rate of the anvil 201514 to fast to rapidly close the anvil 201514. Otherwise the process 201700 continues along the no (N) branch. When the position of the trocar 201510 is located in a third zone 201522, referred to as a verification zone, the process continues along the yes (Y) branch and the control circuit 760 sets 201708 the closure rate of the anvil 201514 to slow to verify full attachment of the anvil 201514 to the trocar 201510. Otherwise the process 201700 continues along the no (N) branch. When the position of the trocar 201510 is located in a fourth zone 201524, referred to as a high closure load zone, the process 201700 continues along the yes (Y) branch and the control circuit 760 sets 201710 the closure rate of the anvil 201514 to a slower rate than in the previous verification zone 201522 during the application of a high closure load. Once the anvil 201514 is fully closed trocar 201510 to capture tissue therebetween, the control circuit 760 actuates the knife 201519 to sever the tissue.

In one aspect, the present disclosure provides a digitally enabled circular stapler adaptive algorithm for determining multi-directional seating motions on the trocar to drive the anvil into proper seating. FIG. 46 is a diagram 201530 of a powered stapling device 201532 and a graph 201534 illustrating detection of closure rates of the trocar 201540 and the anvil 201544, in accordance with at least one aspect of the present disclosure. The powered stapling device 201532 is similar to the motorized circular stapling instrument 201800 described herein with reference to FIGS. 24-30, may be controlled using any of the control circuits described in connection with FIGS. 16-23, and may be employed in a hub and cloud environment as described in connection with FIGS. 1-15. The anvil 201544 includes an anvil head 201545 and an anvil shank 201547. The trocar 201540 can be advanced and retracted in the direction indicated by arrow 201546. In one aspect, if the anvil shank 201547 is detected pulling loose from the trocar 201540, the powered stapling device 210530 could stop retraction or reverse and advance towards an open position 201541 until the instability of the anvil 201544 seating is resolved. If the anvil 201544 is pulled fully off, the powered stapling device 210530 could fully open 201541 indicating to the user to try re-attaching the anvil shank 201547 to the trocar 201540.

The powered stapling device 201532, shown on the left side of FIG. 46, includes a circular stapling head assembly 201536 with a seating collar 201538 that receives the trocar 201540 therethrough. The trocar 201540 engages the anvil 201544 via a locking feature 201542. The trocar 210540 is movable, e.g., advanced and retracted, in the directions indicated by arrow 201546. A cutting element, such as a knife 201548, severs tissue when the circular stapling head assembly 201536 is driven towards the anvil 201544.

In one aspect, the closure rates of the trocar 201540 and the anvil 201544 can be detected and any discrepancy between the closure rates of the two components could generate an automatic extension of the trocar 201540 and then retraction of the trocar 201540 in order to fully seat the anvil 201544 on the trocar 201540. In one aspect, any discrepancy between the closure rates of the trocar 201540 and the anvil 201544 may be provided to a control circuit or processor to operate a motor coupled to the trocar 201540 to generate an automatic extension of the trocar 201540 and then re-retraction in order to fully seat the anvil 201544 on the trocar 201540. If the anvil shank 201547 is detected pulling loose from the trocar 201540 the smart powered stapling device 201532 could stop retraction or even reverse and advance towards open until the instability of seating the anvil 201544 is resolved. If the anvil 201544 were pulled fully off it could even fully open indicating to the user to try re-attaching the anvil shank 201547 to the trocar 201540. As shown FIG. 46, the control algorithm can be configured to extend the trocar 201540 back towards the open position 201541 to reset the anvil 201544 if an anvil 201544 detachment is sensed, prior to then re-verifying attachment of the anvil 201544 and proceeding as normal upon confirming that the anvil 201544 is attached.

Accordingly, the system can be configured for multi-directional seating motions on the trocar 201540 to drive the anvil 201544 into proper seating. For example, if the anvil shank 201547 is detected as pulling loose from the trocar 201540, the smart powered stapling device 201530 could be configured to stop retraction or even reverse and advance towards open until the instability of seating the anvil 201544 is resolved. If the anvil 201544 were pulled fully off, the smart powered stapling device 201532 could even be configured to fully open, indicating to the user to try reattaching the anvil shank 201547 to the trocar 201540.

On the right side of FIG. 46, the graph 201534 illustrates the position of the trocar 201510 as a function of time at certain key points, labeled as "δ Trocar" along the vertical axis and "t" along the horizontal axis, in accordance with at least one aspect of the present disclosure. A trocar 201540 position profile curve 201549 is plotted as a function of time (t). With reference to the trocar 201540 position profile curve 201549, the trocar 201540 moves from a fully open position 201541 towards a fully closed position 201543 over a first period 201556 at a quick closure rate. During a second period 201558, the trocar 201540 moves into the verification zone 201547 where the anvil locking feature 201542 engages the seating collar 201538, at a slow rate to verify that the anvil locking feature 201542 has properly engaged the seating collar 201538. In the illustrated example, an anvil 201544 detached initiation is sensed at time 201552. Upon sensing that the anvil 201544 is detached, the trocar 201540 is advanced towards an open position and back over a third period 201560. The trocar 201540 then moves slowly during a fourth period 201562 until it is confirmed or verified that the anvil 201544 is attached to the trocar 201540 at time 201554. Thereafter, the trocar 201540 moves towards the closed position 201543 very slowly during a fifth period 201564 under high tissue load before the knife 201548 is advanced to sever the tissue captured between the anvil 201544 and the circular stapling head assembly 201536.

FIG. 47 is a logic flow diagram of a process 201720 depicting a control program or a logic configuration to detect multi-directional seating motions on the trocar 201540 to drive the anvil 201544 into proper seating, in accordance with at least one aspect of the present disclosure. This process 201720 may be implemented with any of the control circuits described herein with reference to FIGS. 16-23. This process 201720 may be implemented in a hub or cloud computing environment described with reference to FIGS. 1-15, for example.

In particular, the process 201720 depicted in FIG. 35 will now be described with reference to the control circuit 760 of FIG. 22. The control circuit 760 determines 201722 the closure rate of the trocar 201540 based on information received from position sensor 784. The control circuit 760 then determines 201724 the closure rate of the anvil 201544 based on information received from position sensor 784. Alternatively, the closure rate of the trocar 201540 or the anvil 201544 may be determined based on information received from the sensors 788 or the timer/counter 781 circuit or a combination thereof. The control circuit 760 compares 207126 the closure rates of the trocar 201540 and the anvil 201544. When there is no discrepancy between the closure rates of the trocar 201540 and the anvil 201544, the process 201720 continues along the no (N) branch and loops until there is a discrepancy between the closure rates of the trocar 201540 and the anvil 201544. When there is a discrepancy between the closure rates of the trocar 201540 and the anvil 201544, the process 201720 continues along the yes (Y) branch and the control circuit 760 extends and retracts 207128 the trocar 201540 to reset the anvil 201544. Subsequently, the process 201720 verifies 201130 the attachment of the trocar 201540 and anvil 201544. If the attachment is verified, the process 201720 continues along the yes (Y) branch and the control circuit 760 slows 207132 the closure rate of the trocar 201540 under tissue load. If the attachment is not verified, the process 201720 continues along the no (N) branch and loops until the attachment of the trocar 201540 to the anvil 201544 is verified. Once the anvil 201544 is fully closed on the trocar 201540 to capture tissue therebetween, the control circuit 760 actuates the knife 201548 to sever the tissue.

Adjustment of Knife Speed/End Points Based on Tissue Parameters

In various aspects, the knife speed of a circular stapler and end points can be adjusted based on the sensed toughness or thickness of the tissue between the anvil and cartridge. Accordingly, the circular stapler control algorithm can be configured to detect the tissue gap and force-to-fire to adjust the knife stroke and speed. In one aspect, the present disclosure provides a digitally enabled circular stapler adaptive algorithm for detecting tissue gap and force-to-fire to adjust knife stroke and knife speed, in accordance with at least one aspect of the present disclosure.

Generally, FIGS. 48-50 represent a circular powered stapling device 201610 and a series of graphs depicting force-to-close (FTC) a clamp relative to the position of the anvil 201612 ($\delta_{Anvil}$) and knife 201616 velocity ($V_K$) and knife 201616 force ($F_K$) relative to the position of the knife 201616 ($\delta_{Knife}$), in accordance with at least one aspect of the present disclosure. Using sensed data at different points along length of the shank 201621, a control algorithm can generate a map of tissue gap or reaction force vector of the anvil 201612, monitoring for a high or low side when compressed on tissue. When firing, the system measures forces acting on a compression element 201620 comprising a force sensor and adjusts to act evenly along the force vector of the shank to provide even and complete cutting.

In particular, FIG. 48 is a partial schematic diagram of a circular powered stapling device 201610 showing anvil 201612 closure on the left side and knife 201616 actuation on the right side, in accordance to at least one aspect of the present disclosure. The circular powered stapling device 201610 comprises an anvil 201612 that is movable from a fully open position $\delta_{A2}$ to a fully closed position $\delta_{A0}$. An intermediate position $\delta_{A1}$ represents the point at which the anvil 201612 contacts tissue located between the anvil 201612 and the circular stapler 201614. One or more position sensors located along the length of the anvil shank 201621 monitor the position of the anvil 201612. In one aspect, the position sensor may be located within the seating collar 201618. The compression element 201620 may comprise a force sensor, such as a strain gauge for example, to monitor the force applied to the tissue and to detect the point of initial contact of the anvil 201612 with the tissue, shown as intermediate position $\delta_{A1}$. The position sensor and the force sensor interface with any of the control circuits described herein with reference to FIGS. 16-23, for example, which implement the circular stapler control algorithm. The circular powered stapling device 201610 also comprises a movable cutting element such as a knife 201616 that is movable from a fully retracted position $\delta_{A0}$ to a fully extended position $\delta_{A2}$ to achieve a complete tissue cut. The intermediate position $\delta_{A1}$ of the knife 201616 represents the point at which the knife 201616 contacts with the compression element 201620 comprising a strain gauge or other contact or proximity sensor.

The power stapling device 201610 includes motors, sensors, and control circuits as described herein in connection with FIGS. 16-30. The motors are controlled by the control circuits to move the anvil 201612 and the knife 201616. One or more position sensors located on the power stapling device 201610 provide the position of the anvil 201612 and the knife 201616 to the control circuit. Additional sensors such as force sensors 201620 also provide tissue contact and force acting on the anvil 201612 and the knife 201616 to the control circuit. The control circuit employs the position of the anvil 201612, the position of the knife 201616, initial tissue contact, or force acting of the anvil 201612 or knife 201616 to implement the circular stapler control algorithm described hereinbelow in connection with FIG. 51.

FIG. 49 is a graphical representation 201600 of anvil 201612 displacement along the vertical axis as a function of force-to-close (FTC) a clamp along the horizontal axis, in accordance with at least one aspect of the present disclosure. The vertical line represents a FTC threshold 201606 that indicates tissue toughness. The left side of the FTC threshold 201606 represents tissue having normal toughness and the right side of the FTC threshold 201606 represents tissue having heavy toughness. As the anvil 201612 is retracted from the fully open position $\delta_{A2}$ to the intermediate position $\delta_{A1}$, where the anvil 201612 initially contacts tissue, the FTC is substantially low (~0). As the anvil 201612 continues closing past this point towards the circular stapler 201614 to the fully retracted position $\delta_{A0}$ minus the compressed tissue thickness, the FTC is nonlinear. Each tissue type from normal to heavy toughness will produce a different FTC curve. For example, the first FTC curve 201604, shown in broken line, spans from ~0 to ~100 lbs., where the maximum FTC is below the FTC threshold 201606. The second FTC curve 201602, shown in solid line, spans from ~0 to ~200 lbs., where the maximum FTC exceeds the FTC threshold 201606. As previously discussed, the FTC is measured by force sensors located in the compression element 201620 and coupled to the control circuit.

FIG. 50 is a graphical representation 201630 of knife 201616 displacement ($\delta_{Knife}$) along the vertical axis as a function of knife 201616 velocity ($V_K$ mm/sec) along the horizontal axis on the left and also as a function of knife 201616 force ($F_K$ lbs) along the horizontal axis on the right, in accordance with at least one aspect of the present disclosure. On the left is a graphical representation 201632 of knife 201616 displacement ($\delta_{Knife}$) along the vertical axis as a function of knife 201616 velocity ($V_K$ mm/sec) along the horizontal axis. On the right is a graphical representation 201634 of knife 201616 displacement ($\delta_{Knife}$) along the vertical axis as a function of knife 201616 force ($F_K$ lbs) along the horizontal axis. The curves in dashed line 201638, 20142 in each of the graphical representations 201632, 201634 represent tissue of normal toughness whereas the curves in solid line 201636, 201640 represent tissue of heavy toughness.

Turning to the graphical representation 201632 on the left, for normal tissue toughness, as shown by the normal tissue knife velocity profile 201638, the initial velocity of the knife 201616 for normal tissue toughness starts at a first velocity, e.g., just over 4 mm/sec, at the initial knife position $\delta_{K0}$. The knife 201616 continues at that velocity until it reaches knife position $\delta_{K1}$ where the knife 201616 contacts tissue and slows the velocity of the knife 201616 as it cuts through the tissue until the knife 201616 reaches knife position $\delta_{K2}$ indicating a complete cut and the control circuit stops the motor and hence stops the knife 201616. Turning to the graphical representation 201634 on the right, for normal tissue toughness, as shown by the normal tissue knife force curve 201642, the force acting on the knife 201616 is 0 lbs. at the initial knife position $\delta_{K0}$ and varies nonlinearly until the knife 201616 reaches knife position $\delta_{K2}$ until the cut is complete.

Turning to the graphical representation 201632 on the left, for heavy tissue toughness, as shown by the heavy tissue knife velocity profile 201636, the initial velocity of the knife 201616 for heavy tissue toughness starts at a second velocity, e.g., just over 3 mm/sec, which is lower relative to the first velocity, at the initial knife position $\delta_{K0}$, which is less than the initial velocity for normal tissue toughness. The knife 201616 continues at that velocity until it reaches knife position $\delta_{K1}$ where the knife 201616 contacts tissue. At this point the velocity of the knife 201616 starts to slow down nonlinearly as it cuts through the tissue for a short displacement of the knife 201616. The control circuit detects that the knife 201616 contacted tissue and in response increases the velocity of the motor to increase the velocity of the knife 201616, e.g., to the initial velocity until the knife 201616, until the knife 201616 reaches position $\delta_{K2}$ indicating a complete cut and the control circuit stops the motor and hence stops the knife 201616. This is shown as velocity spike 201644 to improve cutting of tissue of heavy toughness. Turning to the graphical representation 201634 on the right, for heavy tissue toughness, as shown by the heavy tissue knife force curve 201640, the force acting on the knife 201616 is 0 lbs. at the initial knife position $\delta_{K0}$ and varies nonlinearly until the knife 201616 reaches knife position $\delta_{K2}$ and the cut is complete. A comparison of the normal and heavy tissue knife force curves 201640, 201642 shows that, with lower velocity and adding the velocity spike 201644 shortly after tissue contact with the knife 201616, the knife 201616 experiences a lower force when cutting tissue of heavy toughness than it experiences when cutting tissue of normal toughness.

FIG. 51 is a logic flow diagram of a process 201720 depicting a control program or a logic configuration to detect the tissue gap and force-to-fire to adjust the knife stroke and speed, in accordance with at least one aspect of the present disclosure. This process 201750 may be implemented with any of the control circuits described with reference to FIGS. 16-23. This process 201750 may be implemented in a hub or cloud computing environment described with reference to FIGS. 1-15, for example.

In particular, the process 201750 depicted in FIG. 51 will now be described with reference to the control circuit 760 of FIG. 22 and the circular powered stapling device 201610 shown in FIGS. 48-50. The control circuit 760 monitors 201752 the displacement of the anvil 201612 based on position feedback received from the position sensor 784. As previously discussed, in one aspect, the position sensor 784 may be embedded in the shank 201612 of the anvil 201612. As the anvil 201612 is displaced, the control circuit 760 monitors 201754 contact of the anvil 201612 with tissue positioned between the anvil 201612 and the circular stapler 201614. In one aspect, tissue contact may be provided by a force sensor embedded in the compression element 201620. The force sensor is represented as the sensors 788 element of the surgical instrument 790 shown in FIG. 22. The force sensor 788 is employed to monitor 201756 the force-to-close (FTC) a clamp, which is the closing force of the anvil 201612 onto the tissue positioned between the anvil 201612 and the circular stapler 201614. The control circuit 760 compares 201758 the FTC to a predetermined threshold. When the FTC is below the predetermined threshold, the control circuit 760 sets the velocity of the motor 754 to advance 201760 the knife 201616 using a normal tissue toughness velocity profile 201638 as shown in FIG. 50. When the FTC is above the predetermined threshold, the control circuit 760 sets the velocity of the motor 754 to advance 201762 the knife 201616 using a heavy tissue toughness velocity profile 201636 with a velocity spike 201644 as shown in FIG. 50.

FIG. 52 is a logic flow diagram of a process 201762 depicting a control program or a logic configuration to advance 201762 the knife 201616 under a heavy tissue toughness velocity profile 201636 with a velocity spike 201644 as shown in FIG. 50, in accordance with at least one aspect of the present disclosure. This process 201762 may be implemented with any of the control circuits described with reference to FIGS. 16-23. This process 201750 may be implemented in a hub or cloud computing environment described with reference to FIGS. 1-15, for example.

In particular, the process 201762 depicted in FIG. 52 will now be described with reference to the control circuit 760 of FIG. 22 and the circular powered stapling device 201610 shown in FIGS. 48-50. When heavy tissue toughness is detected, the control circuit 760 sets 201770 the initial velocity of the knife 201616 a lower knife velocity relative to the knife velocity used for cutting normal tissue toughness. In one aspect, a slower knife velocity in heavy tissue toughness conditions promotes a better cut. The control circuit 760 monitors 201772 when the knife 201616 contacts the tissue. As previously discussed, tissue contact may be detected by a force sensor embedded in the compression element 201620. As shown in FIG. 50, when the knife 201616 contacts tissue the knife 201616 naturally slows down. Accordingly, once the control circuit 760 detects that the knife 201616 has contacted tissue, the tissue contact is detected, the control circuit 760 increases 201774 the velocity of the motor 754 to increase the velocity of the knife 201616 cutting through the tissue. The control circuit 760 monitors 201776 the completion of the cut and maintains 201778 the velocity of the motor 740 until completion of the cut is detected and then stops 201780 the motor 740.

Varying Reactions Based on Lockout Type and Conditions

The reaction of compulsory electronic lockouts is to prohibit a device function until the situation is resolved. Conversely, the reaction to a discretionary lockout can be more subtle. For example, discretionary lockout could include a warning indication, an alert requiring user consent to proceed, a change in the rate or force of an actuation or wait time, or a prohibition of certain functions being performed until the situation is resolved or stabilized. In operation, compulsory conditions for a circular stapler can include, for example, having the anvil fully seated before clamping or the cartridge being loaded with staples before firing. Viable conditions for a circular stapler can include, for example, being within the acceptable staple height for a given tissue thickness or a minimum tissue compression. Further, different conditions could have both discretionary and compulsory level thresholds on the same parameter, e.g., power level within the battery pack.

In one aspect, a stapling instrument can be configured to implement various control mechanisms for preventing or adjusting the function of the instrument based on the lockout type. In one aspect, compulsory lockouts could be solely electronic, mechanical interlocks, or a combination of the two. In various aspects having two lockouts, the lockouts could be redundant or optionally used based on the settings of the device. In one aspect, discretionary lockouts can be electronic lockouts so that they can be adjustable based on sensed parameters. For example, the discretionary lockouts could be a mechanical interlock that is electronically disabled or they could be a solely electronic lockout.

FIG. 53 is a graphical representation of a first pair of graphs 202000, 202020 depicting anvil gap and tissue compression force F verse time for illustrative firings of a stapling instrument, in accordance with at least one aspect of the present disclosure. The tissue compression force F also may be expressed as force to close (FTC). The top graph 202000 depicts three separate anvil gap curves 202002, 202004, 202006 representative of anvil gap closure over time at three separate tissue compression forces, as shown in the bottom graph 202020, where anvil gap δ is shown along the vertical axis and time is shown along the horizontal axis. The anvil gap curves 202002, 202004, 202006 represent anvil closure of a powered circular stapling device 202080 (FIG. 55) as a function of time t for tissue of variable stiffness, constant thickness, and constant anvil gap δ, until adjustment(s) of the anvil gap δ are made by a control algorithm. A control algorithm implemented by any of the control circuits described herein with reference to FIGS. 1-23 can be configured to adjust the anvil gap according to the sensed tissue compression force F compared to one or more different thresholds.

Turning now briefly to FIG. 55, there is shown a schematic diagram of a powered circular stapling device 202080 illustrating valid tissue gap $δ_y$, actual gap $δ_{actual}$, normal range gap $δ_2$, and out of range gap $δ_3$, in accordance with at least one aspect of the present disclosure. The powered circular stapling device 202080 includes a circular stapler 202082 and an anvil 202084, which is retracted from an open position to a closed position to clamp tissue between the anvil 201084 and the stapler 202082. Once the anvil 202084 is fully clamped on the tissue, there will be a gap δ defined between the anvil 202084 and the stapler 202082. When the circular stapler 202082 is fired (e.g., actuated), the staple formation is dependent upon the tissue gap δ. As shown in FIG. 55, for a normal range gap $δ_2$, the staples 202088 are well formed. When the gap δ is too small, the staples 202086 are too tightly formed and when the gap δ is too large, the staples 202090 are too loosely formed.

Turning back now to FIG. 53, with reference to the top and bottom graphs 202000, 202020 and FIG. 55, at time $t_0$ the anvil 201084 is initially open beyond the maximum anvil gap $δ_{max}$ before the anvil 201084 reaches the initial tissue contact point 202008 at time $t_1$. As shown, due to constant tissue thickness, $t_1$ is a common tissue contact point for tissue having variable tissue stiffness. At time $t_1$, the anvil gap δ is still outside of the ideal firing zone 202016 shown between a maximum anvil gap $δ_{max}$, defining a upper firing lockout threshold 202012, and a minimum anvil gap $δ_{min}$ 202014, defining a lower firing lockout threshold 202014. From the initial tissue contact point 202008 at time $t_1$ as the anvil 201084 continues to close the tissue compression force F starts to increase. The tissue compression force F will vary as a function of the biomechanical properties of tissue in terms of stiffness. As indicated in the bottom graph 202020, tissue of normal stiffness is represented by a first tissue compression force curve 202022, tissue of high stiffness is represented by a second tissue compression force curve 202024, and tissue of low stiffness is represented by a third tissue compression force curve 202026.

As the anvil 201084 continues to close between the maximum anvil gap $δ_{max}$ and the minimum anvil gap $δ_{min}$, the anvil gap δ reaches a point of constant anvil gap 202018 at time $t_2$. As shown in the lower graph 202020, at time $t_2$ the tissue compression force F for tissue of normal stiffness represented by the first tissue compression force curve 202022 is within the ideal firing zone 202036, which is defined between a maximum compression force $F_{max}$, defining an upper warning threshold 202032, and a minimum compression force $F_{min}$, defining a lower warning threshold 202034. At time $t_2$, the tissue compression force F for tissue of high stiffness represented by the second tissue compression force curve 202024 is above the upper warning threshold 202032 outside the ideal firing zone 202036 and the tissue compression force for tissue of low stiffness represented by the third tissue compression force curve 202026 is below the lower warning threshold 202034 outside the ideal firing zone 202036.

From time $t_2$ to time $t_3$, the anvil 201084 is maintained at a constant gap δ, as shown in the upper graph 202000, by the three anvil gap curves 202002, 202004, 202006. This period of constant gap δ, allows for tissue creep, as shown in the lower graph 202020, during which the average tissue compression force F slowly drops as shown by the three tissue compression force curves 202022, 202024, 202026. Tissue creep is a phase that is entered after tissue is grasped and the average tissue compression force F reaches a predetermined threshold and the closure motion of the anvil 201084 such that the anvil 201084 and the stapler 202082 hold the tissue therebetween for a predetermined time before initiating the firing phase in which the staples and knife are deployed. During the tissue creep phase the average tissue compression force F drops over the time period between $t_2$ and $t_3$. Tissue, in part because it is composed of solid and liquid material, tends to elongate when compressed. One way to account for this property is "tissue creep." When tissue is compressed, a certain amount of tissue creep can occur. Affording the compressed tissue an adequate amount of time under certain circumstances to accomplish tissue creep can therefore produce benefits. One benefit can be adequate staple formation. This can contribute to a consistent staple line. Accordingly, a certain time can be given to enable tissue creep prior to firing.

With reference now also to FIG. 23, after a period where the anvil gap δ is maintained constant to allow for tissue creep, at time $t_3$, prior to deploying the staples, the control circuit 760 at point 202010 determines whether a possible adjustment of the anvil 766 relative to the staple cartridge 764 (anvil 201804 and stapler 202084 in FIG. 55) is necessary. Accordingly, the control circuit 760 determines if the tissue compression force F is between the ideal firing zone 202036, above the maximum compression force $F_{max}$ threshold 202032, or below the minimum compression force $F_{min}$ threshold 202034 and makes any necessary adjustments to the anvil gap δ. If the tissue compression force F is between the ideal firing zone 202036, the control circuit 760 deploys the staples in the staple cartridge 768 and deploys the knife 764.

If the tissue compression force F is above the maximum compression force $F_{max}$ threshold 202032, the control circuit 760 is configured to register a warning that the compression force is too tight and to adjust the anvil gap δ, increase the wait time before firing, lower the firing speed, or enable a firing lockout, or any combination thereof. The control circuit 760 can adjust the anvil gap δ by advancing the anvil 766 distally, e.g. away, from the staple cartridge 768 (anvil 201804 and stapler 202084 in FIG. 55) to increase the anvil gap δ as shown by the segment of the anvil gap curve 2002004 beyond time $t_3$. As shown by the segment of the tissue compression force curve 202024 beyond time $t_3$, after the control circuit 760 increases the anvil gap δ, the tissue compression force F decreases into the ideal firing zone 202036.

If the tissue compression force F is below the minimum compression force $F_{min}$ threshold 202034, the control circuit 760 is configured to register a warning that the compression force is too loose and to adjust the anvil gap δ, proceed with caution, or enable a firing lockout, or any combination thereof. The control circuit 760 is configured to adjust the anvil gap δ by retracting the anvil 766 proximally, e.g. toward, the staple cartridge 768 (anvil 201804 and stapler 202084 in FIG. 55) to decrease the anvil gap δ as shown by the segment of the anvil gap curve 2002006 beyond time $t_3$. As shown by the segment of the tissue compression force curve 202026 beyond time $t_3$, after decreasing the anvil gap δ, the tissue compression force F increases into the ideal firing zone 202036.

Turning now to FIG. 54, there is shown a graphical representation of a second pair of graphs 202040, 202060 depicting anvil gap and tissue compression force F verse time for illustrative firings of a stapling instrument, in accordance with at least one aspect of the present disclosure. The top graph 202040 depicts three separate anvil gap curves 202042, 202046, 202046 representative of anvil gap closure over time at three separate tissue thicknesses, where anvil gap δ is shown along the vertical axis and time is shown along the horizontal axis. The anvil gap curves 202042, 202044, 202046 represent anvil closure of a powered circular stapling device 202080 (FIG. 55) as a function of time t for tissue of variable thickness, constant stiffness, and constant anvil gap δ, until adjustment(s) of the anvil gap δ are made by a control algorithm. A control algorithm implemented by any of the control circuits described herein with reference to FIGS. 1-23 can be configured to adjust the anvil gap according to the sensed tissue compression force F compared to one or more different thresholds.

With reference now to the top and bottom graphs 202040, 202060 and FIG. 55, at time $t_0$ the anvil 201084 is initially open beyond the maximum anvil gap $δ_{max}$ before the anvil 201084 reaches a first tissue contact point 202048 for tissue of high thickness at time $t_1$, where the tissue compression force curve 202064 for tissue of high thickness starts to increase. At time $t_1$, the anvil gap δ is still outside of the ideal firing zone 202056 shown between a maximum anvil gap δmax, defining a upper firing lockout threshold 202052, and a minimum anvil gap δmin, defining a lower firing lockout threshold 202054. As shown, due to constant tissue stiffness and variable tissue thickness, the anvil 201084 contacts the tissue at different times. For example, time $t_1$ is a first tissue contact point 202048 for tissue having high tissue thickness, time $t_2$ is a second tissue contact point for tissue of normal thickness, and time $t_3$ is a third tissue contact point 202058 for tissue of low thickness.

The first tissue compression force curve 202062 represents the compression force for tissue of normal thickness and starts to increase at time $t_2$ when tissue of normal thickness initially contacts the anvil 201804. The second tissue compression force curve 202064 represents tissue of high thickness and starts to increase at time $t_1$ when tissue of high thickness initially contacts the anvil 201804. The third tissue compression force curve 202066 represents tissue of low thickness and starts to increase at time $t_3$ when tissue of low thickness initially contacts the anvil 201804. At the second and third tissue contact points at times $t_2$ and $t_3$, for tissue of normal and low thickness, the anvil gap δ is within the ideal firing zone 202056, 202076. The tissue compression force F will vary as a function of the biomechanical properties of tissue thickness. As indicated in the bottom graph 202040, tissue of normal thickness is represented by a first tissue compression force curve 202042, tissue of high thickness is represented by a second tissue compression force curve 202044, and tissue of low stiffness is represented by a third tissue compression force curve 202066. From the initial tissue contact points at times $t_1$, $t_2$, $t_3$ as the anvil 201084 continues to close, the tissue compression forces for each curve 202062, 202064, 2020066 start to increase until time $t_4$ where the anvil gap reaches a predetermined value and remains constant between $t_4$ and $t_5$ until the stapler 202082 is ready to fire.

As the anvil 201084 continues to close between the maximum anvil gap max and the minimum anvil gap δmin, the anvil gap δ reaches a point of constant anvil gap at time $t_4$. As shown in the lower graph 202060, at time $t_4$ the tissue compression force F for tissue of normal thickness represented by the first tissue compression force curve 202062 is within the ideal firing zone 202076, which is defined between a maximum compression force $F_{max}$, defining an upper warning threshold 202072, and a minimum compression force $F_{min}$, defining a lower warning threshold 202074. At time $t_4$ the tissue compression force F for tissue of high thickness represented by the second tissue compression force curve 202064 is above the upper warning threshold 202072 outside the ideal firing zone 202076 and the tissue compression force F for tissue of low thickness represented by the third tissue compression force curve 202066 is below the lower warning threshold 202074 outside the ideal firing zone 202076.

From time $t_4$ to time $t_5$, the anvil 201084 is maintained at a constant gap δ, as shown in the upper graph 202040, by the three anvil gap curves 202042, 202044, 202046. This period of constant gap δ, allows for tissue creep, as shown in the lower graph 202060, during which the average tissue compression force F slowly drops as shown by the three tissue compression force curves 202062, 202064, 202066. Tissue creep is a phase that is entered after tissue is grasped and the average tissue compression force F reaches a predetermined threshold and the closure motion of the anvil 201084 such that the anvil 201084 and the stapler 202082 hold the tissue therebetween for a predetermined time before initiating the firing phase in which the staples and knife are deployed. During the tissue creep phase the average tissue compression force F drops over the time period between $t_2$ and $t_3$. Tissue, in part because it is composed of solid and liquid material, tends to elongate when compressed. One way to account for this property is "tissue creep." When tissue is compressed, a certain amount of tissue creep can occur. Affording the compressed tissue an adequate amount of time under certain circumstances to accomplish tissue creep can therefore produce benefits. One benefit can be adequate staple formation. This can contribute to a consistent staple line. Accordingly, a certain time can be given to enable tissue creep prior to firing.

With reference now also to FIG. 23, after a period where the anvil gap δ is maintained constant to allow for tissue creep, at time t5, prior to deploying the staples, the control circuit 760 at point 202050 determines whether a possible adjustment of the anvil 766 relative to the staple cartridge 764 (anvil 201804 and stapler 202084 in FIG. 55) is necessary. Accordingly, the control circuit 760 determines if the tissue compression force F is between the ideal firing zone 202076, above the maximum compression force $F_{max}$ threshold 202072, or below the minimum compression force $F_{min}$ threshold 202074 and makes any necessary adjustments to the anvil gap δ. If the tissue compression force F is between the ideal firing zone 202076, the control circuit 760 deploys the staples in the staple cartridge 768 and deploys the knife 764.

If the tissue compression force F is above the maximum compression force $F_{max}$ threshold 202072, the control circuit 760 is configured to register a warning that the compression force is too tight and to adjust the anvil gap δ, increase the wait time before firing, lower the firing speed, or enable a firing lockout, or any combination thereof. The control circuit 760 can adjust the anvil gap δ by advancing the anvil 766 distally, e.g. away, from the staple cartridge 768 (anvil 201804 and stapler 202084 in FIG. 55) to increase the anvil gap δ as shown by the segment of the anvil gap curve 2002044 beyond time $t_5$. As shown by the segment of the tissue compression force curve 202064 beyond time $t_5$, after the control circuit 760 increases the anvil gap δ, the tissue compression force F decreases into the ideal firing zone 202076.

If the tissue compression force F is below the minimum compression force $F_{min}$ threshold 202074, the control circuit 760 is configured to register a warning that the compression force is too loose and can adjust the anvil gap δ, proceed with caution, or enable a firing lockout, or any combination thereof. The control circuit 760 is configured to adjust the anvil gap δ by retracting the anvil 766 proximally, e.g. toward, the staple cartridge 768 (anvil 201804 and stapler 202084 in FIG. 55) to decrease the anvil gap δ as shown by the segment of the anvil gap curve 202046 beyond time $t_5$. As shown by the segment of the tissue compression force curve 202066 beyond time $t_5$, after decreasing the anvil gap δ, the tissue compression force F increases into the ideal firing zone 202076.

With reference to FIGS. 53-54, in one aspect, the anvil gap δ may be determined by the controller 620 based on readings from the closure motor 603 as described with reference to FIG. 20, for example. In one aspect, the anvil gap δ may be determined by the control circuit 710 based on readings from the position sensor 734 coupled to the anvil 716 as described with reference to FIG. 21, for example. In one aspect, the anvil gap δ may be determined by the control circuit 760 based on readings from the position sensor 784 coupled to the anvil 766 as described with reference to FIGS. 22-23, for example.

With reference to FIGS. 53-54, in one aspect, the tissue compression force F may be determined by the controller 620 based on readings from the closure motor 603 as described with reference to FIG. 20. For example, the tissue compression force F may be determined based on the current draw of the motor where higher current draw while closing the anvil is related to higher tissue compression force. In one aspect, the tissue compression force F may be determined by the control circuit 710 based on readings from sensors 738, such as strain gauges, coupled to the anvil 716 or the staple cartridge 718 as described with reference to FIG. 21, for example. In one aspect, the tissue compression force F may be determined by the control circuit 760 based on readings from the sensors 788, such as strain gauges, coupled to the anvil 766 as described with reference to FIGS. 22-23, for example.

FIG. 56 is a logic flow diagram of a process 202100 depicting a control program or a logic configuration to provide discretionary or compulsory lockouts according to sensed parameters compared to thresholds, in accordance with at least one aspect of the present disclosure. As depicted in FIG. 56, according to a comparison of the measured anvil gap relative to one or more thresholds and the measured tissue compression force F (otherwise referred to as FTC) relative to one or more thresholds, a control algorithm can allow the instrument to be fired (e.g., actuated) without limitations, implement a discretionary lockout (e.g., provide a warning to the user), or implement a compulsory lockout of the instrument.

Accordingly, with reference to FIGS. 22, 55, and 56, the process 202100 will be described with reference to FIGS. 22-32. The control circuit 760 implements the algorithm to execute the process 202100 where the anvil 766 in FIG. 23 is shown as anvil 202084 in FIG. 55 and the staple cartridge 768 in FIG. 22 is shown as the stapler 202082 in FIG. 55. Additional details regarding the configuration and operation of a powered circular stapling device 202080 are described herein with reference to FIGS. 24-30. Turning back to the process 202100, the control circuit 760 determines the anvil gap δ as described in connection with FIGS. 53 and 54 based on readings from the position sensor 784 coupled to the anvil 766. When the anvil gap δ is $\delta_3 > \delta_{Max}$, the anvil gap is out of range and the control circuit 760 engages a compulsory lockout 202104. When the anvil gap δ is $\delta_{Max} > \delta_2 > \delta_{Min}$, the anvil gap δ is in range and the control circuit 760 determines 202106 the tissue compression force F (FTC) as described with reference to FIG. 58. As described above, the tissue compression force may be determined by the control circuit 760 based on readings from strain gauge sensors 788 coupled to the anvil 766 or the staple cartridge 768. Alternatively, tissue compression force may be determined based current draw by the motor 754.

With reference now to FIGS. 56 and 58, when the FTC is less than an ideal FTC threshold ($X_1$<Ideal FTC), zone A in FIG. 58, the control circuit 760 executes 202108 a no limits electronic lockout. When the FTC is between a maximum FTC threshold and the ideal FTC threshold (Max>$X_2$>Ideal), zone B in FIG. 58, the control circuit 760 executes 202110 discretionary electronic lockouts without limits. In one aspect, under this condition, the control circuit 760 issues a warning in the form of a message or alert (audio, visual, tactile, etc.). When the FTC is greater than a maximum FTC threshold ($X_3$>Margin), zone C in FIG. 58, the control circuit executes 202112 discretionary electronic lockouts with limits. Under this condition, the control circuit 760 issues a warning in the form of a message or alert (audio, visual, tactile, etc.) and applies a wait period before firing. In various aspects, the powered circular stapling device 202080 includes adjustable electronic lockouts as described herein, which can either prevent the actuation of the 202082 stapler or adjust the function of the powered circular stapling device 202080 based on a sensed condition and a secondary measure.

In one aspect, powered circular stapling device 202080 control algorithm described herein as the process 202100 can be configured to initiate discretionary and compulsory lockouts based on marginal and required conditions for the powered circular stapling device 202080 to operate. In one aspect, the process 202100 for the powered circular stapling device 202080 can be configured to implement both compulsory and discretionary lockouts based on sensed parameters within the system. A discretionary lockout pauses the automatic execution of a sequential operation, but can be overridden by the user input, for example. A compulsory lockout prevents the next sequential step, causing the user to back up a step of operation and resolve the lockout condition which induced the lockout, for example. In one aspect, both compulsory and discretionary lockouts can have both upper and lower bounded thresholds. Accordingly, the powered circular stapling device 202080 can comprise a combination of discretionary and compulsory lockouts.

In one aspect, powered circular stapling device 202080 control algorithm described herein as the process 202100 can be configured to adjust electronic lockouts that can either prevent the actuation of a system or adjust its function based on the sensed condition and a secondary measure. The sensed condition may be FTC, anvil displacement, gap δ, formation of staples and the secondary measure can include the severity of failure, a user input, or predefined comparison lookup table, for example.

In one aspect, the reaction of compulsory electronic lockouts is to prohibit the powered circular stapling device 202080 function until the situation is resolved. Conversely, the reaction to a discretionary lockout can be more subtle. For example, discretionary lockout could include a warning indication, an alert requiring user consent to proceed, a change in the rate or force of an actuation or wait time, or a prohibition of certain functions being performed until the situation is resolved or stabilized. In operation, compulsory conditions for the powered circular stapling device 202080 can include, for example, having the anvil 202084 fully seated before clamping or the stapler cartridge being loaded with staples before firing. Viable conditions for the powered circular stapling device 202080 can include, for example, being within the acceptable staple height for a given tissue thickness or a minimum tissue compression. Further, different conditions could have both discretionary and compulsory level thresholds on the same parameter, e.g., power level within the battery pack.

In one aspect, the powered circular stapling device 202080 can be configured to implement various control mechanisms to prevent or adjust the function of the powered circular stapling device 202080 based on the lockout type. In one aspect, compulsory lockouts could be solely electronic, mechanical interlocks, or a combination of the two. In various aspects having two lockouts, the lockouts could be redundant or optionally used based on the settings of the device. In one aspect, discretionary lockouts can be electronic lockouts so that they can be adjustable based on sensed parameters. For example, the discretionary lockouts could be a mechanical interlock that is electronically disabled or they could be a solely electronic lockout.

FIG. 57 is a diagram illustrating the anvil gap ranges and corresponding staple formation, in accordance with at least one aspect of the present disclosure. When the anvil gap 202120 is between an upper limit 202126 and a lower limit 202128, the staple formation is proper and within an acceptable range of staple heights for a given range of tissue thickness or minimum tissue compression force. When the anvil gap 202122 is greater than the upper limit 202126, the staple formation is loose. When the anvil gap 202124 is less than the lower limit 202128, the staple formation is tight.

FIG. 58 is a graphical representation 202150 of three force to close (FTC) curves 202152, 202154, 202156 verse time, in accordance with at least one aspect of the present disclosure. The FTC curves 202152, 202154, 202156 are divided into three phases: clamp, wait, and fire. The camp phase has a common starting point, which means that the tissue has a common thickness and variable tissue stiffness as described in detail in FIG. 31. At the end of the clamp phase, there is a wait period before starting the fire phase to account for tissue creep.

The first FTC curve 202152 corresponds to tissue having a low tissue stiffness. During the clamping phase, the FTC curve 202152 exhibits a rise in tissue compression force that peaks below the ideal FTC threshold 202158 in zone A. At the end of the clamp phase, the powered circular stapling device 202080 (FIG. 55) waits a user controlled period 202162 before initiating the firing phase to account for tissue creep.

The second FTC curve 202154 corresponds to tissue having a normal tissue stiffness. During the clamping phase, the FTC curve 202154 exhibits a rise in tissue compression force that peaks between the ideal FTC threshold 202158 and the maximum FTC threshold 202160 in zone B. At the end of the clamp phase, the powered circular stapling device 202080 (FIG. 55) waits a user controlled period 202164 before initiating the firing phase to account for tissue creep.

The third FTC curve 202154 corresponds to tissue having a high tissue stiffness. During the clamping phase, the FTC curve 202156 exhibits a rise in tissue compression force that peaks above the maximum FTC threshold 202160 in zone C. At the end of the clamp phase, the powered circular stapling device 202080 (FIG. 55) controls a wait period 202166 before initiating the firing phase to account for tissue creep.

FIG. 59 is a detail graphical representation 202170 of a FTC curve 202172 verse time, in accordance with at least one aspect of the present disclosure. As shown, the FTC curve 202172 is divided over three phases: a clamp phase, a wait phase, and a fire phase. During the clamp phase, the FTC curve 202172 exhibits and increase in tissue compression force as indicated by the clamp phase segment 202174. After the clamp phase, there is a wait period 202176 before initiating the fire phase. The wait period 202176 may be either user controlled or device controlled depending on the value of the tissue compression force relative to ideal and maximum compression force thresholds. During the fire phase, the tissue compression force increases as shown by FTC curve segment 202178 and then drops.

Establishment and Alteration of Communication Priorities

Various techniques for establishing hub wireless communication prioritization are described herein.

FIG. 60 depicts a chart 200500 indicating hub communication priorities according to procedure step, in accordance with at least one aspect of the present disclosure. In one aspect, the hub communication priorities can be based on situational awareness of the hub. The hub's situational awareness can determine which step of the procedure is being performed and, accordingly, what the appropriate communication priorities are, as shown in FIG. 60. The communication priorities can be based on a critical failure of a specific step, process, or device operation, for example. Further, the communication priorities can be based on the procedure step and the device needs determined to be integral to that step, for example. Still further, the communication priorities can be based on special requirements of a device given a certain configuration of the device, for example. For example, battery-powered RF devices configured to operate in a high calculation-based mode for improved performance and can require that some supplemental processing be performed by the hub. Still further, prioritization of communication priorities can vary based on the current step of the procedure, as shown in FIG. 60. For example, the priority of communication from a device actively being used for a critical procedure step can have a higher communication priority in general when compared to a device that is on a back table waiting to be used. Still further, the communication priorities can be based on the importance of the connected device.

Still further, the communication priorities can be based on status of the hub itself. For example, if there is a failure of an internal process or program in the hub, there may be a need to verify the authenticity or the integrity of the program before re-initializing it. As another example, a communication with an outside security fob or license server may be required to bring a program back online. In one aspect, it may be required for a hub to communicate with some cloud services in order to verify if any alterations or updates are required for a hub-based program to operate after it has unexpectedly shut down. Such a cloud services communication, for example, may be required to reestablish a predefined link between the hub and any relay device or range extension device used to regain links to attached/paired devices. In some aspects, the communication priorities can be based on the level of importance of an issue being experienced by an attached device. Yet still further, communication priorities can be based on the detection, by the hub, of a device that is capable of communicating with a hub and whether there has been a lack of established identification from that device.

Chart 200500 depicted in FIG. 60 illustrates some examples of communication priorities that may be associated with a first hub and related to surgical procedures. Column 200510 depicts a default set of communication priorities for a first hub associated with a first operating room (OR) in which a generic surgical procedure is active. As depicted in column 200510, the top priority (priority 1) may be given to those functions associated with patient status monitoring (for example, anesthesia, blood pressure monitoring, pulse oximetry monitoring, and similar status indicators). The first hub communications with the generic smart surgical instruments within the first OR may have high communications priorities after patient monitoring. Communications with a second hub located in a second OR, and the instruments associated with the second hub, may generally have lower communications priorities. Communication with devices and/or servers associated with ancillary activities (such as disposables inventory and billing services) may have still lower communication priorities.

Column 200520 of chart 200500 depicts a set of communication priorities for a first hub associated with a first operating room in which a vessel dissection procedure is occurring. As indicated in column 200520, the patient monitoring functions again have the top level priority (priority 1) for the first hub communication. Thereafter, communications with dissection specific devices (such as an advanced energy device, and a powered endoscope grasper) have the next highest communication priorities. In some aspects, a second hub in a second OR may be communicating with medical devices associated with a vessel transection procedure. The second hub, for example, may be communicating with other medical devices such as a powered stapler and a powered endoscopic clip applier. The second hub and its associated medical devices may have a lower communication priority with respect to the first hub Again, as indicated in column 200510, communications with ancillary services may have lower priorities.

Column 200530 of chart 200500 depicts a set of communication priorities for a first hub associated with a first operating room in which a vessel transection procedure is occurring. As indicated in column 200520, the patient monitoring functions again have the top level priority (priority 1) for the first hub communication. Thereafter, communications with dissection specific devices (such as a powered stapler device, and a powered endoscope grasper) have the next highest communication priorities. In some aspects, a second hub in a second OR may be communicating with medical devices associated with a vessel dissection procedure. The second hub, for example, may be communicating with other medical devices such as an advanced energy device and a powered endoscopic clip applier. The second hub and its associated medical devices may have a lower communication priority with respect to the first hub Again, as indicated in column 200510, communications with ancillary services may have lower priorities.

Detection of Necessary Interaction of Two Systems within the Network

In various aspects, the hub can be configured to reprioritize linked processes or products to ensure that needed information has been transmitted to and/or received from the devices.

In one aspect, if an in-use device that requires input from an associated system, but has not been provided the required data, communication with the associated system can be prioritized. For example, if an intelligent advanced energy combo device is in-use, but has not received any information from an advance visualization module on tissue type, thickness, or collagen level and the hub has identified that both systems exist within the network, the hub could be configured to then prioritize the image processing routines and provide the parameters needed by the energy device as the highest priority of both process and communication through the system.

Hub-to-Hub Communication, Processing Control, and Interaction

Various techniques for non-interactive, interactive, and process-sharing hub-to-hub communication are described herein.

In one aspect of non-interactive communication, the hubs can be configured to perform inter-hub sharing of information including, for example, location, geo-fences, and status. In this aspect, hubs can be configured to communicate with adjacent OR hubs and identify/locate different systems. Communication of data, status, or other collected information to the network of hubs can be selectively used by one or more hubs.

In one aspect of interactive control communication, interaction between hubs to distribute data and processing can be effected with a network. Numerous hubs connected via a network can use distributed processing for processing/determining/calculating performance or usage parameters. For example, FIG. 61 is a diagram of a network of surgical hubs 200600 executing a distributed processing system, in accordance with at least one aspect of the present disclosure.

As depicted in FIG. 61, hubs 1, 2, 3, and 4 (200610, 200620, 200630, and 200640, respectively) may be included in a network of surgical hubs 200600. Each hub may be located within a separate operating room. Thus, hub 1 (200610) may be located within OR 1 (200612), hub 2 (200620) may be located within OR 2 (200622), hub 3 (200630) may be located within OR 3 (200632), and hub 4 (200610) may be located within OR 4 (200642).

The distributed processing system allows hubs within the system to distribute processing resources amongst themselves as needed. For example, if a hub within the network is reaching its processing or power cap such that it will need to begin budgeting processing power, and another hub within the network is idle, the first hub could offload high-processing needs to the idle hub, allowing the idle hub to share maximum processing capability and power needs. Examples of such inter-hub communications are depicted in FIG. 61. Thus, hub 1 (200610) may form a communication link 200650a with hub 2 (200620), a communication link 200650b with hub 3 (200630) or a communication link 200650c with hub 4 (200640). Hub 2 (200620) may form a communication link 200650a with hub 1 (200610), or a communication link 200650d with hub 3 (200630), or a communication link 200650e with hub 4 (200640). Hub 3 (200630) may form a communication link 200650b with hub 1 (200610), or a communication link 200650d with hub 2 (200620), or a communication link 200650f with hub 4 (200640). Similarly, hub 4 (200640) may form a communication link 200650c with hub 1 (200610), or a communication link 200650e with hub 2 (200620), or a communication link 200650f with hub 3 (200630). Although each hub in the network of surgical hubs 200600 may form a pair-wise communication connection with any other hub in the network of surgical hubs 200600, it may be recognized that process distribution among the hubs may include more than two hubs in any connection. In one aspect, hubs in the same OR/network may use different communication protocols than are used by hubs in different ORs/networks.

In one aspect of process-sharing between hubs based on the unused capacity of the interconnected systems, processing or communication resources can be distributed or concentrated based on anticipated system impact. For example, the interconnected surgical devices/systems could be configured to compare which device has the module and systems necessary to accomplish a specified surgical task. If the task were process- or communication-intensive, the system could either distribute the needed capacity between multiple devices or consolidate them to a specific portion of the system in order to accomplish the task based on the criticality of the task or its impact on the overall system (and thus its impact on other tasks being performed by the system). Prioritization for sharing can be determined by several factors, such as capacity (i.e., how much is the system being taxed with its current functions), activity level (e.g., hubs that are not in use because the OR is empty or being set up should get priority for sharing), model number (e.g., models with increased capabilities may be more adept at sharing than older models), and so on.

Pairing of Personally Owned Wireless Devices

Various techniques for pairing personally owned wireless devices are described herein. In one aspect, an encrypted key can be used to authenticate a smart phone, wearable, or other personally owned device is supplied to a given user. Defining of the functions a personal device will request of the Hub to do given certain input elements. In one aspect, porting the personally owned device into the system provides a link from the device to the surgical hub to run an internal function. For example, a device can be connected to a hub and the music from a library or playlist on the device to be ported into (i.e., streamed through) the hub's speakers. As another example, a phone or another such device can be connected to a hub and options for the device can be linked through the hub to allow the porting of calls through the hub monitors and speakers. In one application, an auto reply voice or text message can be sent to incoming calls or texts that states that the user is unavailable when the user's device is connected to the hub, unless, e.g., the call or text is from a select subset of numbers (e.g., from other physicians that may call to consult on cases). In another application, a contact list from a linked phone can be stored so that incoming calls to the surgeon's phone during surgery can be answered or ignored according to whether the incoming call is from a number on the contact list.

In one aspect, a surgical hub can be configured to display functional imported data (e.g., data imported from a mobile device) on a secondary display due to the hub's awareness of the type of data and/or how common the use of the data is. In one aspect, the information can be displayed on a secondary display when the data is uploaded/imported to the surgical hub. In another aspect, an interactive menu can become actionable on the primary or in-use display when the data is uploaded/imported to the surgical hub when interaction is available. For example, when a call is received by a mobile device connected to a surgical hub, caller ID information from the mobile device's contact list can pop up on selected monitors visible by surgeon and nurses. As another example, the caller ID information could be displayed on secondary monitor that for displaying ancillary information, such as device settings, or a configurable computer tablet positioned in the sterile field that the surgeon could touch to answer if needed in order to avoid cluttering the main surgical screen with pop-ups. As another example, depending on the particular sensed user, the number of times that user utilizes the secondary device, and other parameters, the hub can be configured to flag the most commonly used and/or most appropriate option or menu according to the particular the interaction. In some aspects, the hub can be configured to display the option or menu on the user interface without interfering with the task at hand.

FIG. 62 depicts an example of a pairing of a personally owned wireless device 200002 with a surgical hub 200006. The wireless device 200002 and the surgical hub 200006 may communicate with each other over a wireless link 200004. As disclosed above, the surgical hub 200006 may display imported data received from the wireless device 200002 on one or more displays visible to the members of the surgical team. In one aspect, the surgical hub 200006 may cause the imported data to be displayed on a primary or in-use display monitor 200008. In another aspect, the surgical hub 200006 may cause the imported data to be displayed on a secondary display monitor 200010.

Smart Cartridge Communication with Hub without Going Through the Attached Device Various techniques for smart cartridge communication with the hub, without utilizing the instrument in which the cartridge is attached as a communication medium, are described herein.

In various aspects, a cartridge can be configured such that there is a wired connection between the device and the cartridge and that physical contact is needed between the instrument and the cartridge is required to transfer power to the cartridge. In one such aspect, the cartridge can include a circuit for identification that includes a portion that requires both the sled of the instrument and at least one staple to make contact thereagainst for there to be continuity. If either of the sled or a staple is not contacting the circuit, the power transfer to the cartridge will not occur and the device will be locked out. In these aspects, the described circuit can be utilized to provide a secondary or backup method of locking out an instrument from being utilized with a spent cartridge.

In various aspects, the cartridge can be configured to communicate with the hub, without requiring any power from the surgical instrument (e.g., a surgical stapler).

In one such aspect, inserting the cartridge into device is configured to supply a momentary amount of power to the cartridge, which is then configured to communicate directly with hub without going through the device. In some aspects, the cartridge includes no battery or power source onboard. In some aspects, the small amount of power can be tapped off upon connection and during transmission, after which the power drain by the cartridge ceases. For example, FIG. 63 is a diagram of a cartridge 200012 configured to wirelessly communicate with a surgical hub 200006, in accordance with at least one aspect of the present disclosure. In one aspect, the communication may be accomplished by a wireless communication circuit 200028 imbedded in the cartridge 200012. In this example, power is wirelessly transferred from the device to the cartridge through inductive coupling. In one aspect, a first wire transmission antenna coil 200014 is printed into the wall 200016 of a channel of the instrument 200018. A second receiver coil 200020 may be printed on a mating surface of the cartridge 200012. Power may be transmitted from the transmission antenna coil 200014 to the receiver coil 200020 when the two coils are proximate to and overlap each other. In some aspects, power 200024 may be supplied to the instrument 200018 and conducted to the transmission coil 200014 via any suitable conductor, such as by a flexible circuit conductor 200026.

FIG. 63A depicts the overlap 200022 of the transmission coil 200014 and the receiver coil 20020. The transmission coil 200014 may receive power 200024 sourced to the instrument 200018. The amount of overlap 200022 and degree of proximity between the transmission coil 200014 and the receiver coil 200020 may determine the amount of power received by the receiver coil 200020. Power in the receiver coil 200020 may be used to power the communication circuit 200028.

In such aspects, the close proximity and alignment of the transmission coil 200014 and the receiver coil 20020 may be achieved with lug features 200030 formed into the body of the cartridge 200012. The lug features 200030 may be configured to align the cartridge 200012 within the channel of the instrument 200018 when the cartridge 200012 is inserted into the instrument 200018. The lug features 200030 may be configured to align the cartridge within the channel of the instrument 200018 by mating with corresponding slot features 200032 fabricated in the channel.

In some aspects, the cartridge and/or instrument further include resonating circuits to increase the efficiency of the power transfer therebetween. For example, FIG. 64 is a block diagram of a resonant inductive wireless power system 200034 in accordance with at least one aspect of the present disclosure. The resonant inductive wireless power system 200034 can include, for example, a transmitter oscillator 200040 that receives power from a power source 200042. The transmitter oscillator 200040 may supply AC current to a transmission coil 200044. The resonant inductive wireless power system 200034 can also include, for example, a rectifier 200046 that may receive power from the a transmission coil 200044 via a receiver coil 200048.

The receiver coil 200048 may be coupled to the transmission coil 200044 through the magnetic (B) field generated by the transmission coil 200044. In some aspects, The rectifier 200046 may convert the AC power received from the transmitter oscillator 200040 to DC power to source to a load 200050. In one example, a load 200050 may include the communication circuit 200028. The resonant inductive wireless power system 200034 may further include, for example, one or more resonance coils 200036a,b made of copper wire for example, that resonate with their internal capacitance (indicated as capacitors 200038a,b in phantom) at a resonant frequency (for example at 10 MHz). In some aspects, the resonance coils 200036a,b may have matched impedances to optimize the power transmission from the transmitter oscillator 200040 to the rectifier 200046.

In another aspect, the cartridge 200012 may include a battery that may power the communication circuit 200028 when the cartridge 200012 is inserted into the instrument

200018. In this aspect, the communication circuit 200028 may be powered regardless of the power status of the instrument 200018.

In another aspect, a sterile scanning pad can be configured to scan an instrument 200018 and/or a cartridge 200012. In operation, the scanning pad can be present on a back table within the operating room (OR) and a health care professional may scan the instrument 200018 or cartridge 200012 by placing the instrument 200018 or cartridge 200012 on the scanning pad. Data from the instrument 200018 or cartridge 200012 may be provided to the hub when the instrument 200018 or cartridge 200012 is opened and placed on the scanning pad. In some aspects, the instrument 200018 or cartridge 200012 may be scanned, for example via radiofrequency (RF), to activate the instrument 200018 or cartridge 200012 and track it by the hub. In some further aspects, there may be a wired connection from the pad to the hub to supply power for scanning.

Detection of Environment and Setting a Geo-Fenced Area

Various techniques for detecting an environment and establishing a geo-fence are described herein.

FIG. 65A is a diagram of a surgical hub detecting an area or room perimeter, for example the perimeter of an operating room (OR) in accordance with at least one aspect of the present disclosure. In one aspect, a perimeter 200052 of a space detectable by a surgical hub 200006 can be defined by one or more freestanding beacons 200054*a-d* with directional antennas. In one aspect, the beacons 200054*a-d* can be placed at desired positions within a room in which the hub 200006 is or will be located. In one aspect, the perimeter 200052 delimited by the beacons 200054*a-d* may form a boundary of a device detection space by the surgical hub 200006. The beacons 200054*a-d* can be used, for example, to define a zone that has a regular three-dimensional shape or an irregular three-dimensional shape. In some applications, as few as three beacons (generically, 200054) can be used to define a simple device detection perimeter, such as the interior of a square or rectangular room. In other aspects, more than three beacons 200054*a-d* may be used to delimit a detection zone having an irregular shape, such as that depicted in FIG. 65A.

In some aspects, the beacons 200054*a-d* may be active or passive. Active beacons 200054*a-d* may actively transmit information for receipt by the hub 200006 without requiring the hub 200006 to transmit any information to them. Passive beacons 200054*a-d* may be activated only on receipt of one or more transmissions from the hub 200006. Passive beacons 200054*a-d* may then respond to an initiating query by the hub 200006 and transmit, in response to receiving the initiating query from the hub 200006, a response signal. The signals transmitted by the beacons 200054*a-d* may be of any suitable form including, without limitation, a wireless signal, an acoustic signal, or a light signal. The signals transmitted by the beacons 200054*a-d* may include any suitable information, such as identification information, locational information, or any other information that the hub 200006 may use to determine the location of the beacons 200054*a-d* and thus permit the hub 200006 to determine the perimeter 200052.

As disclosed above, the perimeter 200052 may define a detection zone in which the hub 200006 may scan for one or more surgical instruments or other devices. Devices within the detection zone may be recognized by the hub 200006 as being potentially associated with a surgical procedure. It may be understood that in this aspect, devices located outside of the detection zone may not be recognized by the hub 200006 as being potentially associated with a surgical procedure. Alternatively, the beacons can be utilized to define an excluded zone in which devices may not be recognized by the hub 200006. In some aspects, the transmission angle of signals from the beacons 200054*a-d* can be adjustable. Starting at about 90 degrees, multiple beacons 200054*a-d* could be placed on the floor or on walls around OR to define the perimeter 200052. In some aspects, the perimeter 200052 may form a surgical instrument detection zone. In some aspects, the detection angle of the beacons can be visually shown with light beam when setting up the beacon assembly.

FIG. 65B depicts some aspects of a geo-fence system that may further include a "jamming" beacon 200056. In some aspects, a spatial region may be protected from receiving a transmission from the hub or devices within the spatial region may be shielded from receiving transmissions from the hub 200006. For example, the "jamming" beacon 200056 may be placed at, near, or within a perimeter that interferes with the hub or a device signal to prevent devices within the excluded region defined by the jamming beacon(s) 200056 from connecting to the surgical hub. In various applications, a "jamming" beacon can be utilized to define a shielded zone, a sterile table, an instrument cabinet 200058 in the OR, or a storage zone between OR rooms, for example.

It may be recognized that the use of a "jamming" beacon 200056 may operate differently than the use of beacons 200054*a-d* to define an exclusion zone. For example, a "jamming" beacon 200056 may be associated with a movable instrument cabinet 200058. The "jamming" function of the "jamming" beacon 200056 may prevent the hub 200006 from establishing communications with medical instruments stored in the instrument cabinet 200058 regardless of the location of the instrument cabinet 200058.

In some applications, positioning the beacons 200054*a-d* along the borders of a room such as an operating room, may establish a controlled means of determining the real-world size and orientation of the OR with respect to the hub 200006. In still other applications, positioning the beacons 200054*a-d* at the boundaries of the sterile field can designate disposable instruments that are opened and ready for use as compared to capital instruments or instruments that are available, but not yet opened.

On-the-Fly Pairing Between Multiple Controllers and Controlled Devices

In one aspect, the hub and/or hub-connectable devices can be configured to wirelessly and interactively pair with each other. Accordingly, multiple controllers and controlled devices can be configured to wirelessly, on-the-fly input pairing, without the need for any direct user control. For example, FIG. 20 is a diagram of user and device pairing 200060 between a hub 200006, a user-worn identifier 200066, and a surgical instrument 200062, in accordance with at least one aspect of the present disclosure. In the depicted aspect, an identifier 200066 can be worn or attached to the hand(s) of each user. The identifier 200066 may interact with a receiver 200064 that is attached to or integral with a surgical device 200062. In one aspect, the receiver 200064 may be integrated within a handle of the surgical device 200062. The identifier 200066 and the receiver 200064 can be configured to communication via near-field communication (NFC) or another such communication protocol.

In operation, whenever a user picks up a device 200062, the receiver 200064 of the device automatically pairs the device 200062 with the identifier 200066. In response to the pairing between the receiver 200064 and the identifier 200066, the hub 200006 recognizes the device 200062 permitting the hub 200006 to control and/or receive status data from the device 200062. In some aspects, the hub 200006 may communicate with the device 200062 directly. In other aspects, the hub 200006 may communicate with the device 200062 via a communication link from the hub 200006 through the identifier 200066 to the device receiver 200064. The NFC linkage allows communication of the surgical device 200062 with the identifier 200066, which in turn communicates with the hub 200006. In some aspects, the identifier 200066 may act as a communications relay 200068 between the hub 200006 and the surgical device 200062, permitting identification and/or sensor information from the surgical device 200062 to be transmitted to the hub 200006, and control data to be transmitted from the hub 200006 to control the surgical device 200062.

In some other aspects, the identifier 200066 may transmit information to either one or both of the hub 200006 and the surgical device 200062. In some aspects, the information from the identifier 200066 may include an identification of the user. In some other aspects, the information from the identifier 200066 may include which hand is using the surgical device 200062. In some additional aspects, the hub 200006 may also provide either one or both of the identifier 200066 and the surgical device 200062 with the appropriate identification information of each device to allow them to communicate with either directly or through the hub 200006 to coordinate activation of a control with activation of a device function.

Methods of Interchanging of Control Paired Instruments Between Two Controllers

In various aspects, control of instruments paired with surgical hubs can be interchangeably switched between different surgical hubs.

Initiation of the control change between the paired instruments and the surgical hubs can be controlled and/or indicated to users/other devices in different manners. In one aspect, a predefined sequence could be used to indicate by the user the release of a controlled device to the control device (e.g., the surgical hub) and/or associated devices (e.g., other devices connected to the surgical hub).

Designation of a new relationship between the control device and the controlled device can be controlled and/or indicated to users/other devices in different manners. In one aspect, once released or when not paired to a control system within the local network of the OR, a series of steps could be used to link two system for the purposes of controlling one system with the other system. In an alternative aspect, the in-sterile field control and interaction device can be utilized to display all the paired links within the OR and to redistribute them in a different order.

Identification and notification of a control change of a device, without used of a control device, can be effected in different manners. In one aspect, the illumination of a built-in display screen of a handheld device could be configured to change from a first color (e.g., blue or green) to a second color (e.g., red) and/or from a first state (e.g., solid color) to a second state (e.g., flashing) to indicate and notify the user in changes to the control state of the device. For example, the first color and/or first state can indicate control of the device (e.g., the device is paired with a surgical hub) and the second color and/or second state can indicate that there is no control device connected to the instrument. Further, the illumination could be around the perimeter of the built-in display of the device. Still further, the illumination could also be through light transmission plastic surrounding a control module. In an alternative aspect, the device could be outlined on the primary display and the color and/or state of the outline around the device (or a component of the device, such as a shaft of an instrument) can indicate its control state (i.e., pairing of the device with a control device or a lack thereof).

In one aspect, control can be shared from more than one control device to a single controlled device. For example, the system could be used to either enable two wireless control devices to both control the same device simultaneously or to control multiple devices from a single control device.

Device Position and Orientation Detection

Various techniques for detecting the position and orientation of devices are described herein.

In one aspect, measurements with respect to a ground coordinate system or with respect to one another can be displayed. In such aspects, a display system can be configured to display user-selectable measurements of the position of the device with respect to the patient, the hub, or a device (e.g., a trocar). FIG. 21 depicts an aspect of a surgical suite 200070 in which surgical instruments (for example, surgical instruments 200072*a,b*) are used as part of a surgical procedure.

In one aspect, the display system could be configured to show the current location of the surgical instruments 200072*a,b* with respect to a local coordinate system. In another aspect, the display system could be configured to calculate whether there is or will be interaction between the surgical instruments 200072*a,b*. In one aspect, the display could switch from displaying the local coordinate measures to the interaction calculation as the surgical instruments 200072*a,b* come closer in proximity to one another or to the tissue. The interaction calculation could be used to avoid inadvertent collisions between the surgical instruments 200072*a,b* or to allow the user(s) to coordinate the motions of two surgical instruments 200072*a,b* specifically to control the interaction between them.

In one aspect, the display system is configured to display the true position of the surgical instruments 200072*a,b* with respect to an outside established frame of reference. For example, triangulation beacons that interface with the hub can be positioned around the OR to establish location and orientation of any devices within the OR (see, for example, FIGS. 65A-B). Further, a beacon could be attached to each of the surgical instruments 200072*a,b* to establish the location of each of the surgical instruments 200072*a,b* with respect to each other, other devices, and/or other beacons. In one aspect, a trocar could be tagged with a beacon, which would allow the hub 200006 to identify which of the surgical instruments 200072*a,b* is currently inserted into the trocar. The display system may display an identifier of a surgical instrument (for example surgical instruments 200072*a,b*) in insure that the surgical instrument and the trocar in which it is inserted is retained on the display.

By determining the relative positions and/or orientation of the surgical instruments 200072*a,b* with respect to each other or with respect to other instruments, the hub 200006 may provide angle, insertion depth, and relative orientation of the surgical instruments 200072a,b and/or an end effector of each of the surgical instruments 200072a,b for a member of the surgical team. In some aspects, the position and/or orientation of the surgical instruments 200072a,b may be determined with respect to the patient, surgical site, or incision site for critical instrument positioning.

As disclosed above, the surgical instruments 200072a,b and/or other devices may include one or more beacons to assist in determining their relative position and/or orientation with respect to each other. Such beacons could be based on RF, magnetics, or another energy waveform capable of penetrating tissue as well as air for sending and receiving triangulation signals. In some aspects, the hub 200006 may receive the triangulation signals emitted by the beacons. In some aspects, the triangulation signals may include identifier information permitting the hub 20006 to determine which beacon is associated with which triangulation signal. In some aspects, an elongated surgical instrument (such as surgical instruments 200072a,b) may have multiple beacons attached to a handle and a shaft so that the orientation of the instrument shaft with respect to the instrument handle may be determined by the hub 200006

As disclosed above, the location and/or orientation of a surgical instrument may be determined relative to a location and/or orientation of another surgical instrument or other surgical device. In another aspect, the location and/or orientation of the surgical instruments 200072a,b may be determined with respect to one or more local references. In some aspects, the one or more local references may include one or more wireless or RF beacons disposed within the surgical suite In another aspect, a local reference may include a magnetic field generator 200074 on a stand within the OR or mounted on a wall or ceiling. The magnetic field generator 200074 can be configured to create a predefined magnetic field within the room, as depicted in FIG. 67. Further, each surgical instrument or medical device may include one or more built-in or attached sensors to detect the magnetic field (or RF field for the use with one or more RF beacons) and determine the device orientation with respect to the magnetic field (or RF field).

Each device (such as surgical instruments 200072a,b) can transmit the location and/or orientation information to the hub 200006 via a wired or a wireless communication system to allow the hub 200006 to track the position and orientation of the device. In one aspect, each of the surgical instruments 200072a,b could include several sensors that would be able to detect their respective distances and orientations with respect to the predefined magnetic field. Multiple sensors may be useful for surgical instruments that include an elongated shaft connected to a hand held unit. For example, magnetic sensors may be disposed with the hand held unit, half-way along a length of the elongated shaft, and at a distal end effector attached to the elongated shaft. The instrument could then report its location and orientation of the elongated shaft and end effector to a central procedural system (executed, e.g., by the hub 200006). The procedureal system could then calculate and track the use and disposition of all of the instruments within the OR and display or highlight to the user on a visual display when interactions or special conditions exist.

In another aspect, each of the surgical instruments 200072a,b may define a coordinate system local to the instrument. In some aspects, the local coordinate systems may be determined with respect to one or more local references, such as a magnetic field generator 200074. In another example, the local coordinate systems may be established with respect to a local ground such as a trocar port on the patient. The use of a local ground, in proximity to the the surgical instruments 200072a,b, can establish a local coordinate system having increased spatial resolution compared to a coordinate system based on a distant beacon (such as the magnetic field generator 200074). Such a finer resolution coordinate system may provide detailed information regarding the location and orientation of a surgical instrument passing through the trocar. Further, trocar positions themselves can be used to aid in understanding of port placement and other operations to inform other systems, both intraoperatively as well as postoperatively, for training purposes.

In one aspect, a first frame of reference is established with respect to a device (e.g., a scope) positioned inside the patient and a second frame of reference is established outside the patient with respect to a predefined position. Further, the system can include a means for linking one frame of reference to the other to be able to establish instrument position to jaw position relative to the tissue. Accordingly, the position and orientation of devices can be determined according to two separate, interrelated coordinate systems.

In one aspect, a coupling sensor could be used to link an internal visualization image within a surgical site to the exterior visualization image of the surgical field in order to coordinate an end effector position of a surgical instrument with respect to patient tissues in the surgical field and an outside position and orientation of a handle of the surgical instrument. For example, the primary internal visualization system could be used to determine positions, distances, and velocities between aspects of the instruments and tissues of interest within the body. In one aspect, a primary internal visualization system may use a specialized frame capture imaging device. Such a device may capture the image of the internal surgical site by using a beam of light that is bounced off an internal structure of the surgical site and any devices disposed therein. Accordingly, the refraction of the beam of light by the tissue can be used to determine the distance between the internal tissue structure(s) and the device(s), rather then the reflectivity of the tissues.

In one aspect, lidar may be used as the measurement method for this type of system. Lidar measurements may use a pulsed laser to create a pattern and then the reflected pulses are measured. In some aspects, such a technique may be referred to as laser scanning. In various aspects, a CMOS array multi laser light source used for advanced visualization may be employed for this technique. For example, FIG. 68 depicts such a system 200076 for using lidar to determine the positions of surgical devices 200078a,b relative to a user-selected measurement site 200080, in accordance with at least one aspect of the present disclosure. As depicted in FIG. 68, the primary internal visualization system may permit a user of the surgical devices 200078a,b to assess a distance 200082 between end effectors of the surgical devices 200078a,b. In some aspects, a surgical hub may display the positions of the end effectors within the surgical site. In some additional aspects, the surgical hub may provide a warning, such as a visual indicator in a display, to warn the user of the surgical devices 200078a,b if the surgical devices 200078a,b are approaching or at a minimum collision distance between them.

In another aspect, RF could be used to determine the locations of end-effectors within the abdomen cavity or within any internal surgical field. FIG. 69 depicts such a system. Radio Frequency time-of-flight would be one measure of determining distance to smart devices. For example, a primary transmitter and receiver could be used on a scope or visualization system 200086. In one aspect, the primary transmitter may include a first antenna 200084a and the receiver may include a second antenna 200084b. In another aspect, the first antenna 200084a may be used as both a transmitting element and as a receiving element. Similarly, the second antenna 200084b may be used as both a transmitting element and as a receiving element. By incorporating the primary transmitter and receiver into an end of the visualization system 200086, the receiver may measure a distance from the visualization system 200086 to a first target device with respect to the visualization focus, thereby allowing the user to measure from a frame of reference based on what the user can see.

In one aspect, an antenna array 200083 associated with the scope or visualization system 200086 may be composed of the first antenna 200084a and the second antenna 200084b. In one aspect, one antenna (such as first antenna 200084a) of the antenna array 200083 can be configured to transmit a signal at one frequency while a second antenna (such as first antenna 200084a) of the antenna array 200083 can be configured to receive a signal transmitted back from a first target surgical instrument 200088. As one example, the frequency of the signal transmitted by the antenna array 200083 may be about 13.56 MHz. In another example, the strength of the signal received by the first target surgical instrument 200088 may be about at about −36 dbm RSSI. In some aspects, a return signal to the antenna array 200083 may be transmitted by the first target surgical instrument 200088 at a frequency that differs from the frequency of the signal transmitted by the antenna array 200083. Such a communication protocol is considered full duplex communication 200090. Separate transmission and reception frequencies may be used to prevent interference of the transmission signal by the reception signal (and vice versa). In addition, separate transmission and reception frequencies may permit the measurement of the round trip time of the signal to and from a first target surgical instrument 200088. In some aspects, the round trip time of the signal to and from a first target surgical instrument 200088 may be used to calculate a distance of the first target surgical instrument 200088 from the antenna array 200083.

In another aspect, the distance of the first target surgical instrument 200088 from the antenna array 200083 to the first target surgical instrument 200088 may be calculated based on the power loss of a signal transmitted by the antenna array 200083 or by a response signal transmitted by the first target surgical instrument 200088. Geometric factors, such as the spread of the transmitted signal over distance, as well as the absorption loss due to the medium between the antenna array 200083 and the first target surgical instrument 200088 may permit such a distance measurement. In general, the distance between the antenna array 200083 and the first target surgical instrument 200088 is proportional to the ratio of the strength of the signal received by the first target surgical instrument 200088 to the strength of the originally transmitted signal by the antenna array 200083. Alternatively, the distance between the antenna array 200083 and the first target surgical instrument 200088 may be calculated from the ratio of the signal strength of the response signal received by the antenna array 200083 to the strength of the signal transmitted by the first target surgical instrument 200088. In some examples of this technique, the signal transmitted by the first target surgical instrument 200088 may incode information regarding the signal strength of transmitted signal.

Accordingly, smart systems could determine relative position by receiving and then returning a signal. The receiving array could include a field-programmable gate array (FPGA) and a microcontroller configured to handle the speed of measurements necessary from multiple instruments in real-time. In one aspect, the receiver antenna array 200083 could consist of two different antennas, for example first antenna 200084a and second antenna 200084b. The system could compare the differences of the signal received on the two antennas (first antenna 200084a and second antenna 200084b) and triangulate the sources position in 3D space, as depicted in FIG. 69. FIG. 69 is a diagram of a system for determining the relative position of devices via a dual-antenna array 200083, in accordance with at least one aspect of the present disclosure. In the system depicted in FIG. 69, the dual-antenna array 200083 is disposed on a scope 200086 and receives either actively transmitted signals or passive signals from devices to determine the relative positions of the devices. In one aspect, the passive signal technique may include the full duplex communication system 200090 depicted with respect to first target surgical instrument 200088. In another aspect, the active signal communication 200092 may involve a second target surgical instrument 200094. The position of the devices can be determined form the detected signal strength, as shown in FIG. 70.

FIG. 70 depicts a graph 200110 of an example of the spatial resolution for determining the position of multiple target surgical instruments based on the detected signal strength. The abscissa represents a ratio of signal strength, in dBm, of a wireless communication between, for example, a target surgical instrument and a transceiver mounted on a reference device. The ordinate is the distance (for example in cm) that can be resolved based on the signal strength ratio. It can be observed in the graph 200110 that a difference between a maximum 200112 distance and a minimum distance 200114 may increase with increasing signal strength ratio.

Returning to FIG. 69, in another aspect, the end effectors of the instruments (for example second target surgical instrument 200094) could include one or more transmitters 200096 that are capable of continuously pinging a receiver of antenna array 200083 affixed to the visualization device 200086. In some non-limiting examples, the transmitter 200096 may transmit a signal at a frequency between about 860 mHz to about 960 mHz. In some examples, the transmitted signal may have a signal strength of about −60 dbm. The the one or more transmitters 200096 could transmit a unique ID, as well as the expected intensity of the signal, so the receiver of antenna array 200083 could then calculate distance based on the received strength. In another aspect, the one or more transmitters 200096 may transmit signals to be received by multiple antennas (for example first antenna 200084a and second antenna 200084b of the antenna array 200083). The difference in the reception time or signal strength of the transmitted signal as determined by the first antenna 200084a and the second antenna 200084b may be used to triangulate the position of the one or more transmitters 200096 and thus the position of the end effector of second target surgical instrument 200094.

In another aspect, an RFID tag could be placed on or in an end effector of each target surgical instrument. The RFID tag could be activated by a signal transmitted by a transmission antenna. In some aspects, the transmission antenna may be part of an antenna array 200083 disposed on a surgical visualization device 200086. In some aspects, each antenna of the antenna array 200083 (for example first antenna 200084a and second antenna 200084b) may act as a separate transmitting antenna. Alternatively, one of the antennae of the antenna array 200083 may be a transmission antenna and another of the antennae of the antenna array 200083 may be a reception antenna. Accordingly, the strength of the transmitted signal received by an RFID tag could be used to determine distance of the RFID tag to the transmitter antenna. In another aspect, the power transmission intensity of the transmitted signal could be varied, allowing the wake-up process of the RFID tag to be used to determine the distance. The wake-up process of the RFID tag may be initiated by the receipt of a radio frequency signal having a power greater than a threshold power. It is recognized that the power of a transmitted signal is attenuated over distance. Thus, an RFID tag disposed at a distance resulting in an attenuated received signal will not enter the wake-up process. However, an RFID tag disposed at a closer distance may receive the transmitted signal at sufficient power to initiate the wake-up process. In either of these examples, the transmitter antenna transmits a power signal for receipt by the passive RFID tag on the end effector. On receipt of a transmitted signal having sufficient power, the RFID tag may wake up and then transmits a return RF signal to be received by the receiver antenna. This return signal could include a unique identifier that the system could use to measure the distance from itself to multiple devices within the operating site.

Returning to FIG. 69, in another aspect, a separate scanning array laser could be used for solely detecting the distances 200098 between itself and structures within the body 200099. The scanning laser array could be cycled out of sequence from the primary visualization system 200086 to prevent interaction of the light from the distance finder and light from the primary visualization means. Alternatively, an energy means outside of the sensing capability of the primary visualization array could be utilized. If the main visualization device could detect near infrared to near ultraviolet EMR, then a light/EMR source that transmits well into the ultraviolet spectrum could be used for the scanning laser array. Alternatively ultrasonic, microwave, or RF could be used to move completely into another energy spectrum area to prevent interference between the scanning array and the visualization device. For example, ultrasonic diffuse and retroreflective sensors could be used determine distance and size of an object within its range through a gas medium (e.g., Senix or Pepperl+Fuchs ultrasonic sensors). As one example, the distance measurement 200098 between the primary visualization system 200086 and a specific structure within the body 200099 may be used along with measurements to determine the position of a first target surgical instrument 200088 to calculate a distance between the first target surgical instrument 200088 and the specific structure within the body 200099. As another example, contact ultrasound sensors could be used to interrogate tissues, fluids, and so on for imaging means. As yet another example, a combination of these two sources could be used to determine the tissue locations and the instrument locations within the insufflation gases of the patient's abdomen.

In another aspect, infrared ID and tracking can be used via projected light and a camera observing the OR. For example, at least two separate reflectors or one reflector with aspect in at least two planes could be used to determine a location and an orientation of a target surgical instrument with respect to a trocar and then with respect to the scope image inside the patient.

Generator Hardware

FIG. 71 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links In one aspect, the surgical instrument 700 may be programmed or configured to individually control a firing member, a closure member, a shaft member, or one or more articulation members, or combinations thereof. The surgical instrument 700 comprises a control circuit 710 configured to control motor-driven firing members, closure members, shaft members, or one or more articulation members, or combinations thereof.

In one aspect, the robotic surgical instrument 700 comprises a control circuit 710 configured to control a clamp arm 716 and a closure member 714 portion of an end effector 702, an ultrasonic blade 718 coupled to an ultrasonic transducer 719 excited by an ultrasonic generator 721, a shaft 740, and one or more articulation members 742a, 742b via a plurality of motors 704a-704e. A position sensor 734 may be configured to provide position feedback of the closure member 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the closure member 714 as determined by the position sensor 734 with the output of the timer/counter 731 such that the control circuit 710 can determine the position of the closure member 714 at a specific time (t) relative to a starting position or the time (t) when the closure member 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the clamp arm 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the closure member 714, clamp arm 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the closure member 714. The position sensor 734 may be or include any type of sensor that is capable of generating position data that indicate a position of the closure member 714. In some examples, the position sensor 734 may include an encoder configured to provide a series of pulses to the control circuit 710 as the closure member 714 translates distally and proximally. The control circuit 710 may track the pulses to determine the position of the closure member 714. Other suitable position sensors may be used, including, for example, a proximity sensor. Other types of position sensors may provide other signals indicating motion of the closure member 714. Also, in some examples, the position sensor 734 may be omitted. Where any of the motors 704a-704e is a stepper motor, the control circuit 710 may track the position of the closure member 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the closure member 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the closure member 714. The transmission 706a comprises movable mechanical elements such as rotating elements and a firing member to control the movement of the closure member 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the closure member 714. A position sensor 734 may be configured to provide the position of the closure member 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the closure member 714 translates distally, the clamp arm 716 closes towards the ultrasonic blade 718.

In one aspect, the control circuit 710 is configured to drive a closure member such as the clamp arm 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the clamp arm 716. The transmission 706b comprises movable mechanical elements such as rotating elements and a closure member to control the movement of the clamp arm 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the clamp arm 716. The position sensor 734 may be configured to provide the position of the closure member as a feedback signal to the control circuit 710. Additional sensors 738 in the end effector 702 may provide the closure force feedback signal to the control circuit 710. The pivotable clamp arm 716 is positioned opposite the ultrasonic blade 718. When ready to use, the control circuit 710 may provide a closure signal to the motor control 708b. In response to the closure signal, the motor 704b advances a closure member to grasp tissue between the clamp arm 716 and the ultrasonic blade 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the clamp arm 716 to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the ultrasonic blade 718 has tissue on it, and (4) the load and position on both articulation rods.

In one aspect, the one or more sensors 738 may comprise a strain gauge, such as a micro-strain gauge, configured to measure the magnitude of the strain in the clamp arm 716 during a clamped condition. The strain gauge provides an electrical signal whose amplitude varies with the magnitude of the strain. The sensors 738 may comprise a pressure sensor configured to detect a pressure generated by the presence of compressed tissue between the clamp arm 716 and the ultrasonic blade 718. The sensors 738 may be configured to detect impedance of a tissue section located between the clamp arm 716 and the ultrasonic blade 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the clamp arm 716 by the closure drive system. For example, one or more sensors 738 can be at an interaction point between the closure tube and the clamp arm 716 to detect the closure forces applied by the closure tube to the clamp arm 716. The forces exerted on the clamp arm 716 can be representative of the tissue compression experienced by the tissue section captured between the clamp arm 716 and the ultrasonic blade 718. The one or more sensors 738 can be positioned at various interaction points along the closure drive system to detect the closure forces applied to the clamp arm 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the clamp arm 716.

In one aspect, a current sensor 736 can be employed to measure the current drawn by each of the motors 704a-704e. The force required to advance any of the movable mechanical elements such as the closure member 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move the closure member 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

FIG. 72 illustrates a schematic diagram of a surgical instrument 750 configured to control the distal translation of a displacement member according to one aspect of this disclosure. In one aspect, the surgical instrument 750 is programmed to control the distal translation of a displacement member such as the closure member 764. The surgical instrument 750 comprises an end effector 752 that may comprise a clamp arm 766, a closure member 764, and an ultrasonic blade 768 coupled to an ultrasonic transducer 769 driven by an ultrasonic generator 771.

The position, movement, displacement, and/or translation of a linear displacement member, such as the closure member 764, can be measured by an absolute positioning system, sensor arrangement, and position sensor 784. Because the closure member 764 is coupled to a longitudinally movable drive member, the position of the closure member 764 can be determined by measuring the position of the longitudinally movable drive member employing the position sensor 784. Accordingly, in the following description, the position, displacement, and/or translation of the closure member 764 can be achieved by the position sensor 784 as described herein. A control circuit 760 may be programmed to control the translation of the displacement member, such as the closure member 764. The control circuit 760, in some examples, may comprise one or more microcontrollers, microprocessors, or other suitable processors for executing instructions that cause the processor or processors to control the displacement member, e.g., the closure member 764, in the manner described. In one aspect, a timer/counter 781 provides an output signal, such as the elapsed time or a digital count, to the control circuit 760 to correlate the position of the closure member 764 as determined by the position sensor 784 with the output of the timer/counter 781 such that the control circuit 760 can determine the position of the closure member 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the closure member 764 via a transmission 756. The transmission 756 may include one or more gears or other linkage components to couple the motor 754 to the closure member 764. A position sensor 784 may sense a position of the closure member 764. The position sensor 784 may be or include any type of sensor that is capable of generating position data that indicate a position of the closure member 764. In some examples, the position sensor 784 may include an encoder configured to provide a series of pulses to the control circuit 760 as the closure member 764 translates distally and proximally. The control circuit 760 may track the pulses to determine the position of the closure member 764. Other suitable position sensors may be used, including, for example, a proximity sensor. Other types of position sensors may provide other signals indicating motion of the closure member 764. Also, in some examples, the position sensor 784 may be omitted. Where the motor 754 is a stepper motor, the control circuit 760 may track the position of the closure member 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the clamp arm 766 during a clamped condition. The strain gauge provides an electrical signal whose amplitude varies with the magnitude of the strain. The sensors 788 may comprise a pressure sensor configured to detect a pressure generated by the presence of compressed tissue between the clamp arm 766 and the ultrasonic blade 768. The sensors 788 may be configured to detect impedance of a tissue section located between the clamp arm 766 and the ultrasonic blade 768 that is indicative of the thickness and/or fullness of tissue located therebetween.

The sensors 788 may be is configured to measure forces exerted on the clamp arm 766 by a closure drive system. For example, one or more sensors 788 can be at an interaction point between a closure tube and the clamp arm 766 to detect the closure forces applied by a closure tube to the clamp arm 766. The forces exerted on the clamp arm 766 can be representative of the tissue compression experienced by the tissue section captured between the clamp arm 766 and the ultrasonic blade 768. The one or more sensors 788 can be positioned at various interaction points along the closure drive system to detect the closure forces applied to the clamp arm 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the clamp arm 766.

A current sensor 786 can be employed to measure the current drawn by the motor 754. The force required to advance the closure member 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a closure member 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or closure member 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical sealing and cutting implements. For example, a motor 754 may drive a displacement member distally and proximally along a longitudinal axis of the end effector 752. The end effector 752 may comprise a pivotable clamp arm 766 and, when configured for use, an ultrasonic blade 768 positioned opposite the clamp arm 766. A clinician may grasp tissue between the clamp arm 766 and the ultrasonic blade 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, the closure member 764 with a cutting element positioned at a distal end, may cut the tissue between the ultrasonic blade 768 and the clamp arm 766.

In various examples, the surgical instrument 750 may comprise a control circuit 760 programmed to control the distal translation of the displacement member, such as the closure member 764, for example, based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the displacement member. Different control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

FIG. 73 illustrates a schematic diagram of a surgical instrument 750 configured to control the distal translation of a displacement member according to one aspect of this disclosure. In one aspect, the surgical instrument 750 is programmed to control the distal translation of a displacement member such as the closure member 764. The surgical instrument 750 comprises an end effector 752 that may comprise a clamp arm 766, a closure member 764, and an ultrasonic blade 768 coupled to an ultrasonic transducer 769 driven by an ultrasonic generator 771.

The position, movement, displacement, and/or translation of a linear displacement member, such as the closure member 764, can be measured by an absolute positioning system, sensor arrangement, and position sensor 784. Because the closure member 764 is coupled to a longitudinally movable drive member, the position of the closure member 764 can be determined by measuring the position of the longitudinally movable drive member employing the position sensor 784. Accordingly, in the following description, the position, displacement, and/or translation of the closure member 764 can be achieved by the position sensor 784 as described herein. A control circuit 760 may be programmed to control the translation of the displacement member, such as the closure member 764. The control circuit 760, in some examples, may comprise one or more microcontrollers, microprocessors, or other suitable processors for executing instructions that cause the processor or processors to control the displacement member, e.g., the closure member 764, in the manner described. In one aspect, a timer/counter 781 provides an output signal, such as the elapsed time or a digital count, to the control circuit 760 to correlate the position of the closure member 764 as determined by the position sensor 784 with the output of the timer/counter 781 such that the control circuit 760 can determine the position of the closure member 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the closure member 764 via a transmission 756. The transmission 756 may include one or more gears or other linkage components to couple the motor 754 to the closure member 764. A position sensor 784 may sense a position of the closure member 764. The position sensor 784 may be or include any type of sensor that is capable of generating position data that indicate a position of the closure member 764. In some examples, the position sensor 784 may include an encoder configured to provide a series of pulses to the control circuit 760 as the closure member 764 translates distally and proximally. The control circuit 760 may track the pulses to determine the position of the closure member 764. Other suitable position sensors may be used, including, for example, a proximity sensor. Other types of position sensors may provide other signals indicating motion of the closure member 764. Also, in some examples, the position sensor 784 may be omitted. Where the motor 754 is a stepper motor, the control circuit 760 may track the position of the closure member 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the clamp arm 766 during a clamped condition. The strain gauge provides an electrical signal whose amplitude varies with the magnitude of the strain. The sensors 788 may comprise a pressure sensor configured to detect a pressure generated by the presence of compressed tissue between the clamp arm 766 and the ultrasonic blade 768. The sensors 788 may be configured to detect impedance of a tissue section located between the clamp arm 766 and the ultrasonic blade 768 that is indicative of the thickness and/or fullness of tissue located therebetween.

The sensors 788 may be is configured to measure forces exerted on the clamp arm 766 by a closure drive system. For example, one or more sensors 788 can be at an interaction point between a closure tube and the clamp arm 766 to detect the closure forces applied by a closure tube to the clamp arm 766. The forces exerted on the clamp arm 766 can be representative of the tissue compression experienced by the tissue section captured between the clamp arm 766 and the ultrasonic blade 768. The one or more sensors 788 can be positioned at various interaction points along the closure drive system to detect the closure forces applied to the clamp arm 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the clamp arm 766.

A current sensor 786 can be employed to measure the current drawn by the motor 754. The force required to advance the closure member 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a closure member 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or closure member 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical sealing and cutting implements. For example, a motor 754 may drive a displacement member distally and proximally along a longitudinal axis of the end effector 752. The end effector 752 may comprise a pivotable clamp arm 766 and, when configured for use, an ultrasonic blade 768 positioned opposite the clamp arm 766. A clinician may grasp tissue between the clamp arm 766 and the ultrasonic blade 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, the closure member 764 with a cutting element positioned at a distal end, may cut the tissue between the ultrasonic blade 768 and the clamp arm 766.

In various examples, the surgical instrument 750 may comprise a control circuit 760 programmed to control the distal translation of the displacement member, such as the closure member 764, for example, based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the displacement member. Different control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

FIG. 73 is a schematic diagram of a surgical instrument 790 configured to control various functions according to one aspect of this disclosure. In one aspect, the surgical instrument 790 is programmed to control distal translation of a displacement member such as the closure member 764. The surgical instrument 790 comprises an end effector 792 that may comprise a clamp arm 766, a closure member 764, and an ultrasonic blade 768 which may be interchanged with or work in conjunction with one or more RF electrodes 796 (shown in dashed line). The ultrasonic blade 768 is coupled to an ultrasonic transducer 769 driven by an ultrasonic generator 771.

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In some examples, the position sensor 784 may be omitted. Where the motor 754 is a stepper motor, the control circuit 760 may track the position of the closure member 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

An RF energy source 794 is coupled to the end effector 792 and is applied to the RF electrode 796 when the RF electrode 796 is provided in the end effector 792 in place of the ultrasonic blade 768 or to work in conjunction with the ultrasonic blade 768. For example, the ultrasonic blade is made of electrically conductive metal and may be employed as the return path for electrosurgical RF current. The control circuit 760 controls the delivery of the RF energy to the RF electrode 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

FIG. 74 illustrates an example of a generator 900, which is one form of a generator configured to couple to an ultrasonic instrument and further configured to execute adaptive ultrasonic blade control algorithms in a surgical data network comprising a modular communication hub. The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled $ENERGY_1$ and RETURN. A second signal of a second energy modality is coupled across a capacitor 910 and is provided to the surgical instrument between the terminals labeled $ENERGY_2$ and RETURN. It will be appreciated that more than two energy modalities may be output and thus the subscript "n" may be used to designate that up to n $ENERGY_n$ terminals may be provided, where n is a positive integer greater than 1. It also will be appreciated that up to "n" return paths $RETURN_n$ may be provided without departing from the scope of the present disclosure.

A first voltage sensing circuit 912 is coupled across the terminals labeled $ENERGY_1$ and the RETURN path to measure the output voltage therebetween. A second voltage sensing circuit 924 is coupled across the terminals labeled $ENERGY_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled $ENERGY_1$/RETURN or the second voltage sensing circuit 924 coupled across the terminals labeled $ENERGY_2$/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality $ENERGY_1$ may be ultrasonic energy and the second energy modality $ENERGY_2$ may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 74 shows a single return path RETURN may be provided for two or more energy modalities, in other aspects, multiple return paths $RETURN_n$ may be provided for each energy modality $ENERGY_n$. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 74, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled $ENERGY_1$ and RETURN as shown in FIG. 74. In one example, a connection of RF bipolar electrodes to the generator 900 output would be preferably located between the output labeled $ENERGY_2$ and RETURN. In the case of monopolar output, the preferred connections would be active electrode (e.g., pencil or other probe) to the $ENERGY_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

FIG. 75 is a simplified block diagram of one aspect of the generator 1100 for providing inductorless tuning as described above, among other benefits. With reference to FIG. 75, the generator 1100 may comprise a patient isolated stage 1520 in communication with a non-isolated stage 1540 via a power transformer 1560. A secondary winding 1580 of the power transformer 1560 is contained in the isolated stage 1520 and may comprise a tapped configuration (e.g., a center-tapped or non-center tapped configuration) to define drive signal outputs 1600*a*, 1600*b*, 1600*c* for outputting drive signals to different surgical devices, such as, for example, an ultrasonic surgical device 1104 and an electrosurgical device 1106. In particular, drive signal outputs 1600*a*, 1600*b*, 1600*c* may output a drive signal (e.g., a 420V RMS drive signal) to an ultrasonic surgical device 1104, and drive signal outputs 1600*a*, 1600*b*, 1600*c* may output a drive signal (e.g., a 100V RMS drive signal) to an electrosurgical device 1106, with output 1600*b* corresponding to the center tap of the power transformer 1560. The non-isolated stage 1540 may comprise a power amplifier 1620 having an output connected to a primary winding 1640 of the power transformer 1560. In certain aspects the power amplifier 1620 may comprise a push-pull amplifier, for example. The non-isolated stage 1540 may further comprise a programmable logic device 1660 for supplying a digital output to a digital-to-analog converter (DAC) 1680, which in turn supplies a corresponding analog signal to an input of the power amplifier 1620. In certain aspects the programmable logic device 1660 may comprise a field-programmable gate array (FPGA), for example. The programmable logic device 1660, by virtue of controlling the power amplifier's 1620 input via the DAC 1680, may therefore control any of a number of parameters (e.g., frequency, waveform shape, waveform amplitude) of drive signals appearing at the drive signal outputs 1600*a*, 1600*b*, 1600*c*. In certain aspects and as discussed below, the programmable logic device 1660, in conjunction with a processor (e.g., processor 1740 discussed below), may implement a number of digital signal processing (DSP)-based and/or other control algorithms to control parameters of the drive signals output by the generator 1100.

Power may be supplied to a power rail of the power amplifier 1620 by a switch-mode regulator 1700. In certain aspects the switch-mode regulator 1700 may comprise an adjustable buck regulator, for example. As discussed above, the non-isolated stage 1540 may further comprise a processor 1740, which in one aspect may comprise a DSP processor such as an ADSP-21469 SHARC DSP, available from Analog Devices, Norwood, Mass., for example. In certain aspects the processor 1740 may control operation of the switch-mode power converter 1700 responsive to voltage feedback data received from the power amplifier 1620 by the processor 1740 via an analog-to-digital converter (ADC) 1760. In one aspect, for example, the processor 1740 may receive as input, via the ADC 1760, the waveform envelope of a signal (e.g., an RF signal) being amplified by the power amplifier 1620. The processor 1740 may then control the switch-mode regulator 1700 (e.g., via a pulse-width modulated (PWM) output) such that the rail voltage supplied to the power amplifier 1620 tracks the waveform envelope of the amplified signal. By dynamically modulating the rail voltage of the power amplifier 1620 based on the waveform envelope, the efficiency of the power amplifier 1620 may be significantly improved relative to a fixed rail voltage amplifier scheme. The processor 1740 may be configured for wired or wireless communication.

In certain aspects, the programmable logic device 1660, in conjunction with the processor 1740, may implement a direct digital synthesizer (DDS) control scheme to control the waveform shape, frequency and/or amplitude of drive signals output by the generator 1100. In one aspect, for example, the programmable logic device 1660 may implement a DDS control algorithm by recalling waveform samples stored in a dynamically-updated look-up table (LUT), such as a RAM LUT which may be embedded in an FPGA. This control algorithm is particularly useful for ultrasonic applications in which an ultrasonic transducer, such as the ultrasonic transducer 1120, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 1100 is impacted by various sources of distortion present in the output drive circuit (e.g., the power transformer 1560, the power amplifier 1620), voltage and current feedback data based on the drive signal may be input into an algorithm, such as an error control algorithm implemented by the processor 1740, which compensates for distortion by suitably pre-distorting or modifying the waveform samples stored in the LUT on a dynamic, ongoing basis (e.g., in real-time). In one aspect, the amount or degree of pre-distortion applied to the LUT samples may be based on the error between a computed motional branch current and a desired current waveform shape, with the error being determined on a sample-by sample basis. In this way, the pre-distorted LUT samples, when processed through the drive circuit, may result in a motional branch drive signal having the desired waveform shape (e.g., sinusoidal) for optimally driving the ultrasonic transducer. In such aspects, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 1540 may further comprise an ADC 1780 and an ADC 1800 coupled to the output of the power transformer 1560 via respective isolation transformers 1820, 1840 for respectively sampling the voltage and current of drive signals output by the generator 1100. In certain aspects, the ADCs 1780, 1800 may be configured to sample at high speeds (e.g., 80 Msps) to enable oversampling of the drive signals. In one aspect, for example, the sampling speed of the ADCs 1780, 1800 may enable approximately 200× (depending on drive frequency) oversampling of the drive signals In certain aspects, the sampling operations of the ADCs 1780, 1800 may be performed by a single ADC receiving input voltage and current signals via a two-way multiplexer. The use of high-speed sampling in aspects of the generator 1100 may enable, among other things, calculation of the complex current flowing through the motional branch (which may be used in certain aspects to implement DDS-based waveform shape control described above), accurate digital filtering of the sampled signals, and calculation of real power consumption with a high degree of precision. Voltage and current feedback data output by the ADCs 1780, 1800 may be received and processed (e.g., FIFO buffering, multiplexing) by the programmable logic device 1660 and stored in data memory for subsequent retrieval by, for example, the processor 1740. As noted above, voltage and current feedback data may be used as input to an algorithm for pre-distorting or modifying LUT waveform samples on a dynamic and ongoing basis. In certain aspects, this may require each stored voltage and current feedback data pair to be indexed based on, or otherwise associated with, a corresponding LUT sample that was output by the programmable logic device 1660 when the voltage and current feedback data pair was acquired. Synchronization of the LUT samples and the voltage and current feedback data in this manner contributes to the correct timing and stability of the pre-distortion algorithm.

In certain aspects, the voltage and current feedback data may be used to control the frequency and/or amplitude (e.g., current amplitude) of the drive signals In one aspect, for example, voltage and current feedback data may be used to determine impedance phase, e.g., the phase difference between the voltage and current drive signals. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the processor 1740, for example, with the frequency control signal being supplied as input to a DDS control algorithm implemented by the programmable logic device 1660.

The impedance phase may be determined through Fourier analysis. In one aspect, the phase difference between the generator voltage $V_g(t)$ and generator current $I_g(t)$ driving signals may be determined using the Fast Fourier Transform (FFT) or the Discrete Fourier Transform (DFT) as follows:

$$V_g(t) = A_1 \cos(2\pi f_0 t + \varphi_1)$$

$$I_g(t) = A_2 \cos(2\pi f_0 t + \varphi_2)$$

$$V_g(f) = \frac{A_1}{2}(\delta(f - f_0) + \delta(f + f_0))\exp\left(j2\pi f \frac{\varphi_1}{2\pi f_0}\right)$$

$$I_g(f) = \frac{A_2}{2}(\delta(f - f_0) + \delta(f + f_0))\exp\left(j2\pi f \frac{\varphi_2}{2\pi f_0}\right)$$

Evaluating the Fourier Transform at the frequency of the sinusoid yields:

$$V_g(f_0) = \frac{A_1}{2}\delta(0)\exp(j\varphi_1) \arg V(f_0) = \varphi_1$$

$$I_g(f_0) = \frac{A_2}{2}\delta(0)\exp(j\varphi_2) \arg I(f_0) = \varphi_2$$

Other approaches include weighted least-squares estimation, Kalman filtering, and space-vector-based techniques. Virtually all of the processing in an FFT or DFT technique may be performed in the digital domain with the aid of the 2-channel high speed ADC 1780, 1800, for example. In one technique, the digital signal samples of the voltage and current signals are Fourier transformed with an FFT or a DFT. The phase angle φ at any point in time can be calculated by:

$$\varphi = 2\pi ft + \varphi_0$$

Where φ is the phase angle, f is the frequency, t is time, and $\varphi_0$ is the phase at t=0.

Another technique for determining the phase difference between the voltage $V_g(t)$ and current $I_g(t)$ signals is the zero-crossing method and produces highly accurate results. For voltage $V_g(t)$ and current $I_g(t)$ signals having the same frequency, each negative to positive zero-crossing of voltage signal $V_g(t)$ triggers the start of a pulse, while each negative to positive zero-crossing of current signal $I_g(t)$ triggers the end of the pulse. The result is a pulse train with a pulse width proportional to the phase angle between the voltage signal and the current signal. In one aspect, the pulse train may be passed through an averaging filter to yield a measure of the phase difference. Furthermore, if the positive to negative zero crossings also are used in a similar manner, and the results averaged, any effects of DC and harmonic components can be reduced. In one implementation, the analog voltage $V_g(t)$ and current $I_g(t)$ signals are converted to digital signals that are high if the analog signal is positive and low if the analog signal is negative. High accuracy phase estimates require sharp transitions between high and low. In one aspect, a Schmitt trigger along with an RC stabilization network may be employed to convert the analog signals into digital signals. In other aspects, an edge triggered RS flip-flop and ancillary circuitry may be employed. In yet another aspect, the zero-crossing technique may employ an eXclusive OR (XOR) gate.

Other techniques for determining the phase difference between the voltage and current signals include Lissajous figures and monitoring the image; methods such as the three-voltmeter method, the crossed-coil method, vector voltmeter and vector impedance methods; and using phase standard instruments, phase-locked loops, and other techniques as described in O'Shea, Peter, "Phase Measurement" 2000 CRC Press LLC, which is incorporated by reference herein in its entirety.

In another aspect, for example, the current feedback data may be monitored in order to maintain the current amplitude of the drive signal at a current amplitude setpoint. The current amplitude setpoint may be specified directly or determined indirectly based on specified voltage amplitude and power setpoints. In certain aspects, control of the current amplitude may be implemented by control algorithm, such as, for example, a proportional-integral-derivative (PID) control algorithm, in the processor 1740. Variables controlled by the control algorithm to suitably control the current amplitude of the drive signal may include, for example, the scaling of the LUT waveform samples stored in the programmable logic device 1660 and/or the full-scale output voltage of the DAC 1680 (which supplies the input to the power amplifier 1620) via a DAC 1860.

The non-isolated stage 1540 may further comprise a processor 1900 for providing, among other things, user interface (UI) functionality. In one aspect, the processor 1900 may comprise an Atmel AT91 SAM9263 processor having an ARM 926EJ-S core, available from Atmel Corporation, San Jose, Calif., for example. Examples of UI functionality supported by the processor 1900 may include audible and visual user feedback, communication with peripheral devices (e.g., via a Universal Serial Bus (USB) interface), communication with a foot switch 1430, communication with an input device 2150 (e.g., a touch screen display) and communication with an output device 2140 (e.g., a speaker). The processor 1900 may communicate with the processor 1740 and the programmable logic device (e.g., via a serial peripheral interface (SPI) bus). Although the processor 1900 may primarily support UI functionality, it may also coordinate with the processor 1740 to implement hazard mitigation in certain aspects. For example, the processor 1900 may be programmed to monitor various aspects of user input and/or other inputs (e.g., touch screen inputs 2150, foot switch 1430 inputs, temperature sensor inputs 2160) and may disable the drive output of the generator 1100 when an erroneous condition is detected.

FIG. 76 illustrates a generator circuit 3500 partitioned into multiple stages where a first stage circuit 3504 is common to the second stage circuit 3506, in accordance with at least one aspect of the present disclosure. In one aspect, the surgical instruments of surgical system 1000 described herein may comprise generator circuit 3500 partitioned into multiple stages. For example, the surgical instruments of surgical system 1000 may comprise the generator circuit 3500 partitioned into at least two circuits: the first stage circuit 3504 and the second stage circuit 3506 of amplification enabling operation of high-frequency (RF) energy only, ultrasonic energy only, and/or a combination of RF energy and ultrasonic energy. A combination modular shaft assembly 3514 may be powered by a common first stage circuit 3504 located within the handle assembly 3512 and a modular second stage circuit 3506 integral to the modular shaft assembly 3514. As previously discussed throughout this description in connection with the surgical instruments of surgical system 1000, a battery assembly 3510 and the shaft assembly 3514 are configured to mechanically and electrically connect to the handle assembly 3512. The end effector assembly is configured to mechanically and electrically connect the shaft assembly 3514.

As shown in the example of FIG. 76, the battery assembly 3510 portion of the surgical instrument comprises a first control circuit 3502, which includes the control circuit 3200 previously described. The handle assembly 3512, which connects to the battery assembly 3510, comprises a common first stage drive circuit 3420. As previously discussed, the first stage drive circuit 3420 is configured to drive ultrasonic, high-frequency (RF) current, and sensor loads. The output of the common first stage drive circuit 3420 can drive any one of the second stage circuits 3506 such as the second stage ultrasonic drive circuit 3430, the second stage high-frequency (RF) current drive circuit 3432, and/or the second stage sensor drive circuit 3434. The common first stage drive circuit 3420 detects which second stage circuit 3506 is located in the shaft assembly 3514 when the shaft assembly 3514 is connected to the handle assembly 3512. Upon the shaft assembly 3514 being connected to the handle assembly 3512, the common first stage drive circuit 3420 determines which one of the second stage circuits 3506 (e.g., the second stage ultrasonic drive circuit 3430, the second stage RF drive circuit 3432, and/or the second stage sensor drive circuit 3434) is located in the shaft assembly 3514. The information is provided to the control circuit 3200 located in the handle assembly 3512 in order to supply a suitable digital waveform to the second stage circuit 3506 to drive the appropriate load, e.g., ultrasonic, RF, or sensor. It will be appreciated that identification circuits may be included in various assemblies 3516 in third stage circuit 3508 such as the ultrasonic transducer 1120, the electrodes 3074a, 3074b, or the sensors 3440. Thus, when a third stage circuit 3508 is connected to a second stage circuit 3506, the second stage circuit 3506 knows the type of load that is required based on the identification information.

FIG. 77 illustrates a diagram of a surgical system 4000, which represents one aspect of the surgical system 1000, comprising a feedback system for use with any one of the surgical instruments of surgical system 1000, which may include or implement many of the features described herein. The surgical system 4000 may include a generator 4002 coupled to a surgical instrument that includes an end effector 4006, which may be activated when a clinician operates a trigger 4010. In various aspects, the end effector 4006 may include an ultrasonic blade to deliver ultrasonic vibration to carry out surgical coagulation/cutting treatments on living tissue. In other aspects the end effector 4006 may include electrically conductive elements coupled to an electrosurgical high-frequency current energy source to carry out surgical coagulation or cauterization treatments on living tissue and either a mechanical knife with a sharp edge or an ultrasonic blade to carry out cutting treatments on living tissue. When the trigger 4010 is actuated, a force sensor 4012 may generate a signal indicating the amount of force being applied to the trigger 4010. In addition to, or instead of a force sensor 4012, the surgical instrument may include a position sensor 4013, which may generate a signal indicating the position of the trigger 4010 (e.g., how far the trigger has been depressed or otherwise actuated). In one aspect, the position sensor 4013 may be a sensor positioned with an outer tubular sheath or reciprocating tubular actuating member located within the outer tubular sheath of the surgical instrument. In one aspect, the sensor may be a Hall-effect sensor or any suitable transducer that varies its output voltage in response to a magnetic field. The Hall-effect sensor may be used for proximity switching, positioning, speed detection, and current sensing applications. In one aspect, the Hall-effect sensor operates as an analog transducer, directly returning a voltage. With a known magnetic field, its distance from the Hall plate can be determined.

A control circuit 4008 may receive the signals from the sensors 4012 and/or 4013. The control circuit 4008 may include any suitable analog or digital circuit components. The control circuit 4008 also may communicate with the generator 4002 and/or a transducer 4004 to modulate the power delivered to the end effector 4006 and/or the generator level or ultrasonic blade amplitude of the end effector 4006 based on the force applied to the trigger 4010 and/or the position of the trigger 4010 and/or the position of the outer tubular sheath described above relative to a reciprocating tubular actuating member located within an outer tubular sheath (e.g., as measured by a Hall-effect sensor and magnet combination). For example, as more force is applied to the trigger 4010, more power and/or higher ultrasonic blade amplitude may be delivered to the end effector 4006. According to various aspects, the force sensor 4012 may be replaced by a multi-position switch.

According to various aspects, the end effector 4006 may include a clamp or clamping mechanism. When the trigger 4010 is initially actuated, the clamping mechanism may close, clamping tissue between a clamp arm and the end effector 4006. As the force applied to the trigger increases (e.g., as sensed by force sensor 4012) the control circuit 4008 may increase the power delivered to the end effector 4006 by the transducer 4004 and/or the generator level or ultrasonic blade amplitude brought about in the end effector 4006. In one aspect, trigger position, as sensed by position sensor 4013 or clamp or clamp arm position, as sensed by position sensor 4013 (e.g., with a Hall-effect sensor), may be used by the control circuit 4008 to set the power and/or amplitude of the end effector 4006. For example, as the trigger is moved further towards a fully actuated position, or the clamp or clamp arm moves further towards the ultrasonic blade (or end effector 4006), the power and/or amplitude of the end effector 4006 may be increased.

According to various aspects, the surgical instrument of the surgical system 4000 also may include one or more feedback devices for indicating the amount of power delivered to the end effector 4006. For example, a speaker 4014 may emit a signal indicative of the end effector power. According to various aspects, the speaker 4014 may emit a series of pulse sounds, where the frequency of the sounds indicates power. In addition to, or instead of the speaker 4014, the surgical instrument may include a visual display 4016. The visual display 4016 may indicate end effector power according to any suitable method. For example, the visual display 4016 may include a series of LEDs, where end effector power is indicated by the number of illuminated LEDs. The speaker 4014 and/or visual display 4016 may be driven by the control circuit 4008. According to various aspects, the surgical instrument may include a ratcheting device connected to the trigger 4010. The ratcheting device may generate an audible sound as more force is applied to the trigger 4010, providing an indirect indication of end effector power. The surgical instrument may include other features that may enhance safety. For example, the control circuit 4008 may be configured to prevent power from being delivered to the end effector 4006 in excess of a predetermined threshold. Also, the control circuit 4008 may implement a delay between the time when a change in end effector power is indicated (e.g., by speaker 4014 or visual display 4016), and the time when the change in end effector power is delivered. In this way, a clinician may have ample warning that the level of ultrasonic power that is to be delivered to the end effector 4006 is about to change.

In one aspect, the ultrasonic or high-frequency current generators of the surgical system 1000 may be configured to generate the electrical signal waveform digitally such that the desired using a predetermined number of phase points stored in a lookup table to digitize the wave shape. The phase points may be stored in a table defined in a memory, a field programmable gate array (FPGA), or any suitable non-volatile memory.

Advanced Enemy Device Control Algorithms

Various control algorithms for ultrasonic surgical instruments and combination energy surgical instruments (e.g., ultrasonic/monopolar surgical instruments, monopolar/bipolar surgical instruments, ultrasonic/bipolar surgical instruments, and other such combination energy devices) are described herein. For the sake of clarity, surgical instruments will be referenced as surgical instrument 7012 in this section of the present disclosure, although the disclosure of this section could also apply to other surgical instruments referenced above such as surgical instrument 112, 700.

In various aspects, a control algorithm for a surgical instrument 7012 can be configured to achieve a constant heat flux along the length of the ultrasonic blade of surgical instrument 7012. The control algorithm can be applied by a control circuit and/or a surgical hub. The control circuit may execute a local computer executable program/algorithm of the surgical instrument 7012 or receive a suitable algorithm (e.g., impedance rate algorithm) from the surgical hub and/or the cloud computing system. Alternatively, the surgical hub could execute the algorithm remotely for the surgical instrument 7012. The constant heat flux may advantageously improve the quality of tissue coagulation, cutting, or sealing. The surgical instrument 7012 could be an ultrasonic and bipolar or a combination energy modality surgical instrument. The control algorithm may involve determining or adjusting clamp force in proportion to the progression of surgical coagulation of the tissue grasped by the surgical instrument 7012. Moreover, the control algorithm could involve variably changing, such as increasing, the clamp arm pressure applied on a tissue bite that has been loaded into the end effector, to produce constant heat flux along the blade length.

In particular, the power of electrosurgical energy delivered by the generator of surgical instrument 7012 as well as the applied clamp arm pressure can be adjusted or determine to attain a predefined heat flux. Additionally or alternatively, these can be adjusted to achieve a predefined amount of power to be applied to the tissue. For example, the control algorithm can comprise varying the RF and ultrasonic power level delivered by the generator in conjunction with varying the clamp arm pressure to achieve a predefined heat flux or power applied to the tissue. The heat flux could be constant or nearly constant over the weld time of the tissue relative to a surgical treatment cycle. The variation implemented by the control algorithm can be based on at least one parameter, which can include, for example, tissue impedance, blade natural frequency, temperature, or some other parameter (e.g., tissue operational parameter). Additionally or alternatively, the variation in clamp pressure and power level can be based on a heat flux controlled threshold. This heat flux controlled threshold can be dynamic so that the threshold adjusts along the blade length based on the progression of the surgical cutting and coagulation. This progression may be assessed by the corresponding focal point, which may be findicative of how well formed a fibrin clot is for coagulation, for example. Accordingly, a constant heat flux along the length of the blade could be generated, with the applied clamp force being proportional or corresponding to coagulation.

The control algorithm might also be configured to achieve constant heat flux by adjusting power over a series of sequential impedance set points based on the time to achieve a set point, in order to mimic impedance rise. In other words, as the generator of the surgical instrument 7012 progressively delivers power according to predetermined power curves (which define a relationship between power delivered to the tissue and the tissue impedance), the control circuit may be configured to determine whether the tissue impedance reaches a certain quantity at a certain time. When the certain quality is reached, the generator may be idle for a period of time and/or switch to a different power curve. If the certain quality is not reached, the generator may switch to a different power curve at that time or upon the control circuit determining that the certain quality will not or likely will not be reached. Additionally or alternatively, the control circuit could select power curves based on forecasting that applying the selected power curve would cause the tissue impedance to reach a particular impedance level at a particular time in the surgical treatment cycle.

The targeted or set tissue impedance points can be dependent on the next target point and/or the time required to reach the last set point. That is, for a series of tissue impedance points, each point can be determined based on its neighboring points, which may be either immediately before or after the subject point. Other points in the series can also be used to determine the value of the subject point. Each set point is defined as a tissue impendence target with an associated power level. For the series of impedance target points, as the delivery of power by the generator causes the tissue impedance to reach the subject point, the next tissue impedance target and power level can be determined. The subsequent impedance target point can be determined or adjusted based on overall tissue impedance level at that moment of the surgical treatment cycle and the time required to attain the previous impedance target point. The set points may include a predefined time, such as a dwell time, at the impedance target points prior to the control circuit determining the next adjustment.

In executing the control algorithm, the control circuit and/or surgical hub may cause the end effector of the surgical instrument 7012 to progressively close while applying a constant or nearly constant clamp force or pressure to the grasped tissue along the length of the ultrasonic blade. That is, the control circuit and/or surgical hub can adjust end effector closure to account for changes in clamp force applied to the tissue that result from the progression of the surgical coagulation and/or cutting treatment. For example, as grasped tissue is coagulated and cut at the proximal portion of the end effector, the corresponding proximal sections of the tissue may experience a greater applied clamp pressure due to the advancement of the surgical coagulation/cutting. Thus, as the control circuit and/or surgical hub senses or determines the progression of this coagulation/cutting action (e.g., via the sealing or weld focal point), it may adjust by increasing the clamp force applied to the distal sections of the tissue. In this way, each section of the grasped tissue may experience a uniform clamp pressure. As the location of the coagulation/cutting focal point shifts along the length of the end effector, the applied clamp force can be further adjusted. Additionally or alternatively, the clamp arm (alternatively referred to as the first jaw) of the end effector could be curved so as to accentuate or amplify the clamp force.

Because the curved clamp arm would result in different clamp pressure applied to tissue, the control algorithm may be executed to compensate for this clamp arm deflection. Thus, as the end effector gradually reaches its full closure stroke, the control circuit and/or surgical hub can execute the control algorithm to compensate for this deflection in order to provide a constant or near constant clamp tissue pressure along the length of the blade (alternatively referred to as the second jaw of the end effector). Accordingly, the end effector may apply relatively greater clamp force at the distal portions of the end effector when the tissue is being treated in a proximal to distal direction. Moreover, the clamp arm deflection may cause variation in heat flux along the length of the end effector. To address this, the control algorithm may involve selectively energizing surgical treatment electrodes (e.g., RF electrodes in the end effector) to compensate or account for this variation. Specifically, the RF electrodes could be segmented into proximal and distal segments and the control circuit and/or surgical hub could control the generator to selectively energize the RF electrode segments as appropriate to obtain a uniform and constant or approximately uniform and constant heat flux.

The control circuit and/or surgical hub can be configured to execute the control algorithm to control the energization of the segmented surgical treatment electrodes. For example, the electrodes may comprise two pairs of RF electrodes on each jaw of the end effector. The control circuit can control the energization in conjunction with the progressive closure of the clamp arm/first jaw to achieve a constant current density along the end effector. Each of the two pairs of RF electrodes could be referred to as a proximal and distal set of electrodes, respectively, and can be energized as a set. The control circuit may control the generator to sequentially energize the proximal and distal set of electrodes so that an equal current density is generated or created in both the proximal and distal portions. In one aspect, the control circuit and/or surgical hub may energize the proximal set of electrodes while causing the end effector to compress the tissue at a first jaw pressure, which results in a predefined current density. When the measured tissue impedance (e.g., measured via a pressure, resistive, or other suitable sensor in the end effector) reaches or exceeds a predetermined threshold, the control circuit and/or surgical hub may energize the distal set of electrodes and de-energize or cease applying power to the proximal set of electrodes. Simultaneously or substantially simultaneously, the clamp force applied by the clamp arm/first jaw may be increased to recreate the predefined current density in the distal area where the distal set of electrodes are located. In this way, the two proximal and distal set of electrodes can be energized or powered sequentially. Moreover, this sequential energizing can occur in conjunction with variable application of clamp force. Additionally or alternatively, as the proximal set of electrodes delivers electrosurgical energy to treat the tissue, the distal set of electrodes may simultaneously receive power from the generator at a lower power level for pre-heating. That is, the distal portion of the end effector may be pre-heated while the proximal portion is used to treat tissue. Similarly, the proximal portion of the end effector may also be pre-heated.

The surgical instrument 7012 may have a tissue (e.g., blood vessel) sealing mode in which a specific tissue impedance change over time or rise rate and predictable coagulation time interval are targeted. During operation of the energy-based surgical instrument 7012, the tissue impedance may be selectively increased in order to "starve" the coagulation cycle. Put differently, by applying electrosurgical energy according to target tissue impedance points and dwell time, the progression of the coagulation cycle can be dynamically halted or "starved" as necessary to achieve the desired impedance rate of change and coagulation time interval. In this way, the generator can adjust power by incrementing or cycling through different load or power curves based on target impedance set points with associated power levels and dwell times in between switching power levels or curves in order to obtain an overall coagulation time interval. The overall coagulation time may include changes in impedance rise rates, as discussed in more detail below. In one aspect, an impedance rise rate such as 50 Ohms ($\Omega$) per second can be achieved adjusting the dwell time at each target to a target time interval such as 2 seconds (e.g., if applying the current power level or curve would otherwise increase the impedance to 100$\Omega$) or increasing the number of targets and spacing them at specified increments such as 50$\Omega$ increments such that each power level or curve is applied until the next 50$\Omega$ target is reached.

Furthermore, selectively achieving tissue impedance rise rates can be performed to attain a predictable sealing time as measured by a surgical coagulation cycle. For example, the generator may apply power to the tissue according to a first power curve (e.g., specifying max power of 200 watts) to reach the target of 100$\Omega$ with a four second dwell time interval. After reaching 100$\Omega$ and dwelling for 4 seconds, the generator may achieve applying a series of power levels or curves. Each power level or curve can be determined and applied until reaching a next target impedance point with an associated power level and a dwell time, in which the target impedance points progressively increase by 100$\Omega$ (i.e., each point is 100$\Omega$ greater than the last). By controlling the generator in this manner, at each subject target impedance point, the applied power level or curve can be changed according to the next target impedance point. The next impedance point can have an associated power level and dwell time before the next impedance point is determined, which can be based on the overall tissue impedance level and time required to achieve the subject target impedance point. In adjusting impedance rise rates according to these dynamically determined target impedance points, a predictable sealing time could be achieved, such as a cycle time of 7 seconds in the example currently being described.

The surgical instrument 7012 may be configured to deliver a composite electrosurgical energy comprising ultrasonic and RF energy to separate treated tissue from a relatively hard or rigid substructure such as the patient's bone. To determine when this particular combination of electrosurgical energy should be applied, the sensors 788 can determine and monitor the natural or resonant frequency of the waveguide (and the blade that the waveguide terminates at). The waveguide natural frequency may be equivalent to the adjustment of the drive frequency made by the generator. In particular, the sensors 788 can detect when the natural frequency experiences a wave or phase shift in order to determine when the end effector may impact a hard substructure (e.g., bone, relatively harder layer of soft tissue, etc.). When such impact or contact is determined, the generator may be controlled to throttle back both the ultrasonic blade amplitude and RF power level. That is, the generator can reduce the transducer current used to vibrate the ultrasonic blade and the power transmitted to the RF electrodes. Accordingly, the surgical instrument 7012 can properly separate tissue from a harder substructure using ultrasonic energy to complement the heat generated by the application of RF energy when the control circuit and/or surgical hub detects bone or differences in soft tissues based on the ultrasonic resonant frequency. The control algorithm could also be configured to detect and throttle back the application of electrosurgical energy upon detection of contact with non-tissue objects such as when underlying clips, staples are encountered or when the surgical instrument 7012 contacts another instrument.

As stated above, the surgical instrument 7012 could be a combination surgical instrument such as a combination monopolar/bipolar electrosurgical instrument in which the type of electrosurgical energy could be ultrasonic, RF, or some other suitable energy modality. In the monopolar modality, the patient being treated acts as the return path or electrical ground (e.g., via return pad on patient's skin) while in the bipolar modality, the ultrasonic blade acts as the second pole for the transmission of the electrosurgical energy. The bipolar modality may generally be preferred for more controlled, localized applications of electrosurgical energy. In this context, the control circuit and/or surgical hub can execute the control algorithm to alter the frequency of the electrosurgical monopolar energy so that it is non-therapeutic (outside treatment range) in order to monitor aspects of the bipolar modality or system. Thus, in aspects in which the surgical instrument 7012 functions as a bipolar tool such as surgical shears, the performance of the control algorithm can provide improved nerve sensing. Specifically, the bipolar and monopolar energy modalities could be applied simultaneously or nearly simultaneously with monopolar energy delivered to the end effector at a non-therapeutic frequency as feedback to the bipolar energy delivery. For example, the generator may deliver a drive signal for nerve stimulation such as a biphasic signal at 100-1000 hertz (Hz) to stimulate the patient's nerves in which the monopolar energy circuit provides monopolar energy at a non-therapeutic frequency while the bipolar energy circuit provides bipolar energy at a range of 200 kilohertz (kHZ) to 3 megahertz (MHz). In this way, the non-therapeutic monopolar component can be used as feedback to the control circuit and/or surgical hub to determine the end effector's proximity to the patient's nerves. Using the determined nerve proximity, the surgical instrument may minimize inadvertent cutting of nerves by the bipolar shears. Alternatively, the delivered bipolar energy could be feedback to the monopolar energy.

Furthermore, the surgical instrument 7012 might regulate the application of bipolar electrosurgical energy based on the change of impedance resulting from the application of monopolar electrosurgical energy. Specifically, the control circuit and/or surgical hub can perform the control algorithm to monitor the relative change of impedance from monopolar energy such that the control settings of the bipolar energy are controlled. The sensors 788, control circuit and/or surgical hub can detect or determine impedance based on a signal transmitted via the monopolar energy circuit. For example, the impedance could be determined by dividing the output of the monopolar voltage sensing circuit by the monopolar current sensing circuit. The bipolar control settings could be settings that define how the bipolar energy is delivered to the end effector. Thus, executing the control algorithm can result in controlling bipolar power using monitored monopolar impedance such as regulating bipolar power level based on changes in the determined monopolar impedance. For example, given an applied clamp arm pressure of 14-17 pounds tip load, the generator can cycle from zero power to full power mode such as 200 watts (W) and use the monopolar to measure the relative impedance increase (e.g., to a particular threshold, such as 80Ω) to control when to shift to a time-based control setting. That is, at the transition from 0 to 200 W, the determined change of 80Ω may be used to trigger a change to the time-based bipolar power control setting that specifies applying a constant amount of power such as 100 W for a predetermined amount of time. Alternatively, the determined change of 80Ω could cause a proportional step power decrease, such as a decrease in full power that is proportional to the increase in monopolar impedance.

The surgical instrument 7012 could also be a combination surgical instrument such as a combination monopolar/ultrasonic electrosurgical instrument in which the monopolar energy is used to sense or monitor surgical treatment using the ultrasonic modality. In particular, the operational frequency of the monopolar energy may be changed in order to monitor aspects of the ultrasonic energy modality. For example, the monopolar energy could initially be output at a therapeutic frequency level and switched to a lower, non-therapeutic frequency and power level to obtain tissue impedance measurements, which can be used for monitoring the ultrasonic energy delivery. Although absolute values of impedance may not be useful, changes in tissue impedance values can be compared against the expected changes in tissue impedance resulting from electrosurgical treatment in order to detect the tissue treatment effects of the delivered ultrasonic energy. In other words, as the tissue is being treated by the ultrasonic energy, there may be an expected change in tissue impedance. The control circuit and/or surgical hub may be configured to determine whether the tissue effects caused by the ultrasonic treatment are consistent with the expected change by using the change in frequency of the monopolar energy, such as by switching to a non-therapeutic frequency level.

The change in operation frequency of the monopolar energy modality for monitoring the ultrasonic energy modality could also be achieved by switching the drive frequency to a very high level, such as greater than 10 MHz to enable tissue monitoring. In this way, the change in monopolar frequency could be used to monitor the therapeutic effect on the tissue resulting from the other energy modality such as the ultrasonic energy modality, as discussed above. In some situations, undesirable parasitic impedances may result. However, the higher drive frequencies of the monopolar energy modality may beneficially negate or minimize parasitic or stray capacitance deriving from the use of a monopolar return pad (e.g., MEGADYNE™ MEGA SOFT™ Reusable Patient Return Electrode). Nonetheless, relatively higher therapeutic monopolar frequencies may also operate effectively even with the monopolar power set to lower levels to detect tissue impedances. As stated above, alternatively, the generator could drive the monopolar output at lower frequencies and sub-therapeutic currents for sensing ultrasonic treatment and the associated effects on treated tissue. Lower frequencies may not result in as many parasitic effects because of cable draping, lengths and other such reasons, but the sensing or monitoring of the ultrasonic energy modality may be limited by the usage of the monopolar return pad.

Although at least some portion of the control algorithm(s) disclosed herein can be performed by surgical hubs (alone or in conjunction with associated control circuits of surgical instruments), the functions of the control algorithm(s) are described as performed by control circuits for the sake of clarity. Also for clarity, the control circuit of surgical instrument 7012 in this portion of the present disclosure is labeled control circuit 710, although control circuit 710 can be the same or similar to control circuits 760, 3200, 3502, 4008. Control circuit 710 may be a part of the generator 4002 itself (referred to as generator 4002 for clarity although generator 4002 can be the same or similar to generator 140, 145, 240, 721, 771, 900, 1100) or another part of the surgical instrument 7012 that is remote from the generator 4002. In various aspects, the surgical instrument 7012 (e.g., ultrasonic surgical instrument) as described in FIGS. 23A-23B, 24A-24B, 25A-25B, 26A-26E, 27A-27F, is configured to operate with situational awareness in a hub environment, such as the surgical hub 106 or 206 (FIGS. 1-11), for example, as depicted by the timeline 5200.

FIGS. 78A-78B are graphs 203500, 203520 including a graph 203500 of clamp force as a function of time and an associated graph 203520 indicating the shift in the location of coagulation and cutting along the length of the blade as a function of time, in accordance with at least one aspect of the present disclosure. As depicted in FIG. 78A-78B, increasing the clamp force as the coagulation/cutting location (e.g., coagulation/cut focal point) on the ultrasonic blade shifts may result in better coupling of the tissue to the ultrasonic blade. The focal point may shift from proximally to distally or distally to proximally depending on the direction of the surgical treatment, for example. Moreover, the focal point might represent the progress of a fibrin clot for coagulation, for example. The clamp arm of the surgical instrument 7012 could be offset, sloped, or otherwise curved to accentuate or amplify the pressure experienced by the tissue, which results from the application of clamp force. The focal point as well as a total sealing or welding time of the surgical operation could be determined by the control circuit 710 based on a sensor signal (e.g., from sensor 788) indicative of a surgical parameter such as tissue impedance, natural frequency, temperature, or some suitable tissue parameter. The control circuit 710 could increase the clamp arm pressure based on the sensor signal. The change in clamp force as a function of surgical coagulation/cutting location could be controlled by the control circuit 710 in conjunction with a variation in electrosurgical power level delivered by the generator in order to attain a predefined heat flux or power applied to the tissue.

The heat flux could be implemented by the control circuit 710 as a heat flux control threshold that may stay the same or change over the duration of the surgical operation performed by the surgical instrument 7012, such as based on the progression of the surgical cutting/coagulation. For example, the control circuit 710 could adjust the heat flux control threshold based on the determined coagulation focal point, progression of the focal point, and/or progression of the cutting. The predefined heat flux may beneficially improve the quality of surgical treatment, such as the tissue seal that is formed. In FIG. 78A, the x-axis 203508 denotes time such as the time over the course of a surgical cycle while y-axis 203510 denotes applied clamp force. As such, the time spanning time $t_0$ to time $t_{10}$ can define a surgical cycle of the surgical instrument 7012. Clamp force can be measured in suitable units such as pounds (lbs). As shown in graph 203500, the y-axis 203510 has annotations for a maximum and minimum clamp force level.

The dashed line 203502 represents the force applied by the clamp arm over time and tracks the application of force by the clamp arm, from the minimum force at time $t_0$ to maximum force at time $t_{10}$. The value or amount of the clamp force may be a function of the process of the tissue coagulation process, which could be tracked based on the location of the coagulation/cut focal point on the end effector as it spans $t_0$ to time $t_{10}$. As illustrated by dashed line 203502, the applied clamp force increases as tissue coagulation/cutting action is sensed. The dashed line 203502 reaches the maximum force at a point close to time $t_6$, where the force stays at its maximum level until time $t_{10}$. The dash-and-dot line 203504 represents the measured tissue impedance over the surgical cycle. As can be seen on graph 203500, the measured tissue impedance decreases from its initial level at time $t_0$ to the low point at around time $t_3$, demonstrating the drop in impedance resulting from the commencement of surgical treatment (the so-called "bathtub" portion of the impedance curve). After time $t_3$, the tissue impedance line 203504 rises as the tissue being treated begins to dry out. This desiccation results in an increase in tissue impedance. FIG. 78A shows how this increase in tissue impedance line 203504 corresponds to an increase in the applied clamp force line 203502. The increase in applied force may assist in cutting the tissue and welding the denatured tissue as the surgical cycle is completed. Also, the clamp arm could be curved to accentuate the tissue pressure resulting from increased clamp force. Additionally, the end effector may progressively close while providing a constant or almost constant tissue clamp pressure along the length of the end effector or ultrasonic blade. The constant or near constant clamp pressure is depicted by solid line 203506, which may correspond to the pressure applied at the leading edge of the end effector, where surgical coagulation and cutting occur. As such, the solid line 203506 stays at an approximately constant level, with minimal or no fluctuations.

FIG. 78B shows that the focal point of the surgical coagulation and cutting operation on the tissue shifts along the length of ultrasonic blade or second jaw 203524 (similar to or the same as ultrasonic blade 718, 768 or other ultrasonic blades described above) over the course of the surgical cycle. As shown in FIG. 78B, the focal point shifts in a proximal to distal direction over time, but the focal point could also shift in a distal to proximal direction. The progress of the tissue coagulation/cutting focal point over the surgical cycle can be represented by the black dots 203522A, 203522B, to 203522N, whose advance corresponds to the advance of time through the surgical cycle spanning time points $t_0$ to time $t_{10}$. That is, each one of the black dots 203522A, 203522B, to 203522N corresponds to a time point in the surgical cycle and also represents the formation of the tissue seal and/or progress of the tissue treatment. For example, the black dots could represent a coagulation focus or focal point determined by the control circuit 710 based on a signal from sensor 788. The sensor signal may be indicative of a surgical parameter such as tissue impedance, a natural frequency of the ultrasonic blade, temperature, or some other tissue parameter. Based on the sensor signal, the control circuit 710 may determine the progression of the tissue seal/weld/coagulation focal point and further determine a tissue weld/seal time for a surgical operation being performed by the surgical instrument 7012.

Moreover, the control circuit 710 may be configured to control the closure of the end effector while compensating for clamp arm deflection, which may result from the curved shape of the end effector. For example, the control circuit 710 could mechanically adjust the force applied by the clamp arm to offset any disproportionate force exerted based on the curvature of the clamp arm so that a constant or near constant tissue pressure is provided along the length of the end effector. Furthermore, the control circuit 710 may selectively energize different segments (e.g., proximal and distal) of RF electrodes such as RF electrodes 796 in order to compensate or adjust for heat flux variation caused by the clamp arm deflection, as described in more detail below. The control circuit 710 could be configured to determine the cut/weld focal point based on one or more of the resonant frequency and electrical continuity feedback measures. A constant heat flux along the length of the ultrasonic blade 203524 may also be achieved. For example, as tissue is coagulated and cut at the proximal sections of the end effector, the delivered electrosurgical power level is relatively higher at those proximal sections. Accordingly, the control circuit 710 might execute the control algorithm to increase the clamp force at the distal sections, which results in higher current density at the distal sections that may compensate for the relatively lower power level at the distal sections. In this way, the heat flux and pressure experienced by the tissue along the ultrasonic blade 203524 may be constant and/or consistent with the heat flux control threshold. The control circuit 710 may receive, from a sensor 788, a sensor signal indicative of a surgical parameter. The surgical parameter may be tissue impedance, a natural frequency of the ultrasonic blade, temperature, or a tissue parameter. The weld time of the surgical operation can be determined by the control circuit 710 based on the sensor signal. The control circuit 710 can vary one or more of a clamp arm pressure applied by the clamp arm and a power level of the electrosurgical energy to maintain one or more of a predefined heat flux or power applied to tissue loaded in the end effector.

FIGS. 79A-79B depict segments of end effector electrodes and an illustration of controlling applied clamp force and delivered electrosurgical energy by the end effector, in accordance with at least one aspect of the present disclosure. FIG. 79A shows the end effector 203540 in an open configuration. The end effector 203540 can be the same or similar to any suitable end effector described above, such as end effector 702, 752, 792, 4006, or some other appropriate end effector. As shown in FIG. 79A, the end effector 203540 comprises two jaws including first jaw (e.g., clamp arm) 203542 and second jaw/ultrasonic blade 203544 (same or similar as ultrasonic blade 203524). The clamp arm 203542 can be the same or similar to any suitable clamp arm described above, such as clamp arm 716, 766, or some other appropriate clamp arm. Each of the first and second jaws 203542, 203544 each comprise electrosurgical electrodes 203546A-203546D, 203548A-203548D, respectively. The electrosurgical electrodes 203546A-203546D, 203548A-203548D can be the same or similar to RF electrodes such as RF electrodes 796 or any other appropriate electrodes described above. The electrosurgical electrodes 203546A-203546D, 203548A-203548D may each be segmented into proximal and distal portions or segments. For example, the electrodes 203546A-203546B, 203548A-203548B may form a proximal electrode pair or segment on the first and second jaws 203542, 203544, respectively. Similarly, the electrodes 203546C-203546D, 203546C-203546D may form a distal electrode pair or segment on the first and second jaws 203542, 203544, respectively. In this way, the electrodes 203546A-203546B, 203548A-203548B could be segmented longitudinally. The longitudinally segmented electrodes may generate a constant current density.

The control circuit 710 may be configured to execute a control algorithm to control the application of power to the segmented electrodes 203546A-203546B, 203548A-203548B by the generator 4002 in conjunction with controlling the progressive closure of the clamp arm 203542 in order to obtain a constant or near constant current density throughout the end effector 203540. FIG. 79B illustrates an example of this. In FIG. 79B, the end effector 203560 applies different clamp pressure on the tissue 203570 based on the different clamp forces resulting from the different end effector closure angles $\theta_1$, $\theta_2$. In particular, the control circuit 710 may control the end effector 203560 to compress the tissue 203570 to a first jaw pressure (which could be predetermined or dynamically determined) while controlling the generator 4002 to energize the proximal set of electrodes 203546A-203546B, 203548A-203548B in order to create a first predefined current density. The generator 4002 could deliver power to one of the proximal electrode pair individually or to both pairs in conjunction. Moreover, the generator 4002 could power the end effector jaws individually such as by only applying power electrode pair 203546A-203546B on first jaw 203542, power them sequentially, or in conjunction. As such, the control circuit 710 may energize the electrode segments 203546A-203546D, 203548A-203548D based on a progressive closure stroke of the clamp arm 203542.

A tissue impedance signal (or signals indicative of current and voltage) may be output by sensor 788 (e.g., pressure, resistive, or other suitable sensor) and transmitted to the control circuit 10 as feedback. When the control circuit 710 determines that the tissue impedance has reached a predetermined or dynamically determined threshold, the control circuit 710 may control the end effector 203560 and generator 4002 to change one or more of clamp force and power level (e.g., to reach a constant heat flux and/or the heat flux control threshold). In particular, the end effector 203560 may be controlled to apply an increased jaw pressure that is higher than the first jaw pressure. Simultaneously or in the same time frame, the control circuit 710 controls the generator 4002 to power off the proximal electrode pair and instead deliver power to one of the distal electrode pair individually or to both pairs in conjunction. That is, the generator 4002 powers one or more of the distal segment of electrodes 203546C-203546D, 203546C-203546D. In this way, the same current density in the clamped tissue may be obtained for the distal electrodes or portion of the end effector 203560 as the proximal electrodes or portion of the end effector 203560. The current density could be predetermined or dynamically determined, as appropriate. As depicted in FIGS. 79A-79B, increasing the clamp load pressure on the tissue 203570 corresponds to an increase in the angle between the clamp arm/first jaw 203562 and the ultrasonic blade/second jaw 203564 to decrease from $\theta_1$ to $\theta_2$. Also as shown in FIGS. 79A-79B, the first and second jaw 203562, 203564 pivot about pivot point 203568 to implement the end effector closure stroke.

FIGS. 80A-80B are graphs 203580, 203600 illustrating controlling the energization or powering of the electrosurgical electrodes 203546A-203546D, 203548A-203548D, in accordance with at least one aspect of the present disclosure. As discussed above, the control circuit 710 may be configured to execute the control algorithm to control the end effector 203560 and generator 4002 to produce or generate a constant current density. During treatment of the proximal portion of the end effector 203560, the control circuit 710 may control the end effector to compress the tissue 203570 in the proximal portion to a first clamp pressure. Simultaneously or in the same time frame, the generator 4002 may deliver power to only the proximal electrode pairs 203546A-203546B, 203548A-203548B to surgically treat the proximal section. Either or both of the electrodes in the first and second jaws 203562, 203564 could be energized such that one or both of the proximal first electrode pair 203546A-203546B and proximal second electrode pair 203548A-203548B could be energized. After surgical treatment of the proximal portion, the generator 4002 may deliver power to the distal electrodes 203546C-203546D, 203548C-203548D to treat the distal portion of the end effector 203560. Either or both of the electrodes in the first and second jaws 203562, 203564 could be energized such that one or both of the distal first electrode pair 203546A-203546B and distal second electrode pair 203548A-203548B could be energized. In this way, the electrosurgical electrodes 203546A-203546D, 203548A-203548D may be sequentially energized by the generator 4002.

FIG. 80A illustrates delivering power to the proximal (referenced as electrode pair "a") and then distal (referenced as electrode pair "b") electrodes sequentially as the clamp pressure experienced by the tissue 203570 is increased in a corresponding manner. The x-axis 203582 of graph 203580 denotes time, such as in units of seconds, which could span the length of a surgical cycle. The y-axes 203584, 203585 respectively denote power level, such as expressed as a percentage of maximum power (100%), and clamp pressure experienced by the tissue 203570 (e.g., measured in pounds). The graph 203580 depicts the sequence of proximal electrode pairs "a" 203546A-203546B, 203548A-203548B being activated and treating tissue for a first period of time indicated on the x-axis 203582 followed by distal electrode pairs "b" 203546C-203546D, 203548C-203548D being activated and treating tissue for a second period of time indicated on the x-axis. The rectangular function of graph 203580 illustrates this sequential energization. The generator 4002 first powers electrode pairs "a" 203546A-203546B, 203548A-203548B according to power level line 203586, deactivates "a," then powers electrode pairs "b" 203546C-203546D, 203548C-203548D according to power level line 203588, and finally deactivates "b." Simultaneously or in the same time frame, the control circuit 710 may be controlling the end effector 203560 to apply clamp pressure at level $P_1$ while electrode pairs "a" are activated and apply clamp pressure at level $P_2$ while electrode pairs "b" are activated. This application of clamp pressure is represented by clamp pressure line 203590. Upon completion of surgical treatment of the proximal and distal portions, the generator 4002 ceases delivering power and the end effector 203560 returns to the open configuration.

FIG. 80B illustrates pre-heating the distal electrode pairs "b" 203546C-203546D, 203548C-203548D. Accordingly, while the proximal portion of the end effector 203560 is being treated, the control circuit 710 may also control the generator 4002 to pre-heat the distal portion. In other words, during the time spanning the activation of electrode pairs "a" 203546A-203546B, 203548A-203548B, the generator 4002 may deliver power to the distal electrode pairs "b" 203546C-203546D, 203548C-203548D at a lower power level to facilitate surgical treatment in the distal portion after completion of surgical treatment in the proximal portion. Graph 203600 depicts this. The x-axis 203602 of graph 203600 denotes time, such as in units of seconds, which could span the length of a surgical cycle. The y-axes 203604, 203605 respectively denote power level, such as expressed as a percentage of maximum power (100%), and clamp pressure experienced by the tissue 203570 (e.g., measured in pounds) The power level line 203606 of graph 203600 shows the sequential activation of electrode pairs "a" similarly to power level line 203586. The power level line 203608 shows a similar activation of electrode pairs "b" except that the generator 4002 may deliver power to the distal electrode pairs "b" 203546C-203546D, 203548C-203548D at a lower power level, e.g., 20% of the maximum power level (100%) applied at the peak of the rectangular function. This applied lower power level enables the distal portion of the end effector 203560 to be pre-heated prior to treatment. Simultaneously or in the same time frame, the control circuit 710 controls the end effector 203560 to apply clamp pressure at level $P_1$ and level $P_2$ as represented by clamp pressure line 203610. Also, the control circuit 710 could control the generator 4002 in an opposite manner so that the proximal portion of the end effector 203560 is pre-heated prior to treatment.

FIGS. 81A-81E are a series of graphs 203620, 203640, 203660, 203680, 203700 illustrating the adjustment of power level to achieve a predictable sealing time, in accordance with at least one aspect of the present disclosure. The x-axis 203622, 203642, 203662, 203682, 203702 denotes tissue impedance which can be measured in units of Ohms (Ω). The y-axis 203624, 203644, 203664, 203684, 203704 denotes the power level applied by the generator 4002. The graphs 203620, 203640, 203660, 203680, 203700 demonstrate how a series of sequential impedance points may be set to mimic an impedance rise corresponding to a particular tissue coagulation time. By attaining a target impedance rise rate and predictable coagulation time interval for the surgical instrument (e.g., in vessel sealing mode), a more secure or otherwise better tissue seal may be achieved. Each impedance point in the sequential series may be set based on the next target power level and/or impedance as well as the time in the surgical cycle required for reaching the immediately preceding or other previously set impedance points. Upon reaching a specific impedance point, the control circuit 710 may determine the next set impedance point and associated power level in order to achieve and/or maintain a desired rise in tissue impedance. In particular, the control circuit 710 might be configured to control the rise in tissue impedance so that the impedance of tissue 203570 changes according to an impedance versus time curve ("bathtub curve") that resembles the shape of a "bathtub." The impedance versus time curve may be characterized by an initial drop in tissue impedance upon initial application of electrosurgical energy until stabilizing (minimum point), which is followed by a rise in tissue impedance corresponding to the desiccation of the tissue 203570. The overall or contemporaneous tissue impedance level relative to this impedance bathtub curve, as assessed by the sensor 788 and control circuit 710, might also be used to adjust the next set impedance point.

The power level associated with each impedance point may be determined based on a power level that achieves a subsequent impedance point which tracks a different impedance versus time curve compared to the default impedance bathtub curve. The different impedance curve may be less (although it could be more as well) aggressive than the bathtub curve, for example. In this way, as each impedance point in the series is achieved and each associated power level is determined according to the desired impedance versus time curve, a desired rise in impedance may be mimicked. This rise in impedance may correspond to the drying out of the tissue 203570, except that the rise may be adjusted relative to the default bathtub curve so that an improved tissue seal may be obtained. Additionally or alternatively, by dynamically determining the set impedance points and associated power levels, the control circuit 710 may implement the surgical treatment according to a predictable coagulation time interval. The associated power level determined for each set impedance point may be one or more power values. In particular, the associated power level may be determined according to a load or power curve. The power curve could be a predetermined power curve stored in the memory of the surgical instrument 7012, a dynamically determined power curve according to a mathematical model or equation (e.g., a change in the variables used in the equation to determine power or a different equation altogether), or some other suitable means, for example.

Accordingly, the impedance points could be dynamically determined or targeted to achieve a selective impedance increase. As discussed above, by controlling the rate of rise of impedance of the tissue 203570 in this way, the tissue coagulation may be more predictable and improved. Also, there could be a dwell time between adjacent impedance set points in the series. This dwell time between impedance points may "starve" the coagulation cycle. That is, during the dwell time, the generator 4002 may not deliver any power to the end effector 203560 such that the impedance of the tissue 203570 does not change significantly during the dwell time. The graph 203620 may show a natural load or power curve (e.g., curve representing power level as a function of tissue impedance) as indicated by the plotted applied power line 203626. The applied power line 203620 also shows the dwell time. The natural power curve could be the desired impedance versus time curve including a desired rise in impedance that is achieved dynamically as impedance points in the series are set. In particular, the graph 203640 portrays the first set impedance point in the series of sequential impedance points.

The first set point occurs at 100Ω such that the generator 4002 delivers the associated power level rising up to maximum power such as 200 Watts (W) to achieve 10052. The associated power level(s) could be determined based on: applying a power curve stored in memory of the surgical instrument 7012, corresponding surgical hub and/or cloud; applying a segment or particular portion of a power curve; or determining an appropriate level such as by reference to the desired natural power curve. As can be seen in graph 203640, the corresponding first power curve is applied as represented by applied power line 203646 to incrementally mimic the natural power curve. The applied power line 203646 also shows the dwell time. As such, the desired rise rate and natural power curve could be used as a guide in conjunction with the elapsed time for determining the next impedance point and associated power level. The remainder of the first power curve or power level(s) is generally represented by the dotted line 203648. Upon reaching the first set impedance point at 100Ω, the generator 4002 may dwell for a suitable period of time. This dwell time could be predefined or contemporaneously determined by the control circuit 710 and may be useful for temporarily pausing or slowing the coagulation cycle. During the dwell time, the control circuit 710 may assess the progress of the tissue coagulation, which might be compared to the desired natural power curve, for example. The dwell time might be four seconds, for example. After dwelling for four seconds, the control circuit 710 may determine that the next set impedance point is 200Ω based on various factors such as reference to the last set point of 100Ω, an estimated next impedance point, and/or the desired natural power curve (e.g., the overall or contemporaneous impedance level of the tissue 203570 relative to the natural power curve).

Also, the control circuit 710 may determine that the corresponding power level is lower than 200 W, such as according to a second power curve that gradually reduces the power level to below 200 W. This second power curve or power level(s) might be different from the first power curve or power level(s) Similar to the first set impedance point, the generator 4002 may deliver power to mimic or follow a desired impedance rise rate and/or in accordance with the natural power curve. That is, the generator 4002 may deliver power so that the second set impedance point is anticipated to be reached in a desired amount of time. The graph 203660 includes applied power line 203666, which shows the application of this second associated power by the generator 4002 to reach 200Ω and the dwell time. The remainder of the second power curve or power level(s) is generally represented by the dotted line 203668. Upon the impedance reaching 200Ω, the control circuit 710 may determine the amount of dwell time that is appropriate. For example, the control circuit 710 might determine that the generator 4002 should dwell for 1 second to pause the tissue coagulation. The control circuit 710 can further determine the next target impedance point is set at 300Ω as the impedance reaches 200Ω. As discussed above, the 300Ω can be determined based on factors such as reference to the last set point of 200Ω, an estimated next impedance point, and/or the desired natural power curve. The associated third power curve or power level(s) to be applied by the generator 4002 can be determined by reference to or in accordance with a desired impedance rise rate and/or natural power curve, as described above. The third power curve or power level(s) could be used to change the relative rate of change of power level as a function of impedance as shown in graph 203680. The remainder of the third power curve or power level(s) is generally represented by the dotted line 203688.

After dwelling for 1 second, the generator 4002 may deliver power according to the corresponding third power curve or power level(s) until reaching the next set impedance point of 300Ω. This is illustrated by graph 203680. In graph 203680, the applied power line 203686 represents delivering power according to the third power curve or power level(s) and the determined dwell time. Similarly to as described above, the control circuit 710 may implement a predetermined or contemporaneously determine dwell time upon reaching 300Ω. Moreover, the control circuit 710 may determine the next impedance point to be set is 400Ω based on the various factors described above. Additionally, the control circuit 710 may change/determine the corresponding power level is a fourth power curve or power level(s). The generator 4002 can deliver power according to this fourth power curve or power level(s), as represented by applied power line 203706, until reaching the next impedance set point. The remainder of the second power curve or power level(s) is generally represented by the dotted line 203708. As the tissue impedance reached the 300Ω set point, the control circuit 710 could determine the next set point is 400Ω, similarly to the determination of previous impedance points in the series. Upon reaching the 400Ω, the control circuit 710 may determine that the tissue coagulation is complete and therefore terminate the coagulation process. This is illustrated by graph 203700. More or less set impedance points could be used, as appropriate. Based on using these dynamically determined series of set impedance points and associated power, the control circuit 710 may mimic a desired impedance rise so as to obtain a predictable coagulation time interval. The impedance points and dwell time can be used to assist in determining an "impromptu" or contemporaneously determined power curve. In other words, the generator 4002 can apply segments or portions of different power curves and/or power level(s) as appropriate. Although FIGS. 81A-81E depict the use of dwell time, in other aspects, dwell time might not be used. In the surgical cycle portrayed in FIGS. 81A-81E, a total dwell time of 7 seconds may be realized during the surgical cycle with a difference of 100Ω between adjacent set impedance points to achieve the desired impedance rise rate. Other desired rise rates could be achieved as well, such as by changing the dwell time to 2 seconds or using differences of 50Ω between adjacent set impedance points, for example.

Thus, the control circuit 710 could execute an impedance rate algorithm, which could be programmed into the memory of the surgical instrument 7012 or received by a surgical hub or cloud computing system. In particular, the control circuit 710 could receive a first tissue impedance point (e.g., given first set impedance point), determine a first power level of the electrosurgical energy that corresponds to the first tissue impedance point, control the generator to deliver the electrosurgical energy at the first power level, determine a second tissue impedance point, adjust the first power level to a second power level of the electrosurgical energy based on a time interval to reach the second tissue impedance point; control the generator to deliver the electrosurgical energy at the second power level. More tissue impedance points in the series of impedance points could be determined or targeted to achieve a selective impedance increase. For example, the control circuit 710 could determine a third tissue impedance point and determine the second tissue impedance point based on the third tissue impedance point and a corresponding time interval to reach the first tissue impedance point. The control circuit 710 may determine the third impedance point and associated power level after controlling the generator 4002 to deliver electrosurgical energy to reach the second impedance point.

Dwell time may also be implemented. For example, the control circuit 710 may dwell for a time before adjusting from the first to second power level and determining the third tissue impedance point. Also, for example, the control circuit may control the generator 4002 to apply power according to the following: applying a first power level to reach a first tissue impedance point; terminating application of the first power level for a first dwell time; determining, by the control circuit, a second tissue impedance point; applying a second power level to reach the second tissue impedance point; terminating application of the second power level for a second dwell time; determining, by the control circuit, a third tissue impedance point; and applying a third power level to reach the third tissue impedance point to achieve the target impedance rise rate. The generator could further terminate application of the third power level for a third dwell time, determine a fourth tissue impedance point; and apply a fourth power level to reach the fourth tissue impedance point. As discussed above, set impedance points in the series can be determined based on prior impedance points and the time of delivering electrosurgical energy to achieve those points. Therefore, the third and fourth impedance points can be determined based on a first and second impedance point and a time to achieve them. The time to achieve the impedance points (e.g., first, second, and third points) can correspond to a predetermined coagulation time interval.

FIGS. 82A-82F are graphs and flow charts 203720, 203740, 203760, 203780, 203800, 203820, illustrating approaches to delivering energy according to power curves, in accordance with at least one aspect of the present disclosure. More details regarding such approaches may be found in U.S. Pat. No. 9,737,355 titled CONTROLLING IMPEDANCE RISE IN ELECTROSURGICAL MEDICAL DEVICES, which is hereby incorporated by reference herein in its entirety; and U.S. Patent App. Pub. No. 20180036065, titled METHODS AND SYSTEMS FOR ADVANCED HARMONIC ENERGY, which is hereby incorporated by reference herein in its entirety.

Figure 82A:
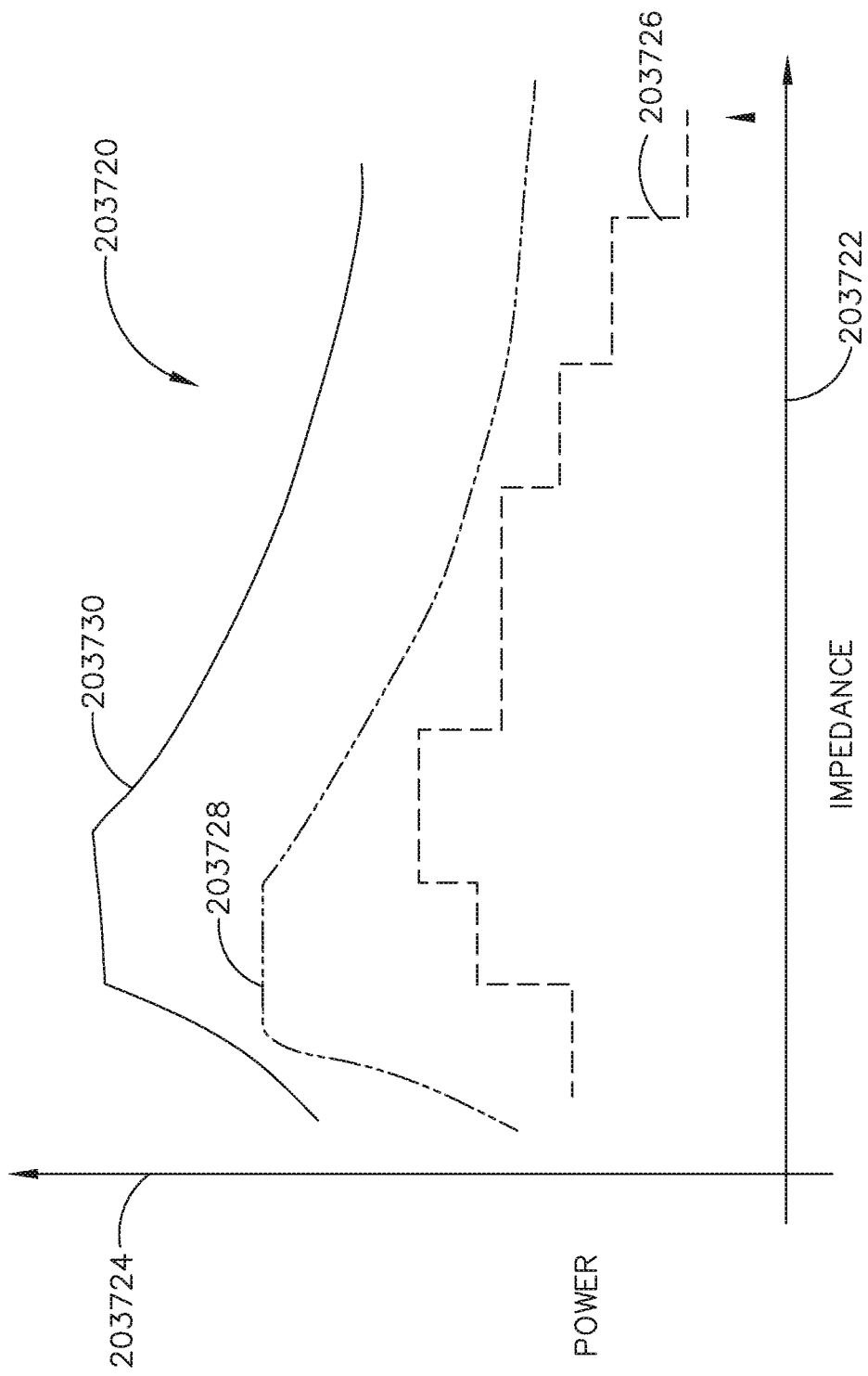

FIG. 82A shows one aspect of a chart 203720 showing example power curves 203726, 203728, 203730. The chart 203720 comprises an impedance x-axis 203722 denotes increasing tissue impedances from left to right. A power y-axis 203724 denotes increasing power from down to up. Each of the power curves 203726, 203728, 203730 may define a set of power levels, on the power y-axis 203724, corresponding to a plurality of potential sensed tissue impedances, in the impedance x-axis 203722. In general, power curves may take different shapes, and this is illustrated in FIG. 82A. Power curve 203726 is shown with a step-wise shape, while power curves 203728, 203730 are shown with curved shapes. It will be appreciated that power curves utilized by various aspects may take any usable continuous or non-continuous shape. The rate of power delivery or aggressiveness of a power curve may be indicated by its position on the chart 203720. For example, power curves that deliver higher power for a given tissue impedance may be considered more aggressive. Accordingly, between two power curves, the curve positioned highest on the power axis 203724 may be the more aggressive. It will be appreciated that some power curves may overlap.

The aggressiveness of two power curves may be compared according to any suitable method. For example, a first power curve may be considered more aggressive than a second power curve over a given range of potential tissue impedances if the first power curve has a higher delivered power corresponding to at least half of the range of potential tissue impedances. Also, for example, a first power curve may be considered more aggressive than a second power curve over a given range of potential tissue impedances if the area under the first curve over the range is larger than the area under the second curve over the range. Equivalently, when power curves are expressed discretely, a first power curve may be considered more aggressive than a second power curve over a given set of potential tissue impedances if the sum of the power values for the first power curve over the set of potential tissue impedances is greater than the sum of the power values for the second power curve over the set of potential tissue impedances.

Some aspects of the surgical instrument 7012 comprise a positive temperature coefficient (PTC) material positioned between one or more of the electrodes of the jaws 203562, 203564. The PTC material may have an impedance profile that remains relatively low and relatively constant until it reaches a threshold or trigger temperature, at which point the impedance of the PTC material may increase. In use, the PTC material may be placed in contact with the tissue while power is applied. The trigger temperature of the PTC material may be selected such that it corresponds to a tissue temperature indicating the completion of welding or coagulation. Accordingly, as a welding or coagulation process is completed, the temperature of the PTC material may increase, causing a corresponding increase in the impedance of the PTC material. This additional series impedance, in series with the tissue, may cause a decrease in power actually provided to the tissue 203570.

It will be appreciated that during the coagulation or welding process, tissue impedance may generally increase. In some aspects, tissue impedance may display a sudden impedance increase indicating successful coagulation. The increase may be due to physiological changes in the tissue, a PTC material reaching its trigger threshold, etc. The amount of energy that may be required to bring about the sudden impedance increase may be related to the thermal mass of the tissue 203570 being acted upon. The thermal mass of any given tissue bite, in turn, may be related to the type and amount of tissue 203570 in the bite. The PTC material could be used to determine a weld time of a surgical operation performed by the surgical instrument 7012. Also, monitoring the PTC material or other sensors 788 in the end effector 203560 may be performed by the control circuit 710 to determine a coagulation focal/focus point and the progression of the surgical treatment (e.g., cutting). Based on these determinations, the control circuit 710 can adjust a heat flux control threshold along the length of the ultrasonic blade 203564.

Various aspects may utilize this sudden increase in tissue impedance to select an appropriate power curve for a given tissue bite. For example, the generator 4012 may select and apply successively more aggressive power curves until the tissue impedance reaches an impedance threshold indicating that the sudden increase has occurred. For example, reaching the impedance threshold may indicate that coagulation is progressing appropriately with the currently applied power curve. The impedance threshold may be a tissue impedance value, a rate of change of tissue impedance, and/or a combination of impedance and rate of change. For example, the impedance threshold may be met when a certain impedance value and/or rate of change are observed. According to various aspects, different power curves may have different impedance thresholds, as described herein.

Figure 82B:
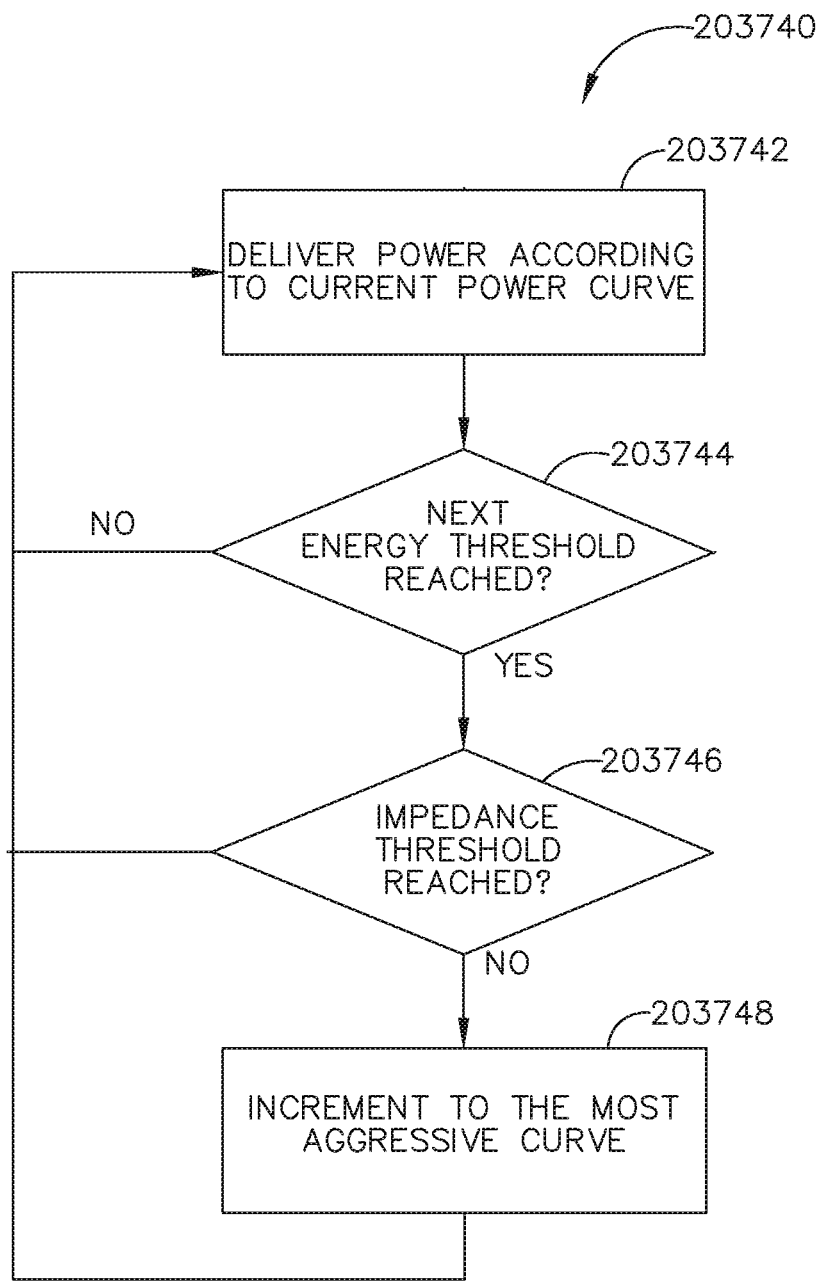

FIG. 82B shows one aspect of a process flow 203740 for applying one or more power curves to a tissue bite of the tissue 203570. Any suitable number of power curves may be used. The power curves may be successively applied in order of aggressiveness until one of the power curves drives the tissue to the impedance threshold. At step 203742, the generator 4002 may apply a first power curve. According to various aspects, the first power curve may be selected to deliver power at a relatively low rate. For example, the first power curve may be selected to avoid tissue searing with the smallest and most vulnerable expected tissue bites.

The first power curve may be applied to the tissue 203570 in any suitable manner. For example, the generator 4002 may generate a drive signal implementing the first power curve. The power curve may be implemented by modulating the power of the drive signal. The power of the drive signal may be modulated in any suitable manner. For example, the voltage and/or current of the signal may be modulated. Also, in various aspects, the drive signal may be pulsed. For example, the generator 4002 may modulate the average power by changing the frequency, pulse width, duty cycle, etc. of the drive signal. The drive signal may be provided to the electrodes of the first and second jaw members 203562, 203564.

While applying the first power curve, the generator 4002 may monitor the total energy provided to the tissue 203570. The impedance of the tissue 203570 may be compared to the impedance threshold at one or more energy thresholds. There may be any suitable number of energy thresholds, which may be selected according to any suitable methodology. For example, the energy thresholds may be selected to correspond to known points where different tissue types achieve the impedance threshold. At step 203744, the generator 4002 may determine whether the total energy delivered to the tissue 203570 has met or exceeded a first energy threshold. If the total energy has not yet reached the first energy threshold, the generator 4002 may continue to apply the first power curve at 203742.

If the total energy has reached the first energy threshold, the generator 4002 may determine whether the impedance threshold has been reached (step 203746). As described above, the impedance threshold may be a predetermined rate of impedance change (e.g., increase) a predetermined impedance, or combination of the two. If the impedance threshold is reached, the generator 4002 may continue to apply the first power curve at step 203742. For example, reaching the impedance threshold in the first power curve may indicate that the aggressiveness of the first power curve is sufficient to bring about suitable coagulation or welding.

In the event that the impedance threshold is not reached at step 203746, the generator 4002 may increment to the next most aggressive power curve at step 203748 and apply the power curve as the current power curve at 203742. In some aspects, incrementing to the next most aggressive power curve may comprise applying a multiplier to a less aggressive power curve such as, for example, the previously implemented power curve. When the next energy threshold is reached at step 203744, the generator 4002 again may determine whether the impedance threshold is reached at step 203746. If it is not reached, the generator 4002 may again increment to the next most aggressive power curve at step 203748 and deliver that power curve at step 203742.

The process flow 203740 may continue until terminated. For example, the process flow 203740 may be terminated when the impedance threshold is reached at step 203746. Upon reaching the impedance threshold, the generator 4002 may apply the then-current power curve until coagulation or welding is complete. Also, for example, the process flow 203740 may terminate upon the exhaustion of all available power curves. Any suitable number of power curves may be used. If the most aggressive power curve fails to drive the tissue to the impedance threshold, the generator 4002 may continue to apply the most aggressive power curve until the process is otherwise terminated (e.g., by a clinician or upon reaching a final energy threshold).

According to various aspects, the process flow 203740 may continue until the occurrence of a termination threshold. The termination threshold may indicate that coagulation and/or welding is complete. For example, the termination threshold may be based on one or more of tissue impedance, tissue temperature, tissue capacitance, tissue inductance, elapsed time, etc. Upon termination, the surgical instrument 7012 and/or surgical hub 5104 may generate an audible tone indicating termination. These may be a single termination threshold or, in various aspects, different power curves may have different termination thresholds. According to various aspects, different power curves may utilize different impedance thresholds. For example, the process flow 203740 may transition from a first to a second power curve if the first power curve has failed to drive the tissue to a first tissue impedance threshold and may, subsequently, shift from the second to a third power curve if the second power curve has failed to drive the tissue to a second impedance threshold. In some aspects, rather than proceeding between power curves in order, the generator 4002 may skip one or more power curves. For example, if the impedance of the tissue at the end of a power curve exceeds a skip threshold, then generator 4002, instead of proceeding to the next power curve, may skip to a more aggressive power curve (e.g., a power curve that provides more energy for a given tissue impedance).

In some aspects utilizing a pulsed drive signal, the generator 4002 may apply one or more composite load curves to the drive signal, and ultimately to the tissue. Composite load curves, like other power curves described herein, may define a level of power to be delivered to the tissue as a function of a measured tissue property or properties. Composite load curves may, additionally, define pulse characteristics, such as pulse width, in terms of the measured tissue properties (e.g., impedance, applied current, applied voltage, temperature, reflectivity, force applied to the tissue, etc.).

Figure 82C:
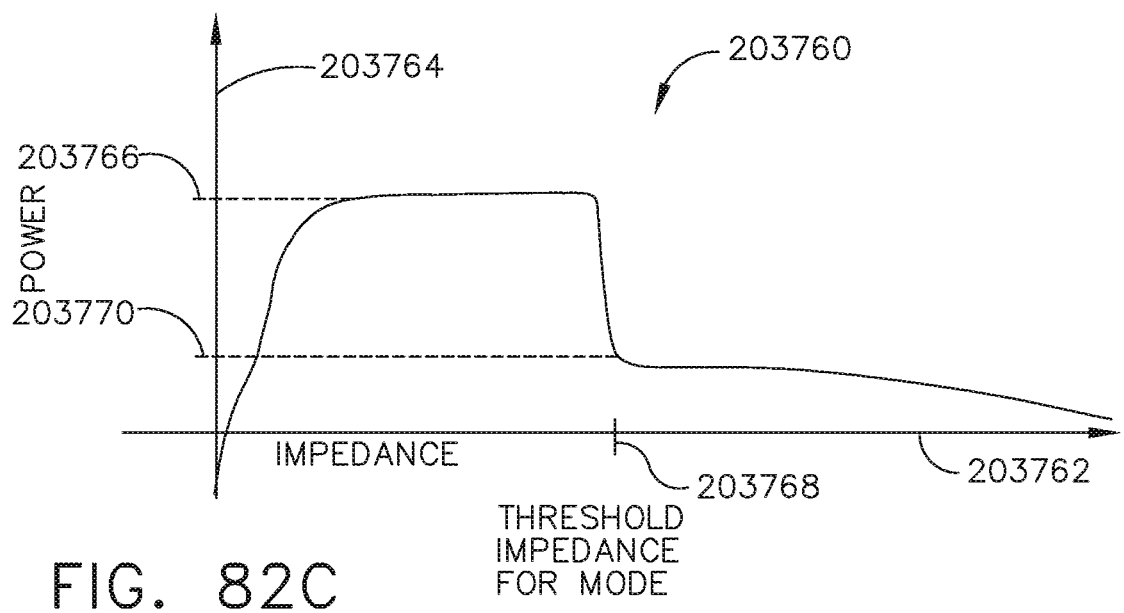

FIG. 82C is a chart 203760 showing power and impedance characteristics of one aspect of a drive signal that may be provided by the generator 4002 during a first mode. In FIG. 82C, impedance is indicated in the x-axis 203762 and power is indicated on the y-axis 203764. During the first mode, the generator 4002 may be configured to provide a first power threshold 203766 to the tissue while the tissue impedance is below a threshold impedance 203768 for the mode. If the impedance of the tissue exceeds the threshold impedance 203768 for the first mode, the generator 4002 may limit the provided power to a second power threshold 203770. In various aspects, the second power threshold 203770 may be less than the maximum power that the generator 4002 is configured to deliver to the tissue. In this way, the first mode may prepare the tissue 203570 for greater power application in later modes. The application period for the first mode may be any suitable value including, for example, one second. It will be appreciated that the drive signal may be pulsed during application of the first mode. For example, the first mode may be applied as a single pulse lasting the duration of the application time period for the first mode, or in multiple shorter pulses. In aspects utilizing multiple pulses in the first mode, each pulse may conform to impedance-determined limits for drive signal power, as described.

Figure 82D:
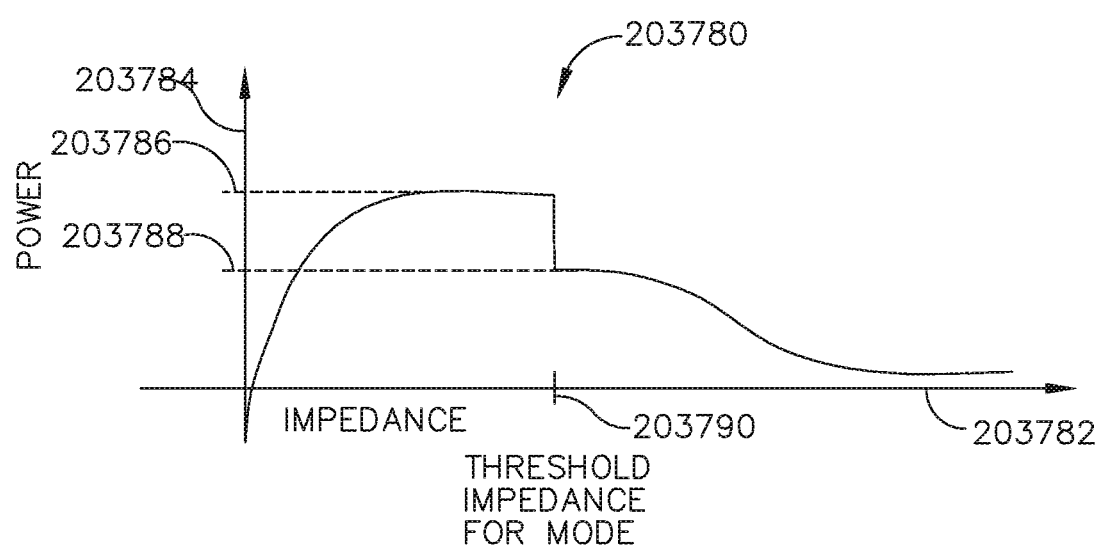

FIG. 82D is a chart 203780 showing power and impedance characteristics of one aspect of a drive signal that may be provided by the generator 4002 during a second mode. In FIG. 82D, impedance is indicated in the x-axis 203782 and power is indicated on the y-axis 203784. In the second mode, the generator 4002 provides a relatively high level of power at the lowest tissue impedances expected to be encountered. For example, in some aspects, the full power available from the generator 4002 (203786 in FIG. 82D) may be provided at tissue impedances below the threshold impedance 203790 for the second mode. Above the threshold impedance 203790, the power may be reduced below a second power threshold 203788 so as to limit the rate of impedance increase. In some aspects, the second power threshold 203788 is greater than the second power threshold 203770 of the first mode. Also, it will be appreciated that the impedance threshold 203768 of the first mode and the impedance threshold 203790 of the second mode may be equal or may take different values depending on the implementation. The application period of the second mode may be longer than that of the first mode so as to allow the provided energy to act on the tissue. For example, in some aspects, the application period of the second period is between four and five seconds. It will be appreciated that the drive signal may also be provided as a single pulse lasting the duration of the application period and/or as multiple pulses Again, when multiple pulses are used, each pulse may conform to the impedance-determined limits for drive signal power.

Figure 82E:
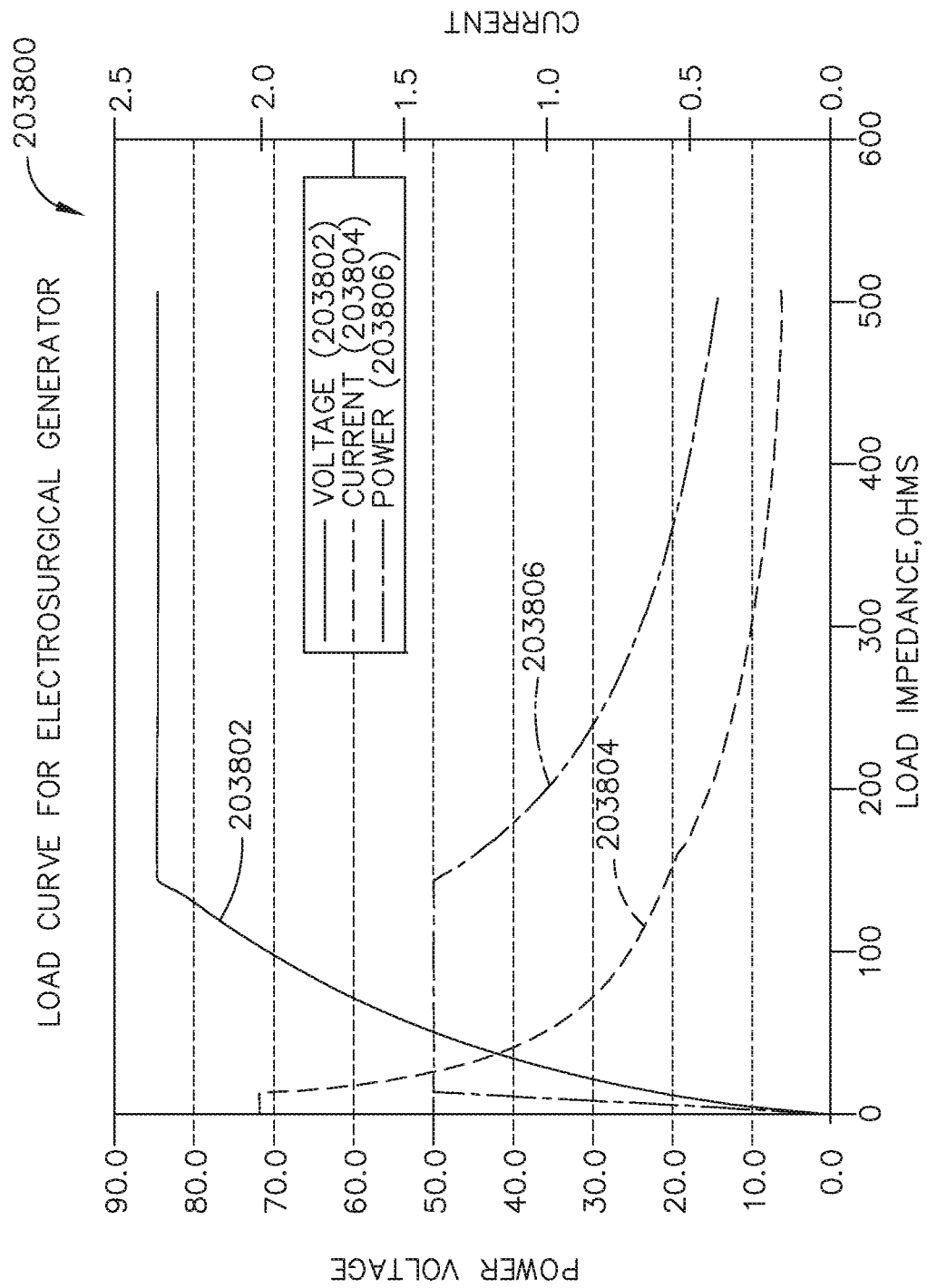

FIG. 82E is a graph 203800 shows an example of a typical load curve for a generator configured to provide power to an electrosurgical system of the present disclosure. In particular, FIG. 82E provides further details of various electrical readings of the surgical instrument system undergoing the sealing procedure during surgery. The left vertical axis represents power (W) and voltage (V), the right vertical axis represents current (A), and the horizontal axis represents load impedance (Ohms). The voltage curve 203802, current curve 203804, and power curve 203806 are shown as functions of load impedance. As shown, the amount of power and voltage applied to tissue typically reaches an impassable threshold, even over ever increasing load impedances. Looked at another way, the amount of energy applied to the tissue at a surgical site has a noticeable effect only up to certain levels of load impedances, and after a certain impedance threshold, such as 175Ω, applying more or sustained power typically has little to no benefit. Graph 203800 therefore provides further detail on why exceeding the transition impedance threshold, as shown in graph 203800, generally represents the cutoff point to which power should continue to be applied.

FIG. 82F is a graph 203820 showing an example power profile of a tapered load curve concept, with additional power characteristics superimposed. In FIG. 82F, the curve 203822 as shown by the thick line represents a measure of voltage as a function of load impedance in the tissue. The curve 203824 as shown by the medium line represents a measure of calculated power applied to the tissue as a function of load impedance. The calculated power may be the measure of power that is determined by the power system of the surgical instrument 7012, while the curve 203826 as shown by the dashed line represents the actual or effective power applied to the tissue. As shown, both of these curves exhibit a power taper that is reduced in a stepwise manner. This may be caused by the power being duty cycled at different rates over time, i.e., via pulse width modulation. The curve 203828 as shown by the thin line represents a measure of current. The scale for the current is shown on the right-hand side, while the scale for power and voltage is shown on the left.

Advanced Enemy Device Control Algorithms

Various control algorithms for ultrasonic surgical instruments and combination energy surgical instruments (e.g., ultrasonic/monopolar surgical instruments, monopolar/bipolar surgical instruments, ultrasonic/bipolar surgical instruments, and other such combination energy devices) are described herein. For the sake of clarity, surgical instruments will be referenced as surgical instrument 7012 in this section of the present disclosure, although the disclosure of this section could also apply to other surgical instruments referenced above such as surgical instrument 112, 700.

In various aspects, a control algorithm for an ultrasonic surgical instrument 7012 can be configured to apply a variable clamp arm pressure over the cycle time or the tissue coagulation/cut process of a surgical operation to create a constant proximal-to-distal pressure profile. The constant pressure profile means that each portion of tissue held within the end effector of surgical instrument 7012 along the proximal to distal end of the end effector experiences the same or substantially same pressure resulting from the force applied by the end effector clamp arm. This may advantageously result in better coagulation of surgically cut tissue. The control algorithm can be applied by a control circuit and/or a surgical hub. The constant proximal-to-distal pressure profile may involve applying the control algorithm to vary the pressure applied by the clamp arm to provide a threshold control pressure at the cut progression location. The cut progression location can be represented by the progression of a corresponding weld/coagulation focal point determined by the control circuit and/or surgical hub. Thus, the pressure may be varied based on the focal point. The threshold control pressure may be a constant pressure applied to the tissue regardless of the amount of the end effector that is active. That is, the applied pressure does not change (or at least does not significantly change) despite any changes in the extent of tissue loading of the end effector.

A tissue bite or portion of tissue may be loaded into the end effector for surgical treatment, such as by loading the distal end of the end effector with tissue first. In this way, contact may initially be made at a distal point of the end effector. A distal portion of one or more of the ultrasonic blade and clamp arm could grasp the tissue at this distal point. The initial pressure applied by the clamp arm may be determined or adjusted (e.g., from a default pressure level) by a control circuit and/or surgical hub based on the size of the tissue bite initially being grasped, which corresponds to an amount of the blade being utilized at the start (an initial tissue loading of the end effector). After surgical cutting of tissue, surgical coagulation/sealing may be performed by the surgical instrument 7012, such as by ultrasonic vibration of the ultrasonic blade and/or delivery of an RF electrical signal waveform output from the generator to RF electrodes. In the coagulation process, the progression of the weld may be used to adjust the applied clamp pressure. Specifically, the pressure of the clamp arm can adjust over the progression of the weld as the cut/weld focal point shifts along the blade.

In order to better grasp the tissue at the distal point, one or more of the blade and clamp arm could be biased or offset to create a preferential initial contact point at the distal end. Subsequently, the remaining portion of the clamp arm may then be broadly loaded in a distal to proximal manner. Stated differently, in this distal start closure stroke configuration, the offset ultrasonic blade may deflect so as to fully close against the tissue and clamp arm fully at the end effector distal end followed by deflecting further in the proximal direction. The deflections of the blade and clamp arm may be approximately equal or balanced relative to each other. The distal start closure stroke configuration is described in more detail below. The clamp arm pressure can also be varied from the initial pressure by the control circuit and/or surgical hub based on the degree that the end effector is loaded with the tissue and the progression through the weld. Also, the clamp arm pressure can be varied based on the measured tissue impedance (e.g., via a pressure, resistive, or other suitable sensor 788 in the end effector). Moreover, depending on which energy modality or modalities of the surgical instrument 7012 are selected, the power level of one or more of RF and ultrasonic energy delivered to the end effector can also be varied based on the measured tissue impedance. Other types of electrosurgical energy besides RF and ultrasonic energy could also be used.

As discussed above, the tissue loading might commence at the tip or distal end of the end effector such that the first contact between the ultrasonic blade and the clamp arm is at the tip. The surgical hub and/or control circuit can be configured to vary pressure applied by the clamp arm based on the extent of blade utilization, which could be determined via position sensor 784 (referred to in this portion of the present disclosure as position sensor 784, although position sensor 784 may also refer to position sensor 734, 4013 or others as described above). In particular, the application of clamp pressure can be controlled so that the clamp arm and ultrasonic blade do not apply pressure at portions of the end effector that do not contain tissue. In other words, the application of clamp pressure is tailored to those portions of the end effector in which tissue is located between the ultrasonic blade and clamp arm. This may advantageously reduce temperatures and heat residing in the ultrasonic blade after activation of the generator of the surgical instrument 7012. To elaborate further, when the generator delivers energy to the end effector, the portions of the end effector in which tissue is not located receive a relatively lower force so energy delivered to these portions is reduced. Consequently, after activating the generator, the peak temperatures and heat of the ultrasonic blade are reduced.

This targeted application of force by the clamp arm can be achieved based on motorized or manual closure control, tip first closure of the end effector, and feedback provided to the control circuit and/or surgical hub. The feedback could include thermally induced changes in the resonant frequency and electrical continuity (or discontinuity). The feedback could be received by the control circuit via circuitry that comprises the ultrasonic blade and a clamp arm/ultrasonic blade interface (e.g., clamp tissue pad). The changes or shift in the resonant frequency of the transducer may be used as feedback to determine the extent of the tissue loading. In this way, the feedback may be used to adjust applied clamp pressure. Furthermore, the control circuit may control the motor of the surgical instrument to implement the closure stroke so that the end effector closes at a point which is distal to the proximal-most point of the grasped tissue. In this way, a gap may be maintained between the clamp arm and ultrasonic blade at a point which is proximal to the proximal-most point of the grasped tissue.

Sensors 788 (referenced as sensors 788 in this portion of the present disclosure, although they could also refer to sensors 738 or other sensors described above) of the surgical instrument 7012 may provide end effector closure signals as input to the control circuit. Using this input, the control circuit can determine the current closure position of the end effector. When the control circuit determines that the end effector is merely closed at the tip portions (e.g., distal tip or proximal tip) or at some other sub-portion of the end effector length (e.g., the distal half of the end effector), the control circuit may reduce displacement of the ultrasonic blade. To this end, power provided to the ultrasonic transducer may be reduced. This reduction in displacement might beneficially prevent or reduce excessive wear of the clamp arm tissue pad at the distal tip. This excessive wear generally is caused by high distal forces or pressure at the distal tip (corresponding to the distal start closure stroke configuration) and inherent high distal displacement corresponding to displacement profiles associated with ultrasonic blades.

In general, when the tissue does not fully occupy the space between the jaws of the end effector, reducing the surface area of the clamp arm being compressed against the blade reduces the wasteful transmission of electrosurgical energy (e.g., including ultrasonic and RF energy) to the clamp arm and/or tissue pad. In other words, the adjustment in clamp arm pressure enables relatively more electrosurgical energy to be directed towards the tissue rather than undesirably being transmitted to other parts of the end effector. Because the pressure applied by the clamp arm is controlled based on the extent of tissue loading, a constant pressure may be applied to the tissue regardless of how much of the end effector is in an active state. The pressure may further be adjusted based on progression of the surgical coagulation/cutting treatment by the surgical instrument 7012.

Furthermore, the feedback circuitry comprising the ultrasonic blade and clamp pad can also comprise sensor 788 for sensing impedance of the tissue located between the clamp arm and the ultrasonic blade. In this case, the ultrasonic blade and associated waveguide that terminates at the blade could serve as part of the return path for the feedback circuitry. The sensed impedance can indicate a status of the coagulation/cut cycle. That is, for example, comparing the tissue impedance to a threshold may be indicative of a weld progression of the tissue, such as a progression of the weld/coagulation focal point. The focal point may be indicative of how well formed a fibrin clot is for coagulation, for example. In this way, the detected tissue impedance can enable the control circuit and/or surgical hub to adjust power provided to the ultrasonic transducer and the force applied by the clamp arm.

Although at least some portion of the control algorithm(s) disclosed herein can be performed by surgical hubs (alone or in conjunction with associated control circuits of surgical instruments), the functions of the control algorithm(s) are described as performed by control circuits for the sake of clarity. Also for clarity, the control circuit of surgical instrument 7012 in this portion of the present disclosure is labeled control circuit 710, although control circuit 710 can be the same or similar to control circuits 760, 3200, 3502, 4008. Control circuit 710 may be a part of the generator 4002 itself (referred to as generator 4002 for clarity although generator 4002 can be the same or similar to generator 140, 145, 240, 721, 771, 900, 1100) or another part of the surgical instrument 7012 that is remote from the generator 4002. In various aspects, the surgical instrument 7012 (e.g., ultrasonic surgical instrument) as described in FIGS. 83A-83B, 84A-84B, 85-86, 87A-87C, 88A-88C, 89A-89C, 90A-90D, 91A-91D, 92A-92E, is configured to operate with situational awareness in a hub environment, such as the surgical hub 106 or 206 (FIGS. 1-11), for example, as depicted by the timeline 5200.

FIG. 83A-83B are graphs 203000, 203020 including a graph of clamp force as a function of time and an associated graph of a coagulation/cut focal point, in accordance with at least one aspect of the present disclosure. In FIG. 83A, the y-axis 203010 denotes force while the x-axis 203008 denotes time. The dashed line 203002 represents the force applied by the clamp arm over time and tracks the application of force by the clamp arm from the minimum force at time $t_0$ to maximum force at time $t_{10}$. Clamp force may be measured in suitable units, such as pounds (lbs). The time spanning initial time $t_0$ to time $t_{10}$ can define a surgical cycle of the surgical instrument 7012. The dash-and-dot line 203004 represents the measured tissue impedance over the surgical cycle. As can be seen on graph 203000, the measured tissue impedance decreases from its initial level at time $t_0$ to the low point at time $t_3$, demonstrating the drop in impedance resulting from the commencement of surgical treatment (the so-called "bathtub" portion of the impedance curve). After time $t_3$, the tissue impedance line 203004 rises as the tissue being treated begins to dry out. This desiccation results in an increase in tissue impedance. FIG. 83A shows how this increase in tissue impedance line 203004 corresponds to an increase in the applied force line 203002. The increase in applied force may assist in cutting the tissue and welding the denatured tissue as the surgical cycle is completed.

In particular, the control circuit 710 may execute the control algorithm to provide a constant proximal-to-distal pressure profile. By providing such a threshold control pressure, the tissue seal formed during the coagulation stage advantageously may be more uniform and secure. Accordingly, the solid line 203006, which indicates a measured pressure applied to the tissue in the end effector, stays the same or roughly constant throughout the surgical cycle. The tissue pressure line 203006 may correspond to the pressure applied at the leading edge of the end effector, where surgical coagulation and cutting occur. Clamp force can be a function of the progress of the tissue coagulation process. This relationship may be used to provide the constant tissue pressure. Thus, while tissue may be coagulated and cut at the proximal sections of the end effector, increasing clamp force at the distal section results in better coupling of the tissue to the distal sections of the ultrasonic blade. In this way, each section of tissue (which spans the proximal to distal sections of the end effector) could experience the same or approximately similar pressure. As the tissue weld progresses, the control circuit may control the clamp arm to progressive closure, which is demonstrated by graph 203000. Also, the clamp arm may be cambered to the ultrasonic wave guide that terminates into the ultrasonic blade.

FIG. 83B shows that the focal point of the surgical coagulation and cutting operation on the tissue shifts along the length of ultrasonic blade 203026 (similar to or the same as ultrasonic blade 718, 768 or other ultrasonic blades described above) over the course of the surgical cycle. As shown in FIG. 83B, the focal point shifts in a proximal to distal direction over time, but the focal point could also shift in a distal to proximal direction. The former possibility corresponds to a proximal start closure stroke configuration while the latter corresponds to a distal start closure stroke configuration. As discussed above, the control circuit 710 may be configured to determine the cut/weld focal point based on one or more of the resonant frequency and electrical continuity feedback measures. Graph 203020 also portrays clamp arm 203022 (similar to the same as clamp arm 716, 766 or other clamp arms described above) Clamp arm 203022 can comprise clamp tissue pad 203024, which may be formed from TEFLON® or some other suitable low-friction material. The pad 203024 may be mounted for cooperation with the blade 203026, with pivotal movement of the clamp arm 203022 positioning the clamp pad 203024 in substantially parallel relationship to, and in contact with, the ultrasonic blade 203026. By this construction, a tissue bite to be clamped may be grasped between the tissue pad 203024 and the ultrasonic blade 203026. The tissue pad 203024 may be provided with a sawtooth-like configuration including a plurality of axially spaced, proximally extending gripping teeth to enhance the gripping of tissue in cooperation with the ultrasonic blade 203026. The control circuit 710 may control the clamp arm 203022 to transition from between an open position and a closed position, including various intermediate positions in between. The control circuit 710 may vary the pressure applied by the clamp arm 203022 based on a shift in the weld focal point along the ultrasonic blade 203026 or an extent of tissue loading in the end effector. The x-axis 203028 of graph 203020 represents the surgical cycle in the same manner that x-axis 203008 does.

FIGS. 84A-84B are graphs 203040, 203060 including a graph 203040 of clamp force as a function of distance from the distal tip of the end effector and a graph 203060 of blade displacement as a function of distance from the distal tip, in accordance with at least one aspect of the present disclosure. FIG. 84A illustrates how the clamp pressure between the ultrasonic blade 203026 and clamp arm 203022 varies as a function of the distance from the distal tip relative to the tissue. Specifically, the graph 203040 includes a plurality of clamp pressure curves 203042A-203042D showing how the control circuit 710 can adjust the applied clamp pressure depending on the position of the tissue. To this end, the control circuit 710 may determine the closure position of one or more of the ultrasonic blade 203026 and clamp arm 203022. The x-axis 203044, 203064 denotes distance from the distal tip of the end effector while the y-axis 203046, 203066 denotes applied clamp force. In the proximal start closure stroke configuration of FIG. 84A, the applied clamp pressure rolls in a distal direction during the closure motion so that the closure stroke is at the fully clamped state at the distal tip. Put differently, the clamp pressure may be maximal when the distance from the distal tip is minimal High amplitude of clamp pressure may be necessarily to surgically manipulate the tissue such as manipulating the structure of a blood vessel as desired.

FIG. 84B illustrates the corresponding displacement profile of the ultrasonic blade 203026 as a function of distance from the tip of the end effector. In the graph 203060, the x-axis 203064 again denotes distance from the distal tip while the y-axis 203066 denotes the magnitude of displacement of the ultrasonic blade 203026. Relatedly, the zero point of the x-axis corresponds an anti-node 203062 while the maximal point corresponds to a node 203068 of the ultrasonic blade 203026. The anti-node 203062 can be defined as a local absolute maximum in which the displacement or vibration of the ultrasonic blade 203026 is maximal. The node 203068 can be defined as a local absolute minimum in which the displacement or vibration of the ultrasonic blade 203026 is minimal In general, the distance between the adjacent node and anti-nodes can be one-quarter wavelength of the drive or resonant frequency of the ultrasonic blade 203026. As illustrated by the graph 203060, at the anti-node 203062, the occurrence of the positive maximum extent of ultrasonic vibration of the ultrasonic blade 203026 overlaps with the maximal distance away from the distal tip. This would also occur at the next anti-node corresponding to the negative maximum extent of ultrasonic vibration, although this is not shown in FIG. 84B. At the point (node 203068) of minimum distance away from the distal tip, the ultrasonic vibration is minimal so as to fully clamp or grasp tissue between the ultrasonic blade 203026 and clamp arm 203022. This change in ultrasonic displacement as a function of distance of tip is represented by displacement line 203070.

In contrast to the proximal start closure stroke configuration, the present disclosure may contemplate a distal start closure stroke configuration in which first closing the distal tip of the end effector ultimately assists in advantageously attaining heat mitigation. Heat mitigation can occur by configuring the control circuit 710 to control clamp pressure according to the extent of tissue loading in the end effector. Specifically, pressure may be provided only at points of intersection where ultrasonic blade 203026 and clamp arm 203022 grasp tissue therebetween. By preventing or reducing pressure at portions of the end effector where no tissue resides, peak temperatures and residual heat after energy delivery from the generator 4002 are reduced. In this way, relatively more energy is transmitted to the tissue instead of the electrically conductive clamp arm tissue pad 203024. The clamp pad 203024 may be formed of a molded, carbon filled polytetraflouroethylene or some other suitable material and additionally may be secured to the underside of clamp arm 203022, as described in U.S. Publication No. 2017/0164997, titled METHOD OF TREATING TISSUE USING END EFFECTOR WITH ULTRASONIC AND ELECTROSURGICAL FEATURES, published on Jun. 15, 2017, which is herein incorporated by reference in its entirety.

Also, the clamp tissue pad 203024 may be electrically conducive based on the use of conductive fillers (e.g. carbon, carbon nanotubes, metallic particles, etc.). Electrical current could flow through the surgical instrument 7012 from the ultrasonic blade 203026 to the tissue pad 203024 via isolated electrical circuitry, which enables the application of therapeutic or sub-therapeutic RF energy to the tissue by the end effector (e.g., via RF electrode 796). When the surgical instrument 7012 includes RF electrode 796, the control circuit 710 can be configured to adjust one or more of a power level of the RF energy and a power level of the electrosurgical energy based on determined tissue impedance. More details regarding conductive pads may be found in U.S. Pat. No. 9,764,164, titled ULTRASONIC SURGICAL INSTRUMENTS, issued on Sep. 19, 2017, which is herein incorporated by reference in its entirety. Other aspects of combination bipolar RF and ultrasonic architectures of surgical instrument 7012 are described in U.S. Pat. No. 9,017,326, titled IMPEDANCE MONITORING APPARATUS, SYSTEM, AND METHOD FOR ULTRASONIC SURGICAL INSTRUMENTS, issued on Apr. 28, 2015; U.S. Pat. No. 10,022,568, titled DEVICES AND TECHNIQUES FOR CUTTING AND COAGULATING TISSUE, issued on Jul. 17, 2018; and U.S. Publication No. 2017/0164997, titled METHOD OF TREATING TISSUE USING END EFFECTOR WITH ULTRASONIC AND ELECTROSURGICAL FEATURES, published on Jun. 15, 2017, all of which are herein incorporated by reference in their entirety.

The control circuit 710 may control the motor of the surgical instrument 7012 to adjust the closure of the clamp arm 203022 and/or the movement of the ultrasonic blade 203026 for heat mitigation and energy efficiency. To this end, only a part of the full length of the end effector could be used to grasp and treat tissue. For example, only the distal end of the end effector could initially close on a tissue bite followed by progressively more tissue loading in the proximal direction. In this distal start closure stroke configuration, the applied force by the clamp arm is increased until reaching the full closure stroke threshold while the clamp arm 203022 and/or ultrasonic blade 203026 gradually deform to fully compress against tissue while maintaining a slight gap therebetween in portions of the end effector that do not contain tissue. When the full closure stroke of the end effector is attained, the clamp tissue pad 203024 may contact the entire length of the tissue treating portion of the ultrasonic blade 203026. In this way, the control circuit can be configured to close the end effector at a distal end of the end effector prior to closing non-distal end portions of the end effector. The pressure profile of the tissue treating or end effecting portion of the ultrasonic blade 203026 is described in more detail below.

An offset, sloping, or otherwise curved ultrasonic blade 203026 can assist in facilitating distal tip first closure of the clamp arm 203022. More detail regarding closing the distal tip of the end effector first (distal start closure stroke configuration) and the offset ultrasonic blade 203026 may be found in U.S. Pat. No. 8,444,663, titled ULTRASONIC SURGICAL SHEARS AND TISSUE PAD FOR THE SAME, issued on May 21, 2013; U.S. Pat. No. 10,004,527, titled ULTRASONIC SURGICAL INSTRUMENT WITH STAGED CLAMPING, issued on Jun. 26, 2018; U.S. Publication No. 2018/0153574, titled HEADPIECE AND BLADE CONFIGURATIONS FOR ULTRASONIC SURGICAL INSTRUMENT, published on Jun. 7, 2018; U.S. Publication No. 2018/0153574, titled HEADPIECE AND BLADE CONFIGURATIONS FOR ULTRASONIC SURGICAL INSTRUMENT, issued on Jun. 7, 2018; and U.S. Publication No. 2018/0014848, titled ULTRASONIC SURGICAL INSTRUMENTS HAVING OFFSET BLADES, published on Jan. 18, 2018, all of which are herein incorporated by reference in their entirety. As discussed above, the ultrasonic blade 203026 and/or clamp arm 203022 may be compliant so that the control circuit 710 causes the ultrasonic blade 203026 and/or clamp arm 203022 to deform as the applied clamp force increases. FIGS. 92A-92E illustrate how this deformation may occur as tissue treatment proceeds. In general, the end effector should be in a full closure state prior to application of electrosurgical energy. Also, a first deflection of the offset ultrasonic blade can correspond to a second deflection of the offset clamp arm. The first and second deflection could be shaped according to a closure pressure profile implemented by the control circuit 710 to provide relatively greater pressure in the proximal portion of the end effector.

The control circuit 710 may use feedback to control the end effector for heat mitigation as described above. For example, the control circuit 710 could monitor the resonant frequency of the ultrasonic blade 203026. In particular, the generator 4002 may include a tuning inductor for tuning out the static capacitance at a resonant frequency so that substantially all of generator's current output flows into the motional branch. The motional branch current, along with the drive voltage, define the impedance and phase magnitude. Accordingly, the current output of the generator 4002 represents the motional branch current, thus enabling the generator 4002 to maintain its drive output at the ultrasonic transducer's resonant frequency. The control circuit 710 can monitor drive signals of the generator 4002 that correlate to the resonant frequency. The generator 4002 may deliver electrosurgical energy to the end effector to weld tissue based on generating the drive signal. As a surgical treatment cycle proceeds, the resonant frequency changes due to changes in the material stiffness of the tissue. In turn, the change in material stiffness occurs because of the rapid accumulation of thermal energy in the ultrasonic blade 203026, as electrosurgical energy is being delivered.

The control circuit 710 is configured to evaluate this dynamic thermal response via frequency changes or frequency slope (e.g., first derivative of frequency or frequency change with respect to time), such as based on comparison to a frequency threshold parameter value. Additionally or alternatively, the control circuit 710 can compare the change in resonant frequency relative to an initial frequency value determined at the start of electrosurgical energy activation, which can be recorded to the memory of the surgical instrument 7012. Based on electrical signals generated by the generator 4002, the control circuit 710 may determine and compare frequency slope or frequency changes against corresponding thresholds. Specifically, the control circuit 710 may determine: (i) when the frequency slope is above the associated threshold parameter value and (ii) when the frequency change is above a frequency floor. Above a frequency floor means, for example, that the drop in frequency does not exceed a predetermined threshold drop relative to the determined initial frequency value. Based on one or more of these determinations, the control circuit 710 (e.g., via the motor) can control the ultrasonic blade 203026 and/or clamp arm 203022 to reduce closure force/stroke when the frequency monitoring conditions (i), (ii) are met. As such, the control circuit 710 may determine a resonant frequency measure indicative of a thermally induced change in resonant frequency to calculate a tissue weld/seal focal point.

In this way, the control circuit 710 causes the applied clamp force or pressure to "back off", to beneficially minimize the delivery of thermal energy to the clamp pad 203024 at locations that are proximal to the proximal extent of the grasped tissue. More details regarding resonant frequency monitoring can be found in U.S. Pat. No. 8,512,365, titled SURGICAL INSTRUMENTS, issued Aug. 20, 2013; and U.S. Pat. No. 9,788,851, titled SURGICAL INSTRUMENT WITH TISSUE DENSITY SENSING, issued on Oct. 17, 2017; both of which are herein incorporated by reference in their entirety. Furthermore, the control circuit 710 can be programmed to follow a set limit defining the permissible extent to which the control circuit 710 backs off on closure force or stroke. The set limit could be determined in order to prevent tissue from slipping out or otherwise escaping from the grasp of the end effector. In addition, the surgical instrument 7012 could be designed to provide user feedback such as visual, audible, tactile, haptic, vibratory, or some other feedback to the user that is indicative of the current closure state. For example, the user feedback (e.g., light emitting diode, graphical user interface, buzzer, computer generated sound, handle vibration etc.) might indicate when the end effector closes at a point proximal the proximal extent of the grasped tissue. In situations where the user selects an override setting for overriding the automatic closure control feature of the surgical instrument 7012, this user feedback can be particularly helpful to inform the user of closure status.

As another example of feedback, the control circuit 710 could monitor the electrical impedance of the surgical instrument 7012. In various aspects, the surgical instrument 7012 may conduct electrical current between the ultrasonic blade 203026 and the clamp arm tissue pad 203024 for delivery of electrosurgical energy. By monitoring this electrical current (or lack thereof), tissue impedance, or transducer impedance based on an end effector sensor 788 and/or drive signal of generator 4002, the control circuit 710 may determine the amount of tissue loading in the end effector. In particular, the control circuit 710 may be programmed to detect and maintain an impedance of the circuit comprising the blade 203026 and the clamp arm tissue pad 203024 above a predetermined threshold. This maintained impedance can correspond or approximately correspond to an electrical short. As such, the electrical short means electrical discontinuity exists between the ultrasonic blade 203026 and the clamp arm tissue pad 203024. Therefore, minimal thermal energy is delivered to the portion of the clamp arm tissue pad 203024 located proximally to the proximal extent of the grasped tissue. To arrive at this desired lack of electrical continuity, the control circuit 710 could perform the reduction or backing off of the closure force or stroke as described above. As such, the control circuit 710 may determine an electrical continuity measure to calculate a tissue weld/seal focal point.

On the other hand, when the end effector is not fully closed, the feedback received by the control circuit 710 may be used to reduce the output of the generator 4002. The output of the generator 4002 might be ultrasonic and/or bipolar RF electrosurgical energy, depending on the energy modality configuration of the surgical instrument 7012. By reducing the ultrasonic displacement of ultrasonic blade 203026 and/or RF power conducted via RF electrode 796, the control circuit 710 may prevent or lower instances of relatively high power densities at the distal tip of the end effector. This is especially true given that the ultrasonic vibration of ultrasonic blade 203026 is generally relatively high at the distal tip. In any case, avoiding these high power densities may advantageously stop or reduce excessive wearing or deterioration of the clamp arm tissue pad 203024. The acoustic drive impedance of the ultrasonic blade 203026 could also be used to assess jaw closure state. Additionally or alternatively, a closure switch of the surgical instrument 7012 such as a handle closure switch could indicate when the clamp arm 203022 and/or ultrasonic blade 203026 is closed, as described for example in U.S. Pat. No. 9,724,118, titled TECHNIQUES FOR CUTTING AND COAGULATING TISSUE FOR ULTRASONIC SURGICAL INSTRUMENTS, issued on Aug. 8, 2017, which is herein incorporated by reference in its entirety. Position sensor 734 or motor current also could be used to determine jaw closure state.

FIG. 85 is a graph 203080 of a clamp force distribution as a function of various sections along the length of the end effector, in accordance with at least one aspect of the present disclosure. The x-axis 203082 denotes a section along the length of the end effector, including section numbers 1 through 5. The y-axis 203084 denotes gradients of pressure measured in suitable units ranging from 1 through 4. The units could be pounds (lbs), for example. Section 1 represents the distal-most portion while section 4 represents the proximal-most portion of the end effector. The measured force can be determined by the control circuit 710 based on the sensor 788, such as a pressure sensor. The pressure output signal of pressure sensor 788 used to generate graph 203080 has been averaged or summed to smooth the clamp pressure line 203086. In other words, peaks and valleys in the pressure line 203086 that might result from irregularities in the pad 203024 (e.g., teeth in the clamp pad 203024) or sensor 788 are softened or smoothed out in graph 203080. As illustrated by graph 203080, the force distribution in the proximal half of the end effector is relatively higher than the force distribution in the distal half of the end effector. In other words, the pressure profile ratio of the end effector is below the value 1.

The pressure profile ratio can be defined as the sum of pressure applied in the distal portion divided by the sum of pressure applied in the proximal portion of the end effector. Therefore, pressure profile ratios>1 indicate that the end effector is distal tip loaded while pressure profile ratios<1 indicate proximal loaded status. A distal tip loaded end effector may have more cumulative pressure on the distal half while a proximal loaded end effector has more cumulative pressure on the proximal half. As demonstrated by graph 203080, the end effector measured by pressure sensor 788 is proximally loaded. The proximally loaded status may be assessed from a position in which no tissue is contained within the end effector. One such example can be seen in FIG. 92A. The relatively higher force applied in the proximal portion of the end effector may result from the greater degree of curvature or offset between the ultrasonic blade 203026 and clamp arm 203022 in the distal portion relative to the proximal portion. Proximally loading the end effector may be desirable because the ultrasonic blade 203026 generally may ultrasonically vibrate to a greater extent towards to the distal portions. That is, the displacement of the ultrasonic blade 203026 might be greater at the distal portion than the proximal portion of the end effector. The relatively high clamp pressure applied at the proximal portion can advantageously ensure a more uniform application of electrosurgical energy to the tissue, thereby attaining a more secure cutting/coagulation surgical treatment.

FIG. 86 is a graph 203100 of blade displacement profile as a function of distance from the distal tip of the end effector, in accordance with at least one aspect of the present disclosure. The x-axis 203102 denotes distance from the distal tip of the end effector, which is shown in units of millimeters (mm) on graph 203100. The y-axis 203104 denotes the normalized velocity (on a scale ranging from 0 to 1) of the ultrasonic blade 203026. When normalized, the velocity profile as shown in 203100 is coterminous or overlaps with the displacement profile of the ultrasonic blade 203026. In addition, the driven resonant frequency 203108 of the ultrasonic blade 203026 defines the effective wavelength of the displacement or velocity profile. As shown in FIG. 86, the driven resonant frequency 203108 is 55.5 kilohertz (kHz), although other suitable resonant frequency values are possible as well. The driven resonant frequency 203108 is a factor of the material, geometry, and thermal condition of the surgical instrument 7012. Also shown in FIG. 86 is the tissue treatment border 203110 of the end effector. The tissue treatment border 203110 indicates the length of the tissue treating (e.g., cutting and coagulation) portion of the end effector and is approximately 15 mm from the distal tip in graph 203100. The velocity-distance line 203106 represents the change in normalized velocity as a function of distance from the distal tip.

Stated another way, the tissue treating portion spans 15 mm from the distal tip of the end effector, as measured in the proximal direction. The velocity and/or displacement profile as portrayed in graph 203100 demonstrates that the velocity and/or displacement of the ultrasonic blade 203026 is maximal at the distal tip and decreases to the minimal value as the distance from the distal tip increases to the maximum. Accordingly, providing a preferential distribution of clamp force towards the proximal portion of the end effector as shown in FIG. 85, can allow for a more uniform power deposition along the length of the end effector. Power deposition is a function of the coefficient of friction, the velocity, and the applied force or pressure. Thus, as discussed above, matching the relatively high distal velocity to a relatively low distal pressure and matching the relatively low proximal velocity to a relatively high proximal pressure can result in more uniform cutting of tissue, as determined with respect to time. When the end effector is fully closed such that it has reached the full closure stroke, the resulting pressure or force profile is higher in the proximal half or quarter of the end effector, so graph 203080 shows how the pressure or force profile ratio is <1. Also, the deflections of the ultrasonic blade 203026 and clamp arm 203022 can be equivalent or match over the course of the closure stroke of the end effector.

FIGS. 87A-87C are sectional views of end effector 203120 that illustrate a closure stroke of the end effector, in accordance with at least one aspect of the present disclosure. The progression of the closure stroke as portrayed in FIGS. 87A-87C demonstrates a proximal start configuration closure stroke. In FIG. 87A, the end effector 203120 (which may be the same or similar to end effectors described above, including end effector 702, 752, 792, 4006) is at a more open position than in FIGS. 87B-87C Clamp arm 203122 includes clamp arm tissue pad 203124, which may be the same or similar as pad 203024. In FIG. 87A, the clamp arm 203122 is spaced away from the ultrasonic blade 203126 so that clamp arm tissue pad 203124 initially begins to contact or touch the blade at the most proximal portion of the clamp arm tissue pad 203124. The clamp arm 203122 is sloped or angled upwards relative to a horizontal axis defined by the end effector 203120. Accordingly, the opening between the clamp arm 203122 and ultrasonic blade 203126 increases in the distal direction away from pivot point 203128. The clamp arm 203122 and ultrasonic blade 203126 may pivot about pivot point 203128.

Although FIG. 87A does not depict tissue grasped by the end effector 203120, in operation, tissue may be located in end effector 203120 such that the end effector 203120 compresses against tissue at the proximal-most extent of pad 203124 to being tissue treatment in FIG. 87A. In FIG. 87B, the clamp arm 203122 is further along in the closure stroke of the end effector 203120. As such, most or all of the proximal portion of the end effector is in the closed position. Accordingly, FIG. 87B shows that the proximal-most extent of the pad 203124 contacts the ultrasonic blade 203126, while the portions of the pad 203124 immediately distal to the proximal-most extent are also almost closed or contacting the ultrasonic blade 203126. Again, the gap between the clamp arm 203122 and the ultrasonic blade 203126 increases in the distal direction away from pivot point 203128. FIG. 87C illustrates the full closure position of the end effector 203120. In FIG. 87C, the full extent of the clamp arm 203122 and pad 203124 contacts the ultrasonic blade 203126 to obtain the full closure stroke. Thus, clamp pressure is applied to all portions of the end effector 203120, as reflected in FIG. 88C. The closure progression of the proximal start configuration as depicted in FIGS. 87A-87C demonstrates how clamp pressure or force rolls in the distal direction.

FIGS. 88A-88C are graphs 203140, 203160, 203180 of clamp force applied between the blade and clamp arm as a function of distance from the distal tip of the end effector 203120 corresponding to the sectional views of FIGS. 87A-87C, in accordance with at least one aspect of the present disclosure. The applied clamp pressure or force plotted in graphs 203140, 203160, 203180 can be measured by pressure sensor 788. In the graphs 203140, 203160, 203180, the x-axis 203144, 203164, 203184 denotes the distance from the distal tip of end effector 203120. The y-axis 203146, 203166, 203186 denotes the clamp arm pressure or force applied between the clamp arm 203122 and the ultrasonic blade 203126. The applied clamp force line 203142, 203162, 203184 illustrates the clamp pressure as a function of distance from the distal tip of end effector 203120. As described above, the applied clamp pressure first begins at the proximal-most extent of clamp arm tissue pad 203124, adjacent to pivot point 203128. This is demonstrated by FIG. 88A. In FIG. 88B, the clamp pressure has begun to spread distally. Accordingly, the applied clamp force line 203162 starts at a more leftward point than that of applied clamp force line 203142. Moreover, the clamp pressure at the proximal-most extent of clamp arm tissue pad 20312 is greater in FIG. 88B than in FIG. 88A. That is, the amplitude at the rightmost portion of the applied clamp force line 203162 is greater than the corresponding amplitude of applied clamp force line 203142.

In FIG. 88C, the applied clamp force line 203182 starts at an even more leftward point than that of applied clamp force line 203162. In fact, clamp pressure is applied at all points spanning the x-axis 203184. The clamp pressure at the proximal-most extent of clamp arm tissue pad 20312 is greater in FIG. 88C than either of FIG. 88B and FIG. 88A. The graph 203180 of FIG. 88C illustrates the applied pressure in a full closure stroke or position of the end effector 203120. In the full closure state of the end effector 203120, it may be desirable for the control circuit 710 to implement computer executable logic or rules that ensure the end effector 203120 reaches the full closure stroke prior to application of energy by the generator 4002. As discussed above, the full closure stroke is achieved when the end effector 203120 closes along its entire available length. By delivering electrosurgical energy to the tissue only after attaining the full closure position, better tissue sealing may be performed. In particular, homeostasis can be maximized or improved based on the full closure stroke laterally displacing the inner layers and approximating the outer layers of the tissue so that these layers may be joined during delivery of electrosurgical energy. That is, optimum vessel sealing may occur when the inner muscle layer of a vessel is separated and moved away from the adventitia layer prior to the application of electrosurgical energy. The outer tissue layers could form more reliable tissue welds or seals (e.g., tunica adventitia, serosal covering, etc.).

One example of such rules executed by the control circuit 710 includes a rule in which if the user activates the large vessel or advanced hemostasis mode of the surgical instrument 7012, the control circuit 710 verifies that the end effector 203120 has reaches the full closure stroke. This verification could occur via a handle closure or full closure switch of the surgical instrument 7012, for example. When the closure switch is not in the closed position, this indicates the end effector 203120 is not fully closed. Consequently, the surgical instrument 7012 may generate an alert such as an audible beeping sound or visual, audible, tactile, haptic, vibratory alert, or some other suitable alert. In some aspects, the surgical instrument 7012 may have mechanical components to control application of relatively high clamp force for displacing vessel structure (e.g., approximating adventitia) and of relatively low clamp force for energy delivery. More details regarding such rules and vessel structure manipulation for cutting and sealing tissue may be found in U.S. Pat. No. 8,779,648, titled ULTRASONIC DEVICE FOR CUTTING AND COAGULATING WITH STEPPED OUTPUT, issued on Jul. 15, 2014; U.S. Pat. No. 9,241,728, titled SURGICAL INSTRUMENT WITH MULTIPLE CLAMPING MECHANISMS, issued on Jan. 26, 2016; U.S. Pat. No. 9,743,947, titled END EFFECTOR WITH A CLAMP ARM ASSEMBLY AND BLADE, issued on Aug. 29, 2017; all of which are herein incorporated by reference in their entirety.

FIGS. 89A-89C are sectional views of the end effector 203200 that illustrate a proximal start closure stroke configuration, in accordance with at least one aspect of the present disclosure. As shown in FIG. 89A, the end effector 203200 starts in an open position in which clamp arm 203202 and ultrasonic blade 203206 define a relatively large gap in between each other Clamp arm 203202 includes clamp arm tissue pad 203204, which may the same or similar as pad 203024, 203124. In FIG. 89B, the clamp arm 203202 has pivoted inwards with respect to pivot point 203208 so that the proximal portion of clamp arm tissue pad 203204 contacts tissue (not shown) located on the pad 203204. In other words, the end effector 203200 closes proximally first so as to apply full clamp pressure to only the proximal portion of the grasped tissue while clamp force progressively rolls or expands in the distal direction. As the end effector 203000 reaches the full closure stroke depicted in FIG. 89C, more clamp pressure is gradually distally. In FIG. 89C, the full closure pressure profile or force distribution is achieved in the full closure position of end effector 203000. As discussed above, relatively more clamp pressure can be applied in the proximal portion of the end effecting portion of the ultrasonic blade 203026 to account for the relatively low proximal velocity of the ultrasonic blade 203026, for example.

Figure 90A:
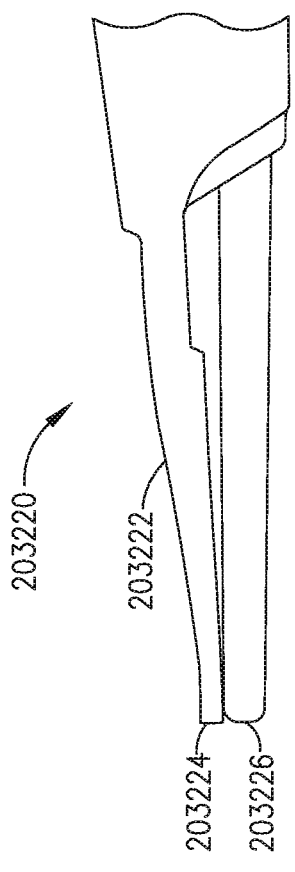
Figure 90B:
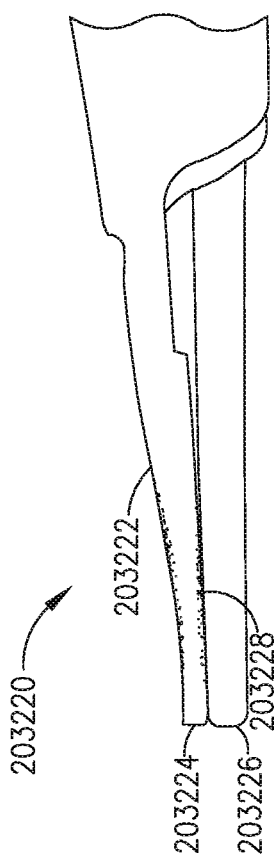
Figure 91B:
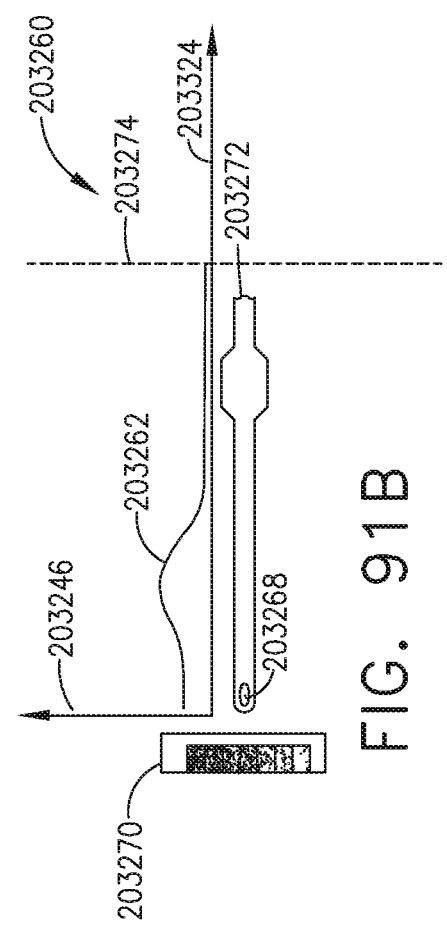
Figure 90D:
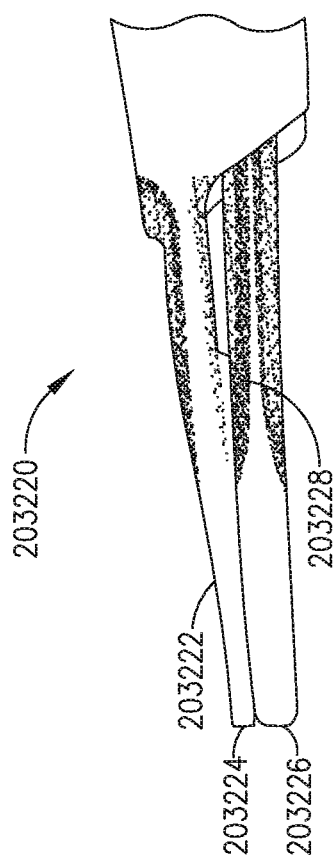
Figure 91D:
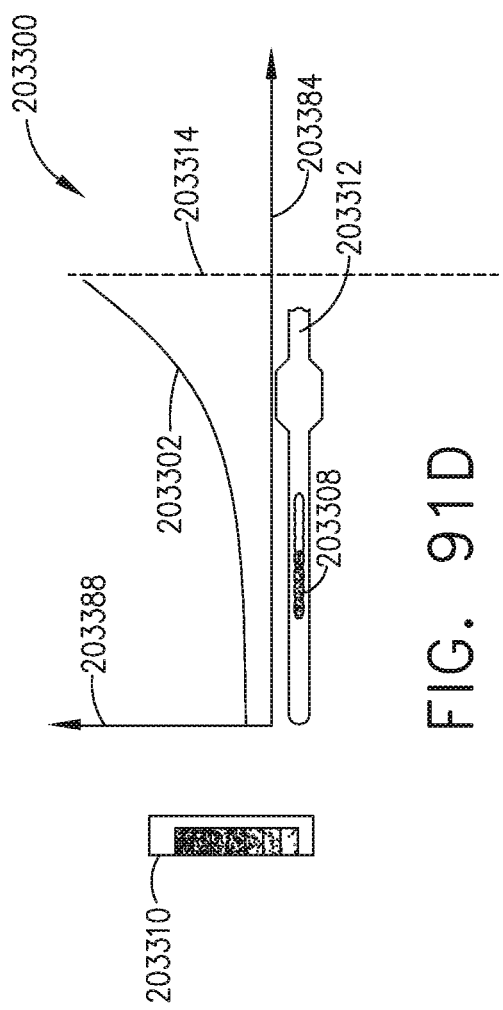

FIGS. 90A-90D are sectional views of the end effector 203220 that illustrate a distal start closure stroke configuration and indicate associated part stresses, in accordance with at least one aspect of the present disclosure. In the distal start closure stroke configuration, the end effector 203220 first closes at the distal tip, as illustrated in FIG. 90A and as described above. Thus, the control circuit is configured to control closure of the clamp arm 203224 by pivoting the clamp arm 203224 to create an initial contact point of the ultrasonic blade 203226 and clamp arm 203224 at a distal end of the end effector 203220. In FIG. 90A the distal tip of clamp arm 203224 contacts ultrasonic blade 203226. In this way, the clamp arm tissue pad 203224 of clamp arm 203224 compresses against the grasped tissue at the distal portion first. Unlike in FIGS. 89A-89C, the applied clamp pressure in FIGS. 90A-90D rolls in the proximal direction. Also, the ultrasonic blade 203226 may be curved, sloped, or otherwise offset to allow for closing at the distal tip first. FIG. 90B depicts the end effector 203220 starting to apply more clamp pressure at the clamp arm tissue pad 203224, moving in the proximal direction. As such, the contours 203228 illustrate the associated part stresses in response to this increased bending of the clamp arm 203224. FIG. 90C shows the continued progression of the applied clamp pressure, in which a majority of the tissue treating portion of the end effector 203220 is in the fully compression position. The tissue treating portion may refer to the portion of the end effector that includes the clamp arm tissue pad 203224. As can be seen in FIGS. 90A-90D, the pad 203224 does not extend to the intersection between the clamp arm 203224 and ultrasonic blade 203226 at the proximal portion of end effector 203220. Based on this configuration, the end effector has a slight proximal gap 203230, which can be beneficial for heat mitigation as described above.

In FIG. 30D, the end effector 203220 has achieved the full closure stroke, while advantageously maintaining the proximal gap 203230. As the end effector 203220 progressively approaches a full closure position, one or more of the clamp arm 203224 and ultrasonic blade 203226 progressively realizes greater part stresses arising from the increased bending force that is exerted. In accordance, the part stresses gradually increase in correspondence with the transition from FIGS. 90A, 90B, 90C to 90D. Consequently, the greatest occurrence of contours 203228 occurs in FIG. 90D. As illustrated in FIGS. 90A-90D and moving in a proximal direction, incrementally more of the clamp arm tissue pad 203224 becomes active as more of the end effector 203220 closes. The depicted closure sequence culminates in FIG. 90D in which the entire available surface area of pad 203224 is used to compress against grasped tissue and ultrasonic blade 203226 while the portion of the end effector 203220 that is proximal to the proximal extent of the pad 203224 and grasped tissue defines the proximal gap 203230. Although the pad 203224 may terminate at the distal-most extent of the proximal gap 203230, the pad 203224 could also extend into the proximal gap 203230. Even where the pad 203224 extends in this way, the clamp arm 203222 is recessed to assist in defining the proximal gap 203230. In the proximal gap 203230, less electrosurgical energy is delivered, which may advantageously reduce the temperatures and heat residing in the ultrasonic blade 203226 after activating energy delivery by the generator 4002. The control circuit 710 may be configured to execute matching or corresponding deflections of the clamp arm 203224 and ultrasonic blade 203226 such that each of the clamp arm 203224 and ultrasonic blade 203226 deform, deflect, or bend to the same extent in transitioning from the configuration of FIG. 90A to FIG. 90D.

Moreover, the applied clamp pressure as well as displacement and velocity of ultrasonic blade 203226 can be controlled depending on the progression of the closure stroke. For example, when the end effector 203220 is only closed at the distal tip or approximately only the distal portion (e.g., in FIGS. 90A-90B), the displacement and/or velocity of the ultrasonic blade 203226 can be reduced in order to prevent excessive wear or deterioration of the pad 203224. Thus, ultrasonic oscillation can be reduced when the end effector 203220 is not fully closed. As described above, displacement may be relatively high at the distal tip portion, so reduction in blade displacement may be desirable for the distal start closure configuration of the end effector 203220. Additionally, the control circuit 710 may be configured to control closure of one or more of the clamp arm 203222 and ultrasonic blade 203226 to vary the pressure applied to provide a threshold control pressure based on the cut progression location (e.g., corresponding weld focal point). For example, as the end effector 203220 advances from FIGS. 90A to 90D, a surgical cut or coagulation focal point may shift along the length of the ultrasonic blade 203226, which can be used to adjust applied clamp pressure. The shift may be proximal or distal, depending on the selected closure stroke configuration, for example. When the focal point is at the center portion of the distal half of the end effector 203220, for example, relatively more pressure may be applied at that center portion while relative less pressure might be applied at locations distal to the center portion.

Additionally or alternatively to adjustments to clamp arm forces based on cut/coagulation focal point, the control circuit 710 may generally apply a relatively lower distal pressure and higher proximal force to address the displacement or velocity profile of the ultrasonic blade 203226. As discussed above, the displacement or velocity of the ultrasonic blade 203226 is relatively higher at distal portions, so applied forces may be lower at those portions compared to proximal portions. The ultrasonic blade 203226 may be made of a suitable material, such as titanium metal or alloy. More specifically, the titanium alloy could be a grade 5 alpha/beta titanium alloy such as Ti-6Al-4V or it could be some other suitable metal. The clamp arm 203224 could also be made of a suitable material such as stainless steel and more particularly, a precipitation-hardened 17-4 stainless steel. Also, the clamp arm tissue pad 203224 may be electrically conductive based on conductive fillers (e.g., carbon, carbon nanotubes, metallic particles) so that the surgical instrument 7012 can conduct electrical current from the ultrasonic blade 203226 to the pad 203224 via isolated electrical conduits after the end effector 203220 is fully closed. This way, electrosurgical energy such as therapeutic or sub-therapeutic RF can be delivered to the grasped tissue.

FIGS. 91A-91D are graphs 203240, 203260, 203280, 203300 of clamp force applied between the ultrasonic blade 203226 and clamp arm 203224 as a function of distance from the distal tip of the end effector 203220 corresponding to the sectional views of FIGS. 90A-90D, in accordance with at least one aspect of the present disclosure. The graphs 203240, 203260, 203280, 203300 contain legends 203250, 203270, 203290, 203310, respectively, which has different dot patterns denoting the associated degree of force due to compression between the ultrasonic blade 203226 and clamp arm 203224, for example. Pressure contours 203308 are plotted along the corresponding blade models 203252, 203272, 203292, 203312, which are a generic depiction of the length of ultrasonic blade 203226. The pressure contours 203308 may be indicative of the amount and location of component stresses applied relative to the distance away from the distal tip of the end effector 203220. The dotted line 203254, 203274, 203294, 203314 denotes the proximal end of the tissue effecting portion (e.g., the proximal end of the pad 203224) of the end effector 203220. As can be seen in FIGS. 91A-91D, the pressure contours 203308 start at the distal tip of the end effector 203220 and transition proximally towards the dotted line 203254, 203274, 203294, 203314. In the graphs 203240, 203260, 203280, 203300, the x-axis 203244, 203264, 203284, 203304 denotes the distance from the distal tip of the end effector 203220.

Figure 91A:
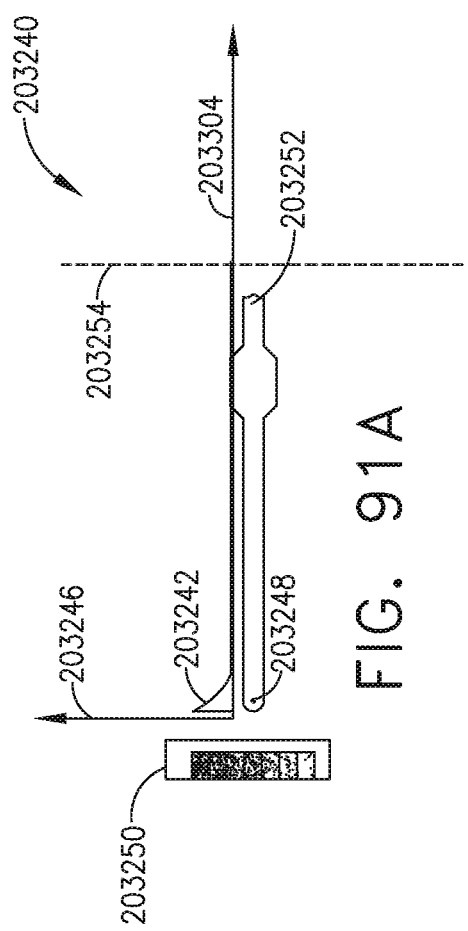

The y-axis 203246, 203266, 203286, 203306 denotes the applied clamp force resulting from contact between the ultrasonic blade 203226 and clamp arm 203224. The applied force is represented by the applied force line 203242, 203262, 203282, 203302. In FIG. 91A, the applied clamp force only occurs at the distal tip, which corresponds to the distal tip first closure of the distal start closure stroke configuration. The application of the clamp force gradually shifts proximally, as illustrated by the change in applied force line 203242, 203262, 203282, 203302 from FIGS. 91A to 91D. Furthermore, the amplitude of the applied clamp force also gradually increases from FIGS. 91A to 91D. The graphs 203240, 203260, 203280, 203300 may display a similar progression in clamp force as that depicted in FIGS. 88A-88C, except that the two series of graphs progress in opposite directions. Nonetheless, the distributed force or pressure profile depicted in graph 203300 may mirror that of graph 203180. That is, although FIGS. 91A to 91D depict applied pressure transitioning proximally while FIGS. 88A-88C depict pressure transitioning distally, the force profile when the full closure stroke is achieved is the same or similar regardless of the selected closure stroke configuration. The component stresses of the closure stroke according to FIGS. 91A-91D are represented by indicators 203248, 203268, 203288, 203308. Additionally, the position sensor 784 or other sensor 788 could be used to detect the vessel location along the length of the ultrasonic blade 203226 for grasped tissue. This detection might be used to adjust the closure stroke in real-time so as to target the blood vessel for application of maximum force on top of the vessel. This detection could also be used to refrain from applying power into portions of the end effector 203220 that do not contact tissue. This could be useful for heat mitigation.

Figures 92A, 92B, 92C, 92D, 92E:
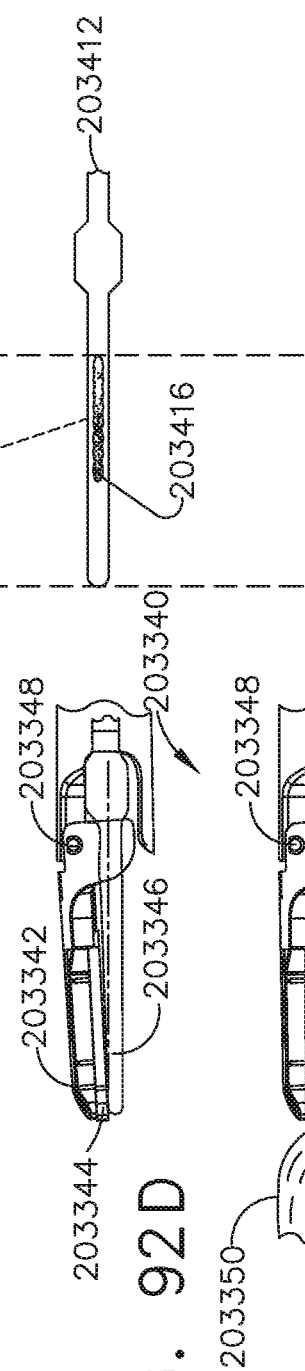

FIGS. 92A-92E are sectional views of the end effector 203340 that illustrate a distal start closure stroke configuration and indicate associated part stresses, in accordance with at least one aspect of the present disclosure. As can be seen in FIG. 92A-92E, the ultrasonic blade 203346 is curved and is deformable so that the curvature of ultrasonic blade 203346 flattens or bottoms out in the full closure stroke, as depicted in FIGS. 92D-92E. Accordingly, the axis of ultrasonic blade 203346 is offset. The ultrasonic blade 203346 and clamp arm 203342 pivot about pivot point 203348. The clamp arm 203342 includes clamp arm tissue pad 203344. FIGS. 92A-92E illustrate the progression of distal tip first closure on tissue 203350 for application of electrosurgical energy through pad 203344. In FIG. 92B, the distal tip of curved ultrasonic blade 203346 contacts the distal tip of clamp arm 203342 based on pivoting one or more of ultrasonic blade 203346 and clamp arm 203342 toward each other. The ultrasonic blade 203346 and clamp arm 203342 may move approximately an equal distance towards each other during the duration of the closure stroke. The end effector 203340 may compress against the proximal-most extent of the tissue 203350 at this point. The control circuit 710 may be configured to determine an initial clamp pressure to be applied based on the size of the tissue 203350 initially loaded into end effector 203340.

As can be seen in FIGS. 92B-92C, the deflection of curved ultrasonic blade 203346 continues and rolls proximally. Simultaneously, more of the tissue 203350 is grasped. The deflection may comprise bottoming out the curved ultrasonic blade 203346 by incrementally reducing the instantaneous curvature of the curved ultrasonic blade 203346. At FIG. 92D, the curved ultrasonic blade 203346 is fully bottomed out such that the end effector 203340 is fully closed (i.e, reached the full closure stroke). A portion of the grasped tissue 203350 is fully compressed against the ultrasonic blade 203346 and clamp arm 203342 in the full closure position so that electrosurgical energy can be delivered through the pad 203344 for cutting and coagulation. The distal to proximal span of the grasped tissue within the end effector 203340 defines the tissue contact area. This tissue contact area may generate a significant amount of heat. For thermal mitigation or reduction, instead of fully bottoming out, the end effector 203340 maintains a deflection of the ultrasonic blade 203346 that is proximal to the proximal most portion of the tissue contact area. This is shown in FIGS. 92A-92E. Thus, the control circuit 7012 may maintain a gap between the ultrasonic blade 203346 and clamp arm 203342 at a point proximal to a proximal end of the tissue. As compared to the fully closed position depicted in FIG. 92D, the portions of the pad 203344 that are not treating tissue (the portions of pad 203344 proximal to the proximal-most extent of tissue contact area) do not receive as much thermal energy. Consequently, peak temperatures and heat residing in the ultrasonic blade 203346 after application of electrosurgical energy is reduced.

Also shown in ultrasonic blade 203346 are blade models 203352, 203372, 203392, 203412, which illustrate the progression of clamp force along the length of the end effector 203340. First dotted line 203356 represents the distal tip while second dotted line 203358 represents the proximal end of the end effector 203340. The second dotted line 203358 also may represent the proximal-most extent of the tissue 203350 or where the tissue 203350 stops. In the blade model 203352, no force is applied to the ultrasonic blade 203346. In the blade model 203372, the distal tip of the ultrasonic blade 203346 contacts the corresponding portion of clamp arm 203342, so some force is applied to the distal portion of the ultrasonic blade 203346. Areas of greater applied force may be denoted by darker shading of the pressure contours 203376, 203396, 203416. Accordingly, relatively high force represented by pressure contour 203376 is applied to the distal tip in blade model 203372. In the blade model 203392, the end effector 203340 is more partially closed in the proximal direction, so the pressure contour 203396 spans a greater length of the end effector 203340. The pressure contour 203396 may vary depending on the location of the cut/weld focal point so as to provide a constant threshold pressure on the tissue 203350. In the blade model 203392, the end effector 203340 is fully closed and applied clamp force has completed moving proximally during the closure motion. Consequently, the pressure contour 203396 spans an even greater length and terminates at the second dotted line 203358.

EXAMPLES

Various aspects of the subject matter described herein are set out in the following numbered examples:

Example 1

A method of adjusting a staple parameter of a surgical stapling instrument, the method comprising: determining, by a control circuit of the surgical stapling instrument, a first stroke length for a first staple driver of the surgical stapling instrument to drive a first row of staples of a circular stapling head assembly of the surgical stapling instrument; detecting, by the control circuit, a malformed staple in the first row of staples; adjusting, by the control circuit, the staple parameter, based on the detection of the malformed staple; and determining, by the control circuit, a second stroke length for a second staple driver of the surgical stapling instrument to drive a second row of staples of the circular stapling head assembly.

Example 2

The method of Example 1, wherein the staple parameter is one or more of: a height of an anvil of the surgical stapling instrument, the second stroke length, and a stroke rate.

Example 3

The method of any one of Examples 1-2, wherein the surgical stapling instrument is a powered circular surgical stapling instrument.

Example 4

The method of any one of Examples 1-3, wherein the second row of staples are driven by the second staple driver following a predetermined delay after driving the first row of staples.

Example 5

The method of any one of Examples 1-4, further comprising: comparing, by the control circuit, the first stroke length to an upper, median, and a lower limit; and determining, by the control circuit, the adjustment to the staple parameter based on comparison.

Example 6

The method of any one of Examples 1-5, further comprising: sensing, by the control circuit, a parameter associated with clamping of the anvil, wherein the parameter comprises a tissue gap, force during closure of the anvil, tissue creep stabilization, or force during firing, or any combination thereof.

Example 7

The method of any one of Examples 1-6, further comprising: adjusting, by the control circuit, a staple height of the first and second rows of staples within a range of selectable staple heights that is varied based on the tissue loading detected during retraction of the anvil.

Example 8

The method of Example 7, further comprising: indicating, by the control circuit, a nominal staple height within a window range; and adjusting, by the control circuit, the window range of an acceptable staple height as compression is increased or tissue gap is decreased.

Example 9

A method of adjusting a cutting parameter of a surgical stapling instrument, the method comprising: receiving, by a control circuit of the surgical stapling instrument, a sensor output signal from a sensor of the surgical stapling instrument; determining, by the control circuit, a parameter associated with clamping of an end effector of the surgical stapling instrument, based on the sensor output signal; and controlling, by the control circuit, a torque applied to a cutting member of the surgical stapling instrument, wherein the motor moves the cutting member between first position and a second position by applying the torque to the cutting member.

Example 10

The method of Example 9, wherein the cutting member is independently actuatable from the end effector.

Example 11

The method of any one of Examples 9-10, wherein the parameter comprises a tissue gap, force during closure of the end effector, tissue creep stabilization, or force during firing, or any combination thereof.

Example 12

The method of any one of Examples 9-11, further comprising: controlling, by the control circuit, an advancement rate at which the motor drives the cutting member according to initial conditions as the motor begins driving the cutting member from the first position.

Example 13

The method of any one of Examples 9-12, further comprising: controlling, by the control circuit, the motor to drive the cutting member in either a load control mode or a stroke control mode according to an adjustable control parameter.

Example 14

The method of any one of Examples 9-13, wherein the control circuit controls the torque applied to the cutting member to adjust one or more of: a torque, a speed, and a distance of the cutting member.

Example 15

The method of any one of Examples 9-14, further comprising: adjusting, by the control circuit, an initial speed of the cutting member based on a toughness of tissue grasped within the end effector.

Example 16

A method of controlling a surgical stapling instrument, the method comprising: receiving, by a control circuit of the surgical stapling instrument, a sensor output signal from a first sensor of the surgical stapling instrument; determining, by the control circuit, a parameter associated with operation of the surgical stapling instrument, based on the sensor output signal; determining, by the control circuit, an anvil gap of an anvil of the surgical stapling instrument, wherein the anvil clamps tissue; comparing, by the control circuit, the anvil gap to a predetermined gap; and executing, by the control circuit, an electronic lockout to prevent actuation of the surgical stapling instrument based on the comparison and the determined parameter.

Example 17

The method of Example 16, further comprising: comparing, by the control circuit, the determined parameter to a first and a second threshold, wherein the determined parameter comprises tissue compression force; executing, by the control circuit, the electronic lockout based on the comparison of the tissue compression force to the first and second threshold.

Example 18

The method of any one of Examples 16-17, wherein the electronic lockout comprises one or more of: a compulsory, a discretionary, and a no limit electronic lockout.

Example 19

The method of any one of Examples 16-18, further comprising: sensing, by a second sensor of the surgical stapling instrument, a secondary measure of the surgical stapling instrument, wherein the secondary measure comprises one or more of a severity of failure, a user input, and a predefined comparison lookup table; controlling, by the control circuit, the electronic lockout based on the secondary measure.

Example 20

The method of any one of Examples 16-19, further comprising: executing, by the control circuit, a predetermined wait period prior to enabling operation of the surgical stapling instrument.

Various additional aspects of the subject matter described herein are set out in the following numbered examples:

Example 1

A surgical hub within a surgical hub network comprising: a controller comprising a processor, wherein the controller is configured to determine a priority of a communication, an interaction, or a processing of information based on a requirement of a system or a device in communication with the surgical hub.

Example 2

The surgical hub of Example 1, wherein the controller is configured to prioritize an order of transmission of one or more communication packets.

Example 3

The surgical hub of Example 2, wherein the one or more communication packets are directed to a device outside of the surgical hub network.

Example 4

The surgical hub of Example 3, wherein the one or more communication packets comprise data to update routines, processes, or data required to execute a critical procedural step executed by the processor.

Example 5

The surgical hub of any one or more of Examples 1-4, wherein the controller is configured to prioritize a communication traffic flow within the surgical hub network.

Example 6

The surgical hub of Example 5, wherein the controller is configured to adjust the communication traffic flow to enable a critical piece of data to take priority thereby insuring the success of a critical device or a hub process or a hub operation.

Example 7

The surgical hub of any one or more of Examples 5-6, wherein the controller is configured to delay or interrupt the communication traffic flow.

Example 8

The surgical hub of Example 7, wherein the controller is configured to interrupt the communication traffic flow and the interruption of the communication traffic flow comprises a short term re-ordering of communication packets.

Example 9

The surgical hub of any one or more of Examples 7-8, wherein the controller is configured to delay the communication traffic flow and the delay of the communication traffic flow comprises a long term adjustment to a data collection or to a transmission rate.

Example 10

The surgical hub of any one or more of Examples 6-9, wherein the adjustment continues for a short period of time.

Example 11

The surgical hub of any one or more of Examples 6-10, wherein the adjustment continues for the duration of the procedure

Example 12

The surgical hub of any one or more of Examples 6-11, wherein the adjustment continues until the prioritization of the communication traffic flow changes.

Example 13

A network of surgical hubs, comprising: a first surgical hub having a first controller; and a second surgical hub having a second controller, wherein the first controller is configured to control one or more interactions between the first surgical hub and the second surgical hub based on one or more capabilities of the first hub and a location of one or more modules within the network of surgical hubs.

Example 14

The network of surgical hubs of Example 13, wherein the control of the one or more interactions comprises a control of one or more task ownerships.

Example 15

The network of surgical hubs of any one or more of Examples 13 through 14, wherein the one or more capabilities of the first hub comprise one or more of a computing capacity of the first hub, a type of the first hub, a type of data associated with the first hub, an interaction of the data needed to perform a specified surgical procedure by the first hub, or a computing requirement of the first hub.

Example 16

The network of surgical hubs of Example 15, wherein a computing capacity comprises one or more of an available processing power, an available processor memory for data storage, an available amount of idle processing cycles, and an available communication bandwidth.

Example 17

The network of surgical hubs of any one or more of Examples 15-16, wherein the location of the one or more modules comprises a location of the one or more modules most critical to an ongoing surgical procedure.

Example 18

The network of surgical hubs of any one or more of Examples 15-17, wherein the first controller is further configured to allow the second controller to control the one or more interactions between the first surgical hub and the second surgical hub based on an anticipated surgical task. are of events occurring within a vicinity of the first surgical device according to data received from a database, a patient monitoring device, or a paired surgical device, or any combination of the database, the patient monitoring device, or the paired surgical device; and wirelessly pair with a second surgical device according to a usage of the first surgical device and the events of which the first surgical device is situationally aware.

Various additional aspects of the subject matter described herein are set out in the following numbered examples:

Example 1

A surgical system comprising: a first surgical device comprising a control circuit, the control circuit configured to: be situationally aware of events occurring within a vicinity of the first surgical device according to data received from a database, a patient monitoring device, or a paired surgical device, or any combination of the database, the patient monitoring device, or the paired surgical device; and wirelessly pair with a second surgical device according to a usage of the first surgical device and the events of which the first surgical device is situationally aware.

Example 2

The surgical system of Example 1, wherein events of which the first surgical device is situationally aware comprise a first user using the first surgical device and a second user using the second surgical device.

Example 3

The surgical system of Example 2, wherein the events comprising the first user using the first surgical device comprise the first user grasping a handle of the first surgical device.

Example 4

The surgical system of Example 3, wherein the events comprising the first user grasping a handle of the first surgical device comprise the first user grasping the handle of the first surgical device thereby allowing a transceiver in the handle of the first surgical device to communicate with an identifier worn by the first user and allowing, by the identifier, a communication between the first surgical device and a surgical hub.

Example 5

The surgical system of any one or more of Examples 2-4, wherein events of which the first surgical device is situationally aware comprise a location of the first surgical device and a location of the second surgical device.

Example 6

The surgical system of Example 5, wherein the control circuit is configured to determine the location of the second surgical device based on a wireless signal transmitted by the second surgical device to the first surgical device.

Example 7

The surgical system of any one or more of Examples 1-6, wherein the control circuit is further configured to simultaneously activate the first surgical device and the second surgical device each for a predetermined period of time when no tissue or patient is sensed.

Example 8

The surgical system of any one or more of Examples 1-7, wherein the first surgical device is located within a sterile field and the second surgical device is located outside the sterile field when the first surgical device wirelessly pairs with the second surgical device.

Example 9

The surgical system of any one or more of Examples 1-8, wherein the control circuit is further configured to wireless pair with a communication device.

Example 10

The surgical system of any one or more of Examples 1-9, wherein events of which the first surgical device is situationally aware comprise a determination of a distance between the first surgical device and a tissue structure within a patient.

Example 11

A method comprising: being situationally aware, by a control circuit within a first surgical device, of events occurring within a vicinity of a first surgical device according to data received from a database, a patient monitoring device, or a paired surgical device, or any combination of the database, the patient monitoring device, or the paired surgical device; and wirelessly pairing, by the control circuit, with a second surgical device according to a usage of the first surgical device and the events of which the first surgical device is situationally aware.

Example 12

The method of Example 11, wherein being situationally aware, by a control circuit within a first surgical device, comprise being situationally aware, by a control circuit within a first surgical device, of a first user using the first surgical device and a second user using the second surgical device.

Example 13

The method of Example 12, wherein being situationally aware, by a control circuit within a first surgical device, of a first user using the first surgical device comprises being situationally aware, by a control circuit within a first surgical device, of a first user grasping a handle of the first surgical device.

Example 14

The method of Example 13, further comprising allowing a transceiver in the handle of the first surgical device to communicate with an identifier worn by the first user and allowing, by the identifier, a communication between the first surgical device and a surgical hub.

Example 15

The method of ay one or more of Examples 12-14, wherein being situationally aware, by a control circuit within a first surgical device, of a first user using the first surgical device and a second user using the second surgical device, comprises being situationally aware, by a control circuit within a first surgical device, of a location of the first surgical device and a location of the second surgical device.

Example 16

The method of Example 15, further comprising determining, by the control circuit, the location of the second surgical device based on a wireless signal transmitted by the second surgical device to the first surgical device.

Example 17

The method of any one or more of Examples 11-16, further comprising activating, by the control circuit, the first surgical device and the second surgical device each for a predetermined period of time when no tissue or patient is sensed.

Example 18

The method of any one or more of Examples 11-17, wherein wirelessly pairing, by the control circuit, with a second surgical device according to a usage of the first surgical device comprises wirelessly pairing, by the control circuit, with a second surgical device outside of a sterile field when the first surgical device is located within the sterile field.

Example 19

The method of any one or more of Examples 11-18, further comprising wirelessly pairing of the control circuit with a communication device.

Example 20

The method of any one or more of Examples 11-19, further comprises determining, by the control circuit, a distance between the first surgical device and a tissue structure within a patient.

Various additional aspects of the subject matter described herein are set out in the following numbered examples:

Example 1

A surgical stapling instrument comprising: an anvil configured to clamp a tissue; a circular stapling head assembly comprising a first row of staples and a second row of staples; a first staple driver configured to drive the first row of staples; a second staple driver configured to drive the second row of staples, wherein the first and second staple drivers are independently actuatable; a motor coupled to the anvil, the motor configured to move the anvil between a first position and a second position; and a control circuit coupled to the motor, the control circuit configured to: set a stroke length for the first and second staple drivers to a first length; detect a malformed staple in the first row of staples; and set the stroke length for the second staple driver to a second length.

Example 2

The surgical stapling instrument of Example 1, wherein the control circuit is further configured to sense a parameter associated with clamping of the anvil.

Example 3

The surgical stapling instrument of Example 2, wherein the parameter comprises a tissue gap, force during closure of the anvil, tissue creep stabilization, or force during firing, or any combination thereof.

Example 4

The surgical stapling instrument of any one of Examples 1-3, wherein the control circuit is further configured to actuate the first staple driver to drive the first row of staples.

Example 5

The surgical stapling instrument of any one of Examples 1-4, wherein the first and second staple drivers are independently actuatable.

Example 6

A surgical stapling instrument comprising: an anvil configured to clamp a tissue; a circular stapling head assembly comprising a first row of staples and a second row of staples; a first staple driver configured to drive the first row of staples; a second staple driver configured to drive the second row of staples; a motor coupled to the anvil, the motor configured to move the anvil between a first position and a second position; and a control circuit coupled to the motor, the control circuit configured to: set a staple height of the first and second rows of staples to a first height; detect a malformed staple in the first row of staples; and set a staple height for the second row of staples to a second height.

Example 7

The surgical stapling instrument of Example 6, wherein the control circuit is further configured to sense a parameter associated with clamping of the anvil.

Example 8

The surgical stapling instrument of Example claim 7, wherein the parameter comprises a tissue gap, force during closure of the anvil, tissue creep stabilization, or force during firing, or any combination thereof.

Example 9

The surgical stapling instrument of any one of Examples 6-8, wherein the control circuit is further configured to actuate the first staple driver to drive the first row of staples.

Example 10

The surgical stapling instrument of any one of Examples 6-9, wherein the first and second staple drivers are independently actuatable.

Example 11

The surgical stapling instrument of any one of Examples 6-10, wherein the control circuit is configured to adjust the staple height of the second row of staples based on a sensed tissue thickness during firing the first row of staples.

Example 12

The surgical stapling instrument of any one of Examples 6-11, wherein the control circuit is configured to adjust the staple height of the second row of staples based on a sensed anvil force to close during firing the first row of staples.

Example 13

The surgical stapling instrument of any one of Examples 6-12, wherein the control circuit is further configured to adjust the staple height within a range of selectable staple heights that is varied based on the tissue loading detected during retraction of the anvil.

Example 14

The surgical stapling instrument of any one of Examples 6-13, wherein the control circuit is configured to adjust a nominal staple height as tissue compression is increased or as tissue gap is decreased.

Example 15

The surgical stapling instrument of Example 14, wherein the control circuit is configured to display the nominal staple height within a window range.

Example 16

The surgical stapling instrument of Example 15, wherein the control circuit is configured to adjust the window range of an acceptable staple height as compression is increased or tissue gap is decreased.

Example 17

A surgical stapling instrument comprising: an anvil configured to clamp a tissue; a circular stapling head assembly comprising a first row of staples and a second row of staples; a first staple driver configured to drive the first row of staples; a second staple driver configured to drive the second row of staples; a motor coupled to the anvil, the motor configured to move the anvil between a first position and a second position; and a control circuit coupled to the motor, the control circuit configured to: set an anvil gap for the first row of staples to a first gap; detect a malformed staple in the first row of staples; and set an anvil gap for the second row of staples to a second gap.

Example 18

The surgical stapling instrument of Example 17, wherein the control circuit is further configured to sense a parameter associated with clamping of the anvil.

Example 19

The surgical stapling instrument of any one of Examples 17-18, wherein the parameter comprises a tissue gap, force during closure of the anvil, tissue creep stabilization, or force during firing, or any combination thereof.

Example 20

The surgical stapling instrument of any one of Examples 17-19, wherein the control circuit is further configured to actuate the first staple driver to drive the first row of staples.

Various additional aspects of the subject matter described herein are set out in the following numbered examples:

Example 1

A surgical stapling instrument comprising: an anvil configured to clamp a tissue; a stapler configured to drive surgical staples through tissue and form against the anvil; a position sensor coupled to the anvil configured to detect anvil gap; a sensor coupled to the anvil configured to detect tissue compression force; a motor coupled to the anvil, the motor configured to move the anvil from a first position and a second position; and a control circuit coupled to the motor and to the position sensor and the sensor, the control circuit configured to: determine the anvil gap; compare the anvil gap to a predetermined gap; determine the tissue compression force; compare the tissue compression force to a predetermined tissue compression force; execute an electronic lockout process to prevent operation of the stapler based on the comparison of the anvil gap to the predetermined gap and the comparison of the tissue compression force to a predetermined tissue compression force.

Example 2

The surgical stapling instrument of Example 1, wherein the control circuit is configured to execute a compulsory electronic lockout process to prevent operation of the stapler when the anvil gap is greater than a predefined maximum anvil gap threshold.

Example 3

The surgical stapling instrument of any one of Examples 1 or 2, wherein the control circuit is configured to execute a no limit electronic lockout process to prevent operation of the stapler when the tissue compression force is below an ideal tissue compression force threshold.

Example 4

The surgical stapling instrument of any one of Examples 1-3, wherein the control circuit is configured to execute a discretionary electronic lockout process without limits to prevent operation of the stapler when the tissue compression force is between an ideal tissue compression force threshold and a maximum tissue compression force threshold.

Example 5

The surgical stapling instrument of any one of Examples 1-4, wherein the control circuit is configured to execute a discretionary electronic lockout process with limits to prevent operation of the stapler when the tissue compression force is greater than a maximum tissue compression force threshold.

Example 6

The surgical stapling instrument of Example 5, wherein the control circuit is configured to execute a predetermined wait period prior to enabling operation of the stapler.

Example 7

A surgical stapling instrument comprising: an anvil configured to clamp a tissue; a stapler configured to drive surgical staples through tissue and form against the anvil; a first sensor to sense a first parameter of the surgical stapling instrument; a second sensor to sense a second parameter of the surgical stapling instrument; a motor coupled to the anvil, the motor configured to move the anvil from a first position and a second position; and a control circuit coupled to the motor and the first and second sensor, the control circuit configured to execute an electronic lockout process to prevent operation of the stapler based on the first and second sensed parameters.

Example 8

The surgical stapling instrument of Example 7, wherein the control circuit is configured to execute a compulsory electronic lockout process to prevent operation of the stapler when the first sensed parameter is greater than a predefined maximum threshold value for the first parameter.

Example 9

The surgical stapling instrument of any one of Examples 7 or 8, wherein the control circuit is configured to execute a no limit electronic lockout process to prevent operation of the stapler when the second sensed parameter is below an ideal threshold value for the second parameter.

Example 10

The surgical stapling instrument of any one of Examples 7-9, wherein the control circuit is configured to execute a discretionary electronic lockout process without limits to prevent operation of the stapler when the second sensed parameter is between an ideal threshold value for the second parameter and a maximum threshold value for the second parameter.

Example 11

The surgical stapling instrument of any one of Examples 7-10, wherein the control circuit is configured to execute a discretionary electronic lockout process with limits to prevent operation of the stapler when the second sensed parameter is greater than a maximum threshold value for the second parameter.

Example 12

The surgical stapling instrument of Example 11, wherein the control circuit is configured to execute a predetermined wait period prior to enabling operation of the stapler.

Example 13

A surgical stapling instrument comprising: an anvil configured to clamp a tissue; a circular stapler configured to drive surgical staples through tissue and form against the anvil; a first sensor to sense a condition of the surgical stapling instrument; a second sensor to sense a secondary measure of the surgical stapling instrument; a motor coupled to the anvil, the motor configured to move the anvil from a first position and a second position; and a control circuit coupled to the motor and the first and second sensor, the control circuit configured to execute an adjustable electronic lockout process to prevent actuation of the stapler based on the sensed condition and the secondary measure.

Example 14

The surgical stapling instrument of Example 13, wherein the adjustable electronic lockout process disables operation of a mechanical lockout.

Example 15

The surgical stapling instrument of any one of Examples 13 or 14, wherein the adjustable electronic lockout process disables operation of an electronic lockout.

Example 16

The surgical stapling instrument of any one of Examples 13-15, wherein the sensed condition is anvil gap and the secondary measure is tissue compression force.

Example 17

The surgical stapling instrument of Example 16, wherein when the anvil gap is between a minimum and maximum anvil gap thresholds and the tissue compression force is above a maximum tissue compression force threshold, the control circuit is configured to: increase the anvil gap; increase a predetermined wait period prior to actuating the circular stapler; reduce the speed at which the circular stapler is actuated; or execute the adjustable electronic lockout process to prevent actuation of the stapler.

Example 18

The surgical stapling instrument of Example 16, wherein when the anvil gap is between a minimum and maximum anvil gap thresholds and the tissue compression force is below a minimum tissue compression force threshold, the control circuit is configured to: decrease the anvil gap; proceed with caution; or execute the adjustable electronic lockout process to prevent actuation of the stapler.

Various additional aspects of the subject matter described herein are set out in the following numbered examples:

Example 1

A surgical stapling instrument comprising: an end effector configured to clamp a tissue; a cutting member; a motor coupled to the cutting member, the motor configured to move the cutting member between a first position and a second position; and a control circuit coupled to the motor, the control circuit configured to: sense a parameter associated with clamping of the end effector; and control the motor to adjust a torque applied to the cutting member by the motor.

Example 2

The surgical stapling instrument of Example 1, wherein the cutting member is independently actuatable from the end effector.

Example 3

The surgical stapling instrument of any one of Examples 1-2, wherein the parameter comprises a tissue gap, force during closure of the end effector, tissue creep stabilization, or force during firing, or any combination thereof.

Example 4

The surgical stapling instrument of any one of Examples 1-3, wherein the control circuit is configured to control the motor to drive the cutting member in either a load control mode or a stroke control mode according to an adjustable control parameter.

Example 5

The surgical stapling instrument of any one of Examples 1-4, wherein the control circuit is configured to control an advancement rate at which the motor drives the cutting member according to initial conditions as the motor begins driving the cutting member from the first position.

Example 6

The surgical instrument of any one of Examples 1-5, wherein the control circuit is configured to control the motor to adjust a speed at which the motor drives the cutting member.

Example 7

The surgical instrument of any one of Examples 1-6, wherein the control circuit is configured to control the motor to adjust a distance to which the motor drives the cutting member according to the parameter.

Example 8

The surgical instrument of any one of Examples 1-7, wherein the control circuit is configured to control the motor to adjust any combination of the torque, the speed, or the distance.

Example 9

A surgical stapling instrument comprising: an end effector configured to clamp a tissue; a cutting member; a motor coupled to the cutting member, the motor configured to move the cutting member between a first position and a second position; and a control circuit coupled to the motor, the control circuit configured to: sense a parameter associated with firing of the cutting member; and control the motor to adjust a torque applied to the cutting member by the motor.

Example 10

The surgical stapling instrument of Example 9, wherein the cutting member is independently actuatable from the end effector.

Example 11

The surgical stapling instrument of any one of Examples 9-10, wherein the parameter comprises a tissue gap, force during closure of the end effector, tissue creep stabilization, or force during firing, or any combination thereof.

Example 12

The surgical stapling instrument of any one of Examples 9-11, wherein the control circuit is configured to control the motor to drive the cutting member in either a load control mode or a stroke control mode according to an adjustable control parameter.

Example 13

The surgical stapling instrument of any one of Examples 9-12, wherein the control circuit is configured to control an advancement rate at which the motor drives the cutting member according to initial conditions as the motor begins driving the cutting member from the first position.

Example 14

The surgical instrument of any one of Examples 9-13, wherein the control circuit is configured to control the motor to adjust a speed at which the motor drives the cutting member.

Example 15

The surgical instrument of any one of Examples 9-14, wherein the control circuit is configured to control the motor to adjust a distance to which the motor drives the cutting member according to the parameter.

Example 16

The surgical instrument of any one of Examples 9-15, wherein the control circuit is configured to control the motor to adjust any combination of the torque, the speed, or the distance.

Example 17

A powered stapling device, comprising: a circular stapling head assembly; an anvil; a trocar coupled to the anvil and coupled to a motor, wherein the motor in configured to advance and retract the trocar; and a control circuit coupled to the motor, wherein the control circuit is configured to: determine a position of the trocar in one of a plurality of zones; and set an anvil closure rate based on the determined position of the trocar.

Example 18

The powered stapling device of Example 17, wherein the plurality of zones comprises: a first zone during attachment of the trocar to the anvil; a second zone during retraction of the trocar and closure of the anvil; a third zone during verification of attachment of the trocar to the anvil; and a fourth zone during application of a high closure load.

Example 19

The powered stapling device of any one of Examples 17-18, wherein the control circuit is configured to: set the closure rate of the anvil to a first velocity when the trocar is in the first zone to ensure proper attachment of the trocar to the anvil; set the closure rate of the anvil to a second velocity, which is greater than the first velocity, when the trocar is in the second position during the retraction of the trocar and the closure of the anvil; set the closure rate of the anvil to a third velocity, which is less than the second velocity, to verify attachment of the trocar to the anvil; set the closure rate of the anvil to a fourth velocity, which is less than the third velocity, when the trocar is the fourth zone during application of a high closure load.

Example 20

The powered stapling device of any one of Examples 17-19, wherein the control circuit is configured to: determine the closure rate of the trocar; determine the closure rate of the anvil; compare the closure rate of the trocar to the closure rate of the anvil to determine a difference between the closure rate of the trocar to the closure rate of the anvil; and at a difference greater than a predetermined value, extend and retract the trocar to reset the anvil.

Example 21

The powered stapling device of any one of Examples 17-20, wherein the control circuit is configured to verify attachment of the trocar to the anvil and to slow the closure rate of the trocar under tissue load.

Example 22

The powered stapling device of any one of Examples 17-21, further comprising: a knife coupled to the motor; a sensor located on the anvil, wherein the sensor is configured to detect tissue contact and force applied to the anvil, wherein the sensor is coupled to the anvil, wherein the control circuit is configured to: monitor anvil displacement; monitor tissue contact with the anvil; monitor a force to close of the anvil; compare the force to close to a predetermined threshold; and set a first initial knife velocity and advance the knife at a first velocity profile suitable for cutting normal tissue toughness when the force to close is less than the predetermined threshold; or set a second initial knife velocity and advance the knife at a second velocity profile suitable for cutting heavy tissue toughness when the force to close is greater than or equal to the predetermined threshold.

Example 23

The powered stapling device of any one of Examples 17-22, wherein to advance the knife at the second velocity profile, the control circuit is further configured to: set the second initial knife velocity to a velocity that is less than the first initial knife velocity; monitor knife contact with tissue; increase motor velocity to increase knife velocity when tissue contact is detected; monitor completion of cut; and stop the motor when completion of cut is detected.

Various additional aspects of the subject matter described herein are set out in the following numbered examples:

Example 1

A surgical instrument comprises an end effector, an electrode, an ultrasonic transducer, a sensor coupled to a control circuit, and the control circuit coupled to the end effector. The end effector comprises: an ultrasonic blade configured to ultrasonically oscillate against tissue; and a clamp arm configured to pivot relative to the ultrasonic blade. The electrode is configured to receive electrosurgical energy from a generator and to apply the received electrosurgical energy to the end effector to weld tissue based on the generator generating a drive signal. The ultrasonic transducer is acoustically coupled to the ultrasonic blade. The ultrasonic transducer is configured to ultrasonically oscillate the ultrasonic blade in response to the drive signal. The sensor is configured to output a signal indicative of a surgical parameter to the control circuit. The control circuit is configured to: receive the sensor signal; determine a weld time of a surgical operation performed by the surgical instrument based on the sensor signal; and vary one or more of a clamp arm pressure applied by the clamp arm and a power level of the electrosurgical energy to maintain one or more of a predefined heat flux or power applied to tissue loaded in the end effector.

Example 2

The surgical instrument of Example 1, wherein the surgical parameter is one or more of tissue impedance, a natural frequency of the ultrasonic blade, temperature, and a tissue parameter.

Example 3

The surgical instrument of Examples 1 or 2, wherein the control circuit is further configured to vary one or more of the clamp arm pressure applied by the clamp arm and the power level of the electrosurgical energy based on a heat flux control threshold.

Example 4

The surgical instrument of Example 3, wherein the control circuit is further configured to adjust the heat flux control threshold along a length of the ultrasonic blade based on one or more of a coagulation focus point and a progression of a surgical cut.

Example 5

The surgical instrument of Examples 1, 2, 3, or 4, wherein the electrode comprises a plurality of electrodes positioned longitudinally to generate a constant current density.

Example 6

The surgical instrument of Example 5, wherein the control circuit is further configured to energize the plurality of electrodes sequentially to generate a first current density in a proximal portion of the plurality of electrodes and a second current density in a distal portion of the plurality of electrodes, and wherein the first and second current density are equal.

Example 7

The surgical instrument of Example 5, further comprising the generator configured to deliver the electrosurgical energy to the end effector, wherein the control circuit is further configured to control the generator to energize the plurality of electrodes by providing a first power level to a first portion of the plurality of electrodes and a second power level to a second portion of the plurality of electrodes, and wherein the first power level is lower than the second power level.

Example 8

The surgical instrument of any one of Examples 1-7 wherein the clamp arm is an offset clamp arm and control circuit is further configured to increase the clamp arm pressure based on the sensor signal.

Example 9

A surgical system comprising a surgical hub configured to receive an impedance rate algorithm transmitted from a cloud computing system and a surgical instrument communicatively coupled to the surgical hub. The surgical hub is communicatively coupled to the cloud computing system. The surgical instrument comprises an end effector, electrode, ultrasonic transducer, and a control circuit. The end effector comprises an ultrasonic blade configured to ultrasonically oscillate against tissue; and a clamp arm configured to pivot relative to the ultrasonic blade. The electrode is configured to receive electrosurgical energy from a generator and apply the received electrosurgical energy to the end effector to weld tissue based on the generator generating a drive signal. The ultrasonic transducer is acoustically coupled to the ultrasonic blade. The ultrasonic transducer is configured to ultrasonically oscillate the ultrasonic blade in response to the drive signal. The control circuit is coupled to the end effector. The control circuit is configured to perform the impedance rate algorithm to: receive a first tissue impedance point; determine a first power level of the electrosurgical energy that corresponds to the first tissue impedance point; control the generator to deliver the electrosurgical energy at the first power level; determine a second tissue impedance point; adjust the first power level to a second power level of the electrosurgical energy based on a time interval to reach the second tissue impedance point; and control the generator to deliver the electrosurgical energy at the second power level.

Example 10

The surgical system of Example 9, wherein the control circuit is configured to perform the impedance rate algorithm to further determine a third tissue impedance point; and determine the second tissue impedance point based on the third tissue impedance point and a corresponding time interval to reach the first tissue impedance point.

Example 11

The surgical system of Example 10, wherein the control circuit is configured to perform the impedance rate algorithm to further determine the third tissue impedance point and a third power level of the electrosurgical energy corresponding to the third tissue impedance point upon controlling the generator to deliver the electrosurgical energy at the second power level to reach the second tissue impedance point.

Example 12

The surgical system of Example 11, wherein the control circuit is configured to perform the impedance rate algorithm to further adjust the third tissue impedance point based on an overall tissue impedance level and the time interval to reach the second tissue impedance point.

Example 13

The surgical system of Example 10, wherein the control circuit is configured to perform the impedance rate algorithm to further determine a dwell time and control the generator to deliver the electrosurgical energy at the first power level for the dwell time prior to adjusting the first power level to the second power level of the electrosurgical energy and determining the third tissue impedance point.

Example 14

The surgical system of any one of Examples 9-13 wherein the electrode comprises a plurality of electrode segments positioned longitudinally to generate a constant current density.

Example 15

The surgical system of Example 14, wherein the control circuit is configured to perform the impedance rate algorithm to further energize the plurality of electrode segments based on a progressive closure stroke of the clamp arm.

Example 16

A method of using a surgical instrument to deliver electrosurgical energy according to a target impedance rise rate, wherein the surgical instrument comprises an end effector, a generator, an electrode configured to deliver the electrosurgical energy to the end effector, an ultrasonic transducer acoustically coupled to the ultrasonic blade, and a control circuit coupled to the end effector. The generator is configured to deliver electrosurgical energy to the end effector based on generating a drive signal. The ultrasonic transducer is configured to ultrasonically oscillate the ultrasonic blade in response to the drive signal. The end effector comprises an ultrasonic blade configured to ultrasonically oscillate against tissue; and a clamp arm configured to pivot relative to the ultrasonic blade. The method comprises: controlling, by the control circuit, the generator to apply power according to a tissue impedance algorithm comprising the steps of: applying, by the generator, a first power level to reach a first tissue impedance point; terminating, by the generator, application of the first power level for a first dwell time; determining, by the control circuit, a second tissue impedance point; applying, by the generator, a second power level to reach the second tissue impedance point; terminating, by the generator, application of the second power level for a second dwell time; determining, by the control circuit, a third tissue impedance point; and applying, by the generator, a third power level to reach the third tissue impedance point to achieve the target impedance rise rate.

Example 17

The method of Example 16, further comprising: terminating, by the generator, application of the third power level for a third dwell time; determining, by the control circuit, a fourth tissue impedance point; and applying, by the generator, a fourth power level to reach the fourth tissue impedance point.

Example 18

The method of Example 17, wherein the third and fourth tissue impedance point are determined based on one or more of first and second tissue impedance point and a time to achieve each of the first and second tissue impedance point.

Example 19

The method of any one of Examples 16-18, wherein a time to achieve the first, second, and third tissue impedance point corresponds to a predetermined coagulation time interval.

Example 20

The method of any one of Examples 16-19, wherein the electrode comprises a plurality of electrode segments positioned longitudinally to generate a constant current density.

Various additional aspects of the subject matter described herein are set out in the following numbered examples:

Example 1

A surgical instrument comprises an end effector, an ultrasonic transducer, a control circuit, and the control circuit coupled to the end effector. The end effector comprises: an ultrasonic blade configured to ultrasonically oscillate against tissue; and a clamp arm configured to pivot relative to the ultrasonic blade. The ultrasonic transducer is acoustically coupled to the ultrasonic blade. The ultrasonic transducer is configured to ultrasonically oscillate the ultrasonic blade in response to a drive signal from a generator. The end effector is configured to receive electrosurgical energy from the generator to treat tissue based on the drive signal. The control circuit is configured to: determine one or more of a resonant frequency measure indicative of a thermally induced change in resonant frequency and an electrical continuity measure; calculate a weld focal point based on one or more of the resonant frequency measure and electrical continuity measure; control closure of the clamp arm to vary a pressure applied by the clamp arm to provide a threshold control pressure to the tissue loaded into the end effector, wherein the pressure is varied based on a corresponding weld focal point; and maintain a gap between the ultrasonic blade and clamp arm at a point proximal to a proximal end of the tissue.

Example 2

The surgical instrument of Example 1, wherein the control circuit is further configured to determine an initial pressure applied by the clamp arm based on a size of the tissue initially loaded into the end effector.

Example 3

The surgical instrument of Examples 1 or 2, wherein the control circuit is further configured to vary the pressure applied by the clamp arm based on a shift in the weld focal point along the ultrasonic blade.

Example 4

The surgical instrument of Example 3, wherein the control circuit is further configured to vary the pressure applied by the clamp arm based on an extent of the tissue loaded into the end effector.

Example 5

The surgical instrument of any one of Examples 1-4, wherein the control circuit is further configured to control closure of the clamp arm by pivoting the clamp arm to create an initial contact point of the ultrasonic blade and clamp arm at a distal end of the end effector.

Example 6

The surgical instrument of any one of Examples 1-5, further comprising the generator configured to deliver electrosurgical energy to the end effector to treat tissue based on generating the drive signal.

Example 7

The surgical instrument of any one of Examples 1-6, further comprising a radio frequency (RF) electrode configured to deliver RF energy to the tissue, wherein the control circuit is further configured to adjust one or more of a power level of the RF energy and a power level of the electrosurgical energy based on tissue impedance.

Example 8

A method of using a surgical instrument to provide a threshold control pressure, wherein the surgical instrument comprises: an end effector comprising: a ultrasonic blade configured to ultrasonically oscillate against tissue; and a clamp arm configured to pivot relative to the ultrasonic blade; an ultrasonic transducer acoustically coupled to the ultrasonic blade, the ultrasonic transducer configured to ultrasonically oscillate the ultrasonic blade in response to the drive signal; and a control circuit coupled to the end effector, wherein the end effector is configured to receive electrosurgical energy from a generator to weld tissue based on a generated drive signal and wherein the method comprises: determining, by the control circuit, one or more of a resonant frequency measure indicative of a thermally induced change in resonant frequency and a electrical continuity measure; calculating, by the control circuit, a weld focal point based on one or more of the resonant frequency measure and electrical continuity measure; controlling, by the control circuit, closure of the clamp arm to vary a pressure applied by the clamp arm to provide the threshold control pressure to the tissue loaded into the end effector, wherein the pressure is varied based on a corresponding weld focal point; and maintaining, by the control circuit, a gap between the ultrasonic blade and clamp arm at a point proximal to a proximal end of the tissue.

Example 9

The method of Example 8, further comprising determining, by the control circuit, an initial pressure applied by the clamp arm based on a size of the tissue initially loaded into the end effector.

Example 10

The method of Examples 8 or 9, further comprising varying, by the control circuit, the pressure applied by the clamp arm based on a shift in the weld focal point along the ultrasonic blade.

Example 11

The method of Example 10, further comprising varying, by the control circuit, the pressure applied by the clamp arm based on an extent of the tissue loaded into the end effector.

Example 12

The method of any one of Examples 8-11 further comprising controlling, by the control circuit, closure of the clamp arm by pivoting the clamp arm to create an initial contact point of the ultrasonic blade and clamp arm at a distal end of the end effector.

Example 13

The method of any one of Examples 8-12, further comprising loading the tissue into the end effector from the distal end to a proximal end of the end effector.

Example 14

The method of any one of Examples 8-13, further comprising adjusting, by the control circuit, one or more of a power level of RF energy and a power level of the electrosurgical energy based on tissue impedance, wherein the surgical instrument further comprises a radio frequency (RF) electrode configured to deliver RF energy to the tissue.

Example 15

A surgical system comprising: a surgical hub configured to receive a clamp pressure algorithm transmitted from a cloud computing system, wherein the surgical hub is communicatively coupled to the cloud computing system; and a surgical instrument communicatively coupled to the surgical hub, wherein the surgical instrument comprises: an end effector comprising: an offset ultrasonic blade configured to ultrasonically oscillate against tissue; and an offset clamp arm configured to pivot relative to the ultrasonic blade; and an ultrasonic transducer acoustically coupled to the ultrasonic blade, the ultrasonic transducer configured to ultrasonically oscillate the ultrasonic blade in response to a drive signal from a generator, wherein the end effector is configured to receive electrosurgical energy from the generator to weld tissue based on the drive signal; and a control circuit configured to perform the clamp pressure algorithm to: determine one or more of a resonant frequency measure indicative of a thermally induced change in resonant frequency and a electrical continuity measure; calculate an extent of tissue loaded into the end effector based on one or more of the resonant frequency measure and electrical continuity measure; and vary pressure applied by the clamp arm according to a closure pressure profile comprising a first pressure in a proximal half of the end effector that is greater than a second pressure in a distal half of the end effector and to maintain a gap between the ultrasonic blade and clamp arm at a point proximal to a proximal end of the tissue loaded into the end effector when the end effector is fully closed.

Example 16

The surgical system of Example 15, wherein the control circuit is further configured to close the end effector at a distal end of the end effector prior to closing non-distal end portions of the end effector.

Example 17

The surgical system of Examples 15 or 16, further comprising: terminating, by the generator, application of the third power level for a third dwell time; determining, by the control circuit, a fourth tissue impedance point; and applying, by the generator, a fourth power level to reach the fourth tissue impedance point.

Example 18

The surgical system of Example 17, wherein the first and second deflection are shaped according to the closure pressure profile to provide the first pressure.

Example 19

The surgical system of any one of Examples 15-18, wherein the control circuit is further configured to determine a closure position of the clamp arm.

Example 20

The method of Example 19, wherein the control circuit is further configured to reduce the ultrasonic oscillation of the ultrasonic blade when the end effector is not in fully closed.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e g, carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A method of adjusting a staple parameter of a surgical stapling instrument, the method comprising:
   determining, by a control circuit of the surgical stapling instrument, a first stroke length for a first staple driver of the surgical stapling instrument to drive a first row of staples of a circular stapling head assembly of the surgical stapling instrument;
   detecting, by the control circuit, a malformed staple in the first row of staples;
   adjusting, by the control circuit, the staple parameter, based on the detection of the malformed staple; and
   determining, by the control circuit, a second stroke length for a second staple driver of the surgical stapling instrument to drive a second row of staples of the circular stapling head assembly.

2. The method of claim 1, wherein the staple parameter is one or more of: a height of an anvil of the surgical stapling instrument, the second stroke length, and a stroke rate.

3. The method of claim 1, wherein the surgical stapling instrument is a powered circular surgical stapling instrument.

4. The method of claim 1, wherein the second row of staples are driven by the second staple driver following a predetermined delay after driving the first row of staples.

5. The method of claim 1, further comprising:
   comparing, by the control circuit, the first stroke length to an upper, median, and a lower limit; and
   determining, by the control circuit, the adjustment to the staple parameter based on comparison.

6. The method of claim 1, further comprising:
   sensing, by the control circuit, a parameter associated with clamping of an anvil, wherein the parameter comprises a tissue gap, force during closure of the anvil, tissue creep stabilization, or force during firing, or any combination thereof.

7. The method of claim 1, further comprising:
   adjusting, by the control circuit, a staple height of the first rows of staples and the second row of staples within a range of selectable staple heights that is varied based on the tissue loading detected during retraction of an anvil.

8. The method of claim 7, further comprising:
   indicating, by the control circuit, a nominal staple height within a window range; and
   adjusting, by the control circuit, the window range of an acceptable staple height as compression is increased or tissue gap is decreased.

9. A method of adjusting a cutting parameter of a circular surgical stapler, the method comprising:
   receiving, by a control circuit of the circular surgical stapler, a sensor output signal from a sensor of the circular surgical stapler during a tissue clamping motion;
   determining, by the control circuit, a tissue toughness parameter associated with clamping of an end effector of the circular surgical stapler during the tissue clamping motion, based on the sensor output signal; and
   controlling, by the control circuit, a torque applied to a cutting member of the circular surgical stapler, wherein a motor of the circular surgical stapler moves the cutting member between a first position and a second position by applying the torque to the cutting member, wherein the torque corresponds to a first velocity profile when the tissue toughness parameter is less than a threshold parameter, and wherein the torque corresponds to a second velocity profile when the tissue toughness parameter is greater than the threshold parameter.

10. The method of claim 9, wherein the cutting member is independently actuatable from the end effector.

11. The method of claim 9, wherein the threshold parameter comprises a tissue gap, force during closure of the end effector, tissue creep stabilization, force during firing, or any combination thereof.

12. The method of claim 9, further comprising:
    controlling, by the control circuit, an advancement rate at which the motor drives the cutting member according to initial conditions as the motor begins driving the cutting member from the first position.

13. The method of claim 9, further comprising:
    controlling, by the control circuit, the motor to drive the cutting member in either a load control mode or a stroke control mode according to an adjustable control parameter.

14. The method of claim 9, wherein the control circuit controls the torque applied to the cutting member to adjust one or more of: a torque, a speed, and a distance of the cutting member.

15. The method of claim 9, further comprising:
    adjusting, by the control circuit, an initial speed of the cutting member based on a toughness of tissue grasped within the end effector.

16. A method of controlling a circular surgical stapler, the method comprising:
    receiving, by a control circuit of the circular surgical stapler, a sensor output signal from a first sensor of the circular surgical stapler;
    determining, by the control circuit, a parameter associated with operation of the circular surgical stapler, based on the sensor output signal;
    determining, by the control circuit, an anvil gap of an anvil of the circular surgical stapler, wherein the anvil clamps tissue;
    comparing, by the control circuit, the anvil gap to a predetermined gap; and
    executing, by the control circuit, an electronic lockout to prevent actuation of the circular surgical stapler based on the comparison and the determined parameter, wherein the electronic lockout corresponds to a compulsory lockout when the comparison falls within a first range, and wherein the electronic lockout corresponds to a discretionary lockout when the comparison falls within a second range.

17. The method of claim 16, further comprising:
    comparing, by the control circuit, the determined parameter to a first threshold and a second threshold, wherein the determined parameter comprises tissue compression force; and
    executing, by the control circuit, the electronic lockout based on the comparison of the tissue compression force to the first threshold and the second threshold.

18. The method of claim 16, further comprising:
    sensing, by a second sensor of the circular surgical stapler, a secondary measure of the circular surgical stapler, wherein the secondary measure comprises one or more of a severity of failure, a user input, and a predefined comparison lookup table; and
    controlling, by the control circuit, the electronic lockout based on the secondary measure.

19. The method of claim 16, further comprising:
executing, by the control circuit, a predetermined wait period prior to enabling operation of the circular surgical stapler.

* * * * *